US011031562B2

(12) United States Patent
Stoessel et al.

(10) Patent No.: US 11,031,562 B2
(45) Date of Patent: Jun. 8, 2021

(54) METAL COMPLEXES

(71) Applicant: Merck Patent GmbH, Darmstadt (DE)

(72) Inventors: Philipp Stoessel, Frankfurt am Main (DE); Nils Koenen, Griesheim (DE); Christian Ehrenreich, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 600 days.

(21) Appl. No.: 15/754,779

(22) PCT Filed: Jul. 27, 2016

(86) PCT No.: PCT/EP2016/001299
§ 371 (c)(1),
(2) Date: Feb. 23, 2018

(87) PCT Pub. No.: WO2017/032439
PCT Pub. Date: Mar. 2, 2017

(65) Prior Publication Data
US 2018/0254416 A1 Sep. 6, 2018

(30) Foreign Application Priority Data

Aug. 25, 2015 (EP) .................................... 15182264

(51) Int. Cl.
| | |
|---|---|
| *H01L 51/00* | (2006.01) |
| *C07D 401/14* | (2006.01) |
| *C07F 15/00* | (2006.01) |
| *H01L 51/50* | (2006.01) |
| *C07D 213/40* | (2006.01) |
| *C07D 213/68* | (2006.01) |
| *C07D 213/75* | (2006.01) |
| *C07D 215/12* | (2006.01) |
| *C07D 213/82* | (2006.01) |
| *C07D 213/30* | (2006.01) |
| *C09K 11/06* | (2006.01) |

(52) U.S. Cl.
CPC ........ *H01L 51/0085* (2013.01); *C07D 213/30* (2013.01); *C07D 213/40* (2013.01); *C07D 213/68* (2013.01); *C07D 213/75* (2013.01); *C07D 213/82* (2013.01); *C07D 215/12* (2013.01); *C07D 401/14* (2013.01); *C07F 15/0033* (2013.01); *C09K 11/06* (2013.01); *H01L 51/5016* (2013.01); *C09K 2211/185* (2013.01)

(58) Field of Classification Search
CPC .. C07D 213/30; C07D 213/40; C07D 213/68; C07D 213/75; C07D 213/82; C07D 215/12; C07D 401/14; C07F 15/0033; C09K 11/06; C09K 2211/185; H01L 51/0085; H01L 51/5016
See application file for complete search history.

(56) References Cited

U.S. PATENT DOCUMENTS

| | | | |
|---|---|---|---|
| 7,728,137 | B2 | 6/2010 | Stossel et al. |
| 9,673,405 | B2 | 6/2017 | Yasukawa et al. |
| 2004/0026663 | A1 | 2/2004 | Heuer et al. |
| 2005/0170207 | A1 | 8/2005 | Ma et al. |
| 2008/0027220 | A1 | 1/2008 | Stossel et al. |
| 2011/0108821 | A1 | 5/2011 | Kaiser et al. |
| 2013/0092879 | A1 | 4/2013 | Fortte et al. |
| 2014/0371825 | A1 | 12/2014 | Anemian et al. |
| 2015/0243910 | A1 | 8/2015 | De Cola et al. |
| 2017/0170413 | A1 | 6/2017 | Stoessel et al. |
| 2018/0026209 | A1 | 1/2018 | Stoessel et al. |

FOREIGN PATENT DOCUMENTS

| | | |
|---|---|---|
| CN | 102076640 A | 5/2011 |
| CN | 102947304 A | 2/2013 |
| CN | 104053746 A | 9/2014 |
| DE | 4217588 | * 12/1993 |
| JP | 2007524585 A | 8/2007 |
| JP | 2008-505925 A | 2/2008 |
| JP | 2008506652 A | 3/2008 |
| JP | 2012195554 A | 10/2012 |
| JP | 2013243234 A | 12/2013 |
| JP | 2013247174 A | 12/2013 |
| JP | 2018-510903 A | 4/2018 |
| TW | 200415956 A | 8/2004 |
| TW | 201425524 A | 7/2014 |
| WO | 2005076380 A2 | 8/2005 |
| WO | 2006014599 A2 | 2/2006 |
| WO | WO-2015117718 A1 | 8/2015 |
| WO | 2016124304 A1 | 8/2016 |

OTHER PUBLICATIONS

Royal Society of Chem., Dalton Transactions, (2012), 41(23), pp. 7005-7012. (Year: 2012).*
JACS, 1988, 110(8), pp. 2457-2464. (Year: 1988).*
New Journal of Chemistry, (2001), 25(2), pp. 275-282. (Year: 2001).*
Stibrany et al., "A Tris(pyrazolyl) η6-Arene Ligand That Selects Cu(I) over Cu(II)," Inorganic Chemistry, vol. 45, No. 24, pp. 9713-9720 (2006).
Tominaga et al., "Construction and Structural Investigation of Helical Coordination Network Formed by the Self-assembly of Triple Helicate with Macrocyclic Framework and Lanthanum Cations," Chemistry Letters, vol. 35, No. 7, pp. 718-719 (2006).
Kotova et al., "Cross-Linking the Fibers of Supramolecular Gels Formed from a Tripodal Terpyridine Derived Ligand with d-Block Metal Ions", Inorganic Chemistry, pp. 7735-7741, vol. 54 (2015).
Durr et al., "Highly Photostable Sensitizers for Artificial Photosynthesis. Ruthenium(II)-3,3'-Bis(diazine)-6,6'-oligo (ethylene glycol) Complexes and a New Class of Podates", Journal of the American Chemical Society, pp. 12362-12365, vol. 115 (1993).
European Office Action dated Mar. 14, 2019 in European Application No. 16747860.1.
Chinese Office Action dated Dec. 24, 2019 in Chinese Application No. 201680048857.8.

(Continued)

*Primary Examiner* — Dawn L Garrett
(74) *Attorney, Agent, or Firm* — Faegre Drinker Biddle & Reath LLP

(57) ABSTRACT

The present invention relates to metal complexes and to electronic devices, especially organic electroluminescent devices, comprising these metal complexes.

15 Claims, No Drawings

(56) References Cited

OTHER PUBLICATIONS

Chinese Search Report dated Dec. 24, 2019 in Chinese Application No. 201680048857.8.
Barigelletti, F., et al., "Caged and Uncaged Ruthenium(II)-Polypyridine Complexes. Comparative Study of the Photochemical, Photophysical, and Electrochemical Properties", J. Am. Chem. Soc., 1989, vol. 111, pp. 4662-4668.
De Cola, L., et al., "Mononuclear, Dinuclear, and Trinuclear Ruthenium(II) Complexes of a Tris(bipyridine) Bridging Ligand: Syntheses, Absorption Spectra, Redox Potentials, and Photophysical Properties", Inorganic Chemistry, 1990, vol. 29, No. 3, pp. 495-499.
Kropf, M., et al., "Biomimetic Models of the Photosynthetic Reaction Center Based on Ruthenium-Polypyridine Complexes", J. Phys. Chem. A, 1998, vol. 102, pp. 5499-5505.
Gross et al., "Concave Hydrocarbons", Chemistry A European Journal., vol. 2, No. 12, 1996, pp. 1585-1595.
Pierre et al., "Fraternal twin iridium hemicage chelates", Dalton Transactions, vol. 40, 2011, pp. 11726-11731.

\* cited by examiner

METAL COMPLEXES

RELATED APPLICATIONS

This application is a national stage entry, filed pursuant to 35 U.S.C. § 371, of PCT/EP2016/001299, filed Jul. 27, 2016, which claims the benefit of European Patent Application No. 15182264.0, filed Aug. 25, 2015, which is incorporated herein by reference in its entirety.

The present invention relates to metal complexes suitable for use as emitters in organic electroluminescent devices.

According to the prior art, triplet emitters used in phosphorescent organic electroluminescent devices (OLEDs) are iridium complexes in particular, especially bis- and tris-ortho-metallated complexes having aromatic ligands, where the ligands bind to the metal via a negatively charged carbon atom and an uncharged nitrogen atom or via a negatively charged carbon atom and an uncharged carbene carbon atom. Examples of such complexes are tris(phenylpyridyl) iridium(III) and derivatives thereof. Additionally known is a multitude of related ligands and iridium complexes, for example complexes with 1- or 3-phenylisoquinoline ligands, with 2-phenylquinolines or with phenylcarbenes.

An improvement in the stability of the complexes was achieved by the use of polypodal ligands, as described, for example, in WO 2004/081017, WO 2006/008069 or U.S. Pat. No. 7,332,232. Even though these complexes having polypodal ligands show advantages over the complexes which otherwise have the same ligand structure except that the individual ligands therein do not have polypodal bridging, there is still a need for improvement. This lies especially in the more complex synthesis of the compounds, such that, for example, the complexation reaction requires very long reaction times and high reaction temperatures. Furthermore, in the case of the complexes having polypodal ligands too, improvements are still desirable in relation to the properties on use in an organic electroluminescent device, especially in relation to efficiency, voltage and/or lifetime.

The problem addressed by the present invention is therefore that of providing novel metal complexes suitable as emitters for use in OLEDs. It is a particular object to provide emitters which exhibit improved properties in relation to efficiency, operating voltage and/or lifetime. It is a further object of the present invention to provide metal complexes which can be synthesized under milder synthesis conditions, especially in relation to reaction time and reaction temperature, compared in each case to complexes having structurally comparable ligands. It is a further object of the present invention to provide metal complexes which do not exhibit any facial-meridional isomerization, which can be a problem in the case of complexes according to the prior art.

It has been found that, surprisingly, this object is achieved by metal complexes having a hexadentate tripodal ligand wherein the bridge of the ligand that joins the individual sub-ligands has the structure described below, which are of very good suitability for use in an organic electroluminescent device. The present invention therefore provides these metal complexes and organic electroluminescent devices comprising these complexes.

The invention thus provides a monometallic metal complex containing a hexadentate tripodal ligand in which three bidentate sub-ligands which may be the same or different coordinate to a metal and the three bidentate sub-ligands are joined to one another via a bridge of the following formula (1):

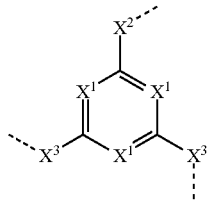

Formula (1)

where the dotted bond represents the bond of the bidentate sub-ligands to this structure and the symbols used are as follows:

$X^1$ is the same or different at each instance and is CR or N;

$X^2$ is the same or different at each instance and is —CR'=CR'—, —CR'=N—, —C(=O)—O—, —C(=O)—NR"—, —C(=O)—S—, —C(=S)—O—, —C(=S)—NR"— or —C(=S)—S—;

$X^3$ is the same or different at each instance and is $X^2$ or a —CR=CR— group;

R, R' is the same or different at each instance and is H, D, F, Cl, Br, I, $N(R^1)_2$, CN, $NO_2$, $OR^1$, $SR^1$, COOH, $C(=O)N(R^1)_2$, $Si(R^1)_3$, $B(OR^1)_2$, $C(=O)R^1$, $P(=O)(R^1)_2$, $S(=O)R^1$, $S(=O)_2R^1$, $OSO_2R^1$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more $R^1$ radicals, where one or more nonadjacent $CH_2$ groups may be replaced by $R^1C=CR^1$, $C\equiv C$, $Si(R^1)_2$, $C=O$, $NR^1$, O, S or $CONR^1$, or an aromatic or heteroaromatic ring system which has 5 to 40 aromatic ring atoms and may be substituted in each case by one or more $R^1$ radicals; at the same time, the two R' radicals when $X^2=$—CR'=CR'— may also together form an aliphatic or heteroaliphatic ring system; in addition, two R radicals when $X^3=$—CR=CR— may also together form an aliphatic, heteroaliphatic, aromatic or heteroaromatic ring system;

R" is the same or different at each instance and is H, D, a straight-chain alkyl group having 1 to 20 carbon atoms or a branched or cyclic alkyl group having 3 to 20 carbon atoms, where the alkyl group in each case may be substituted by one or more $R^1$ radicals and where one or more nonadjacent $CH_2$ groups may be replaced by $Si(R^1)_2$, or an aromatic or heteroaromatic ring system which has 5 to 40 aromatic ring atoms and may be substituted in each case by one or more $R^1$ radicals;

$R^1$ is the same or different at each instance and is H, D, F, Cl, Br, I, $N(R^2)_2$, CN, $NO_2$, $OR^2$, $SR^2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more $R^2$ radicals, where one or more nonadjacent $CH_2$ groups may be replaced by $R^2C=CR^2$, $C\equiv C$, $Si(R^2)_2$, $C=O$, $NR^2$, O, S or $CONR^2$, or an aromatic or heteroaromatic ring system which has 5 to 40 aromatic ring atoms and may be substituted in each case by one or more $R^2$ radicals; at the same time, two or more $R^1$ substituents together may also form an aliphatic, heteroaliphatic, aromatic or heteroaromatic ring system;

$R^2$ is the same or different at each instance and is H, D, F or an aliphatic, aromatic and/or heteroaromatic organic radical, especially a hydrocarbyl radical, having 1 to 20 carbon atoms, in which one or more hydrogen atoms may also be replaced by F;

at the same time, the three bidentate ligands, apart from by the bridge of the formula (1), may also be ring-closed by a further bridge to form a cryptate.

According to the invention, the ligand is thus a hexadentate tripodal ligand having three bidentate sub-ligands. The structure of the hexadentate tripodal ligand is shown in schematic form by the following formula (Lig):

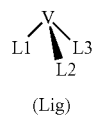

(Lig)

where V represents the bridge of formula (1) and L1, L2 and L3 are the same or different at each instance and are each bidentate sub-ligands. "Bidentate" means that the particular sub-ligand in the complex coordinates or binds to the metal via two coordination sites. "Tripodal" means that the ligand has three sub-ligands bonded to the bridge V or the bridge of the formula (1). Since the ligand has three bidentate sub-ligands, the overall result is a hexadentate ligand, i.e. a ligand which coordinates or binds to the metal via six coordination sites. The expression "bidentate sub-ligand" in the context of this application means that this unit would be a bidentate ligand if the bridge of the formula (1) were not present. However, as a result of the formal abstraction of a hydrogen atom in this bidentate ligand and the attachment to the bridge of the formula (1), it is no longer a separate ligand but a portion of the hexadentate ligand which thus arises, and so the term "sub-ligand" is used therefor.

The metal complex M(Lig) formed with this ligand of the formula (Lig) can thus be represented schematically by the following formula:

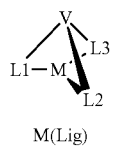

M(Lig)

where V represents the bridge of formula (1), L1, L2 and L3 are the same or different at each instance and are each bidentate sub-ligands and M is a metal. As can be inferred from the schematic drawing, all three bidentate sub-ligands coordinate to the metal via both coordination sites in each case in the compounds of the invention.

"Monometallic" in the context of the present invention means that the metal complex contains just a single metal atom, as also represented schematically by M(Lig). Metal complexes in which, for example, each of the three bidentate sub-ligands is coordinated to a different metal atom are thus not encompassed by the invention.

The bond of the ligand to the metal may either be a coordinate bond or a covalent bond, or the covalent fraction of the bond may vary according to the ligand and metal. When it is said in the present application that the ligand or sub-ligand coordinates or binds to the metal, this refers in the context of the present application to any kind of bond of the ligand or sub-ligand to the metal, irrespective of the covalent fraction of the bond.

Preferably, the compounds of the invention are characterized in that they are uncharged, i.e. electrically neutral. This is achieved in a simple manner by selecting the charges of the three bidentate sub-ligands such that they compensate for the charge of the metal atom complexed. Thus, for example, if a metal atom in the +3 oxidation state is used, charge neutrality can be achieved by virtue of each of the three bidentate sub-ligands being monoanionic.

Preferred embodiments of the group of the formula (1) are detailed hereinafter. The $X^2$ group may be an alkenyl group, an imine group, an amide group, an ester group or the corresponding sulphur analogues of amide and ester groups. The $X^3$ group, when $X^3$ is —CR=CR— and the R radicals together form an aromatic or heteroaromatic ring system, may also be an ortho-bonded aryl or heteroaryl group. In the case of unsymmetric $X^2$ or $X^3$ groups, any orientation of the groups is possible. This is shown hereinafter by the example of $X^2=X^3=$—C(=O)—O—. This gives rise to the following possible orientations of $X^2$ and $X^3$, all of which are encompassed by the present invention:

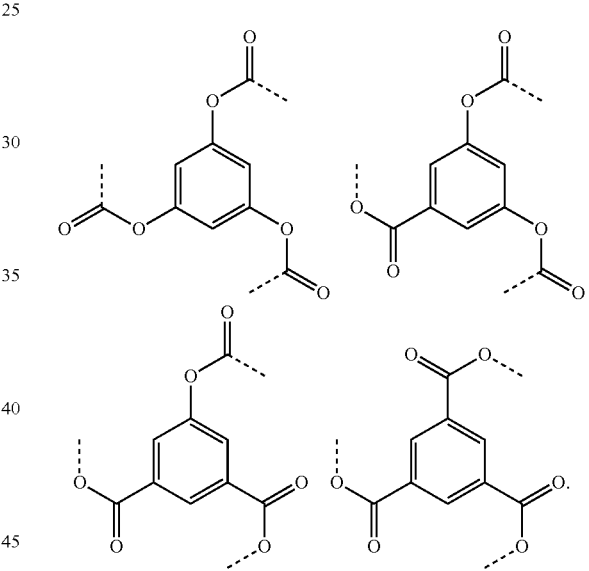

When $X^2$ or $X^3$ is an alkenyl group or an imine group, these are cis-bonded alkenyl or imine groups.

The wording that two or more radicals together may form a ring, in the context of the present description, shall be understood to mean, inter alia, that the two radicals are joined to one another by a chemical bond with formal elimination of two hydrogen atoms. This is illustrated by the following scheme:

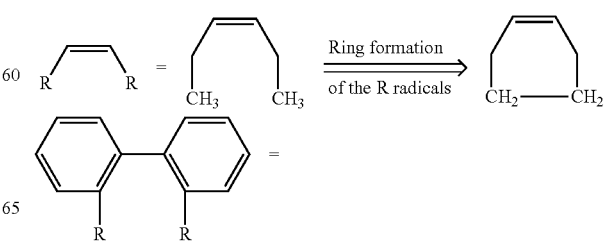

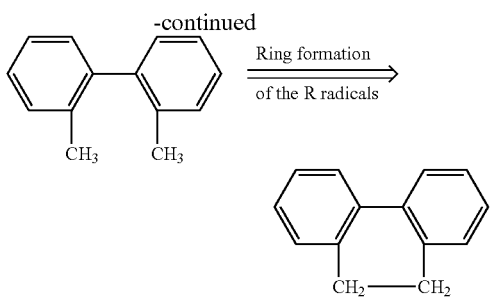

In addition, the abovementioned wording shall also be understood to mean that, if one of the two radicals is hydrogen, the second radical binds to the position to which the hydrogen atom was bonded, forming a ring. This is illustrated by the following scheme:

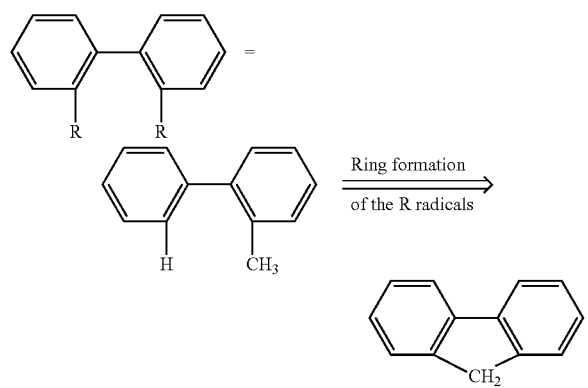

An aryl group in the context of this invention contains 6 to 40 carbon atoms; a heteroaryl group in the context of this invention contains 2 to 40 carbon atoms and at least one heteroatom, with the proviso that the sum total of carbon atoms and heteroatoms is at least 5. The heteroatoms are preferably selected from N, O and/or S. An aryl group or heteroaryl group is understood here to mean either a simple aromatic cycle, i.e. benzene, or a simple heteroaromatic cycle, for example pyridine, pyrimidine, thiophene, etc., or a fused aryl or heteroaryl group, for example naphthalene, anthracene, phenanthrene, quinoline, isoquinoline, etc.

An aromatic ring system in the context of this invention contains 6 to 40 carbon atoms in the ring system. A heteroaromatic ring system in the context of this invention contains 1 to 40 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be interrupted by a nonaromatic unit (preferably less than 10% of the atoms other than H), for example a carbon, nitrogen or oxygen atom or a carbonyl group. For example, systems such as 9,9'-spirobifluorene, 9,9-diarylfluorene, triarylamine, diaryl ethers, stilbene, etc. shall also be regarded as aromatic ring systems in the context of this invention, and likewise systems in which two or more aryl groups are interrupted, for example, by a linear or cyclic alkyl group or by a silyl group. In addition, systems in which two or more aryl or heteroaryl groups are bonded directly to one another, for example biphenyl, terphenyl, quaterphenyl or bipyridine, shall likewise be regarded as an aromatic or heteroaromatic ring system.

A cyclic alkyl, alkoxy or thioalkoxy group in the context of this invention is understood to mean a monocyclic, bicyclic or polycyclic group.

In the context of the present invention, a $C_1$- to $C_{20}$-alkyl group in which individual hydrogen atoms or $CH_2$ groups may also be replaced by the abovementioned groups are understood to mean, for example, the methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclohex-1-yl, 1-(n-butyl)cyclohex-1-yl, 1-(n-hexyl)cyclohex-1-yl, 1-(n-octyl)cyclohex-1-yl and 1-(n-decyl)cyclohex-1-yl radicals. An alkenyl group is understood to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is understood to mean, for example, ethynyl, propynyl, butynyl, pentynyl, hexynyl, heptynyl or octynyl. A $C_1$- to $C_{40}$-alkoxy group is understood to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system which has 5-40 aromatic ring atoms and may also be substituted in each case by the abovementioned radicals and which may be joined to the aromatic or heteroaromatic system via any desired positions is understood to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

Suitable embodiments of the group of the formula (1) are the structures of the following formulae (2) to (5):

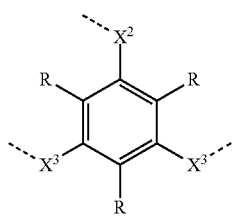

Formula (2)

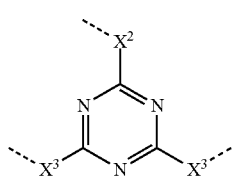

Formula (3)

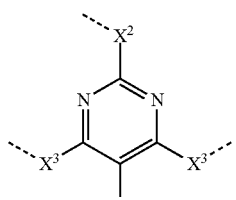

Formula (4)

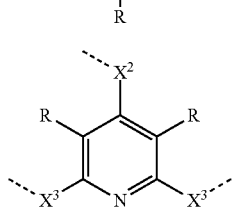

Formula (5)

where the symbols used have the definitions given above.

In a preferred embodiment of the invention, all $X^1$ groups in the group of the formula (1) are CR, and so the central trivalent cycle of the formula (1) is an optionally substituted benzene. More preferably, all $X^1$ groups are CH. In a further preferred embodiment of the invention, all $X^1$ groups are a nitrogen atom, and so the central trivalent cycle of the formula (1) is a triazine. Preferred embodiments of the formula (1) are thus the structures of the formulae (2) and (3).

Preferred R radicals on $X^1$ and especially on the trivalent central benzene ring of the formula (2) are as follows:
R is the same or different at each instance and is H, D, F, CN, $OR^1$, a straight-chain alkyl group having 1 to 10 carbon atoms or an alkenyl group having 2 to 10 carbon atoms or a branched or cyclic alkyl group having 3 to 10 carbon atoms, each of which may be substituted by one or more $R^1$ radicals, or an aromatic or heteroaromatic ring system which has 5 to 24 aromatic ring atoms and may be substituted in each case by one or more $R^1$ radicals;

$R^1$ is the same or different at each instance and is H, D, F, CN, $OR^2$, a straight-chain alkyl group having 1 to 10 carbon atoms or an alkenyl group having 2 to 10 carbon atoms or a branched or cyclic alkyl group having 3 to 10 carbon atoms, each of which may be substituted by one or more $R^2$ radicals, or an aromatic or heteroaromatic ring system which has 5 to 24 aromatic ring atoms and may be substituted in each case by one or more $R^2$ radicals;

$R^2$ is the same or different at each instance and is H, D, F or an aliphatic, aromatic and/or heteroaromatic organic radical having 1 to 20 carbon atoms, in which one or more hydrogen atoms may also be replaced by F.

Particularly preferred R radicals on $X^1$ and especially on the trivalent central benzene ring of the formula (2) are as follows:
R is the same or different at each instance and is H, D, F, CN, a straight-chain alkyl group having 1 to 4 carbon atoms or a branched or cyclic alkyl group having 3 to 6 carbon atoms, each of which may be substituted by one or more $R^1$ radicals, or an aromatic or heteroaromatic ring system which has 6 to 12 aromatic ring atoms and may be substituted in each case by one or more $R^1$ radicals;

$R^1$ is the same or different at each instance and is H, D, F, CN, a straight-chain alkyl group having 1 to 4 carbon atoms or a branched or cyclic alkyl group having 3 to 6 carbon atoms, each of which may be substituted by one or more $R^2$ radicals, or an aromatic or heteroaromatic ring system which has 6 to 12 aromatic ring atoms and may be substituted in each case by one or more $R^2$ radicals;

$R^2$ is the same or different at each instance and is H, D, F or an aliphatic or aromatic hydrocarbyl radical having 1 to 12 carbon atoms.

More preferably, the structure of the formula (2) is especially a structure of the following formula (2'):

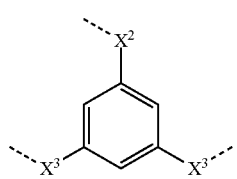

Formula (2')

where the symbols used have the definitions given above.

There follows a description of preferred bivalent $X^2$ or $X^3$ groups as occur in the structures of the formulae (1) to (5).

In a preferred embodiment of the invention, the $X^2$ symbol is the same or different at each instance and is —CR'=CR'—, —C(=O)—O— or —C(=O)—NR''—. In a further preferred embodiment of the invention, the $X^3$ symbol is the same or different at each instance and is —CR'=CR'—, —C(=O)—O— or —C(=O)—NR''—. Preferred combinations of $X^2$ and $X^3$ are:

| $X^2$ | $X^3$ | $X^3$ |
|---|---|---|
| —CR'=CR— | —CR=CR— | —CR=CR— |
| —C(=O)—O— | —C(=O)—O— | —C(=O)—O— |
| —C(=O)—O— | —C(=O)—O— | —CR=CR— |
| —C(=O)—O— | —CR=CR— | —CR=CR— |
| —C(=O)—NR''— | —C(=O)—NR''— | —C(=O)—NR''— |

-continued
| $X^2$ | $X^3$ | $X^3$ |
|---|---|---|
| —C(=O)—NR″— | —C(=O)—NR″— | —CR=CR— |
| —C(=O)—NR″— | —CR=CR— | —CR=CR— |
The group of the formula (1) may preferably be represented by the following formulae (1a) to (1m):
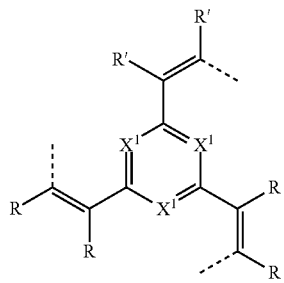
Formula (1a)
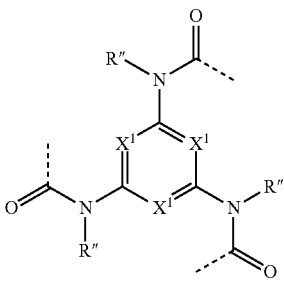
Formula (1b)
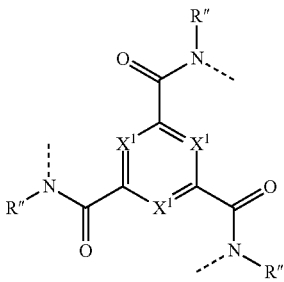
Formula (1c)
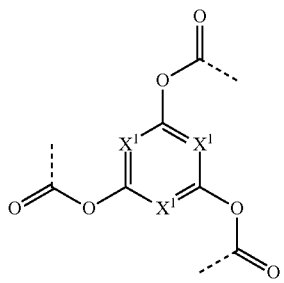
Formula (1d)
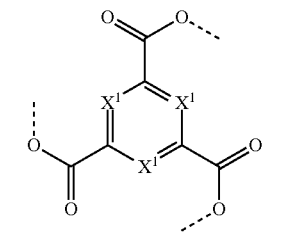
Formula (1e)
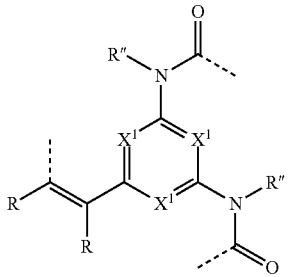
Formula (1f)
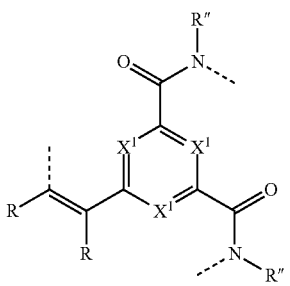
Formula (1g)
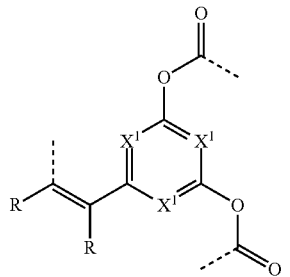
Formula (1h)
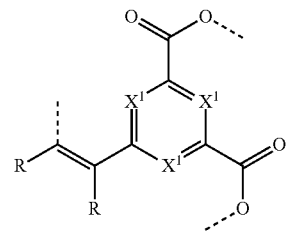
Formua (1i)
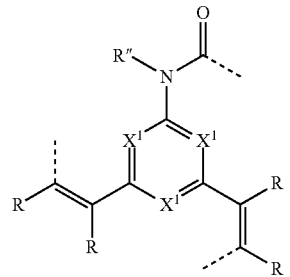
Formula (1j)

Formula (1k)

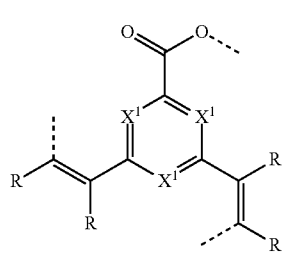

Formula (1l)

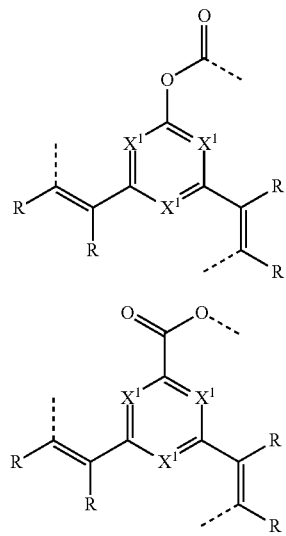

Formula (1m)

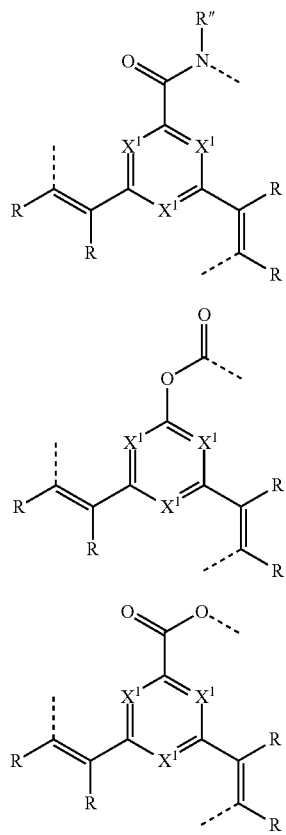

where the symbols have the definitions given above. At the same time, the R radicals in the formulae (1f) to (1m) preferably form an aromatic or heteroaromatic ring system with one another.

The groups of the formulae (2) to (5) are correspondingly preferably selected from the groups of the following formulae (2a) to (5e):

Formula (2a)

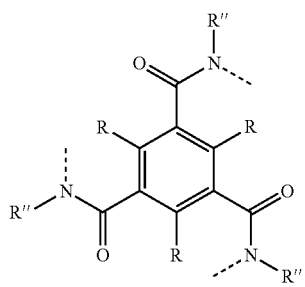

Formula (2b)

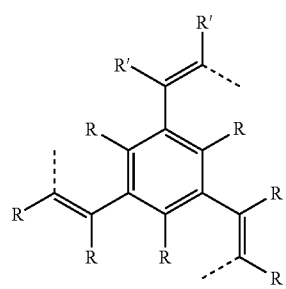

Formula (2c)

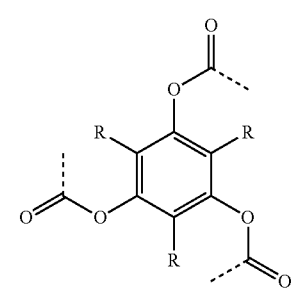

Formula (2d)

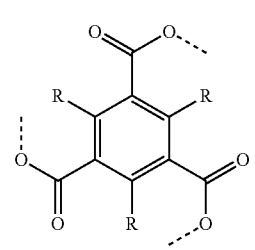

Formula (2e)

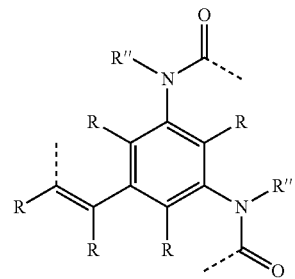

Formula (2f)

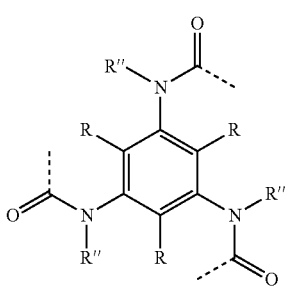

Formula (2g)

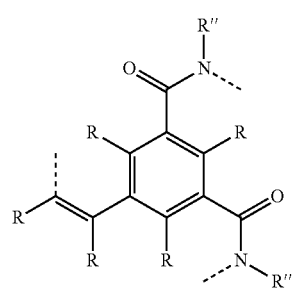

Formula (2h)
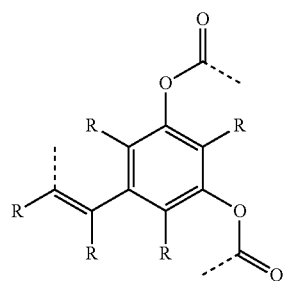
Formula (2i)
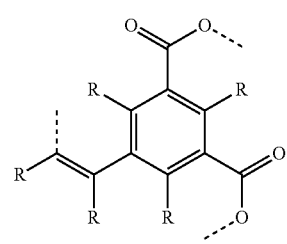
Formula (2j)
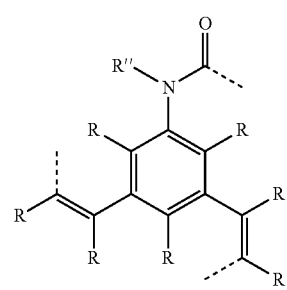
Formula (2k)
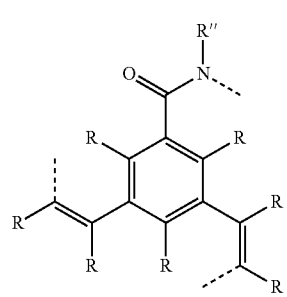
Formula (2l)
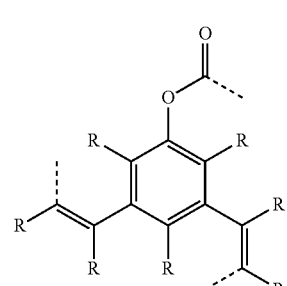
Formula (2m)
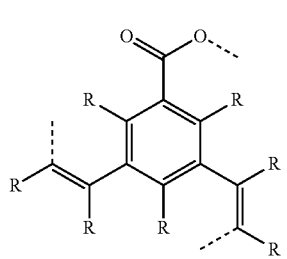
Formula (3a)
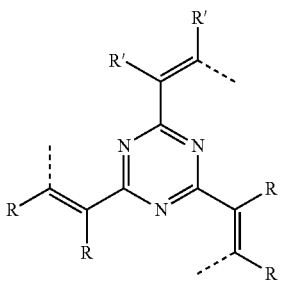
Formula (3b)
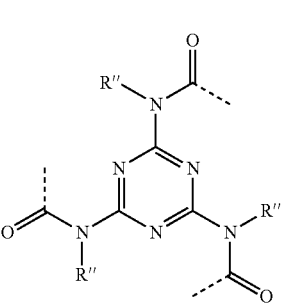
Formula (3c)
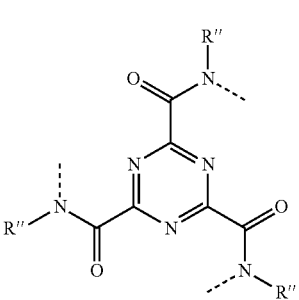
Formula (3d)
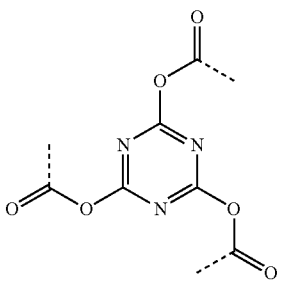
Formula (3e)
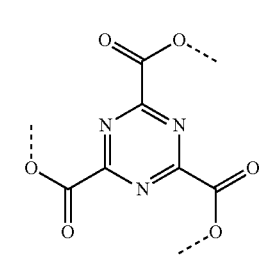

Formula (3f)
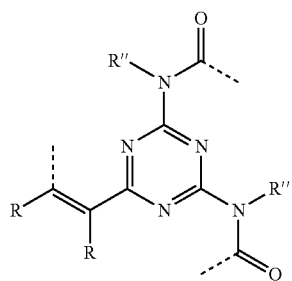
Formula (3g)
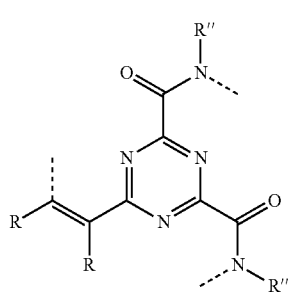
Formula (3h)
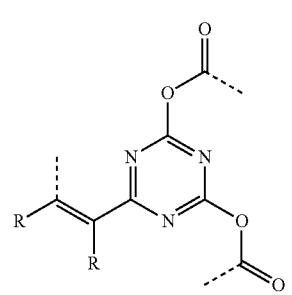
Formula (3i)
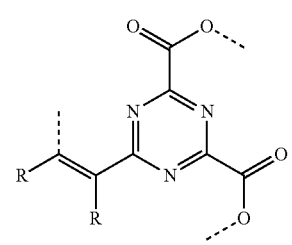
Formula (3j)
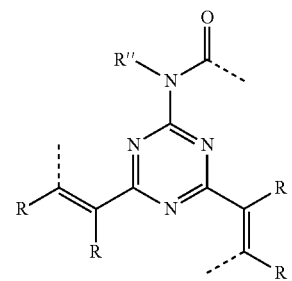
Formula (3k)
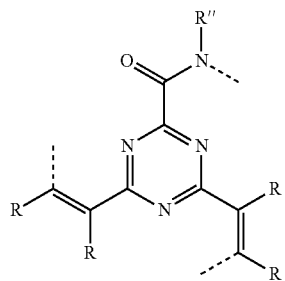
Formula (3l)
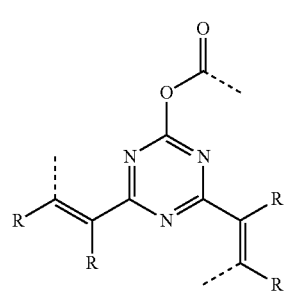
Formula (3m)
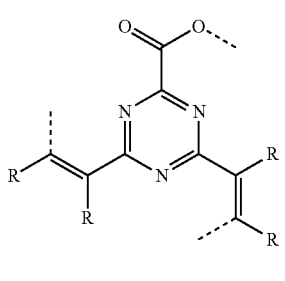
Formula (4a)
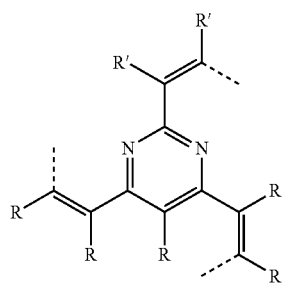
Formula (4b)
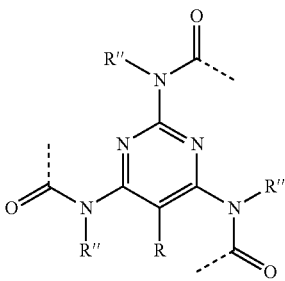

where the symbols have the definitions given above. At the same time, the R radicals in the formulae (2f) to (2m) and (3f) to (3m) preferably form an aromatic or heteroaromatic ring system with one another.

Particular preference is given to the groups of the following formulae (2a') to (2m'):

Formula (2c')
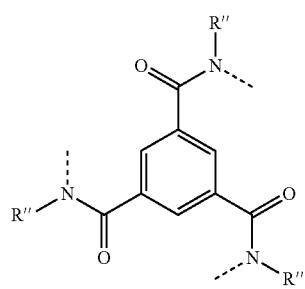
Formula (2d')
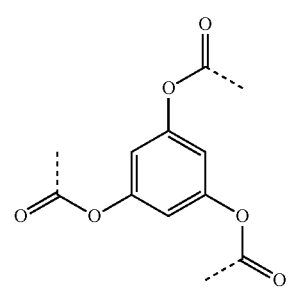
Formula (2e')
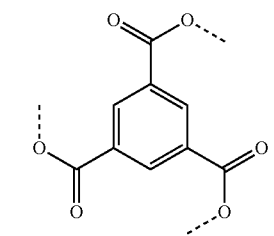
Formula (2f')
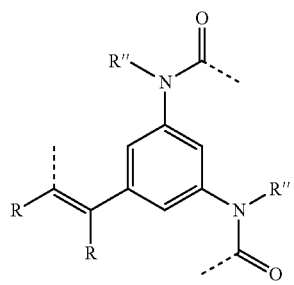
Formula (2g')
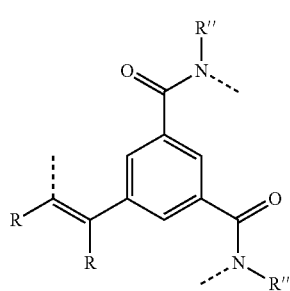
Formula (2h')
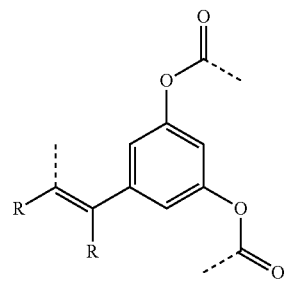
Formula (2i')
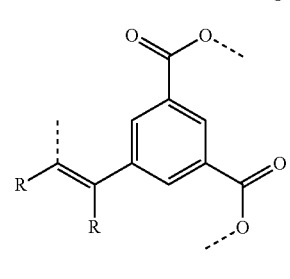
Formula (2j')
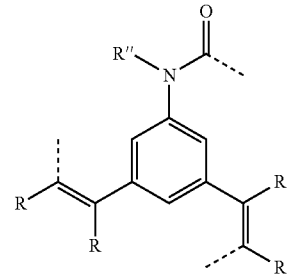
Formula (2k')
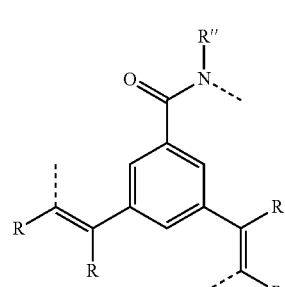
Formula (2l')
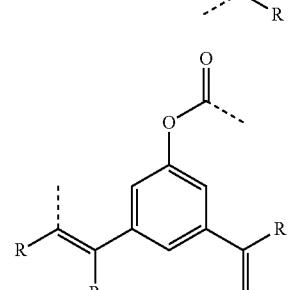
Formula (2m')
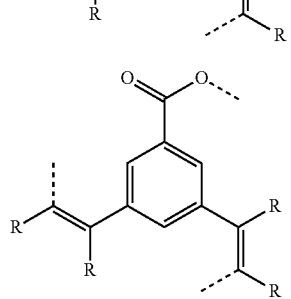

where the symbols have the definitions given above. At the same time, the R radicals in the formulae (2f') to (2m') preferably form an aromatic or heteroaromatic ring system with one another.

When $X^2$ or $X^3$ is —C(=O)—NR"—, R" is preferably the same or different at each instance and is a straight-chain alkyl group having 1 to 10 carbon atoms or a branched or cyclic alkyl group having 3 to 10 carbon atoms or an aromatic or heteroaromatic ring system having 6 to 24 aromatic ring atoms, each of which be substituted by one or more $R^1$ radicals. More preferably, R" is the same or different at each instance and is a straight-chain alkyl group having 1 to 5 carbon atoms or a branched or cyclic alkyl group having 3 to 6 carbon atoms or an aromatic or heteroaromatic ring system having 6 to 12 aromatic ring atoms, each of which be substituted by one or more $R^1$ radicals, but is preferably unsubstituted.

When the $X^2$ group is a cis-bonded alkenyl group —CR'=CR'—, it may be preferable when the R' radicals form an aliphatic or heteroaliphatic ring system with one another. The manner in which the substituents form such a ring is described in detail further down.

When the $X^3$ group is an alkenyl group —CR=CR— and the R radicals do not form an aromatic or heteroaromatic ring system with one another, preferred embodiments of the group are the same as detailed above and hereinafter for $X^2$.

When $X^3$ is —CR=CR— and the R substituents form an aromatic or heteroaromatic ring system with one another, the group is preferably an aryl or heteroaryl group which has 5 to 13 aromatic ring atoms and preferably contains not more than two heteroatoms, more preferably not more than one heteroatom, where the heteroatoms are selected from N, O and S, preferably N and O, more preferably N. This does not mean that any substituents bonded to this group cannot also contain heteroatoms.

Preferred embodiments for $X^3$=—CR=CR— in which the substituents form an aromatic or heteroaromatic ring system are the structures of the following formulae (6) to (22):

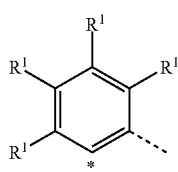

Formula (6)

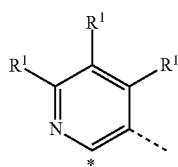

Formula (7)

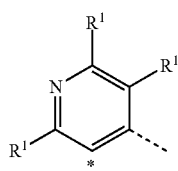

Formula (8)

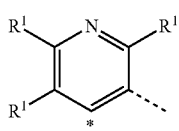

Formula (9)

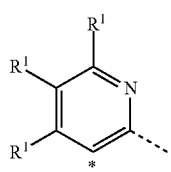

Formula (10)

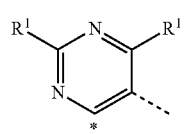

Formula (11)

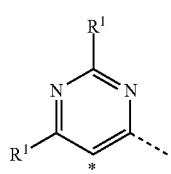

Formula (12)

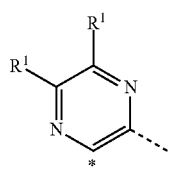

Formula (13)

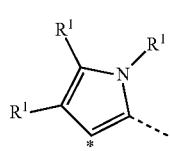

Formula (14)

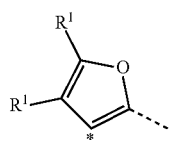

Formula (15)

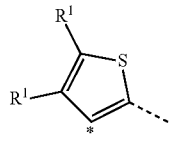

Formula (16)

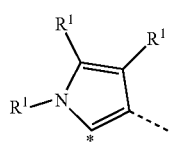

Formula (17)

Formula (18)
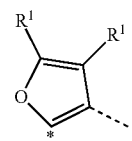

Formula (19)
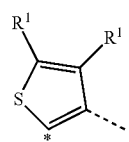

Formula (20)
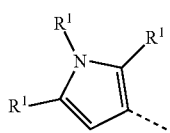

Formula (21)
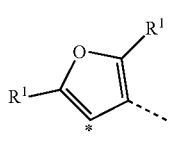

Formula (22)
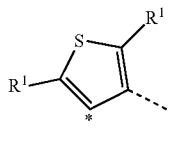

where the dotted bond in each case represents the position of the bond of the bidentate sub-ligands to this structure, * represents the position of the linkage of the unit of the formula (6) to (22) to the central trivalent aryl or heteroaryl group and the further symbols used have the definitions given above.

Particular preference is given to the optionally substituted six-membered aromatic rings and six-membered heteroaromatic rings of the formulae (6) to (10) depicted above. Very particular preference is given to ortho-phenylene, i.e. a group of the abovementioned formula (6).

At the same time, as also described above, it is also possible for adjacent substituents together to form a ring system, such that fused structures, including fused aryl and heteroaryl groups, for example naphthalene, quinoline, benzimidazole, carbazole, dibenzofuran or dibenzothiophene, can form. Such ring formation is shown schematically below in groups of the abovementioned formula (6), which leads to groups of the following formulae (6a) to (6j):

Formula (6a)
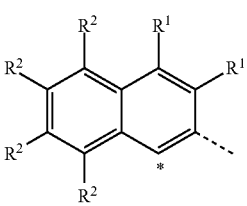

Formula (6b)
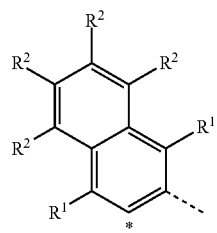

Formula (6c)
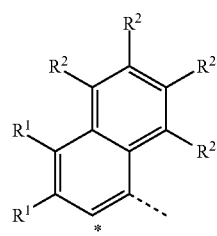

Formula (6d)
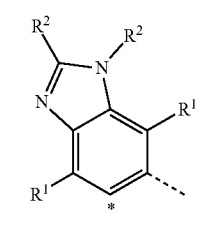

Formula (6e)
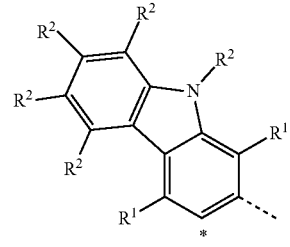

Formula (6f)
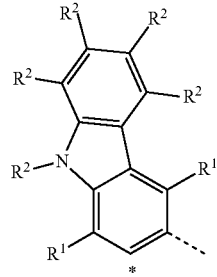

Formula (6g)
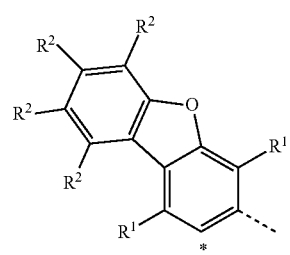

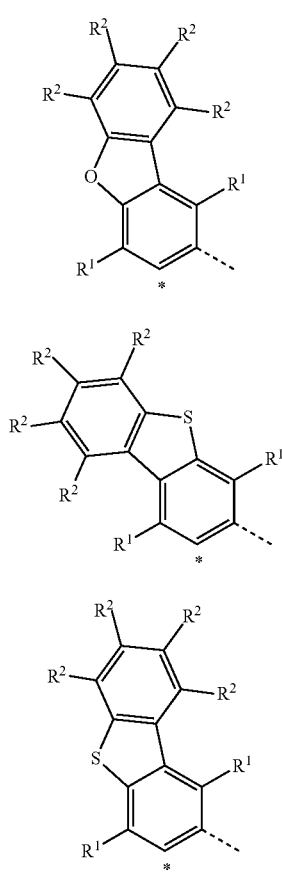

Formula (6h)

Formula (6i)

Formula 6j)

where the symbols used have the definitions given above.

It is generally the case that the three $X^2$ and $X^3$ groups present in the unit of the formulae (15) to (5) may be the same or different. In a preferred embodiment of the invention, all three $X^2$ and $X^3$ groups are the same and also have identical substitution. The reason for this preference is the better synthetic accessibility. In a further preferred embodiment of the invention, the $X^2$ and $X^3$ groups are different, where the two $X^3$ groups may likewise be the same or different. The reason for this preference is the better solubility and generally lower sublimation temperature of the compounds.

There follows a description of the preferred metals in the metal complex of the invention. In a preferred embodiment of the invention, the metal is a transition metal, where transition metals in the context of the present invention do not include the lanthanides and actinides, or is a main group metal. When the metal is a main group metal, it is preferably selected from metals of the third and fourth main groups, preferably Al(III), In(III), Ga(III) or Sn(IV), especially Al(III). When the metal is a transition metal, it is preferably selected from the group consisting of chromium, molybdenum, tungsten, rhenium, ruthenium, osmium, rhodium, iridium, iron, cobalt, nickel, palladium, platinum, copper, silver and gold, especially molybdenum, tungsten, rhenium, ruthenium, osmium, iridium, copper, platinum and gold. Very particular preference is given to iridium. The metals may be present in different oxidation states. Preference is given to the abovementioned metals in the following oxidation states: Cr(0), Cr(III), Cr(VI), Mo(0), Mo(III), Mo(VI), W(0), W(III), W(VI), Re(I), Re(III), Re(IV), Ru(II), Ru(III), Os(II), Os(III), Os(IV), Rh(III), Ir(III), Ir(IV), Fe(II), Fe(III), Co(II), Co(III), Ni(II), Ni(IV), Pt(IV), Cu(II), Cu(III), Au(III) and Au(V). Particular preference is given to Mo(0), W(0), Re(I), Ru(II), Os(II), Rh(III) and Ir(III). Very particular preference is given to Ir(III). Especially in the case of use of heavy transition metals, for example Ir(III), the compounds of the invention are phosphorescent compounds.

It is particularly preferable when the preferred embodiments of the sub-ligands as laid out in more detail below and of the bridge of the formula (1) are combined with the preferred embodiments of the metal. Particular preference is thus given to metal complexes in which the metal is Ir(III) and which have a bridge of the formula (2) to (5) or (2a) to (5e) and the $X^2$ or $X^3$ group in formula (2) to (5) or the preferred embodiments have the preferred embodiments detailed above.

There follows a description of the bidentate sub-ligands joined to the bridge of the formula (1) or the abovementioned preferred embodiments. The preferred embodiments of the bidentate sub-ligands especially depend on the particular metal used. The three bidentate sub-ligands may be the same or different. When all three bidentate sub-ligands selected are the same, this results in $C_3$-symmetric metal complexes when the unit of the formula (1) also has $C_3$ symmetry, which is advantageous in terms of the synthesis of the ligands. However, it may also be advantageous to select the three bidentate sub-ligands differently or to select two identical sub-ligands and a different third sub-ligand, so as to give rise to $C_1$-symmetric metal complexes, because this permits greater possible variation of the ligands, such that the desired properties of the complex, for example the HOMO and LUMO position or the emission colour, can be varied more easily. Moreover, the solubility of the complexes can thus also be improved without having to use long aliphatic or aromatic solubility-imparting groups. In addition, unsymmetric complexes frequently have a lower sublimation temperature than similar symmetric complexes.

In a preferred embodiment of the invention, either the three bidentate sub-ligands are selected identically or two of the bidentate sub-ligands are selected identically and the third bidentate sub-ligand is different from the first two bidentate sub-ligands. In this context "identical sub-ligands" means firstly that the ligand structure selected itself is the same, and secondly that these structures also have the same substitution.

In a preferred embodiment of the invention, each of the bidentate sub-ligands is the same or different and is either monoanionic or uncharged. More preferably, each of the bidentate sub-ligands is monoanionic.

In a further preferred embodiment of the invention, the coordinating atoms of the bidentate sub-ligands are the same or different at each instance and are selected from C, N, P, O, S and/or B, more preferably C, N and/or O.

When the metal is selected from the main group metals, the coordinating atoms of the bidentate sub-ligands are preferably the same or different at each instance and are selected from N, O and/or S. More preferably, the bidentate sub-ligands have two nitrogen atoms or two oxygen atoms or one nitrogen atom and one oxygen atom per sub-ligand as coordinating atoms. In this case, the coordinating atoms of each of the three sub-ligands may be the same, or they may be different.

When the metal is selected from the transition metals, the coordinating atoms of the bidentate sub-ligands are preferably the same or different at each instance and are selected from C, N, O and/or S, more preferably C, N and/or O and most preferably C and/or N. The bidentate sub-ligands preferably have one carbon atom and one nitrogen atom or two carbon atoms or two nitrogen atoms or two oxygen atoms or one oxygen atom and one nitrogen atom per sub-ligand as coordinating atoms. In this case, the coordinating atoms of each of the three sub-ligands may be the same, or they may be different. More preferably, at least one of the bidentate sub-ligands has one carbon atom and one nitrogen atom or two carbon atoms as coordinating atoms, especially one carbon atom and one nitrogen atom. Most preferably, at least two of the bidentate sub-ligands and especially all three bidentate sub-ligands have one carbon atom and one nitrogen atom or two carbon atoms as coordinating atoms, especially one carbon atom and one nitrogen atom. This is especially true when the metal is Ir(III). When the metal is Ru, Co, Fe, Os, Cu or Ag, particularly preferred coordinating atoms in the bidentate sub-ligands are also two nitrogen atoms.

In a particularly preferred embodiment of the invention, the metal is Ir(III) and two of the bidentate sub-ligands each coordinate to the iridium via one carbon atom and one nitrogen atom and the third of the bidentate sub-ligands coordinates to the iridium via one carbon atom and one nitrogen atom or via two nitrogen atoms or via one nitrogen atom and one oxygen atom or via two oxygen atoms, especially via one carbon atom and one nitrogen atom. Particular preference is thus given to an iridium complex in which all three bidentate sub-ligands are ortho-metallated, i.e. form a metallacycle with the iridium in which a metal-carbon bond is present.

It is further preferable when the metallacycle which is formed from the metal and the bidentate sub-ligand is a five-membered ring, which is preferable particularly when the coordinating atoms are C and N, N and N, or N and O. When the coordinating atoms are O, a six-membered metallacyclic ring may also be preferred. This is shown schematically hereinafter:

Five-membered ring   Six-membered ring where M is the metal, N is a coordinating nitrogen atom, C is a coordinating carbon atom and O represents coordinating oxygen atoms, and the carbon atoms shown are atoms of the bidentate ligand.

There follows a description of the structures of the bidentate sub-ligands which are preferred when the metal is a transition metal.

In a preferred embodiment of the invention, at least one of the bidentate sub-ligands, more preferably at least two of the bidentate sub-ligands, most preferably all three of the bidentate sub-ligands, are the same or different at each instance and are a structure of the following formulae (L-1), (L-2), (L-3) and (L-4):

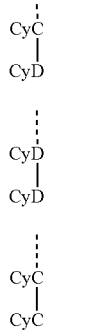

Formula (L-1)

Formula (L-2)

Formula (L-3)

Formula (L-4)

where the dotted bond represents the bond of the sub-ligand to the bridge of the formulae (1) to (5) or the preferred embodiments and the other symbols used are as follows:

CyC is the same or different at each instance and is an optionally substituted aryl or heteroaryl group which has 5 to 14 aromatic ring atoms and coordinates in each case to the metal via a carbon atom and which is bonded in each case to CyD via a covalent bond;

CyD is the same or different at each instance and is an optionally substituted heteroaryl group which has 5 to 14 aromatic ring atoms and coordinates to the metal via a nitrogen atom or via a carbene carbon atom and which is bonded to CyC via a covalent bond;

at the same time, two or more of the optional substituents together may form a ring system; in addition, the optional radicals are preferably selected from the abovementioned R radicals.

At the same time, CyD in the sub-ligands of the formulae (L-1) and (L-2) preferably coordinates via an uncharged nitrogen atom or via a carbene carbon atom. Further preferably, one of the two CyD groups in the ligand of the formula (L-3) coordinates via an uncharged nitrogen atom and the other of the two CyD groups via an anionic nitrogen atom. Further preferably, CyC in the sub-ligands of the formulae (L-1), (L-2) and (L-4) coordinates via anionic carbon atoms.

Particular preference is given to the bidentate sub-ligands of the formulae (L-1) and (L-2).

When two or more of the substituents, especially two or more R radicals, together form a ring system, it is possible for a ring system to be formed from substituents bonded to directly adjacent carbon atoms. In addition, it is also possible that the substituents on CyC and CyD in the formulae (L-1) and (L-2) or the substituents on the two CyD groups in formula (L-3) or the substituents on the two CyC groups in formula (L-4) together form a ring, as a result of which CyC and CyD or the two CyD groups or the two CyC groups may also together form a single fused aryl or heteroaryl group as bidentate ligands.

In a preferred embodiment of the present invention, CyC is an aryl or heteroaryl group having 6 to 13 aromatic ring atoms, more preferably having 6 to 10 aromatic ring atoms, most preferably having 6 aromatic ring atoms, which coordinates to the metal via a carbon atom, which may be substituted by one or more R radicals and which is bonded to CyD via a covalent bond.

Preferred embodiments of the CyC group are the structures of the following formulae (CyC-1) to (CyC-20):

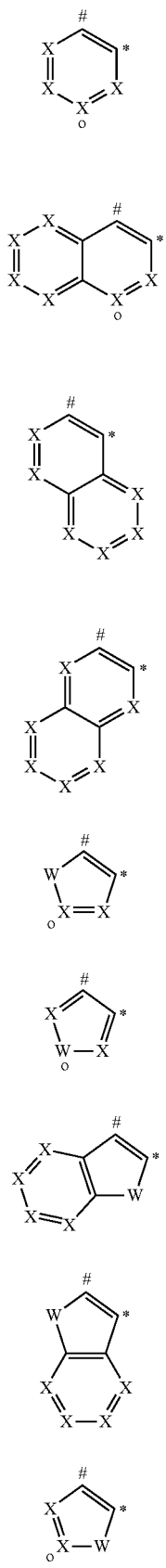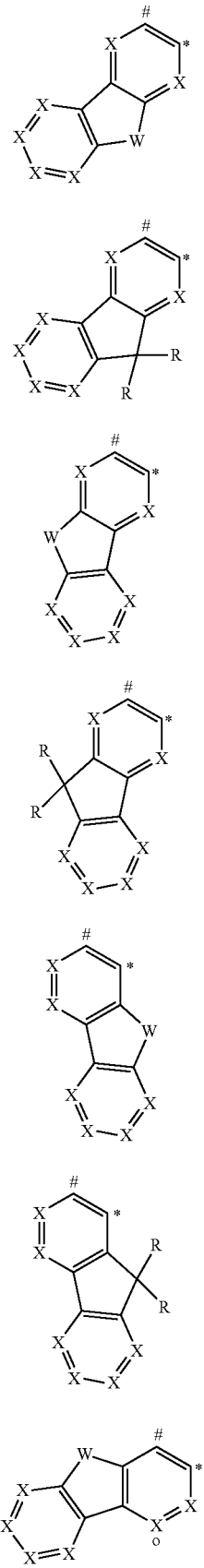

-continued

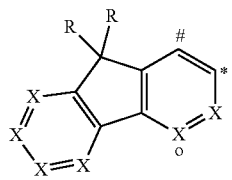
(CyC-17)

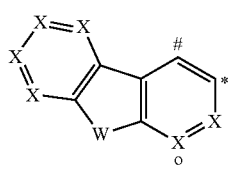
(CuC-18)

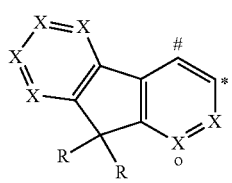
(CyC-19)

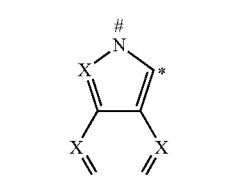
(CyC-20)

where the group binds in each case to the position in CyD indicated by # in (L-1) or (L-2), or in CyC in (L-4), and coordinates to the metal at the position indicated by *, R has the definitions given above and the further symbols used are as follows:
X is the same or different at each instance and is CR or N, with the proviso that not more than two symbols X per cycle are N;
W is the same or different at each instance and is NR, O or S;
with the proviso that, when the bridge of the formulae (1) to (5) or the preferred embodiments is bonded to CyC, one symbol X is C and the bridge of the formulae (1) to (5) or the preferred embodiments is bonded to this carbon atom. When the CyC group is bonded to the bridge of the formulae (1) to (5) or the preferred embodiments, the bond is preferably via the position marked by "o" in the formulae depicted above, and so the symbol X marked by "o" in that case is preferably C. The above-depicted structures which do not contain any symbol X marked by "o" are preferably not bonded directly to the bridge of the formulae (1) to (5) or the preferred embodiments, since such a bond to the bridge is not advantageous for steric reasons. Such CyC groups are preferably incorporated only in formula (L-1), or as the lower group in formula (L-4).

Preferably, a total of not more than two symbols X in CyC are N, more preferably not more than one symbol X in CyC is N, and most preferably all symbols X are CR, with the proviso that, when the bridge of the formulae (1) to (5) or the preferred embodiments is bonded to CyC, one symbol X is C and the bridge of the formulae (1) to (5) or the preferred embodiments is bonded to this carbon atom.

Particularly preferred CyC groups are the groups of the following formulae (CyC-1a) to (CyC-20a):

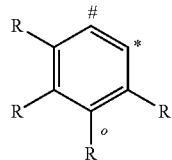
(Cyc-1a)

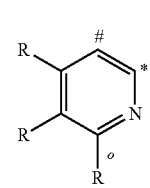
(CyC-1b)

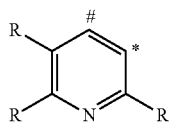
(CyC-1c)

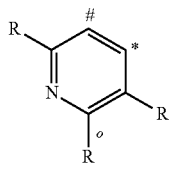
(CyC-1d)

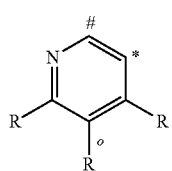
(CyC-1e)

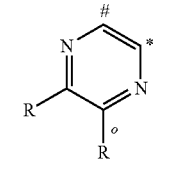
(CyC-1f)

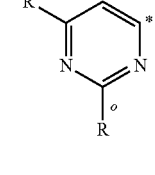
(CyC-1g)

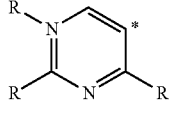
(CyC-1h)

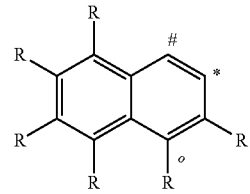
(CyC-2a)

-continued
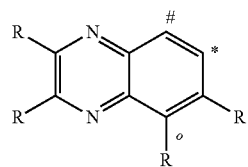
(CyC-2b)
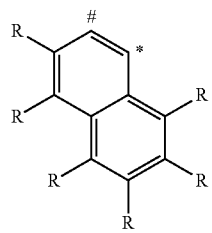
(CyC-3a)
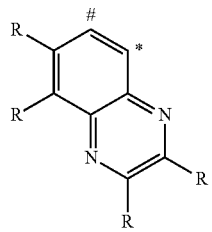
(CyC-3b)
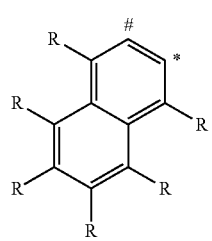
(CyC-4a)
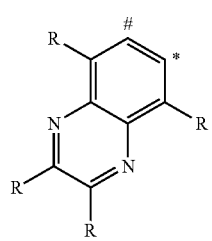
(CyC-4b)
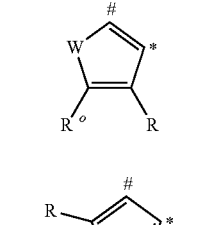
(CyC-5a)
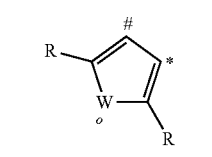
(CyC-6a)
-continued
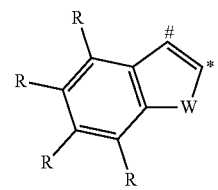
(CyC-7a)
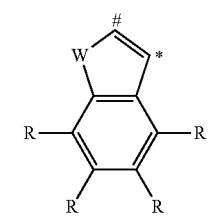
(CyC-8a)
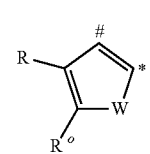
(CyC-9a)
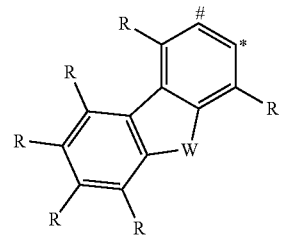
(CyC-10a)
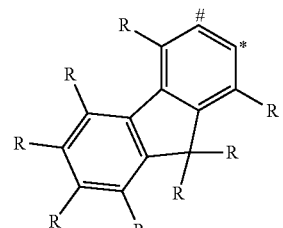
(CyC-11a)
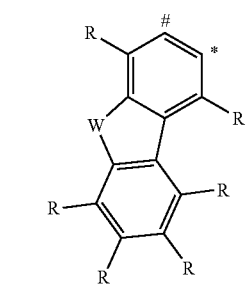
(CyC-12a)

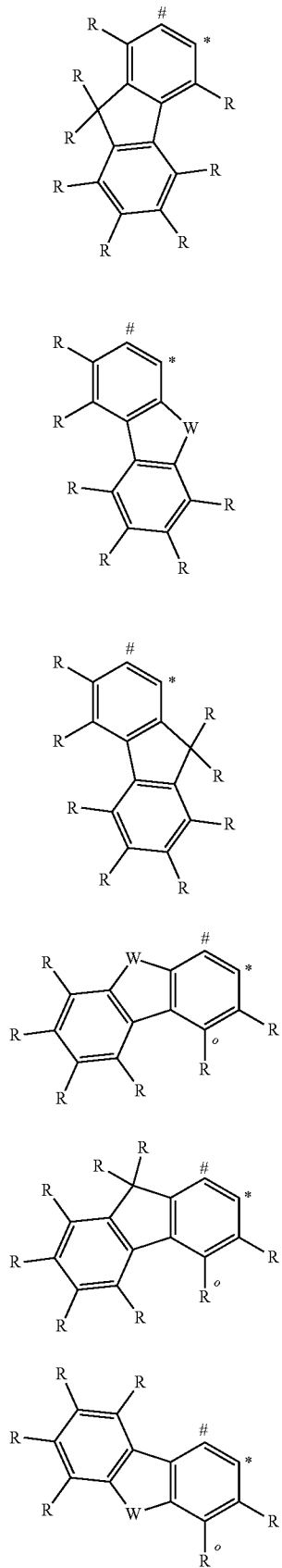

(CyC-13a)

(CyC-14a)

(CyC-15a)

(CyC-16a)

(CyC-17a)

(CyC-18a)

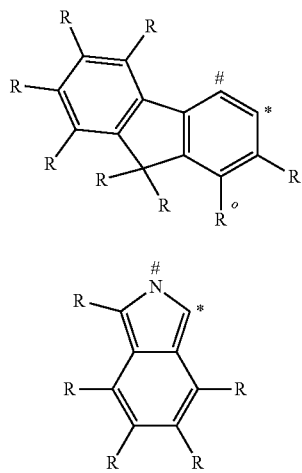

(CyC-19a)

(CyC-20a)

where the symbols used have the definitions given above and, when the bridge of the formulae (1) to (5) or the preferred embodiments is bonded to CyC, one R radical is not present and the bridge of the formulae (1) to (5) or the preferred embodiments is bonded to the corresponding carbon atom. When the CyC group is bonded to the bridge of the formulae (1) to (5) or the preferred embodiments, the bond is preferably via the position marked by "o" in the formulae depicted above, and so the R radical in this position in that case is preferably absent. The above-depicted structures which do not contain any carbon atom marked by "o" are preferably not bonded directly to the bridge of the formulae (1) to (5) or the preferred embodiments.

Preferred groups among the (CyC-1) to (CyC-19) groups are the (CyC-1), (CyC-3), (CyC-8), (CyC-10), (CyC-12), (CyC-13) and (CyC-16) groups, and particular preference is given to the (CyC-1a), (CyC-3a), (CyC-8a), (CyC-10a), (CyC-12a), (CyC-13a) and (CyC-16a) groups.

In a further preferred embodiment of the invention, CyD is a heteroaryl group having 5 to 13 aromatic ring atoms, more preferably having 6 to 10 aromatic ring atoms, which coordinates to the metal via an uncharged nitrogen atom or via a carbene carbon atom and which may be substituted by one or more R radicals and which is bonded via a covalent bond to CyC.

Preferred embodiments of the CyD group are the structures of the following formulae (CyD-1) to (CyD-14):

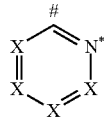

(CyD-1)

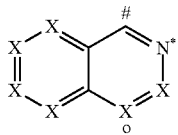

(CyD-2)

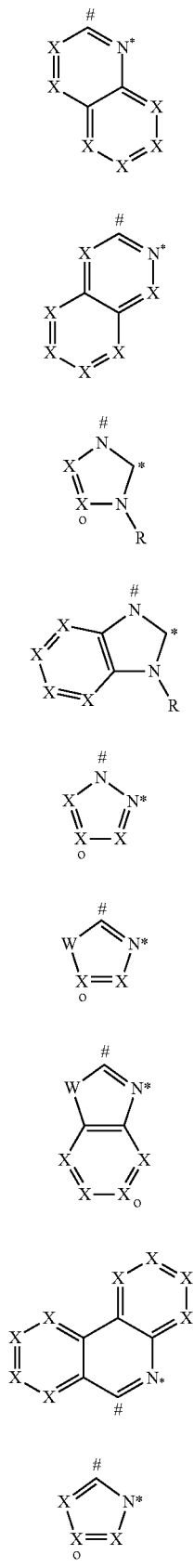
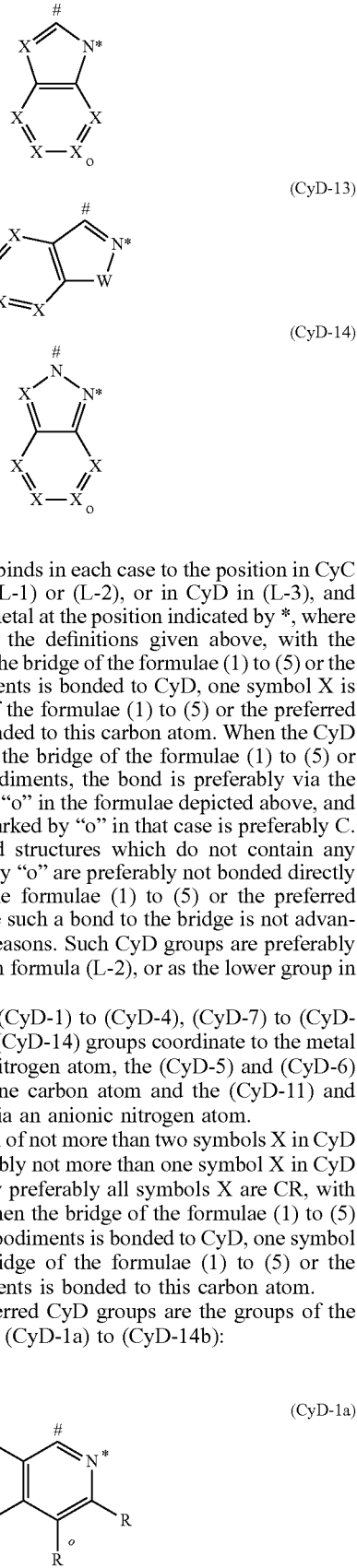

where the group binds in each case to the position in CyC indicated by # in (L-1) or (L-2), or in CyD in (L-3), and coordinates to the metal at the position indicated by *, where X, W and R have the definitions given above, with the proviso that, when the bridge of the formulae (1) to (5) or the preferred embodiments is bonded to CyD, one symbol X is C and the bridge of the formulae (1) to (5) or the preferred embodiments is bonded to this carbon atom. When the CyD group is bonded to the bridge of the formulae (1) to (5) or the preferred embodiments, the bond is preferably via the position marked by "o" in the formulae depicted above, and so the symbol X marked by "o" in that case is preferably C. The above-depicted structures which do not contain any symbol X marked by "o" are preferably not bonded directly to the bridge of the formulae (1) to (5) or the preferred embodiments, since such a bond to the bridge is not advantageous for steric reasons. Such CyD groups are preferably incorporated only in formula (L-2), or as the lower group in formula (L-3).

In this case, the (CyD-1) to (CyD-4), (CyD-7) to (CyD-10), (CyD-13) and (CyD-14) groups coordinate to the metal via an uncharged nitrogen atom, the (CyD-5) and (CyD-6) groups via a carbene carbon atom and the (CyD-11) and (CyD-12) groups via an anionic nitrogen atom.

Preferably, a total of not more than two symbols X in CyD are N, more preferably not more than one symbol X in CyD is N, and especially preferably all symbols X are CR, with the proviso that, when the bridge of the formulae (1) to (5) or the preferred embodiments is bonded to CyD, one symbol X is C and the bridge of the formulae (1) to (5) or the preferred embodiments is bonded to this carbon atom.

Particularly preferred CyD groups are the groups of the following formulae (CyD-1a) to (CyD-14b):

(CyD-2a) 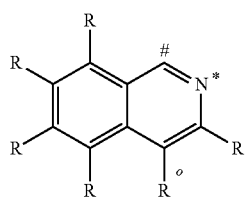
(CyD-3a) 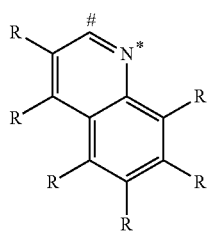
(CyD-3b) 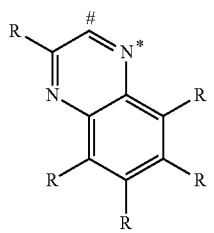
(CyD-4a) 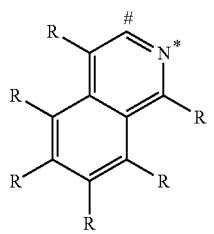
(CyD-5a) 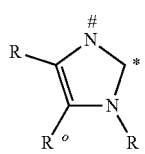
(CyD-6a) 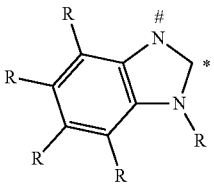
(CyD-7a) 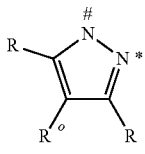
(CyD-8a) 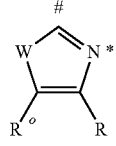
(CyD-9a) 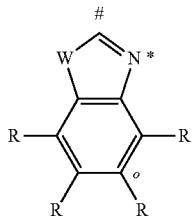
(CyD-10a) 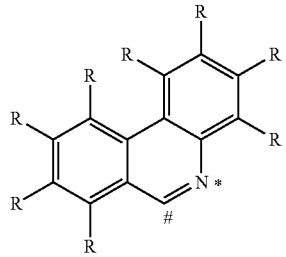
(CyD-11a) 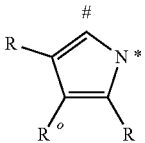
(CyD-11b) 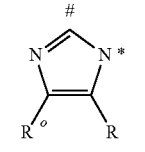
(CyC-11c) 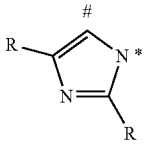
(CyD-11d) 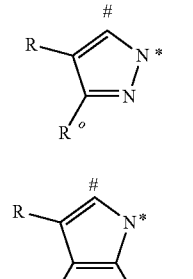
(CyD-12a) 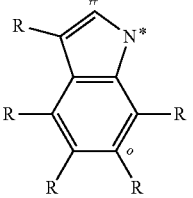
(CyD-12b) 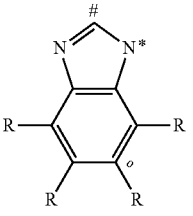

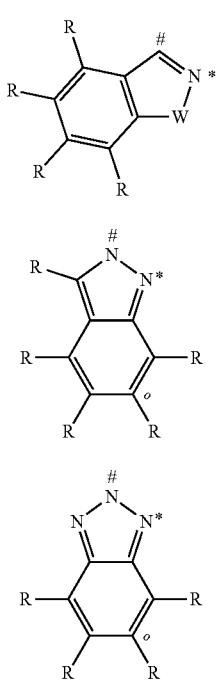

(CyD-13a)

(CyD-14a)

(CyD-14b)

where the symbols used have the definitions given above and, when the bridge of the formulae (1) to (5) or the preferred embodiments is bonded to CyD, one R radical is not present and the bridge of the formulae (1) to (5) or the preferred embodiments is bonded to the corresponding carbon atom. When the CyD group is bonded to the bridge of the formulae (1) to (5) or the preferred embodiments, the bond is preferably via the position marked by "o" in the formulae depicted above, and so the R radical in this position in that case is preferably absent. The above-depicted structures which do not contain any carbon atom marked by "o" are preferably not bonded directly to the bridge of the formulae (1) to (5) or the preferred embodiments.

Preferred groups among the (CyD-1) to (CyD-10) groups are the (CyD-1), (CyD-2), (CyD-3), (CyD-4), (CyD-5) and (CyD-6) groups, especially (CyD-1), (CyD-2) and (CyD-3), and particular preference is given to the (CyD-1a), (CyD-2a), (CyD-3a), (CyD-4a), (CyD-5a) and (CyD-6a) groups, especially (CyD-1a), (CyD-2a) and (CyD-3a).

In a preferred embodiment of the present invention, CyC is an aryl or heteroaryl group having 6 to 13 aromatic ring atoms, and at the same time CyD is a heteroaryl group having 5 to 13 aromatic ring atoms. More preferably, CyC is an aryl or heteroaryl group having 6 to 10 aromatic ring atoms, and at the same time CyD is a heteroaryl group having 5 to 10 aromatic ring atoms. Most preferably, CyC is an aryl or heteroaryl group having 6 aromatic ring atoms, and CyD is a heteroaryl group having 6 to 10 aromatic ring atoms. At the same time, CyC and CyD may be substituted by one or more R radicals.

The abovementioned preferred (CyC-1) to (CyC-20) and (CyD-1) to (CyD-14) groups may be combined with one another as desired in the sub-ligands of the formulae (L-1) and (L-2), provided that at least one of the CyC or CyD groups has a suitable attachment site to the bridge of the formulae (1) to (5) or the preferred embodiments, suitable attachment sites being signified by "o" in the formulae given above.

It is especially preferable when the CyC and CyD groups specified above as particularly preferred, i.e. the groups of the formulae (CyC-1a) to (CyC-20a) and the groups of the formulae (CyD1-a) to (CyD-14b), are combined with one another, provided that at least one of these groups has a suitable attachment site to the bridge of the formulae (1) to (5) or the preferred embodiments, suitable attachment sites being signified by "o" in the formulae given above. Combinations in which neither CyC nor CyD has such a suitable attachment site for the bridge of the formulae (1) to (5) or the preferred embodiments are therefore not preferred.

It is very particularly preferable when one of the (CyC-1), (CyC-3), (CyC-8), (CyC-10), (CyC-12), (CyC-13) and (CyC-16) groups and especially the (CyC-1a), (CyC-3a), (CyC-8a), (CyC-10a), (CyC-12a), (CyC-13a) and (CyC-16a) groups is combined with one of the (CyD-1), (CyD-2) and (CyD-3) groups and especially with one of the (CyD-1a), (CyD-2a) and (CyD-3a) groups.

Preferred sub-ligands (L-1) are the structures of the following formulae (L-1-1) and (L-1-2), and preferred sub-ligands (L-2) are the structures of the following formulae (L-2-1) to (L-2-3):

(L-1-1)

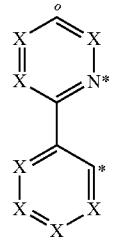

(L-1-2)

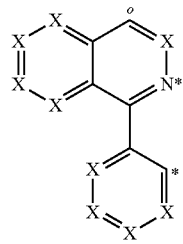

(L-2-1)

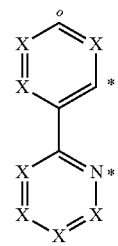

(L-2-2)

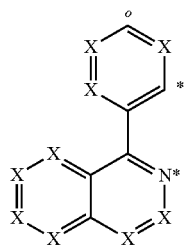

(L-2-3)

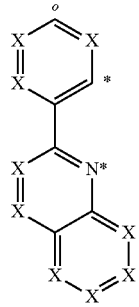

where the symbols used have the definitions given above and "o" represents the position of the bond to the bridge of the formulae (1) to (5) or the preferred embodiments.

Particularly preferred sub-ligands (L-1) are the structures of the following formulae (L-1-1a) and (L-1-2b), and particularly preferred sub-ligands (L-2) are the structures of the following formulae (L-2-1a) to (L-2-3a):

(L-1-1a)

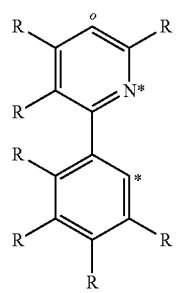

(L-1-2a)

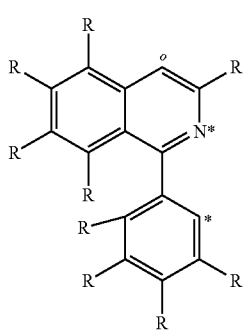

(L-2-1a)

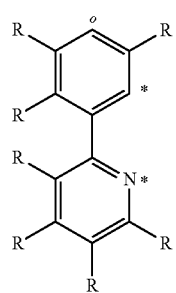

(L-2-2a)

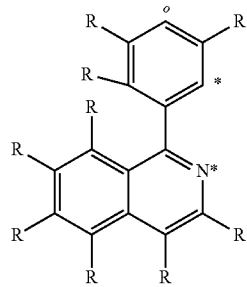

(L-2-3a)

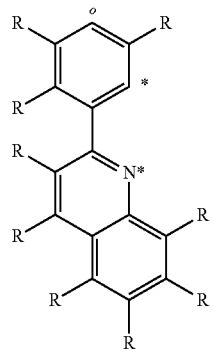

where the symbols used have the definitions given above and "o" represents the position of the bond to the bridge of the formulae (1) to (5) or the preferred embodiments.

It is likewise possible for the abovementioned preferred CyD groups in the sub-ligands of the formula (L-3) to be combined with one another as desired, it being preferable to combine an uncharged CyD group, i.e. a (CyD-1) to (CyD-10), (CyD-13) or (CyD-14) group, with an anionic CyD group, i.e. a (CyD-11) or (CyD-12) group, provided that at least one of the preferred CyD groups has a suitable attachment site to the bridge of the formulae (1) to (5) or the preferred embodiments, suitable attachment sites being signified by "o" in the formulae given above.

It is likewise possible to combine the abovementioned preferred CyC groups with one another as desired in the sub-ligands of the formula (L-4), provided that at least one of the preferred CyC groups has a suitable attachment site to the bridge of the formulae (1) to (5) or the preferred embodiments, suitable attachment sites being signified by "o" in the formulae given above.

When two R radicals, one of them bonded to CyC and the other to CyD in the formulae (L-1) and (L-2) or one of them bonded to one CyD group and the other to the other CyD group in formula (L-3) or one of them bonded to one CyC group and the other to the other CyC group in formula (L-4), form a ring system with one another, this may result in bridged sub-ligands and, for example, also in sub-ligands which represent a single larger heteroaryl group overall, for example benzo[h]quinoline, etc. The ring formation between the substituents on CyC and CyD in the formulae (L-1) and (L-2) or between the substituents on the two CyD groups in formula (L-3) or between the substituents on the two (CyC) groups in formula (L-4) is preferably via a group according to one of the following formulae (23) to (32):

Formel (23)
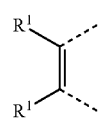

Formel (24)
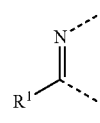

Formel (25)
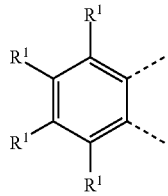

Formel (26)
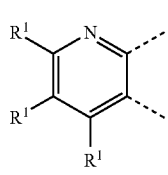

Formel (27)
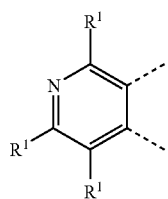

Formel (28)
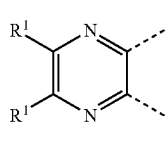

Formel (29)
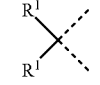

Formel (30)
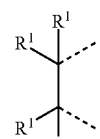

Formel (31)
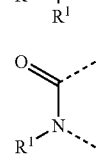

Formel (32)
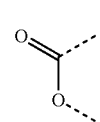

where $R^1$ has the definitions given above and the dotted bonds signify the bonds to CyC or CyD. At the same time, the unsymmetric groups among those mentioned above may be incorporated in each of the two possible options; for example, in the group of the formula (32), the oxygen atom may bind to the CyC group and the carbonyl group to the CyD group, or the oxygen atom may bind to the CyD group and the carbonyl group to the CyC group.

At the same time, the group of the formula (29) is preferred particularly when this results in ring formation to give a six-membered ring, as shown below, for example, by the formulae (L-23) and (L-24).

Preferred ligands which arise through ring formation between two R radicals in the different cycles are the structures of the formulae (L-5) to (L-32) shown below:

(L-5)
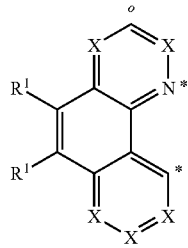

(L-6)
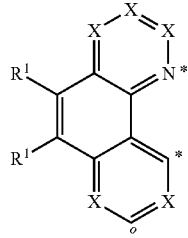

(L-7)
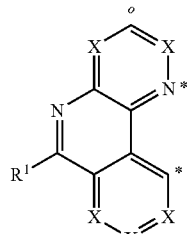

(L-8)
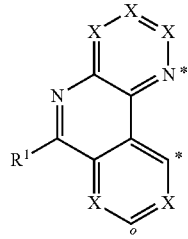

(L-9)
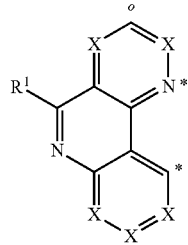

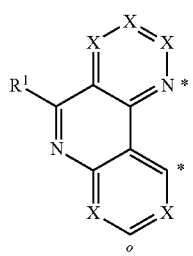 (L-10)
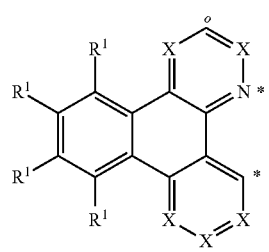 (L-11)
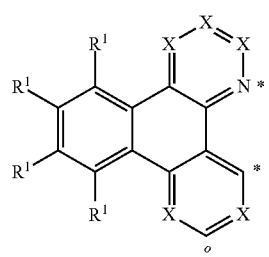 (L-12)
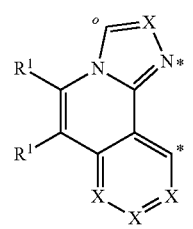 (L-13)
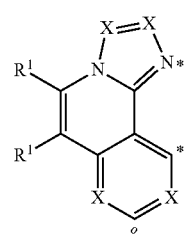 (L-14)
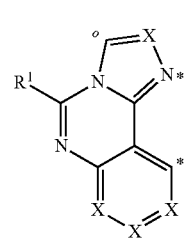 (L-15)
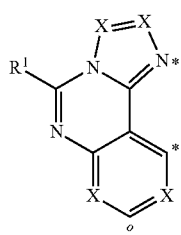 (L-16)
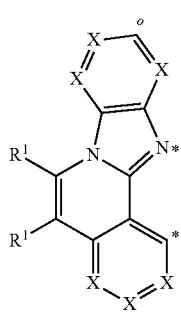 (L-17)
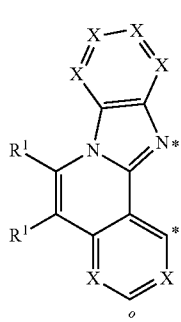 (L-18)
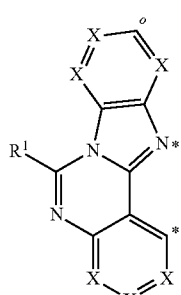 (L-19)
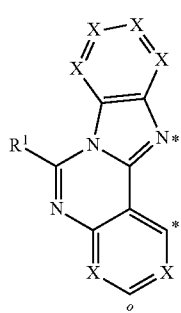 (L-20)

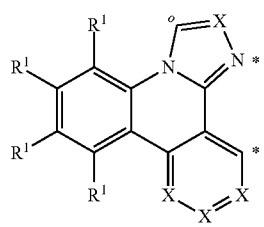 (L-21)
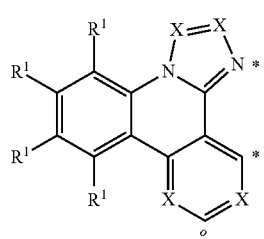 (L-22)
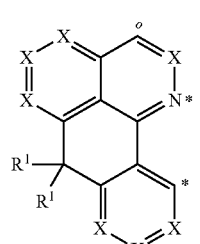 (L-23)
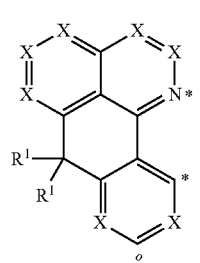 (L-24)
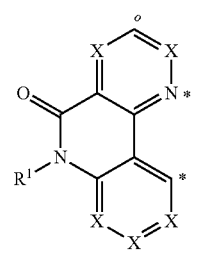 (L-25)
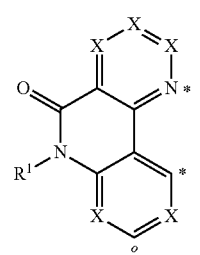 (L-26)
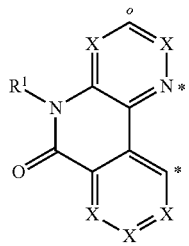 (L-27)
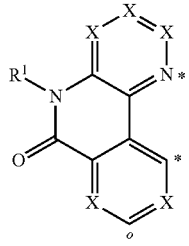 (L-28)
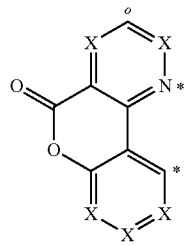 (L-29)
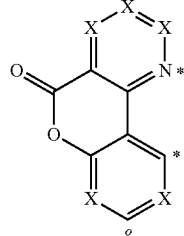 (L-30)
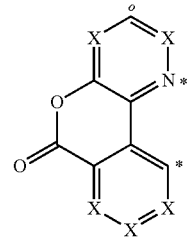 (L31)
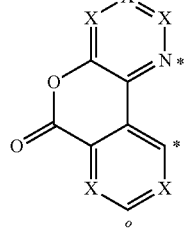 (L-32)

where the symbols used have the definitions given above and "o" indicates the position at which this sub-ligand is joined to the group of the formulae (1) to (5) or the preferred embodiments.

In a preferred embodiment of the sub-ligands of the formulae (L-5) to (L-32), a total of one symbol X is N and the other symbols X are CR, or all symbols X are CR. More preferably, all symbols X are CR.

In a further embodiment of the invention, it is preferable if, in the groups (CyC-1) to (CyC-20) or (CyD-1) to (CyD-14) or in the sub-ligands (L-5) to (L-32), one of the atoms X is N when an R group bonded as a substituent adjacent to this nitrogen atom is not hydrogen or deuterium. This applies analogously to the preferred structures (CyC-1a) to (CyC-20a) or (CyD-1a) to (CyD-14b) in which a substituent bonded adjacent to a non-coordinating nitrogen atom is preferably an R group which is not hydrogen or deuterium.

This substituent R is preferably a group selected from CF$_3$, OCF$_3$, alkyl or alkoxy groups having 1 to 10 carbon atoms, especially branched or cyclic alkyl or alkoxy groups having 3 to 10 carbon atoms, a dialkylamino group having 2 to 10 carbon atoms, aromatic or heteroaromatic ring systems or aralkyl or heteroaralkyl groups. These groups are sterically demanding groups. Further preferably, this R radical may also form a cycle with an adjacent R radical.

A further suitable bidentate sub-ligand for metal complexes in which the metal is a transition metal is a sub-ligand of the following formula (L-33) or (L-34):

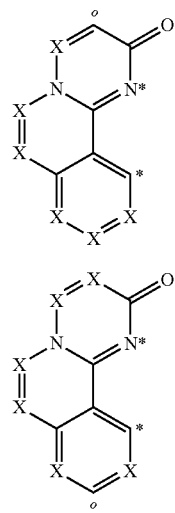

where R has the definitions given above, * represents the position of coordination to the metal, "o" represents the position of linkage of the sub-ligand to the group of the formulae (1) to (5) or the preferred embodiments and the other symbols used are as follows:

X is the same or different at each instance and is CR or N, with the proviso that not more than one symbol X per cycle is N, and with the additional proviso that one symbol X is C and the group of the formulae (1) to (5) or the preferred embodiments is bonded to this carbon atom.

When two R radicals bonded to adjacent carbon atoms in the sub-ligands (L-33) and (L-34) form an aromatic cycle with one another, this cycle together with the two adjacent carbon atoms is preferably a structure of the following formula (33):

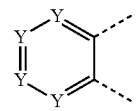

Formula (33)

where the dotted bonds symbolize the linkage of this group within the sub-ligand and Y is the same or different at each instance and is CR$^1$ or N and preferably not more than one symbol Y is N.

In a preferred embodiment of the sub-ligand (L-33) or (L-34), not more than one group of the formula (33) is present. The sub-ligands are thus preferably sub-ligands of the following formulae (L-35) to (L-40):

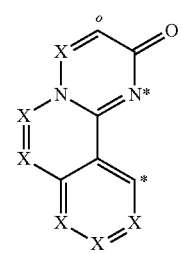
(L-35)

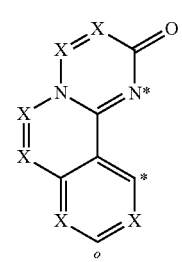
(L-36)

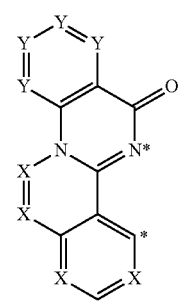
(L-37)

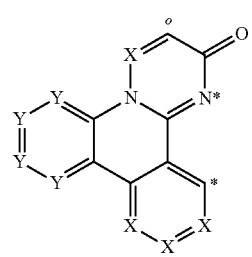
(L-38)

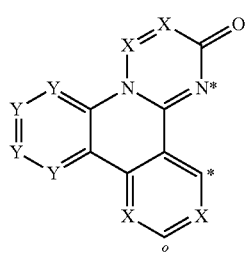
(L-39)

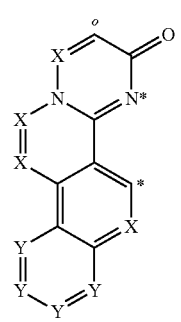
(L-40)

where X is the same or different at each instance and is CR or N, but the R radicals together do not form an aromatic or heteroaromatic ring system and the further symbols have the definitions given above.

In a preferred embodiment of the invention, in the sub-ligand of the formulae (L-33) to (L-40), a total of 0, 1 or 2 of the symbols X and, if present, Y are N. More preferably, a total of 0 or 1 of the symbols X and, if present, Y are N.

Preferred embodiments of the formulae (L-35) to (L-40) are the structures of the following formulae (L-35a) to (L-40f):

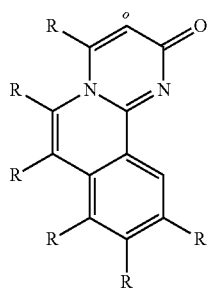
(L-35a)

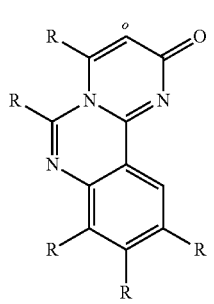
(L-35b)

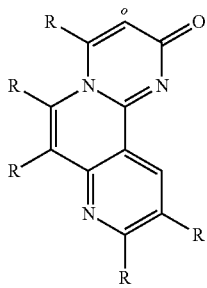
(L-35c)

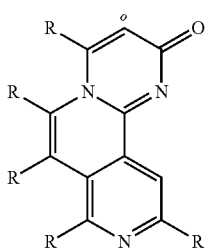
(L-35d)

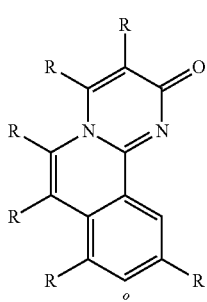
(L-36a)

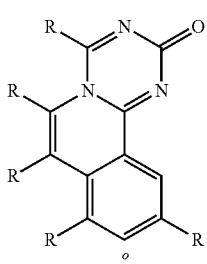
(L-36b)

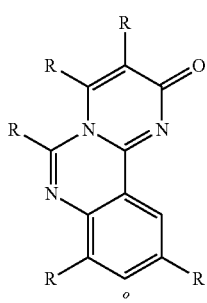
(L-36c)

(L-36d)
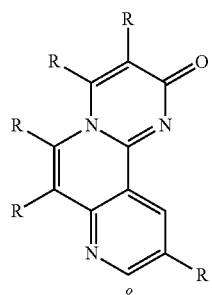
(L-37a)
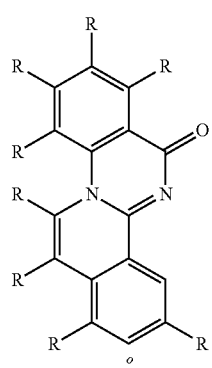
(L-37b)
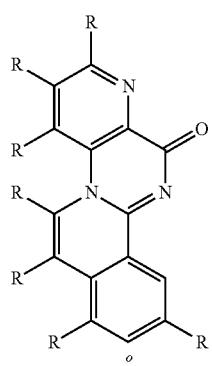
(L-37c)
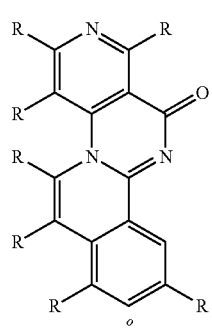
(L-37d)
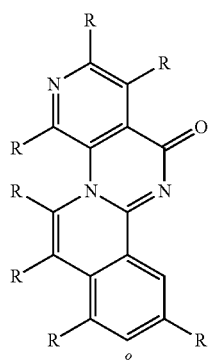
(L-37e)
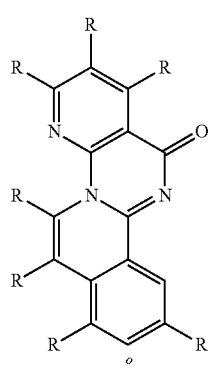
(L-37f)
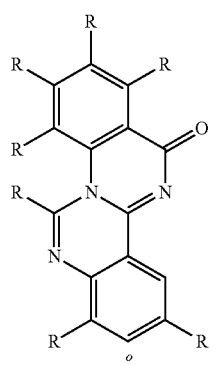
(L-37g)
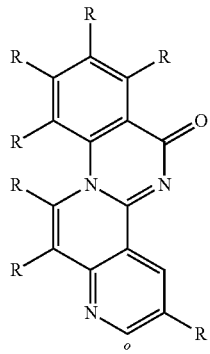

(L-38a)
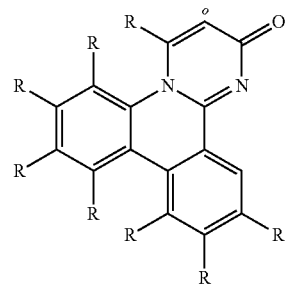
(L-38b)
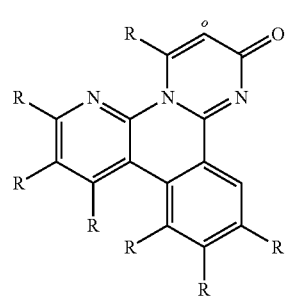
(L-38c)
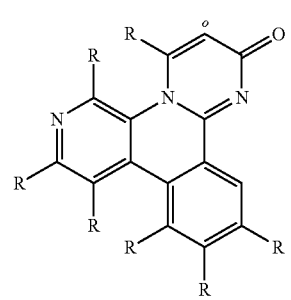
(L-38d)
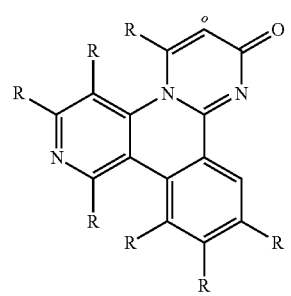
(L-38e)
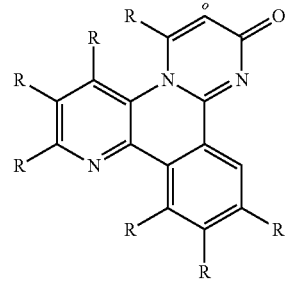
(L-38f)
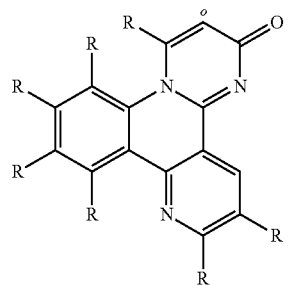
(L-38g)
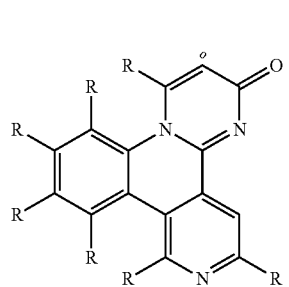
(L-39a)
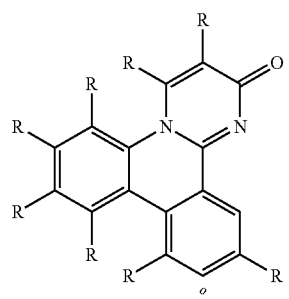
(L-39b)
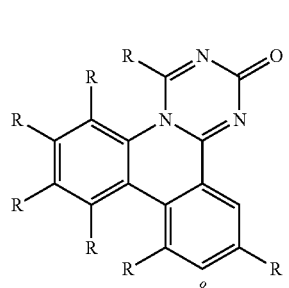
(L-39c)
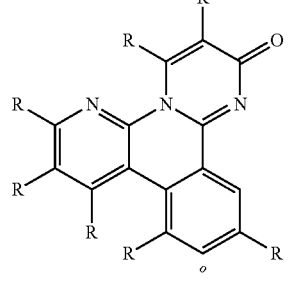

(L-39d)
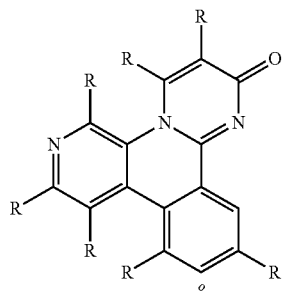
(L-39e)
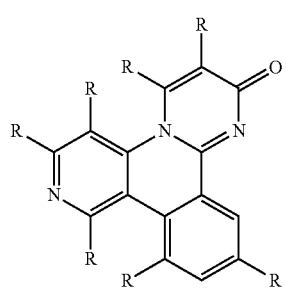
(L-39f)
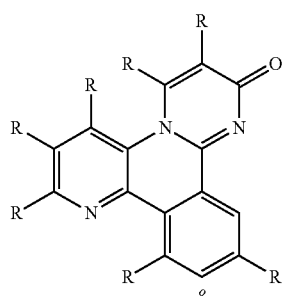
(L-39g)
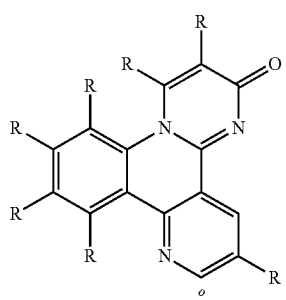
(L-40a)
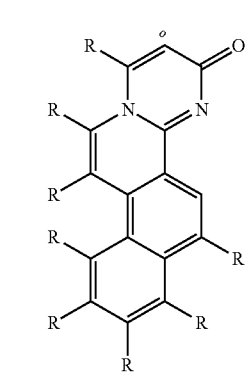
(L-40b)
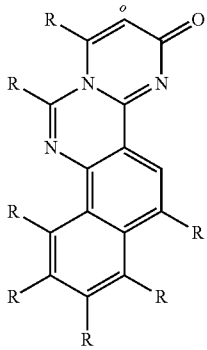
(L-40c)
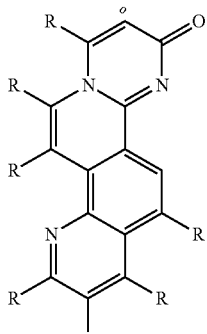
(L-40d)
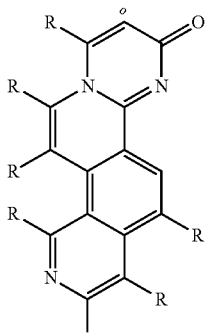
(L-40e)
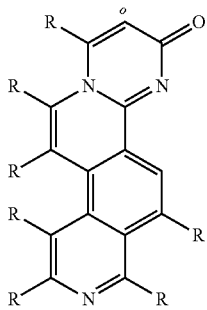

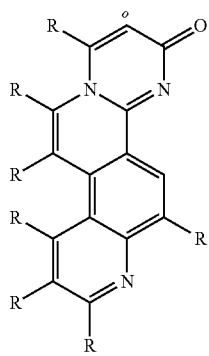
(L-40f)

where the symbols used have the definitions given above and "o" indicates the position of the linkage to the group of the formulae (1) to (5) or the preferred embodiments.

In a preferred embodiment of the invention, the X group in the ortho position to the coordination to the metal is CR. In this radical, R bonded in the ortho position to the coordination to the metal is preferably selected from the group consisting of H, D, F and methyl.

In a further embodiment of the invention, it is preferable, if one of the atoms X or, if present, Y is N, when a substituent bonded adjacent to this nitrogen atom is an R group which is not hydrogen or deuterium.

This substituent R is preferably a group selected from $CF_3$, $OCF_3$, alkyl or alkoxy groups having 1 to 10 carbon atoms, especially branched or cyclic alkyl or alkoxy groups having 3 to 10 carbon atoms, a dialkylamino group having 2 to 10 carbon atoms, aromatic or heteroaromatic ring systems or aralkyl or heteroaralkyl groups. These groups are sterically demanding groups. Further preferably, this R radical may also form a cycle with an adjacent R radical.

When the metal in the complex of the invention is a main group metal, especially Al or Ga, preferably at least one of the bidentate sub-ligands, preferably at least two of the bidentate sub-ligands and more preferably all three bidentate sub-ligands are the same or different at each instance and are selected from the sub-ligands of the following formulae (L-41) to (L-44):

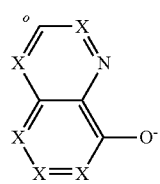
(L-41)

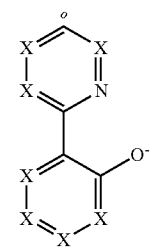
(L-42)

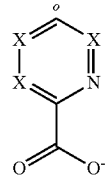
(L-43)

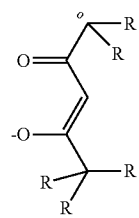
(L-44)

where the sub-ligands (L-41) to (L-43) each coordinate to the metal via the nitrogen atom explicitly shown and the negatively charged oxygen atom, and the sub-ligand (L-44) coordinates via the two oxygen atoms, X has the definitions given above and "o" indicates the position via which the sub-ligand is joined to the group of the formulae (1) to (5) or the preferred embodiments.

These sub-ligands may also be preferred for transition metals in combination with two sub-ligands which coordinate to the metal via one carbon atom and one nitrogen atom or via two carbon atoms, especially the sub-ligands (L-1) to (L-40).

In the sub-ligands of the formulae (L-41) to (L-43), preferably not more than two symbols X are N, more preferably not more than one symbol X. Most preferably, all symbols X are CR. Preferred sub-ligands of the formulae (L-41) to (L-43) are therefore the sub-ligands of the following formulae (L-41a) to (L-43a):

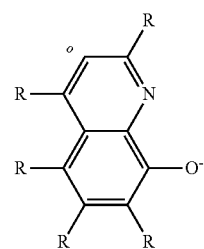
(L-41a)

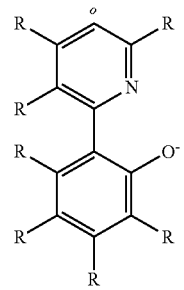
(L-42a)

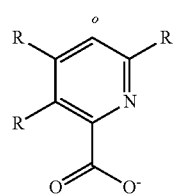
(L-43a)

where the symbols used have the definitions given above and "o" indicates the position via which the sub-ligand is joined to the group of the formulae (1) to (5) or the preferred embodiments.

More preferably, in these formulae, R is hydrogen, where "o" indicates the position via which the sub-ligand is joined to the group of the formulae (1) to (5) or the preferred embodiments, and so the structures are those of the following formulae (L-41 b) to (L-43b):

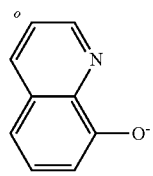
(L-41b)

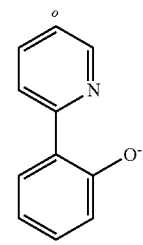
(L-42b)

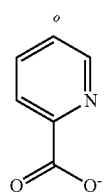
(L-43b)

where the symbols used have the definitions given above.

There follows a description of preferred substituents as may be present in the sub-ligands described above. These substituents may additionally also be present as substituents on the $X^2$ or $X^3$ group. More particularly, it is also preferable when the aliphatic or heteroaliphatic ring structures described below are present on the $X^2$ and/or $X^3$ groups.

In a preferred embodiment of the invention, the metal complex of the invention contains two R or R' substituents which are bonded to adjacent carbon atoms and together form an aliphatic or heteroaliphatic ring according to one of the formulae described hereinafter. At the same time, the two R substituents which form this aliphatic ring may be present on one or more of the bidentate sub-ligands. It is likewise possible for the two R or R' substituents to be present on one or more of the $X^2$ and/or $X^3$ groups. The aliphatic or heteroaliphatic ring which is formed by the ring formation by two R substituents together or two R' substituents together is preferably described by one of the following formulae (34) to (40):

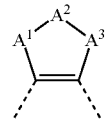
Formula (34)

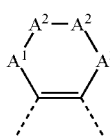
Formula (35)

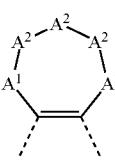
Formula (36)

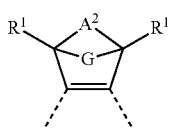
Formula (37)

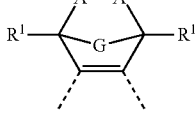
Formula (38)

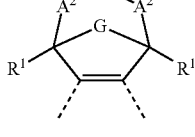
Formula (39)

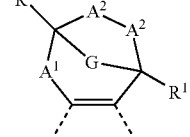
Formula (40)

where $R^1$ and $R^2$ have the definitions given above, the dotted bonds signify the linkage of the two carbon atoms in the ligand and, in addition:

$A^1$, $A^3$ is the same or different at each instance and is $C(R^3)_2$, O, S, $NR^3$ or C(=O);

$A^2$ is $C(R^1)_2$, O, S, $NR^3$ or C(=O);

G is an alkylene group which has 1, 2 or 3 carbon atoms and may be substituted by one or more $R^2$ radicals, —$CR^2$=$CR^2$— or an ortho-bonded arylene or heteroarylene group which has 5 to 14 aromatic ring atoms and may be substituted by one or more $R^2$ radicals;

$R^3$ is the same or different at each instance and is H, D, F, a straight-chain alkyl or alkoxy group having 1 to 10 carbon atoms, a branched or cyclic alkyl or alkoxy group having 3 to 10 carbon atoms, where the alkyl or alkoxy group may be substituted in each case by one or more $R^2$ radicals, where one or more nonadjacent $CH_2$ groups may be replaced by $R^2C$=$CR^2$, C≡C, $Si(R^2)_2$, C=O, NR², O, S or CONR², or an aromatic or heteroaromatic ring system which has 5 to 24 aromatic ring atoms and may be substituted in each case by one or more R² radicals, or an aryloxy or heteroaryloxy group which has 5 to 24 aromatic ring atoms and may be substituted by one or more R² radicals; at the same time, two R³ radicals bonded to the same carbon atom together may form an aliphatic or aromatic ring system and thus form a spiro system; in addition, R³ with an adjacent R or R¹ radical may form an aliphatic ring system;

with the proviso that no two heteroatoms in these groups are bonded directly to one another and no two C=O groups are bonded directly to one another.

In a preferred embodiment of the invention, R³ is not H or D.

In the above-depicted structures of the formulae (34) to (40) and the further embodiments of these structures specified as preferred, a double bond is formed in a formal sense between the two carbon atoms. This is a simplification of the chemical structure when these two carbon atoms are incorporated into an aromatic or heteroaromatic system and hence the bond between these two carbon atoms is formally between the bonding level of a single bond and that of a double bond. The drawing of the formal double bond should thus not be interpreted so as to limit the structure; instead, it will be apparent to the person skilled in the art that this is an aromatic bond.

When adjacent radicals in the structures of the invention form an aliphatic ring system, it is preferable when the latter does not have any acidic benzylic protons. Benzylic protons are understood to mean protons which bind to a carbon atom bonded directly to the ligand. This can be achieved by virtue of the carbon atoms in the aliphatic ring system which bind directly to an aryl or heteroaryl group being fully substituted and not containing any bonded hydrogen atoms. Thus, the absence of acidic benzylic protons in the formulae (34) to (36) is achieved by virtue of A' and A³, when they are C(R³)₂, being defined such that R³ is not hydrogen. This can additionally also be achieved by virtue of the carbon atoms in the aliphatic ring system which bind directly to an aryl or heteroaryl group being the bridgeheads in a bi- or polycyclic structure. The protons bonded to bridgehead carbon atoms, because of the spatial structure of the bi- or polycycle, are significantly less acidic than benzylic protons on carbon atoms which are not bonded within a bi- or polycyclic structure, and are regarded as non-acidic protons in the context of the present invention. Thus, the absence of acidic benzylic protons in formulae (37) to (40) is achieved by virtue of this being a bicyclic structure, as a result of which R¹, when it is H, is much less acidic than benzylic protons since the corresponding anion of the bicyclic structure is not mesomerically stabilized. Even when R¹ in formulae (37) to (40) is H, this is therefore a non-acidic proton in the context of the present application.

In a preferred embodiment of the structure of the formulae (34) to (40), not more than one of the A¹, A² and A³ groups is a heteroatom, especially O or NR³, and the other groups are C(R³)₂ or C(R¹)₂, or A¹ and A³ are the same or different at each instance and are O or NR³ and A² is C(R¹)₂. In a particularly preferred embodiment of the invention, A' and A³ are the same or different at each instance and are C(R³)₂, and A² is C(R¹)₂ and more preferably C(R³)₂ or CH₂.

Preferred embodiments of the formula (34) are thus the structures of the formulae (34-A), (34-B), (34-C) and (34-D), and a particularly preferred embodiment of the formula (34-A) is the structures of the formulae (34-E) and (34-F):

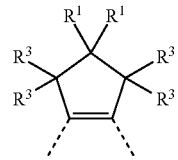

Formulal (34-A)

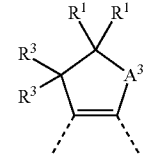

Formulal (34-B)

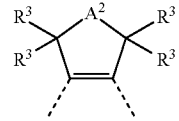

Formulal (34-C)

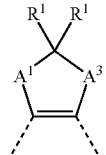

Formulal (34-D)

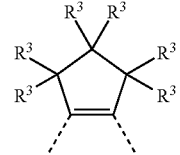

Formulal (34-E)

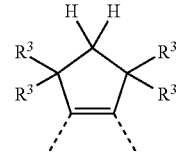

Formulal (34-F)

where R¹ and R³ have the definitions given above and A¹, A² and A³ are the same or different at each instance and are O or NR³.

Preferred embodiments of the formula (35) are the structures of the following formulae (35-A) to (35-F):

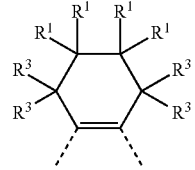

Formulal (35-A)

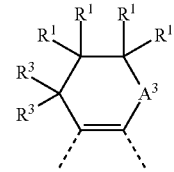

Formulal (35-B)

-continued

Formulal (35-C)
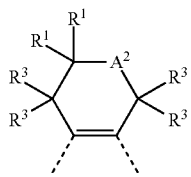

Formulal (35-D)
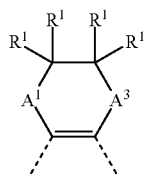

Formulal (35-E)
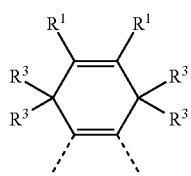

Formulal (35-F)
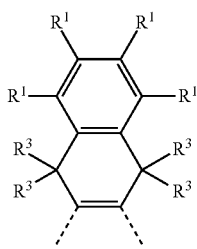

where $R^1$ and $R^3$ have the definitions given above and $A^1$, $A^2$ and $A^3$ are the same or different at each instance and are O or $NR^3$.

Preferred embodiments of the formula (36) are the structures of the following formulae (36-A) to (36-E):

Formulal (36-A)
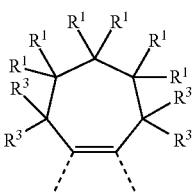

Formulal (36-B)
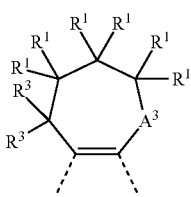

Formulal (36-C)
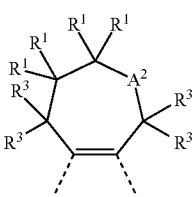

-continued

Formulal (36-D)
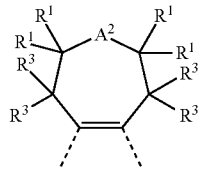

Formulal (36-E)
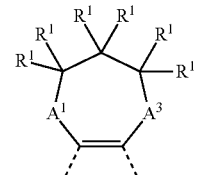

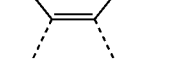

where $R^1$ and $R^3$ have the definitions given above and $A^1$, $A^2$ and $A^3$ are the same or different at each instance and are O or $NR^3$.

In a preferred embodiment of the structure of formula (37), the $R^1$ radicals bonded to the bridgehead are H, D, F or $CH_3$. Further preferably, $A^2$ is $C(R^1)_2$ or O, and more preferably $C(R^3)_2$. Preferred embodiments of the formula (37) are thus structures of the formulae (37-A) and (37-B), and a particularly preferred embodiment of the formula (37-A) is a structure of the formula (37-C):

Formulal (37-A)
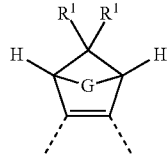

Formulal (37-B)
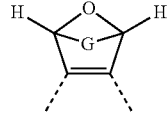

Formulal (37-C)
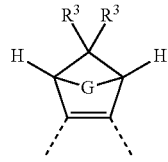

where the symbols used have the definitions given above.

In a preferred embodiment of the structure of formulae (38), (39) and (40), the $R^1$ radicals bonded to the bridgehead are H, D, F or $CH_3$. Further preferably, $A^2$ is $C(R^1)_2$. Preferred embodiments of the formula (38), (39) and (40) are thus the structures of the formulae (38-A), (39-A) and (40-A):

Formel (38-A)
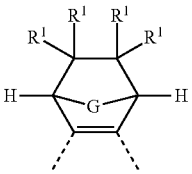

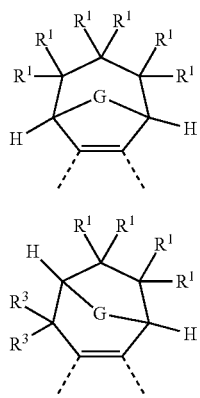

Formel (39-A)

Formel (40-A)

where the symbols used have the definitions given above.

Further preferably, the G group in the formulae (37), (37-A), (37-B), (37-C), (38), (38-A), (39), (39-A), (40) and (40-A) is a 1,2-ethylene group which may be substituted by one or more $R^2$ radicals, where $R^2$ is preferably the same or different at each instance and is H or an alkyl group having 1 to 4 carbon atoms, or an ortho-arylene group which has 6 to 10 carbon atoms and may be substituted by one or more $R^2$ radicals, but is preferably unsubstituted, especially an ortho-phenylene group which may be substituted by one or more $R^2$ radicals, but is preferably unsubstituted.

In a further preferred embodiment of the invention, $R^3$ in the groups of the formulae (34) to (40) and in the preferred embodiments is the same or different at each instance and is F, a straight-chain alkyl group having 1 to 10 carbon atoms or a branched or cyclic alkyl group having 3 to 20 carbon atoms, where one or more nonadjacent $CH_2$ groups in each case may be replaced by $R^2C=CR^2$ and one or more hydrogen atoms may be replaced by D or F, or an aromatic or heteroaromatic ring system which has 5 to 14 aromatic ring atoms and may be substituted in each case by one or more $R^2$ radicals; at the same time, two $R^3$ radicals bonded to the same carbon atom may together form an aliphatic or aromatic ring system and thus form a spiro system; in addition, $R^3$ may form an aliphatic ring system with an adjacent R or $R^1$ radical.

In a particularly preferred embodiment of the invention, $R^3$ in the groups of the formulae (34) to (40) and in the preferred embodiments is the same or different at each instance and is F, a straight-chain alkyl group having 1 to 3 carbon atoms, especially methyl, or an aromatic or heteroaromatic ring system which has 5 to 12 aromatic ring atoms and may be substituted in each case by one or more $R^2$ radicals, but is preferably unsubstituted; at the same time, two $R^3$ radicals bonded to the same carbon atom may together form an aliphatic or aromatic ring system and thus form a spiro system; in addition, $R^3$ may form an aliphatic ring system with an adjacent R or $R^1$ radical.

Examples of particularly suitable groups of the formula (34) are the structures listed below:

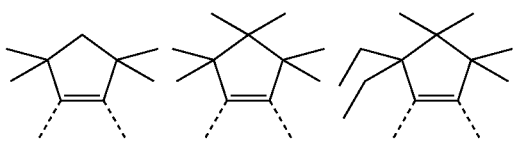

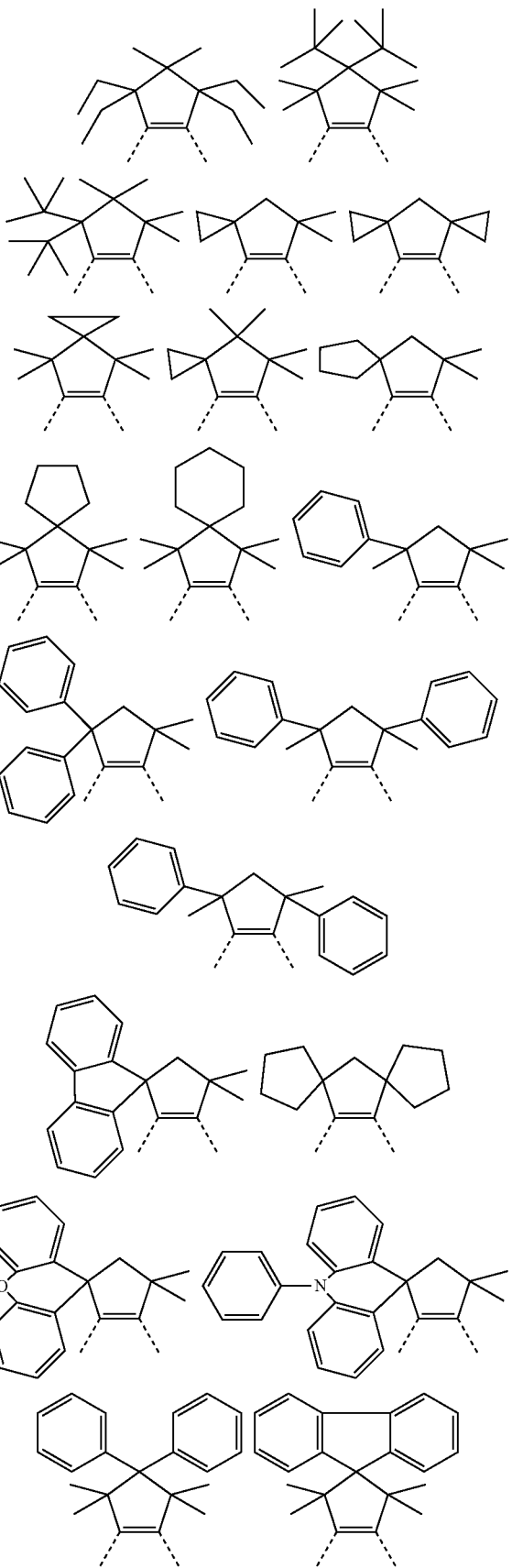

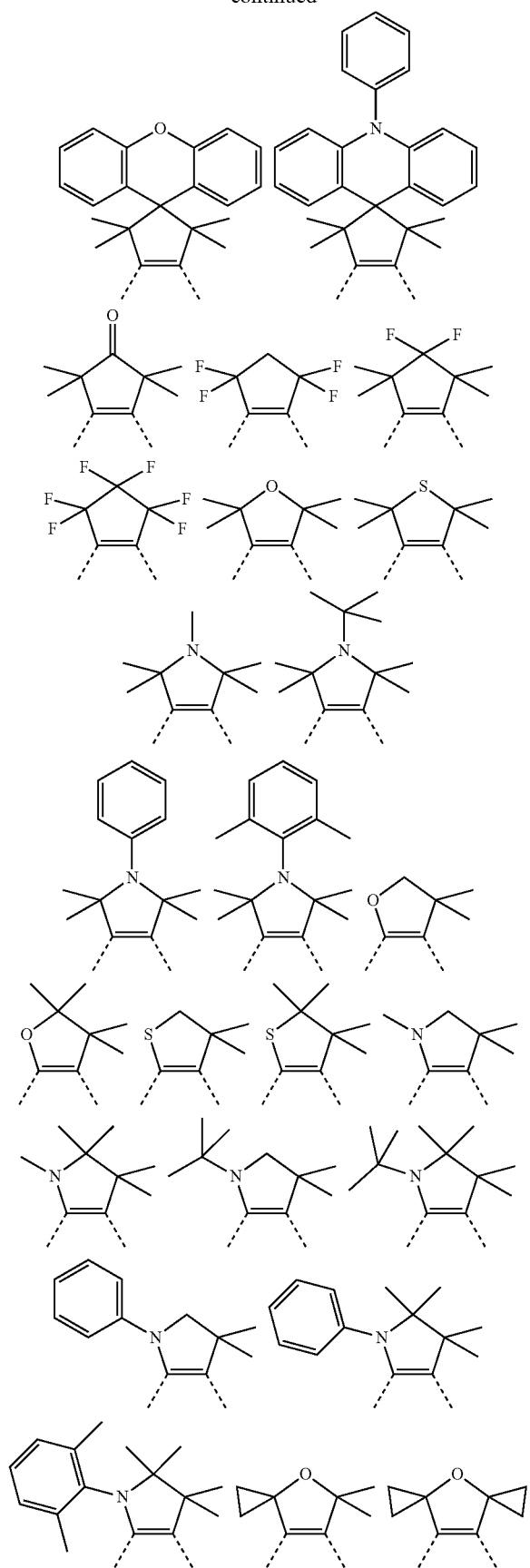
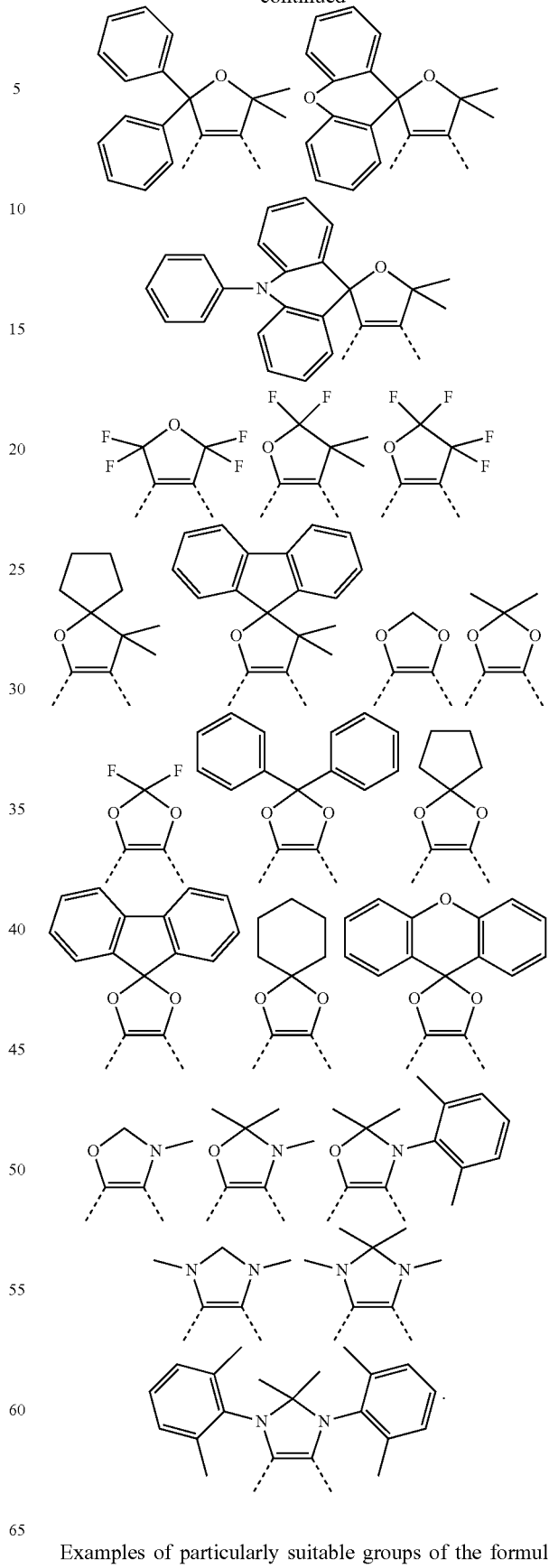
Examples of particularly suitable groups of the formula (34) are the structures listed below:

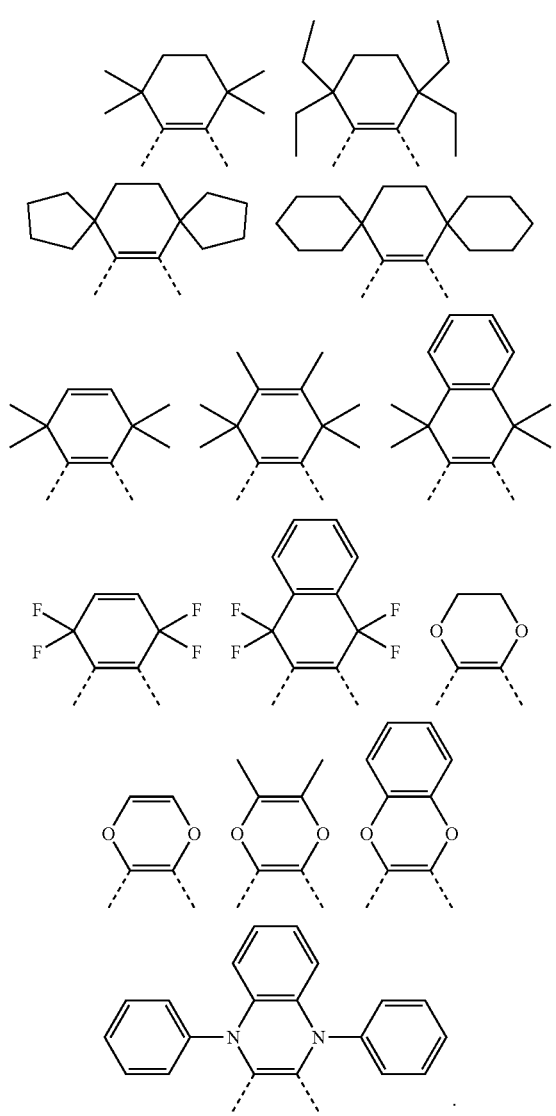

Examples of particularly suitable groups of the formulae (36), (39) and (40) are the structures listed below:

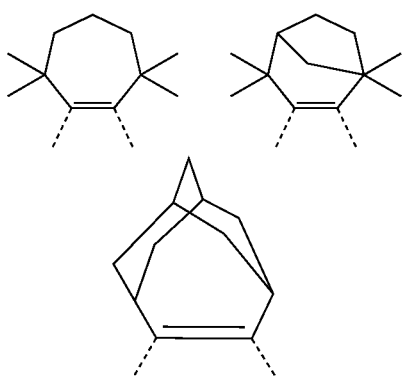

Examples of particularly suitable groups of the formula (37) are the structures listed below:

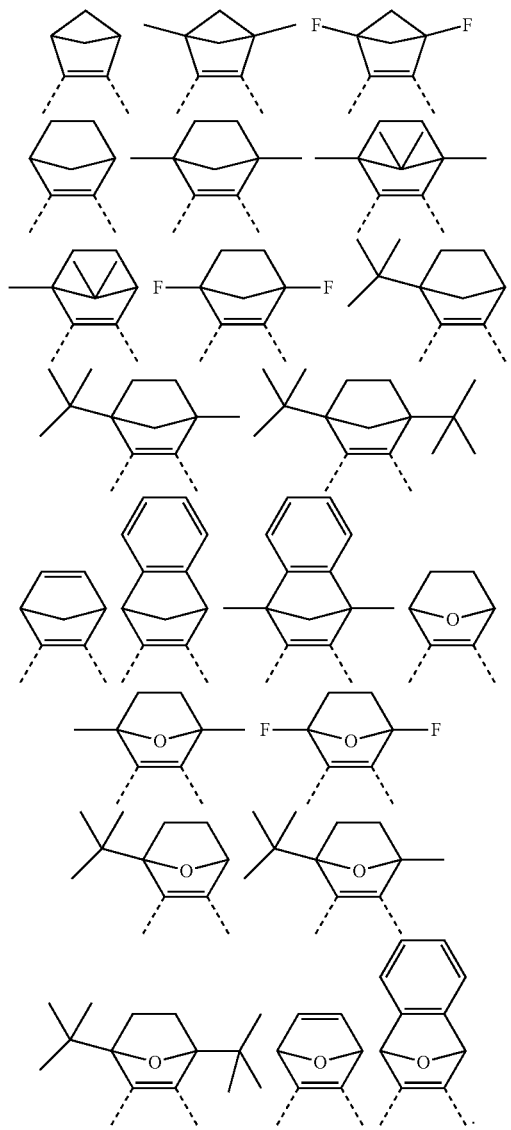

Examples of particularly suitable groups of the formula (38) are the structures listed below:

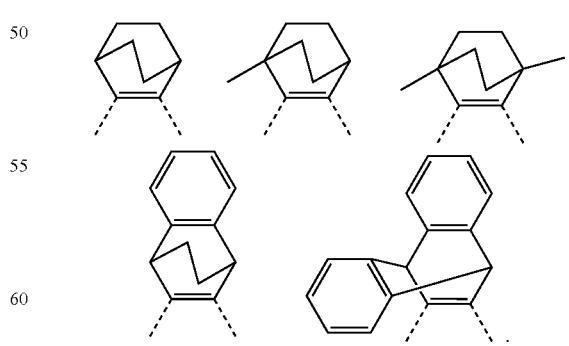

When R radicals are incorporated within the bidentate sub-ligands, these R radicals are the same or different at each instance and are preferably selected from the group consisting of H, D, F, Br, I, $N(R^1)_2$, CN, $Si(R^1)_3$, $B(OR^1)_2$, C(=O)R¹, a straight-chain alkyl group having 1 to 10 carbon atoms or an alkenyl group having 2 to 10 carbon atoms or a branched or cyclic alkyl group having 3 to 10 carbon atoms, where the alkyl or alkenyl group may be substituted in each case by one or more R¹ radicals, or an aromatic or heteroaromatic ring system which has 5 to 30 aromatic ring atoms and may be substituted in each case by one or more R¹ radicals; at the same time, two adjacent R radicals together or R together with R¹ may also form a mono- or polycyclic, aliphatic or aromatic ring system. More preferably, these R radicals are the same or different at each instance and are selected from the group consisting of H, D, F, N(R¹)₂, a straight-chain alkyl group having 1 to 6 carbon atoms or a branched or cyclic alkyl group having 3 to 10 carbon atoms, where one or more hydrogen atoms may be replaced by D or F, or an aromatic or heteroaromatic ring system which has 5 to 24 aromatic ring atoms and may be substituted in each case by one or more R¹ radicals; at the same time, two adjacent R radicals together or R together with R¹ may also form a mono- or polycyclic, aliphatic or aromatic ring system.

Preferred R¹ radicals bonded to R are the same or different at each instance and are H, D, F, N(R²)₂, ON, a straight-chain alkyl group having 1 to 10 carbon atoms or an alkenyl group having 2 to 10 carbon atoms or a branched or cyclic alkyl group having 3 to 10 carbon atoms, where the alkyl group may be substituted in each case by one or more R² radicals, or an aromatic or heteroaromatic ring system which has 5 to 24 aromatic ring atoms and may be substituted in each case by one or more R² radicals; at the same time, two or more adjacent R¹ radicals together may form a mono- or polycyclic aliphatic ring system. Particularly preferred R¹ radicals bonded to R are the same or different at each instance and are H, F, CN, a straight-chain alkyl group having 1 to 5 carbon atoms or a branched or cyclic alkyl group having 3 to 5 carbon atoms, each of which may be substituted by one or more R² radicals, or an aromatic or heteroaromatic ring system which has 5 to 13 aromatic ring atoms and may be substituted in each case by one or more R² radicals; at the same time, two or more adjacent R¹ radicals together may form a mono- or polycyclic aliphatic ring system.

Preferred R² radicals are the same or different at each instance and are H, F or an aliphatic hydrocarbyl radical having 1 to 5 carbon atoms or an aromatic hydrocarbyl radical having 6 to 12 carbon atoms; at the same time, two or more R² substituents together may also form a mono- or polycyclic aliphatic ring system.

The compounds of the invention may also be closed by a second bridging unit to form cryptates. In this case, the second bridging unit binds to each of the three bidentate sub-ligands. In a preferred embodiment of the present invention, the second bridging unit which closes the compound to form a cryptate is a group of the following formula (41):

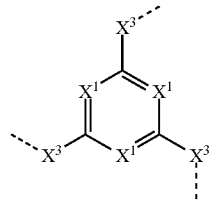

Formula (41)

where the symbols used have the definitions given above. Preferably, X¹ in formula (41) is CR, more preferably CH. Preferably, in addition, X³ in formula (41) is the same or different at each instance and is —CR=CR—, where the R radicals together form an aromatic or heteroaromatic ring system, —C(=O)—O— or —C(=O)—NR"—.

The metal complexes of the invention are chiral structures. If the tripodal ligand of the complexes is additionally also chiral, the formation of diastereomers and multiple enantiomer pairs is possible. In that case, the complexes of the invention include both the mixtures of the different diastereomers or the corresponding racemates and the individual isolated diastereomers or enantiomers.

If C₃- or C₃ᵥ-symmetric ligands are used in the ortho-metalation, what is obtained is typically a racemic mixture of the C₃-symmetric complexes, i.e. of the Δ and Λ enantiomers. These may be separated by standard methods (chromatography on chiral materials/columns or optical resolution by crystallization). This is shown in the scheme which follows using the example of a C₃-symmetric ligand bearing three phenylpyridine sub-ligands and also applies analogously to all other C₃- or C₃ᵥ-symmetric ligands.

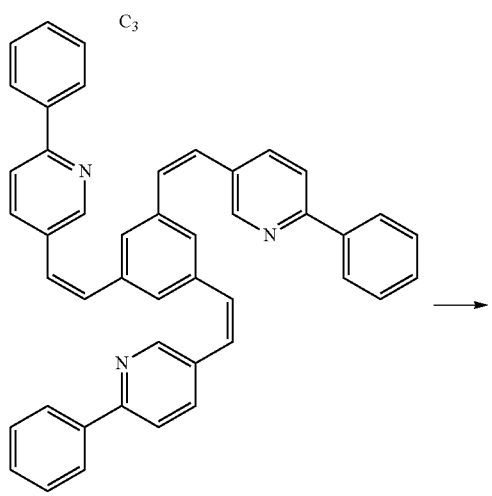

-continued
Racemate from the o-metallation

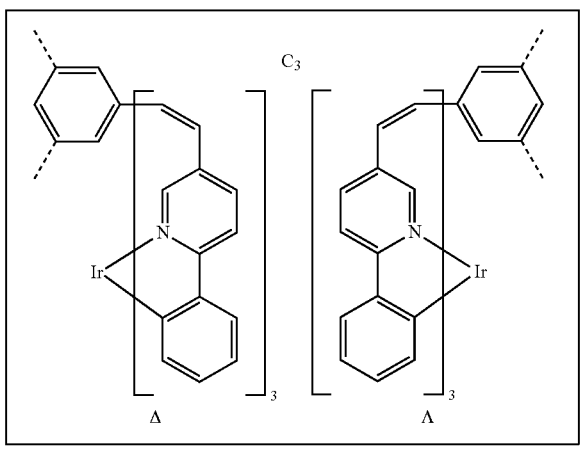

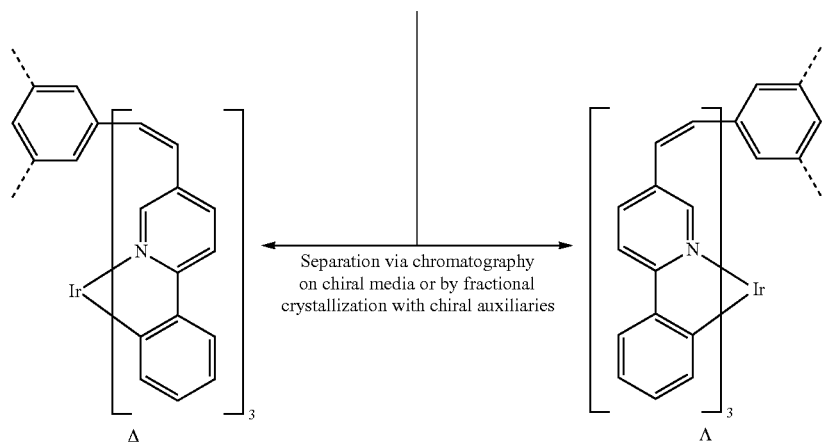

Optical resolution via fractional crystallization of diastereomeric salt pairs can be effected by customary methods. One option for this purpose is to oxidize the uncharged Ir(III) complexes (for example with peroxides or $H_2O_2$ or by electrochemical means), add the salt of an enantiomerically pure monoanionic base (chiral base) to the cationic Ir(IV) complexes thus produced, separate the diastereomeric salts thus produced by fractional crystallization, and then reduce them with the aid of a reducing agent (e.g. zinc, hydrazine hydrate, ascorbic acid, etc.) to give the enantiomerically pure uncharged complex, as shown schematically below:

Analogous processes can also be conducted with complexes of $C_s$-symmetric ligands.

If $C_1$-symmetric ligands are used in the complexation, what is typically obtained is a diastereomer mixture of the complexes which can be separated by standard methods (chromatography, crystallization).

Enantiomerically pure $C_3$-symmetric complexes can also be synthesized selectively, as shown in the scheme which follows. For this purpose, an enantiomerically pure $C_3$-sym-

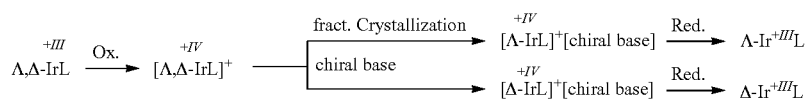

In addition, an enantiomerically pure or enantiomerically enriching synthesis is possible by complexation in a chiral medium (e.g. R- or S-1,1-binaphthol).

metric ligand is prepared and complexed, the diastereomer mixture obtained is separated and then the chiral group is detached.

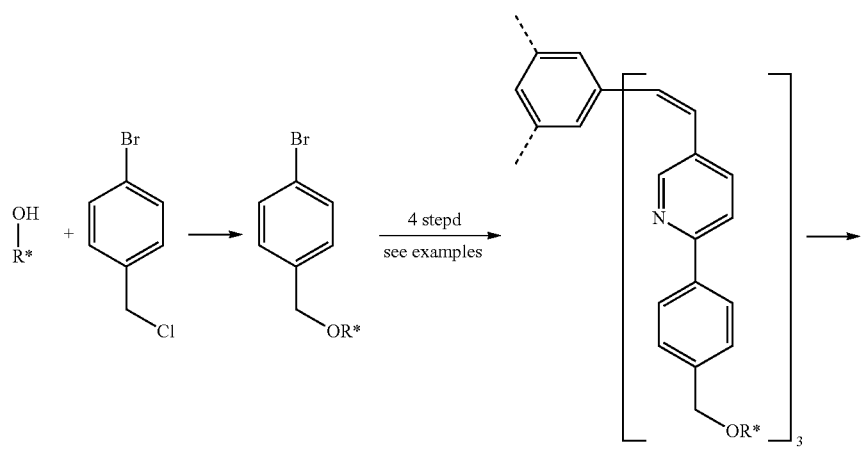
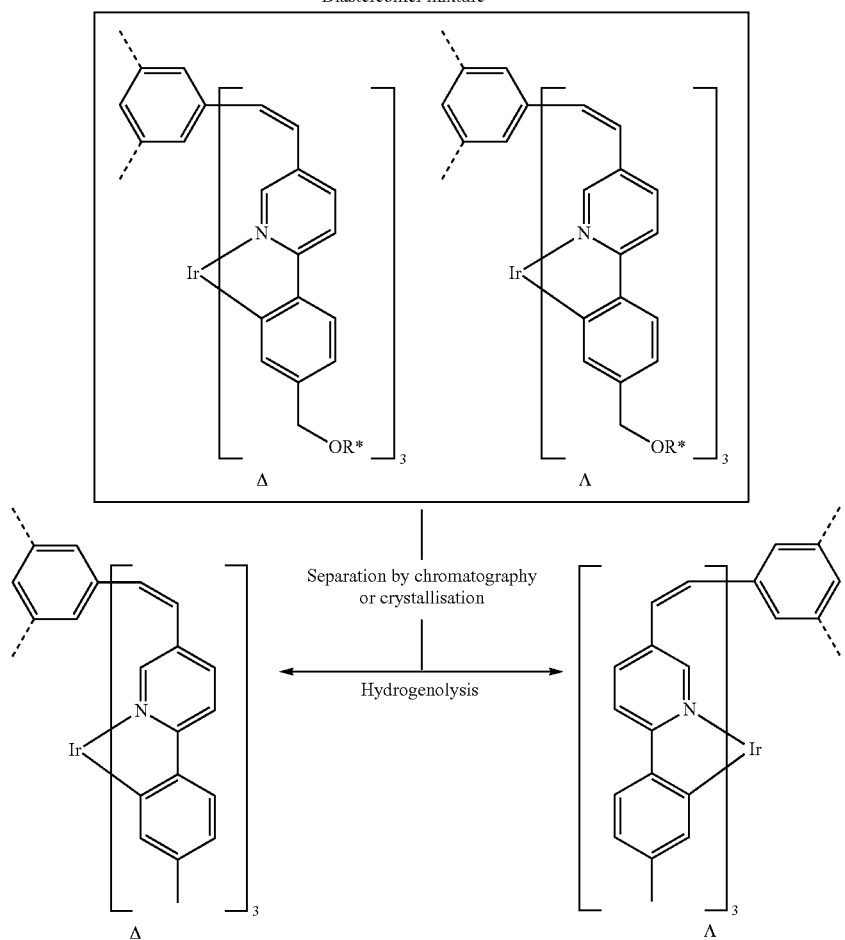
R* = enantiomerically pure radicalt
The abovementioned preferred embodiments can be combined with one another as desired. In a particularly preferred embodiment of the invention, the abovementioned preferred embodiments apply simultaneously.
Examples of suitable metal complexes of the invention are adduced hereinafter.

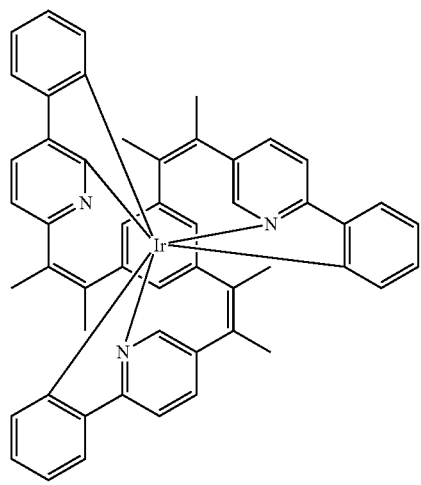
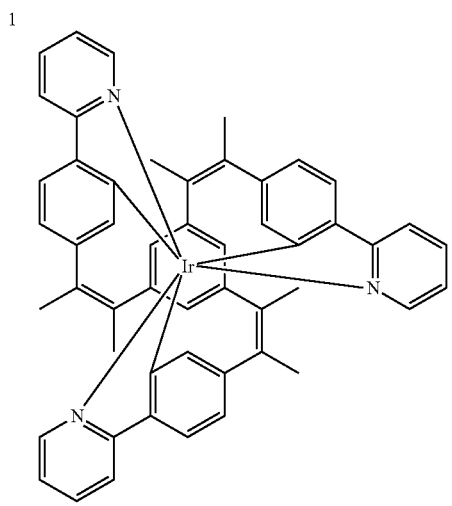
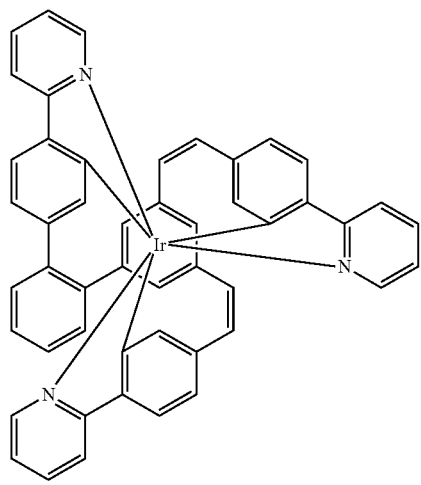
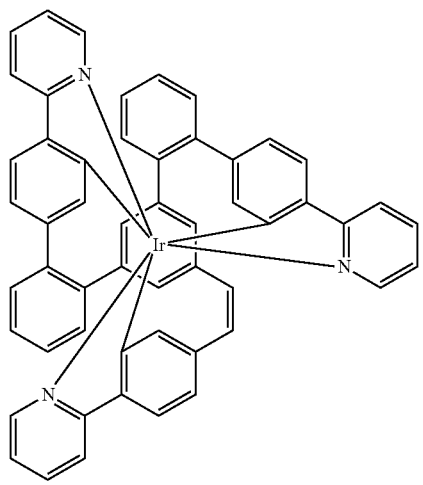
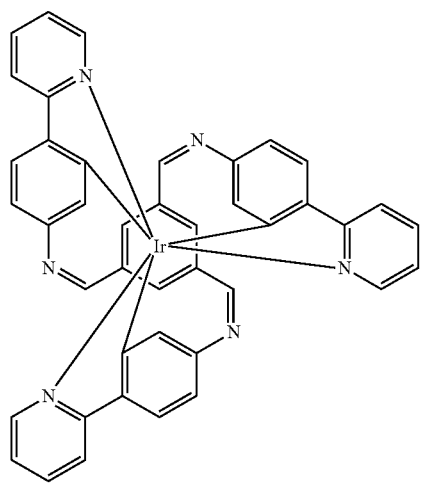
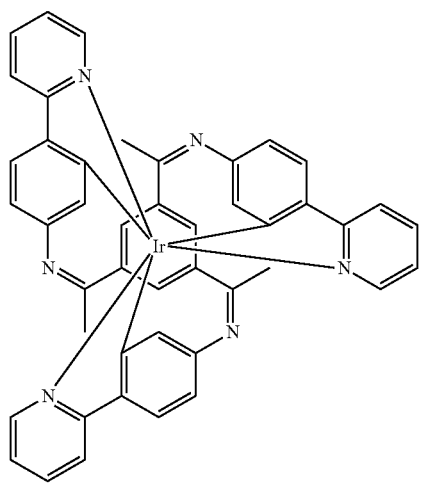

-continued
7
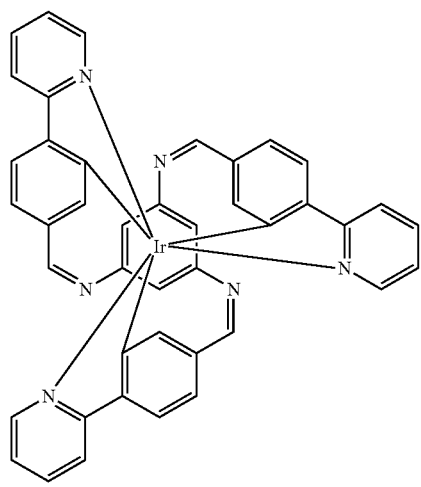
8
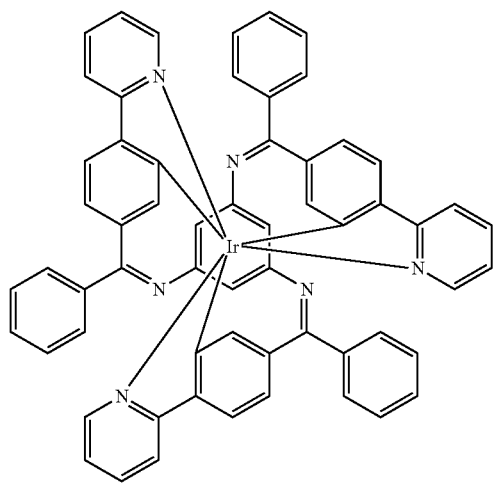
9
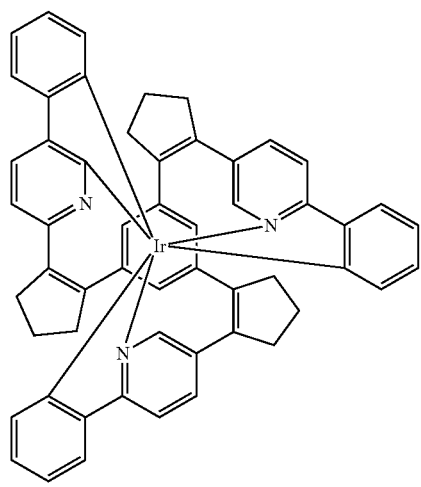
10
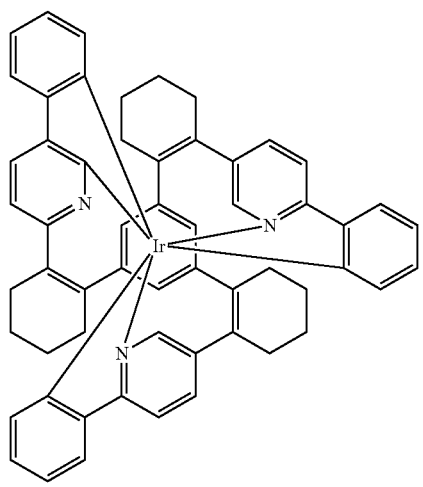
11
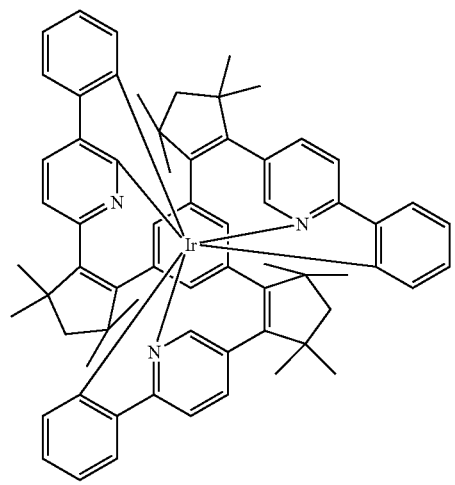
12
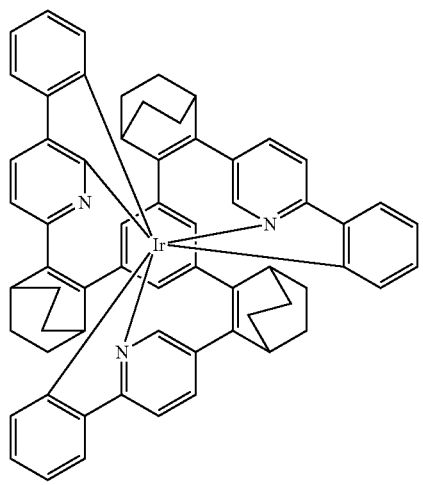

-continued
13
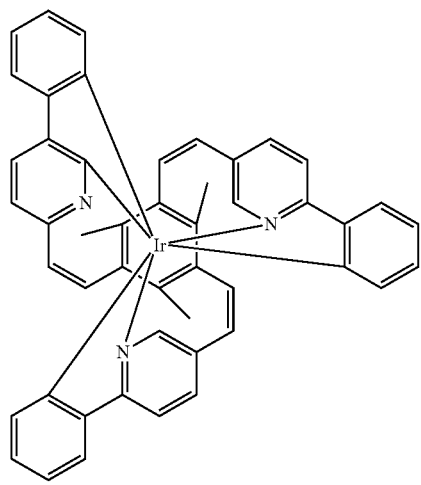
14
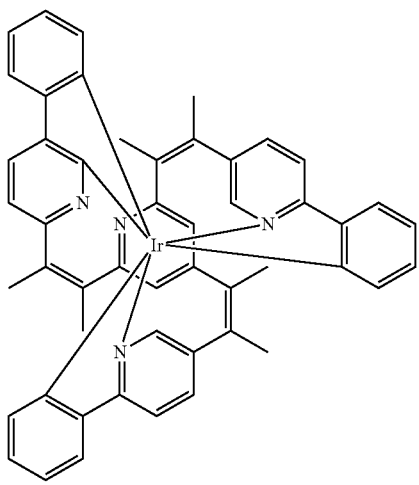
15
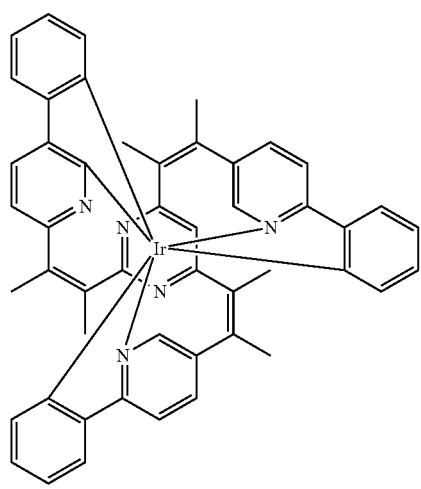
16
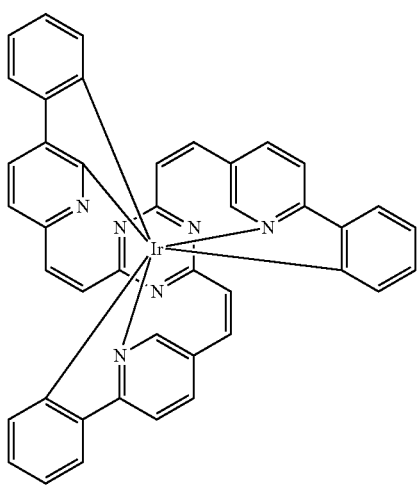
17
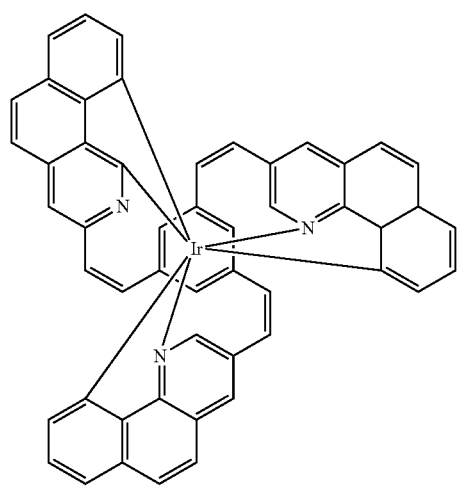
18
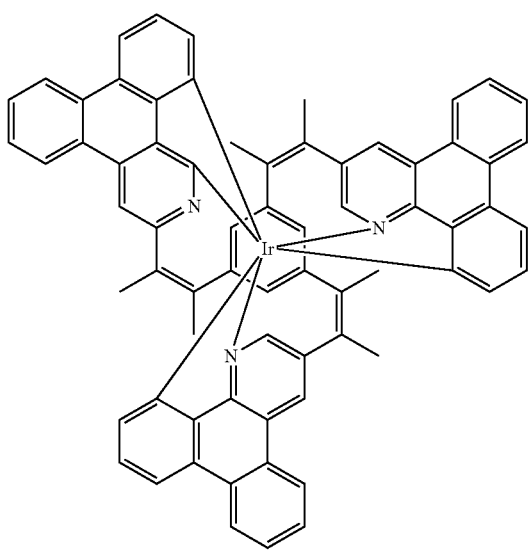

19
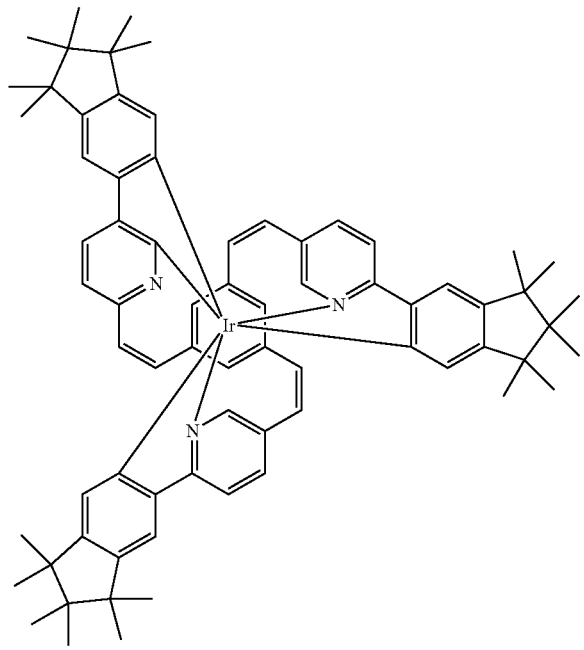
20
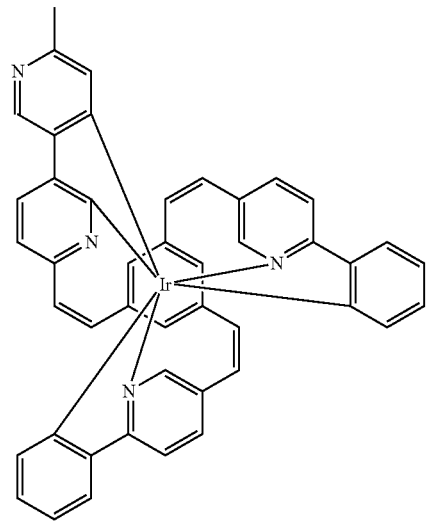
21
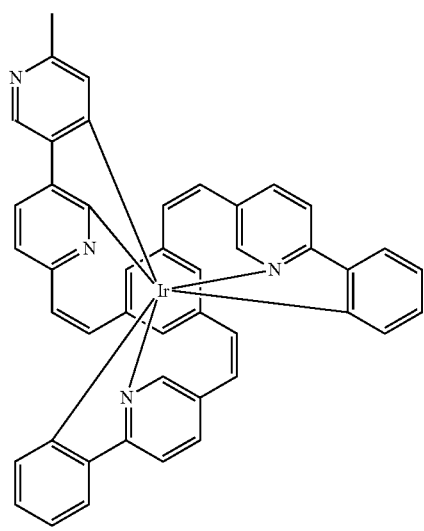
22
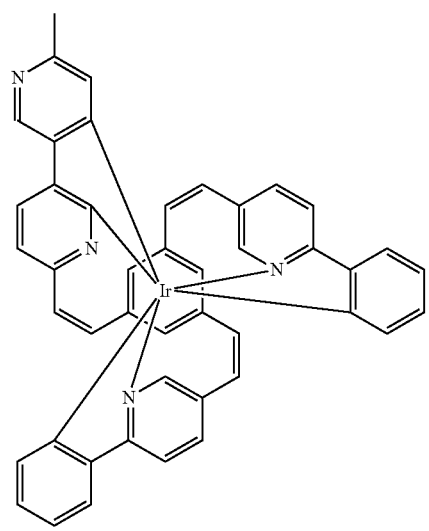

-continued
23
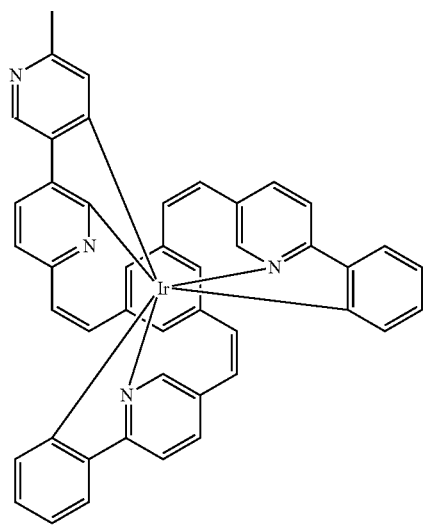
24
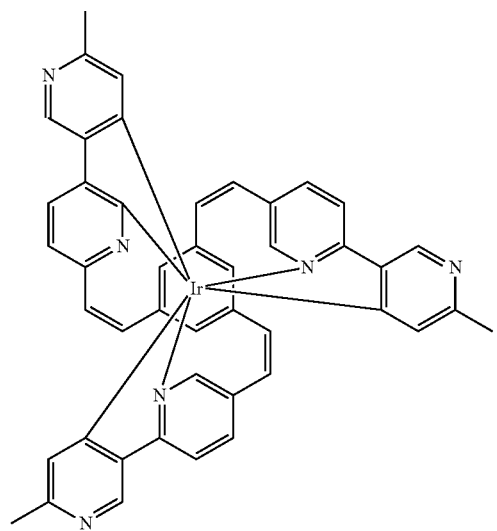
25
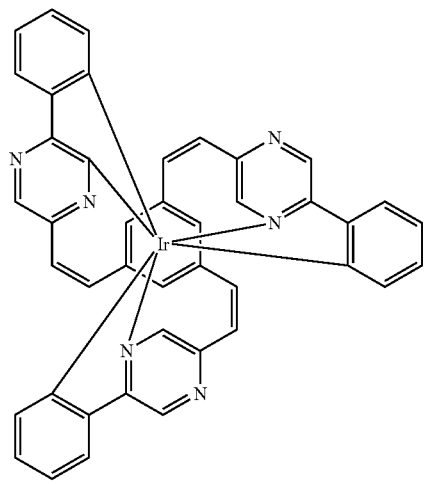
26
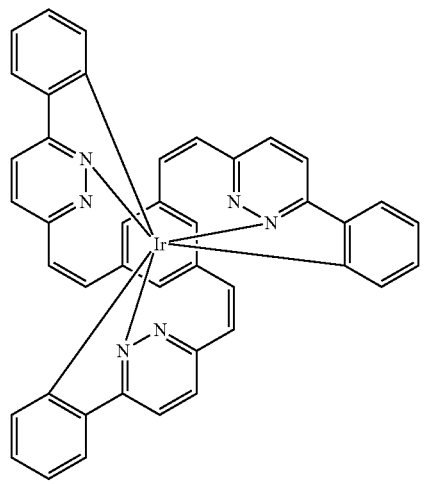
27
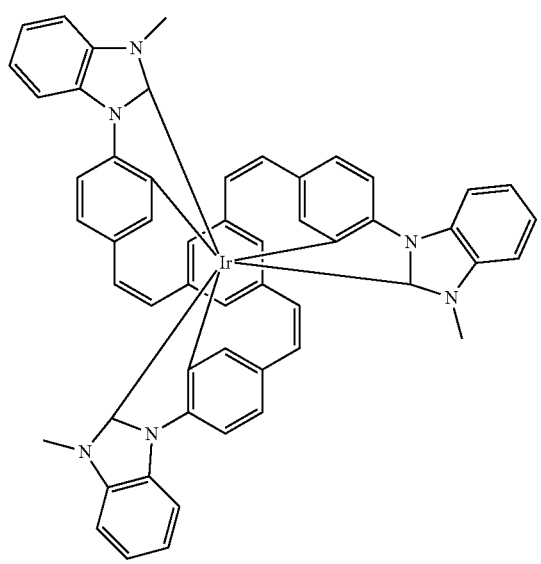
28
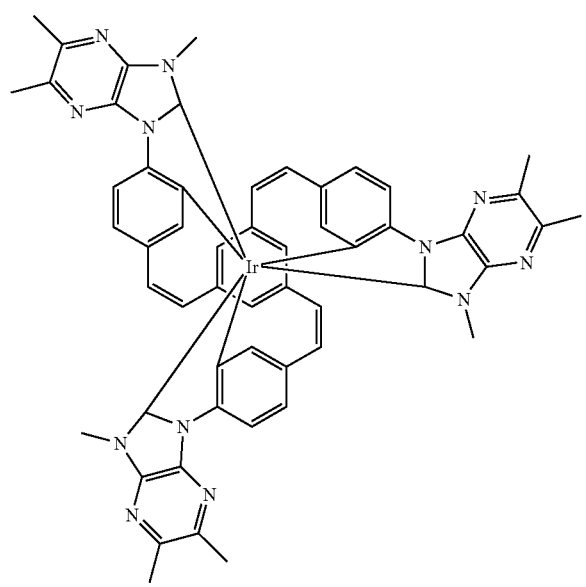

-continued
29
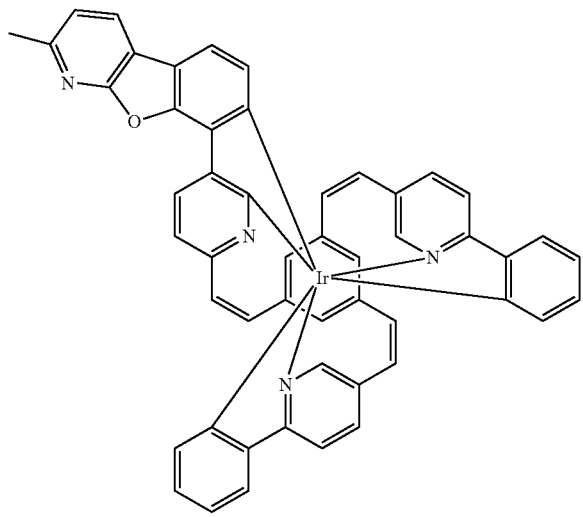
30
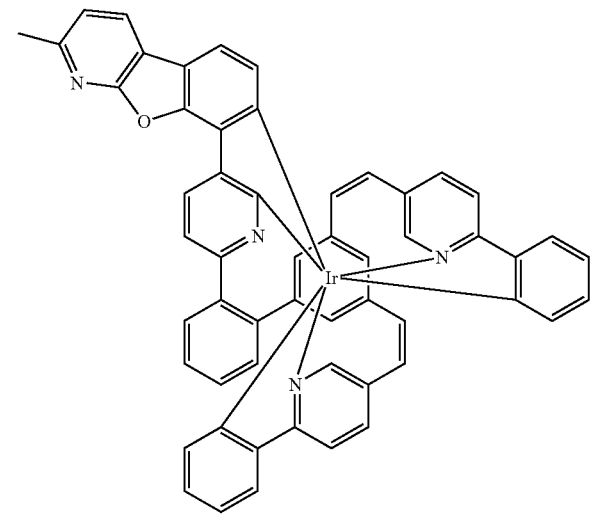
31
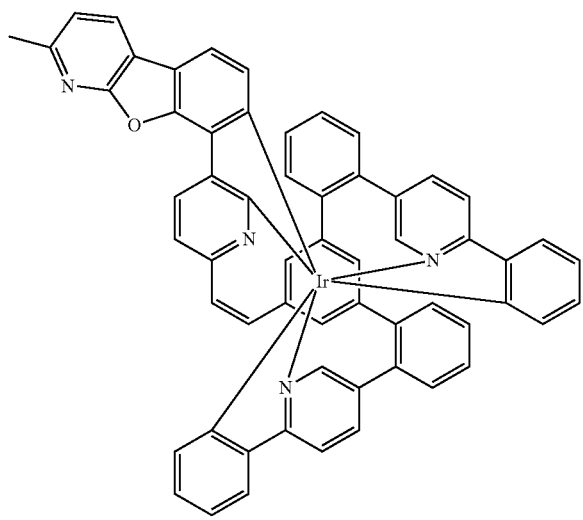
32
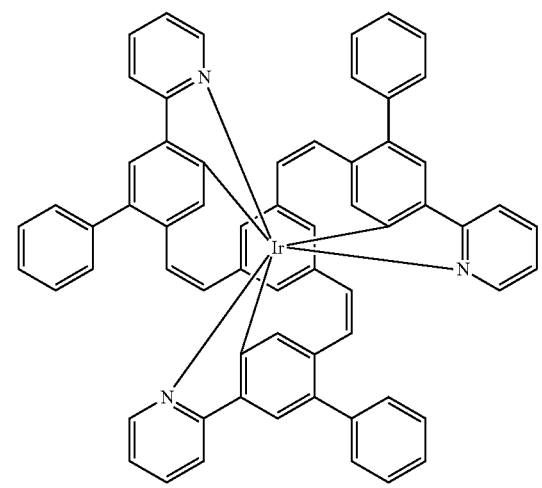
33
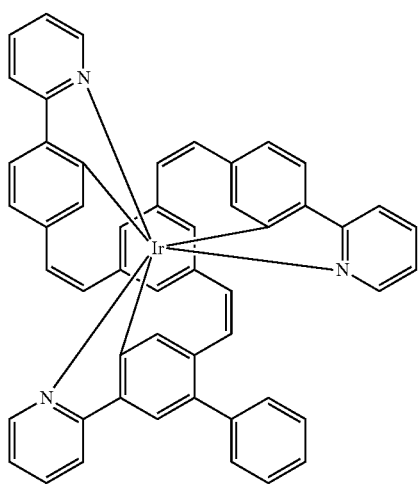
34
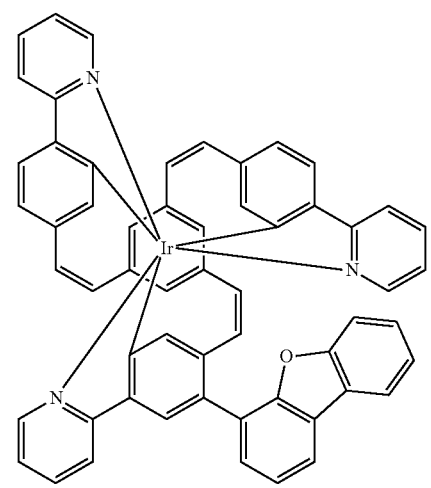

-continued
35
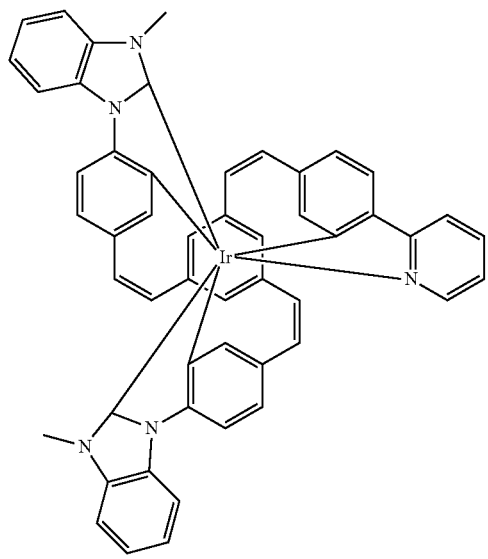
36
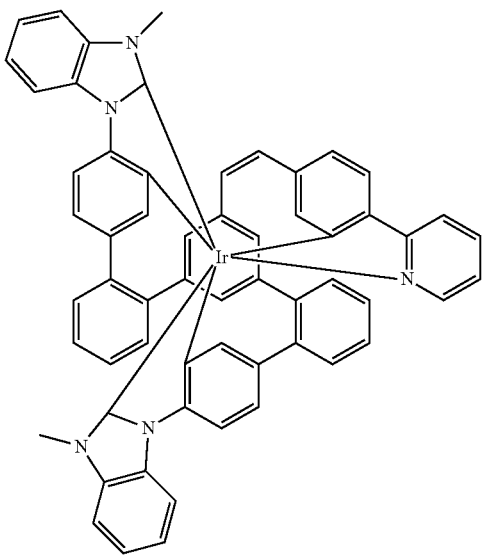
37
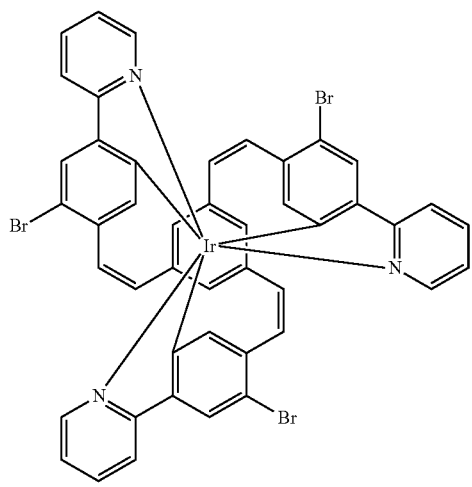
38
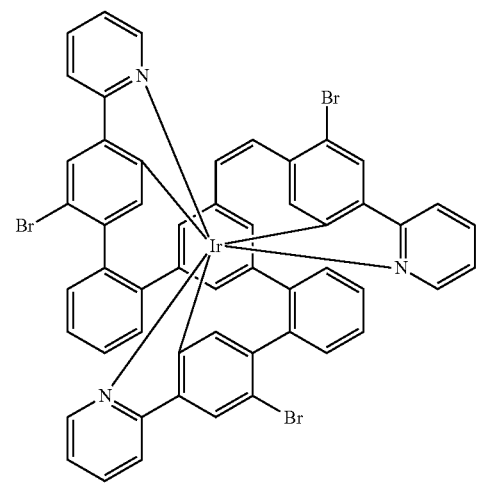
39
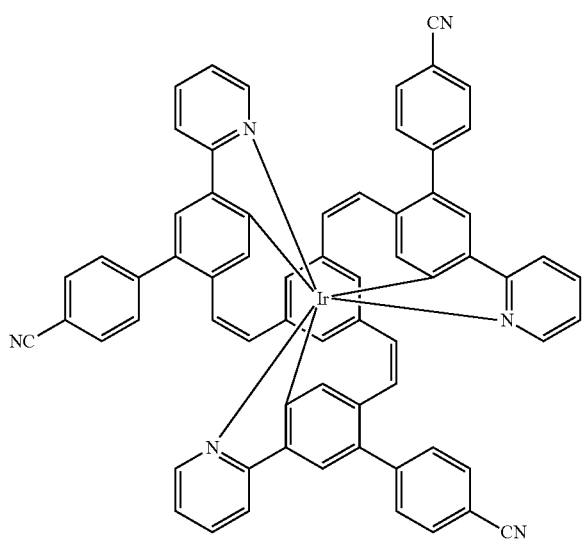
40
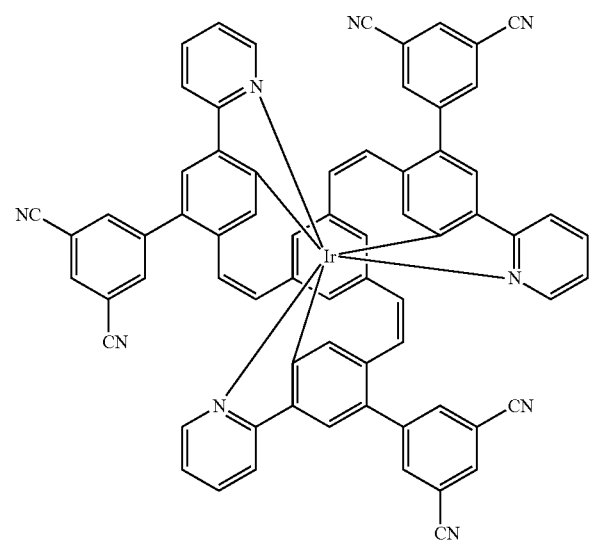

41
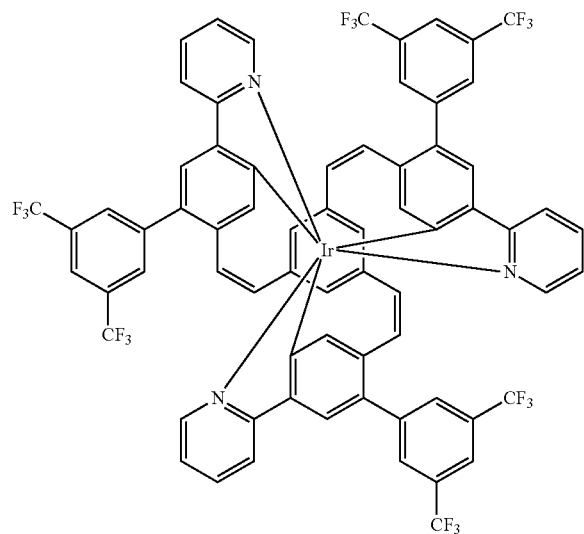
42
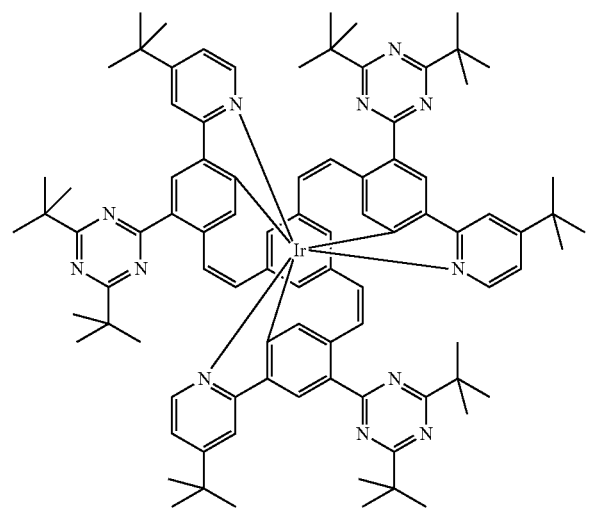
43
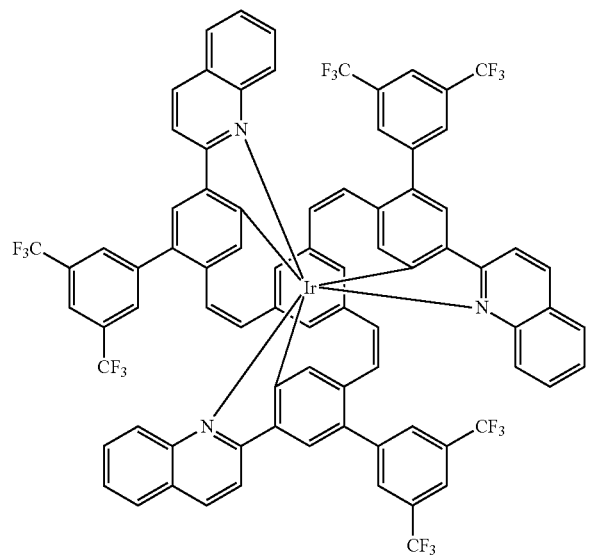
44
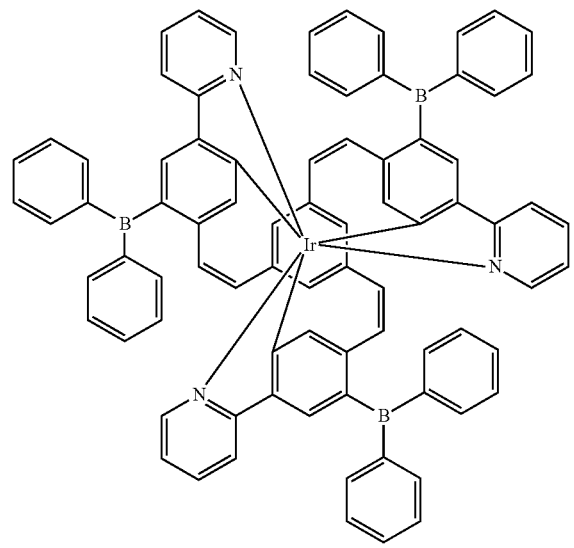

45
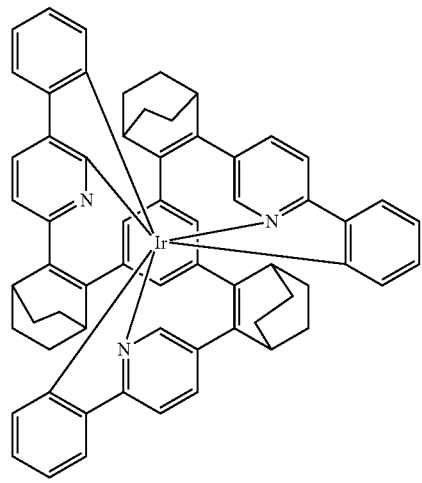
46
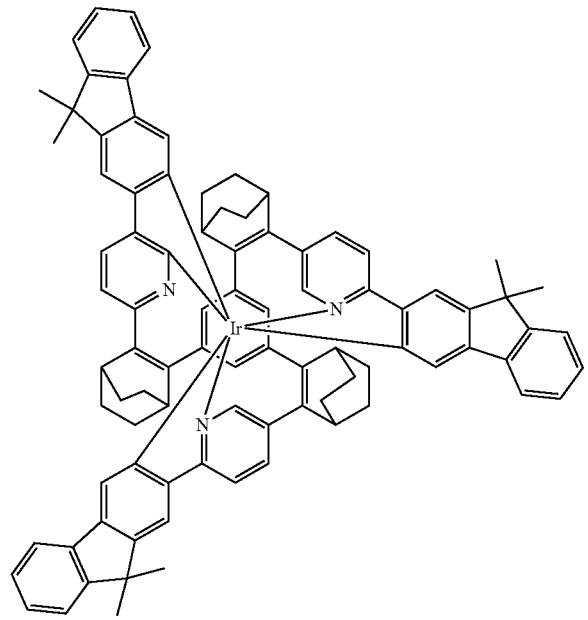
47
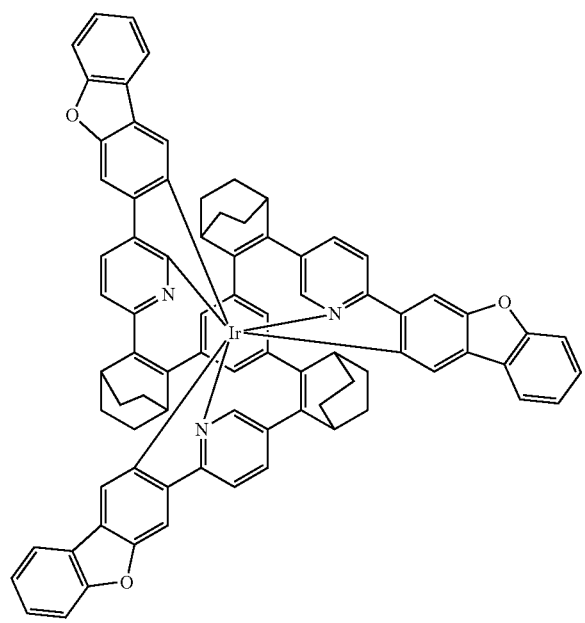
48
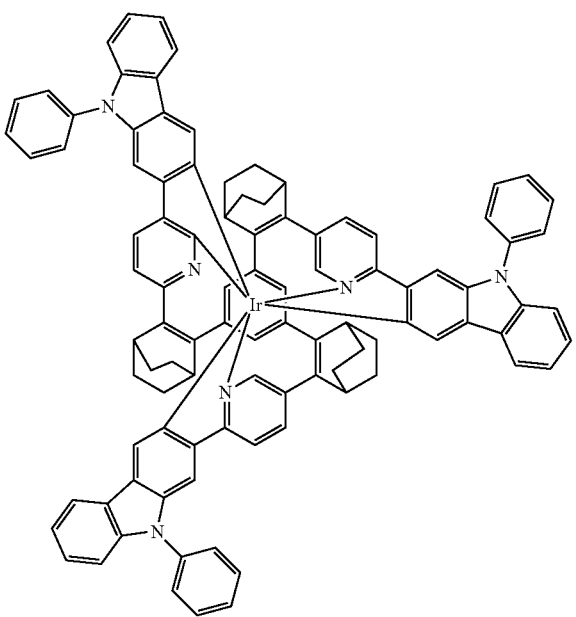

-continued
49
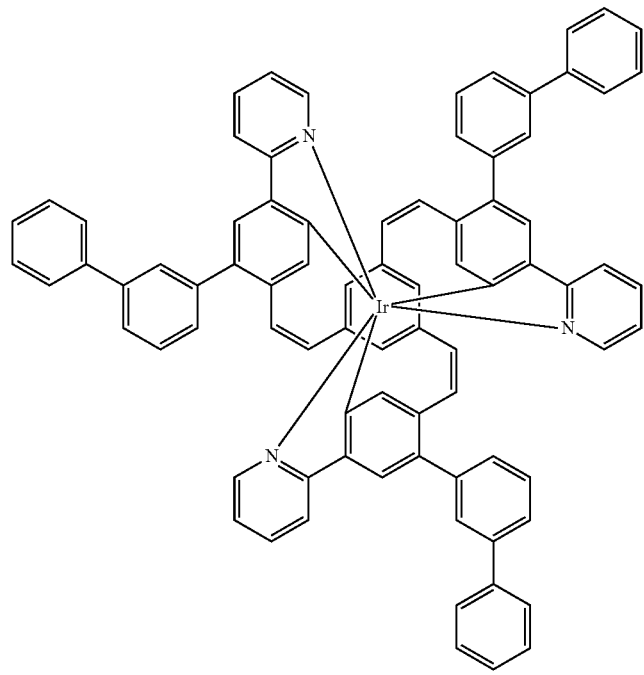
50
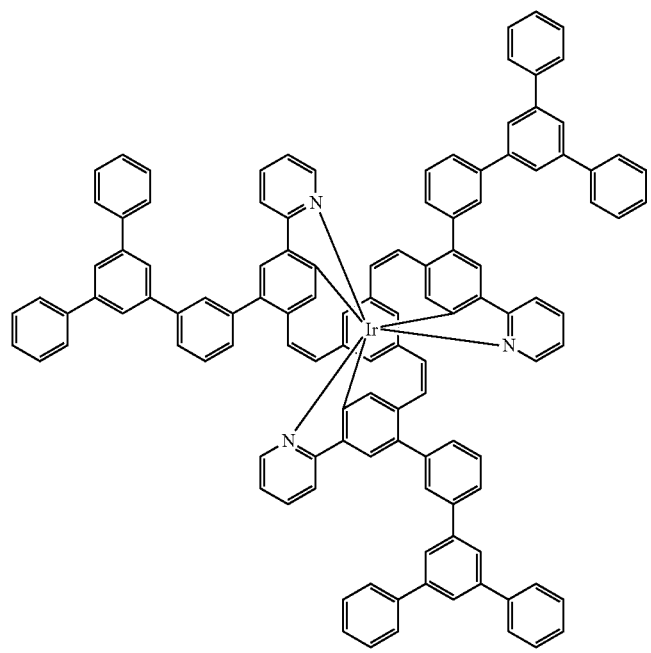

101  102
-continued
51  52
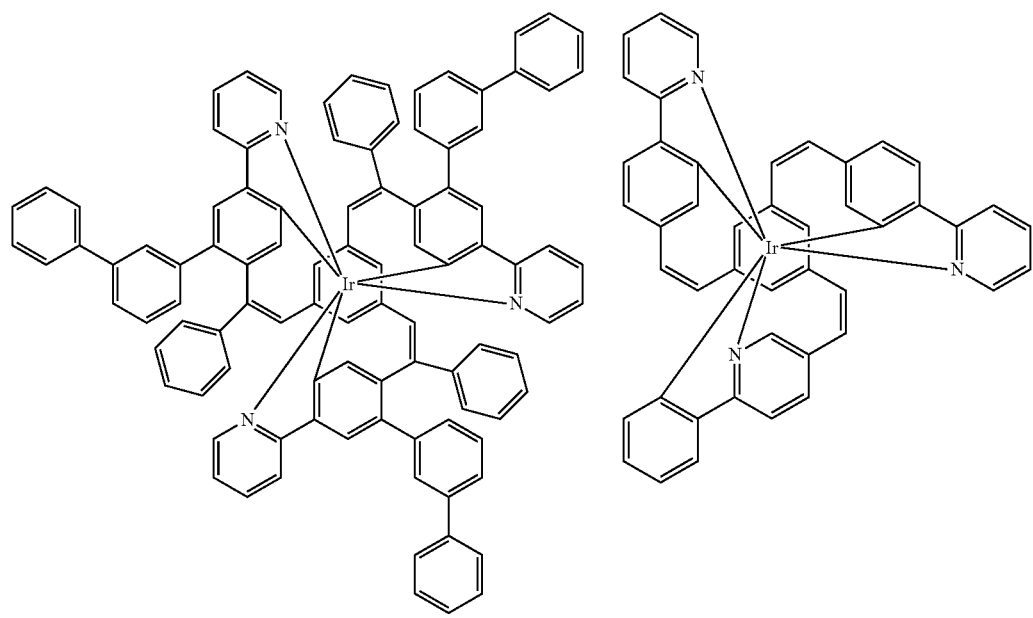
53
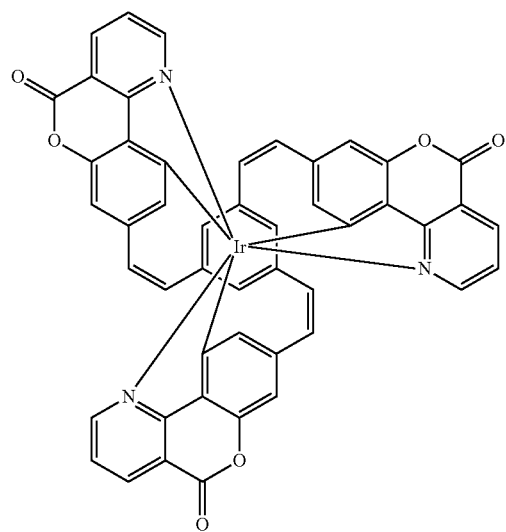

-continued
54
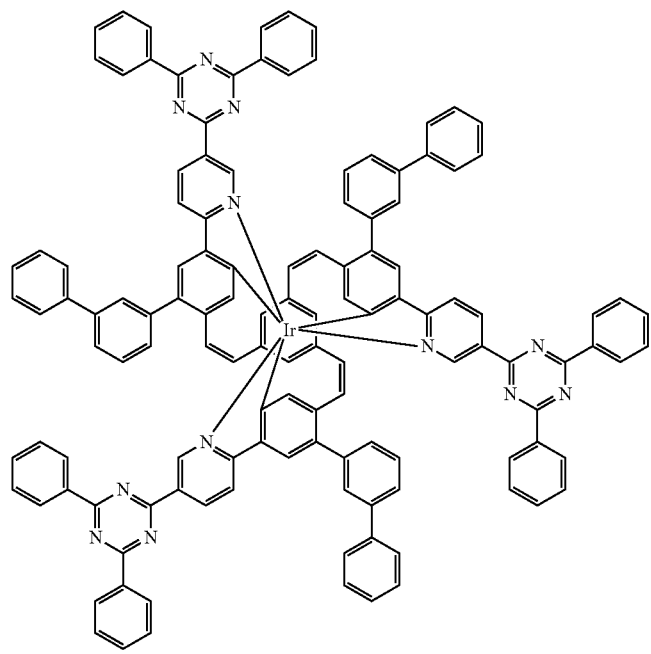
55
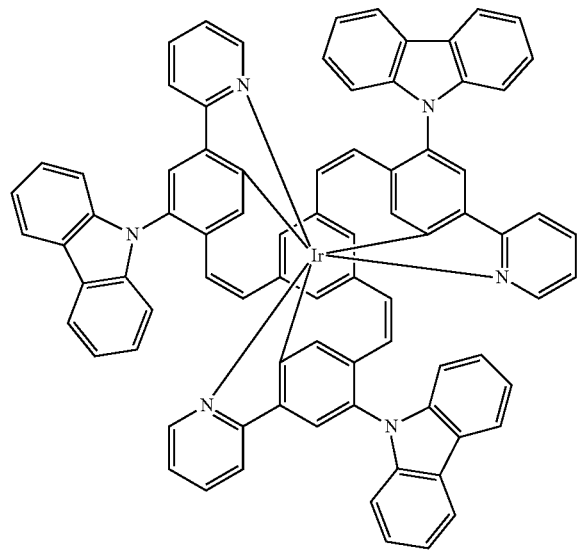

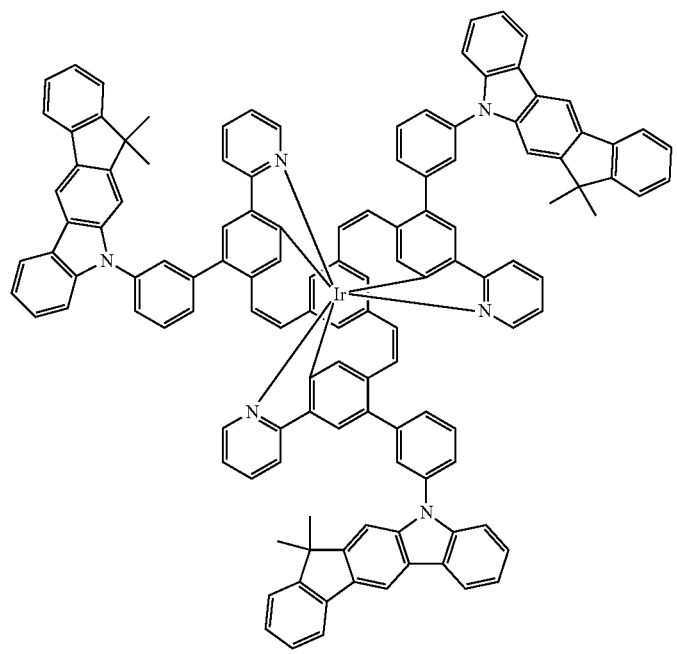
56
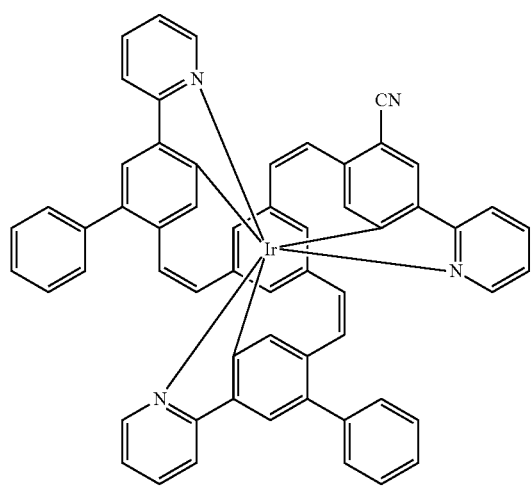
57
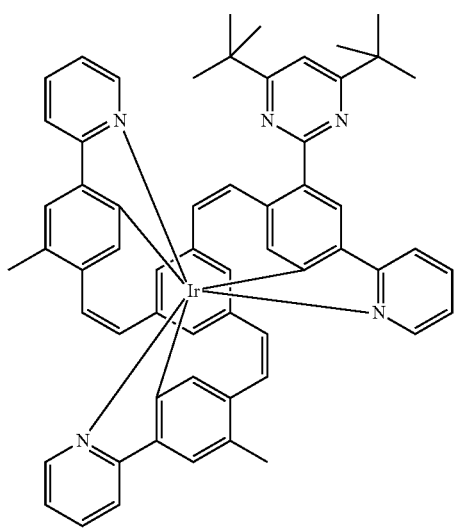
58
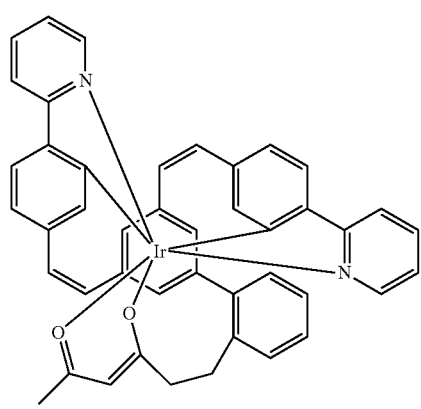
59
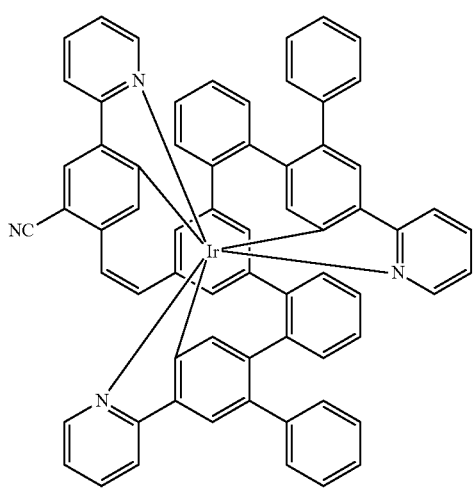
60

-continued
61
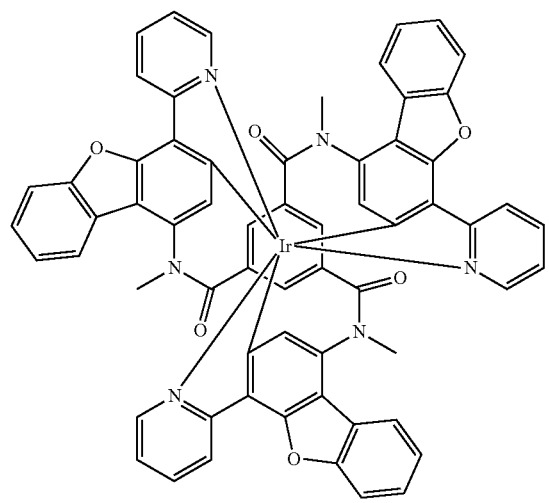
62
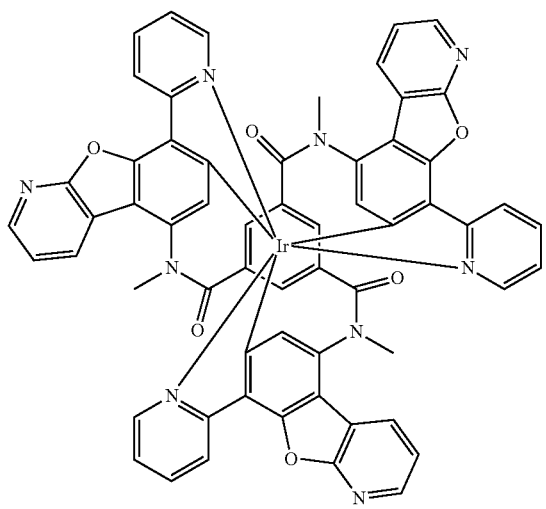
63
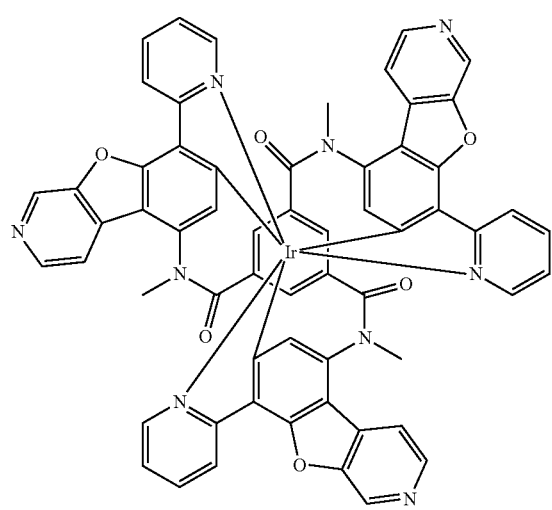
64
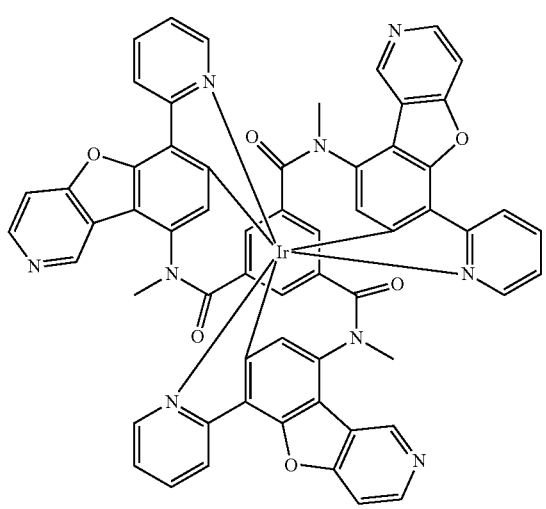
65
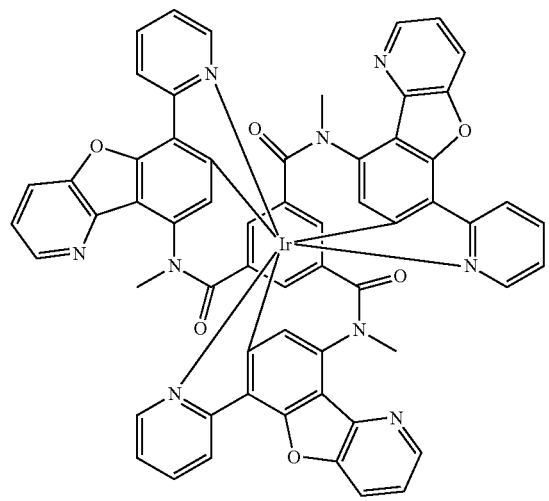
66
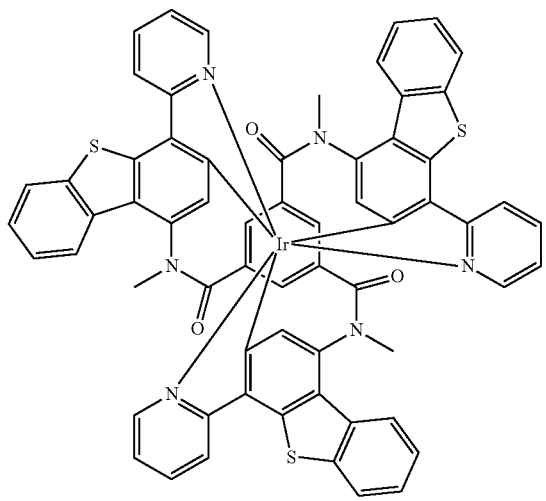

-continued
67
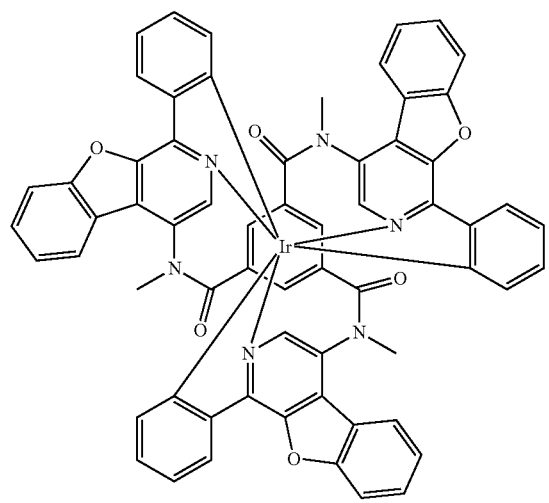
68
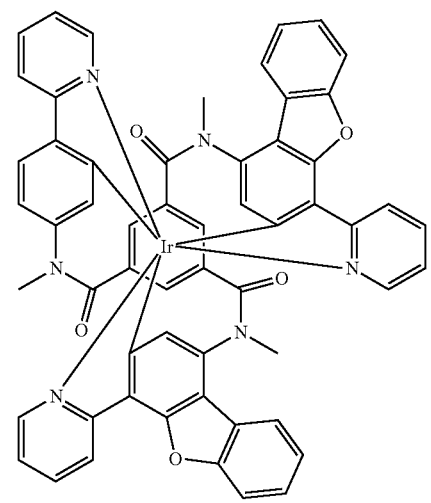
69
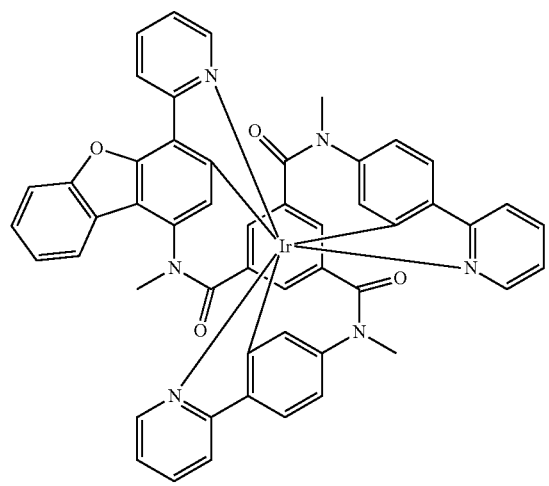
70
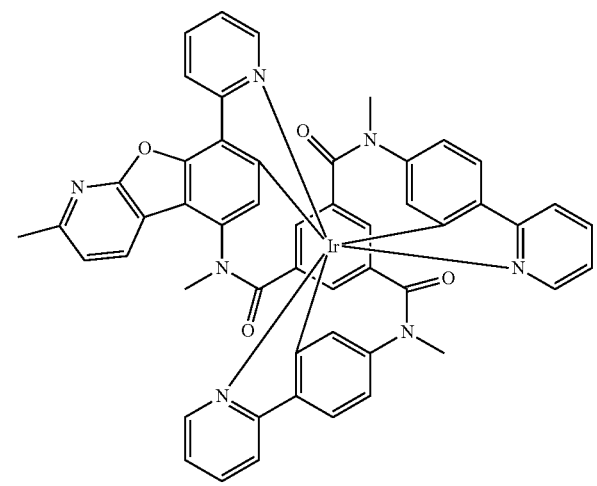
71
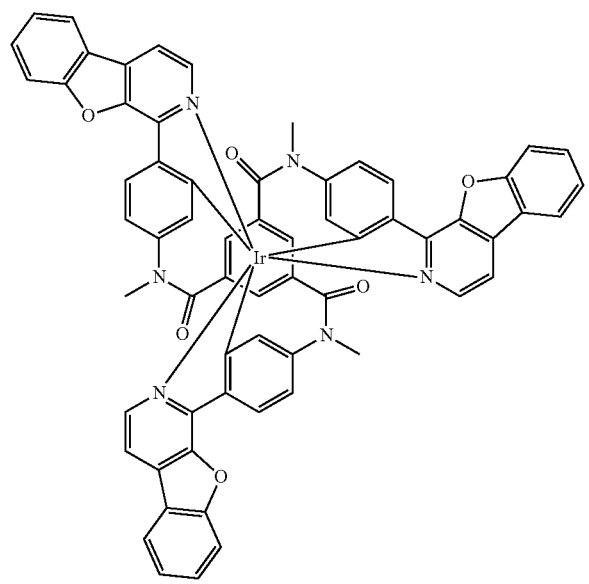
72
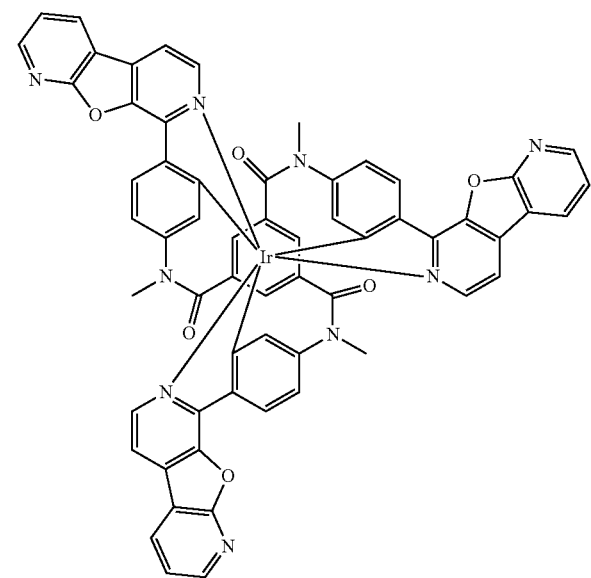

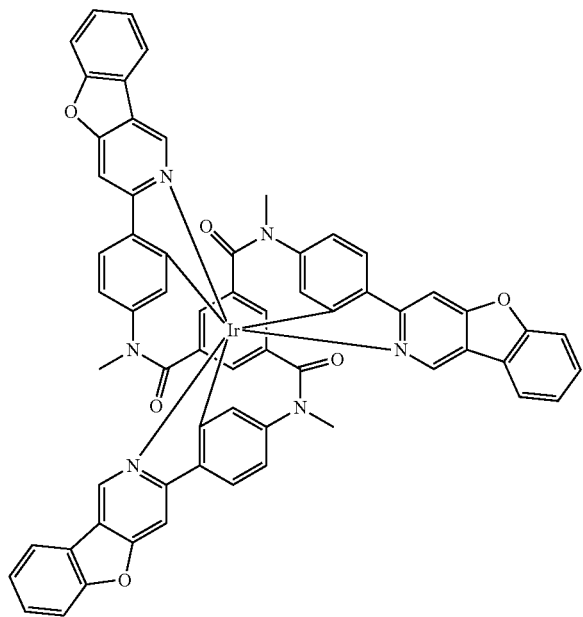
73
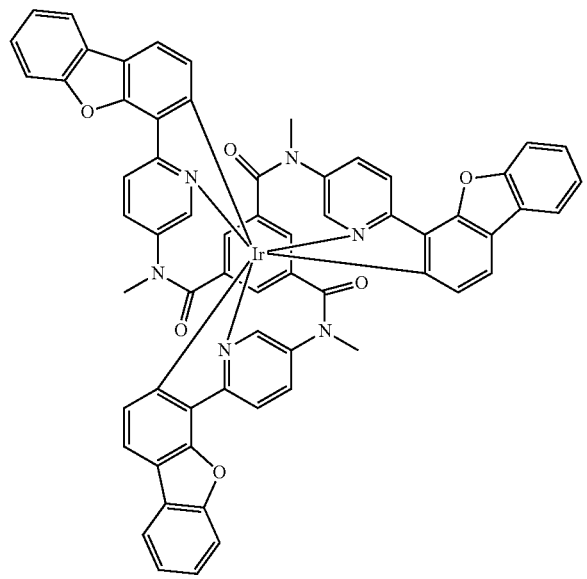
74
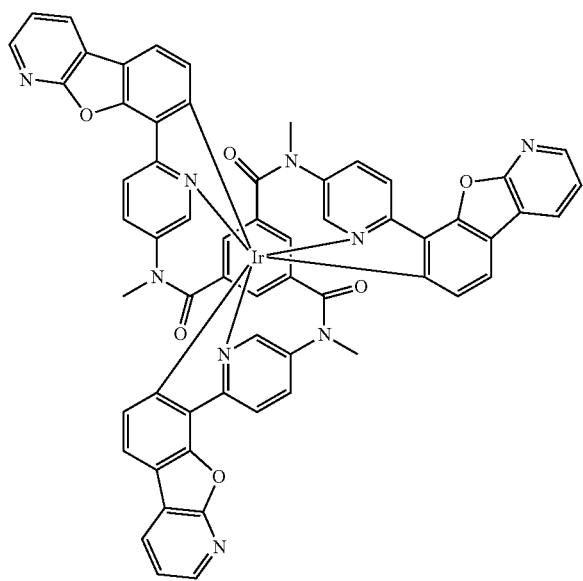
75
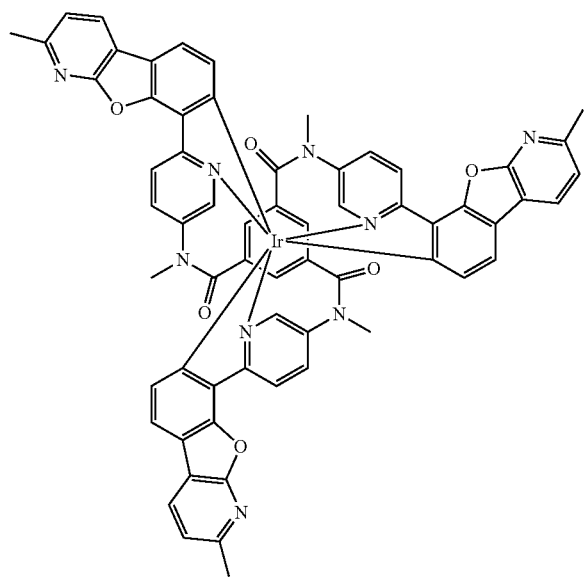
76

77
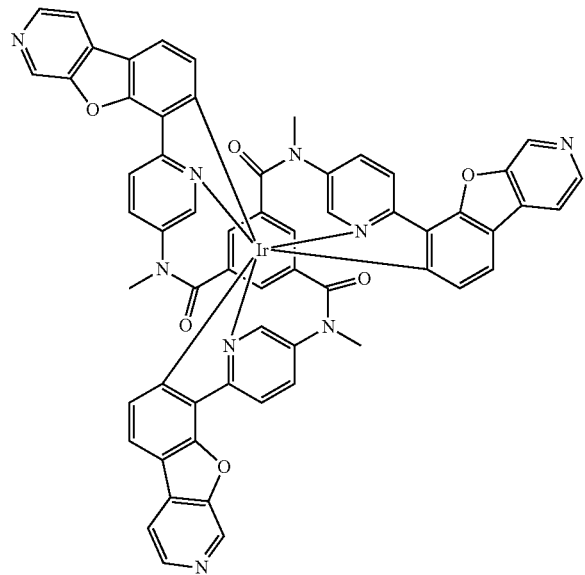
78
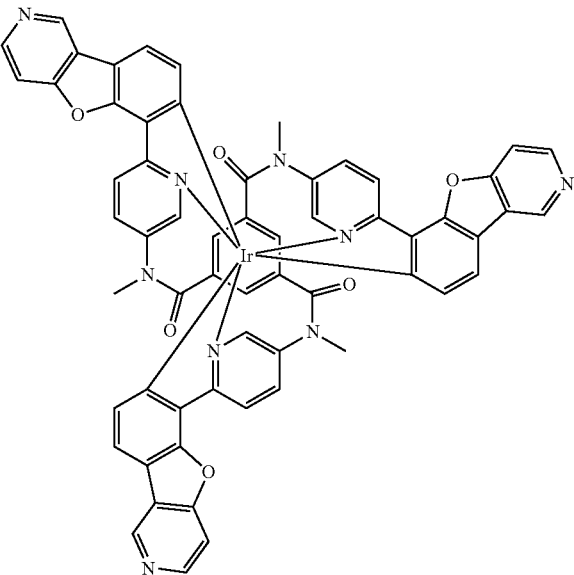
79
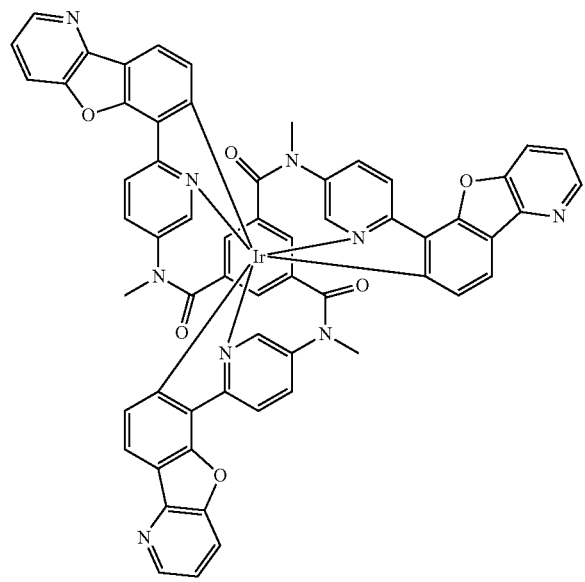
80
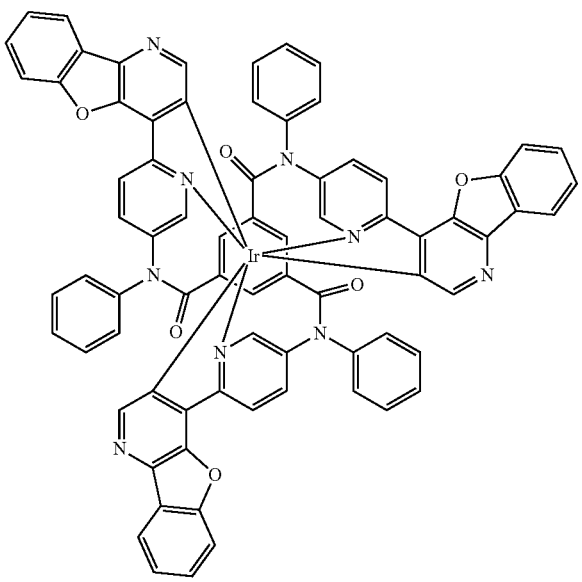

-continued
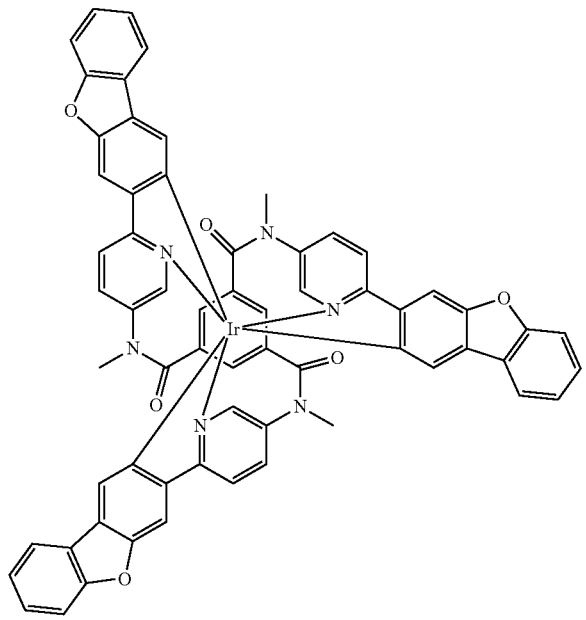
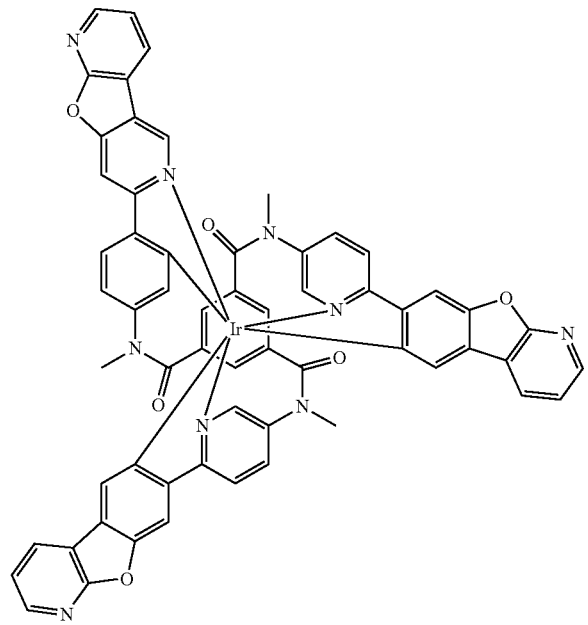
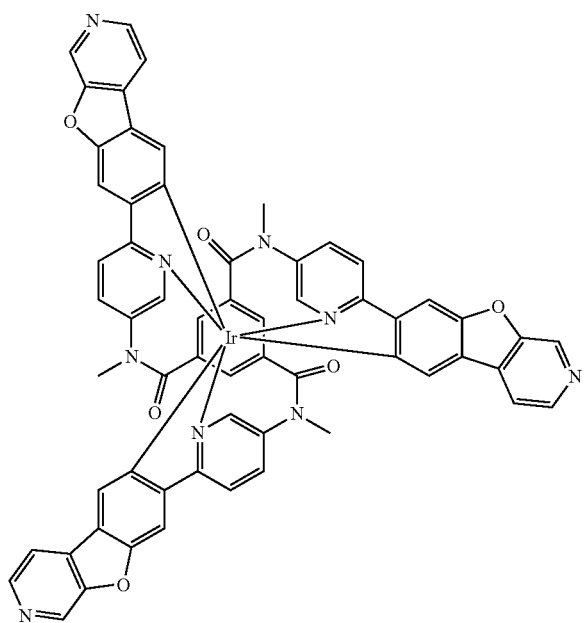
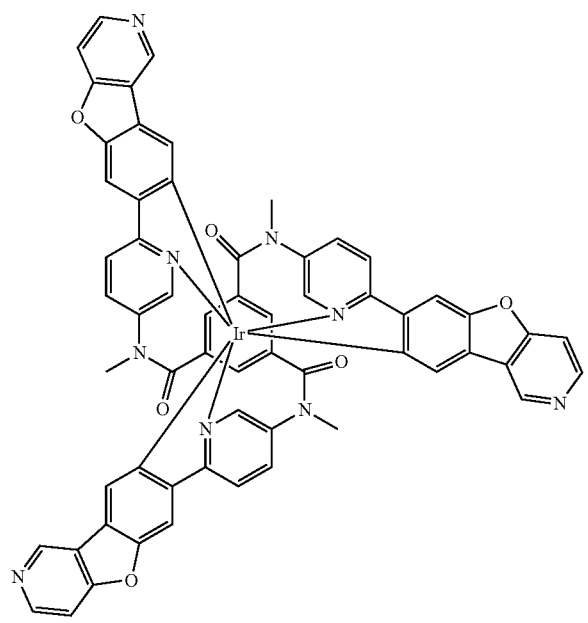

117 118
-continued
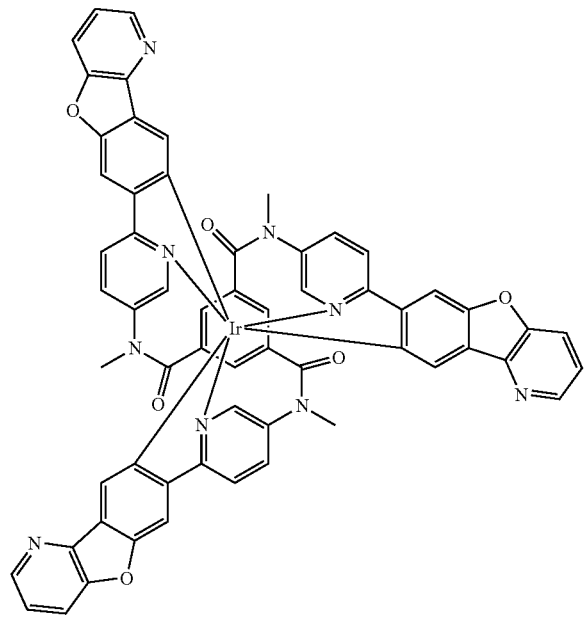
85
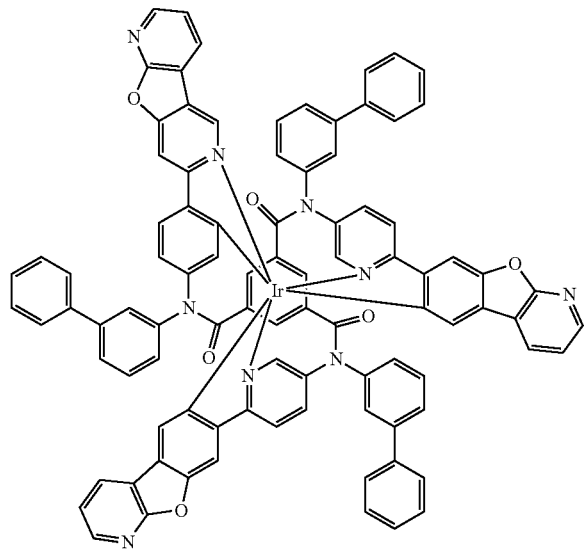
86
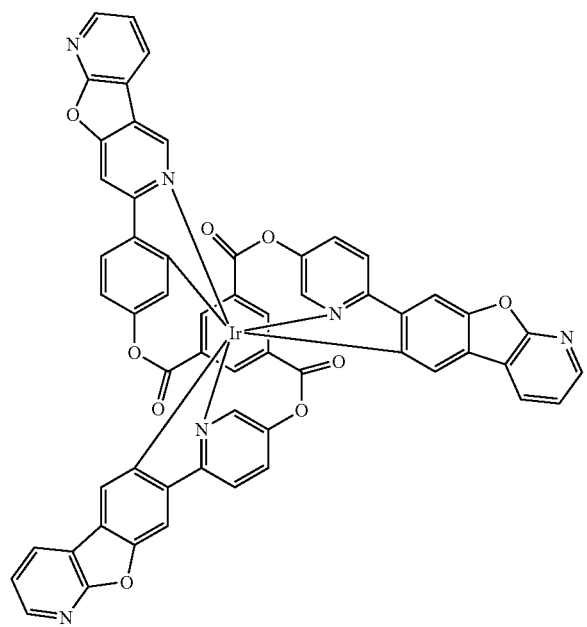
87
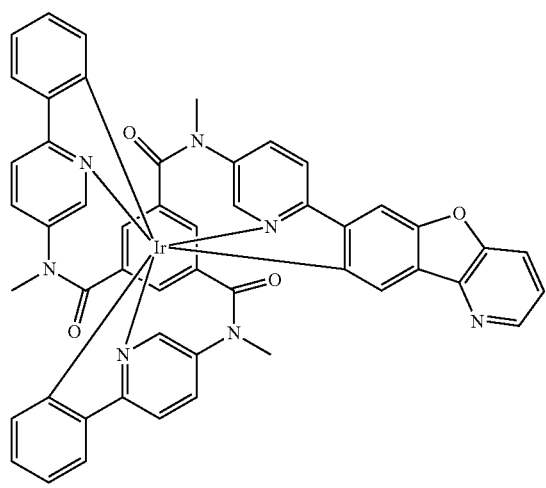
88

-continued
89
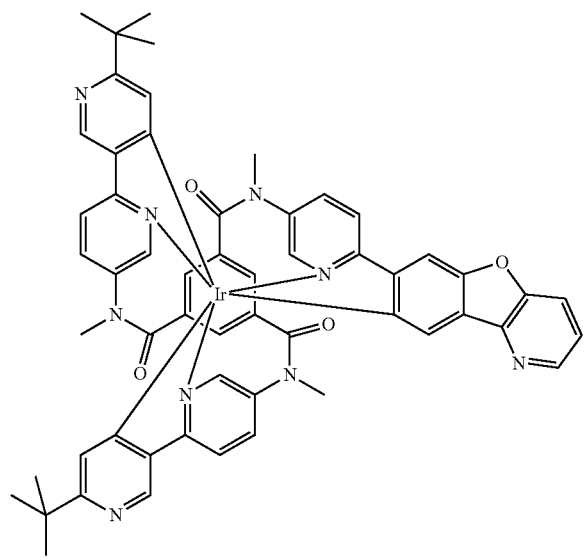
90
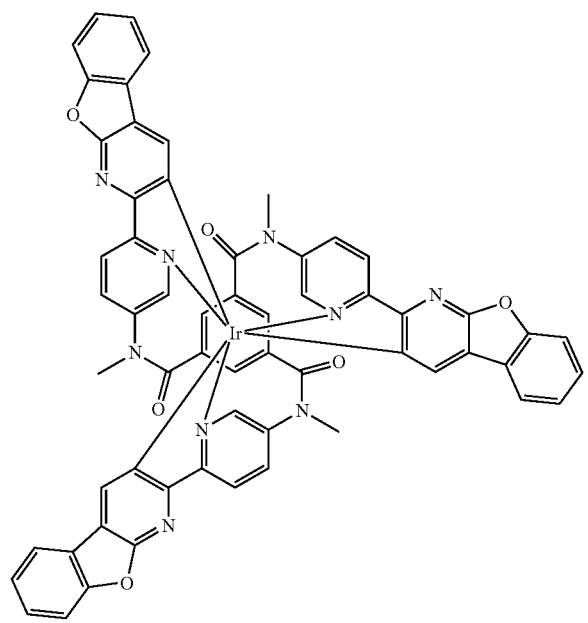
91
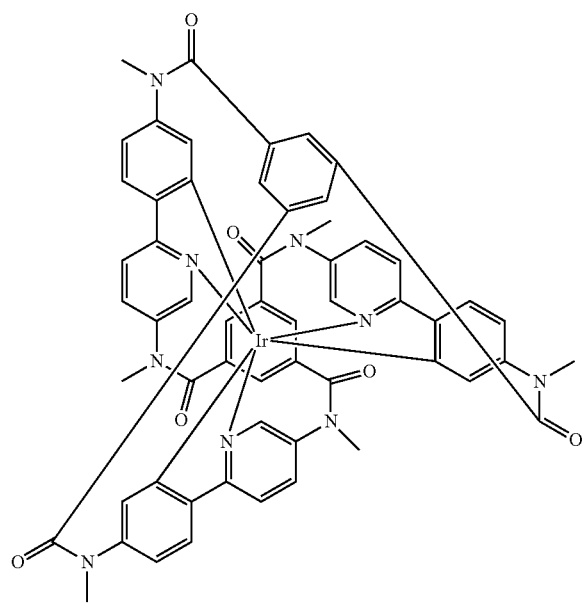
92
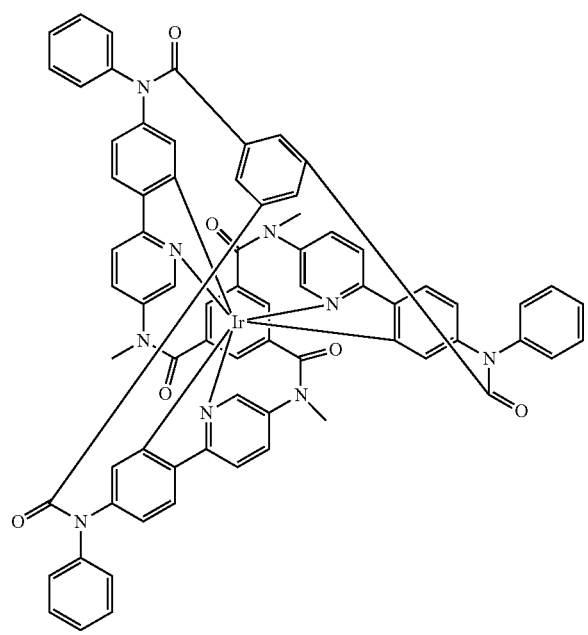

-continued
93
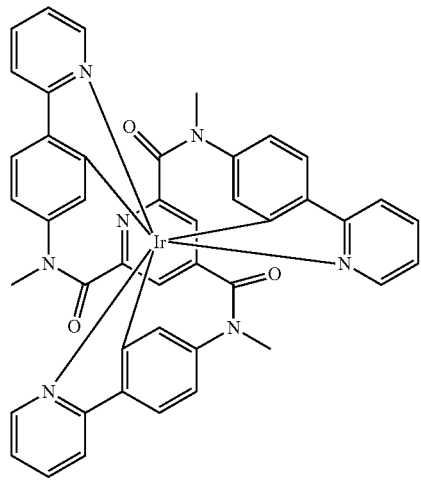
94
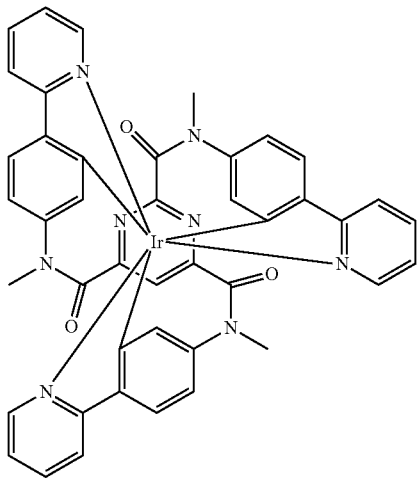
95
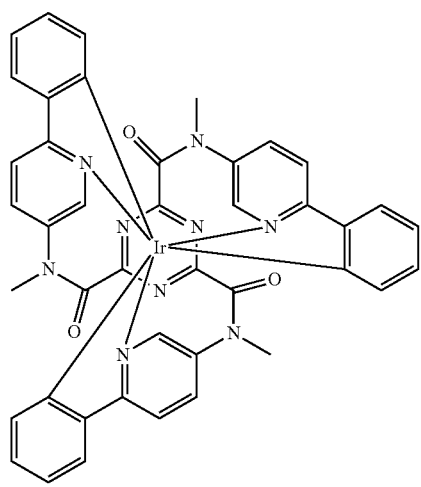
96
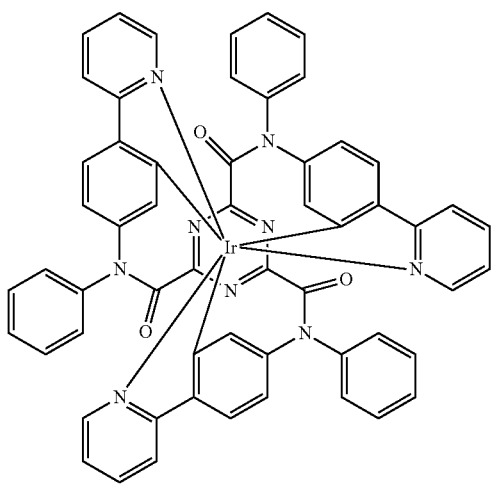
97
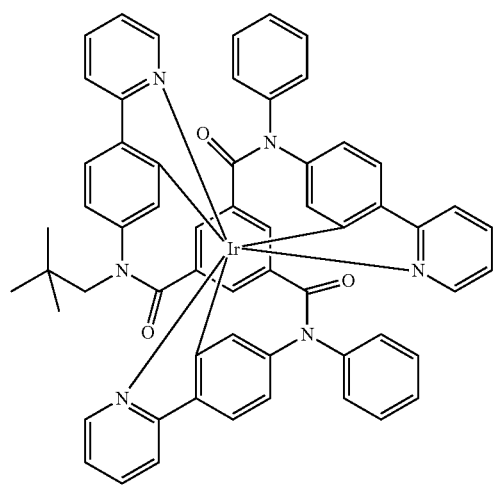
98
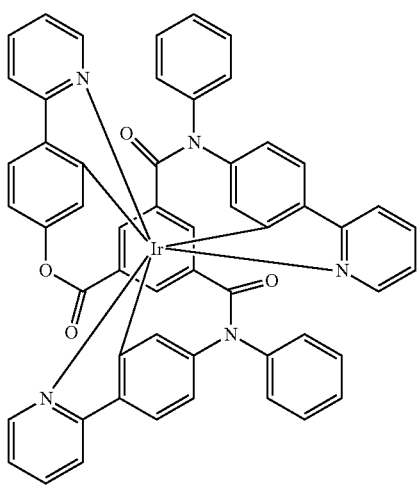

123 124
-continued
99
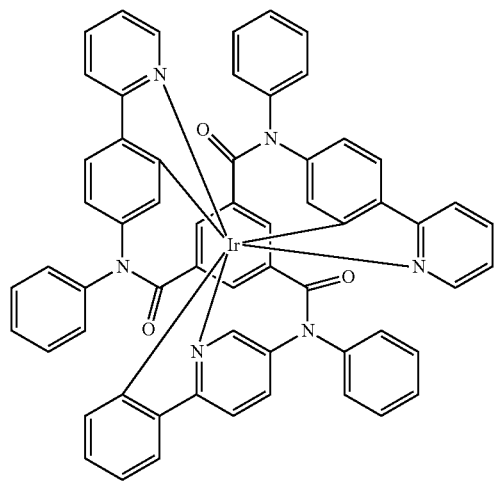
100
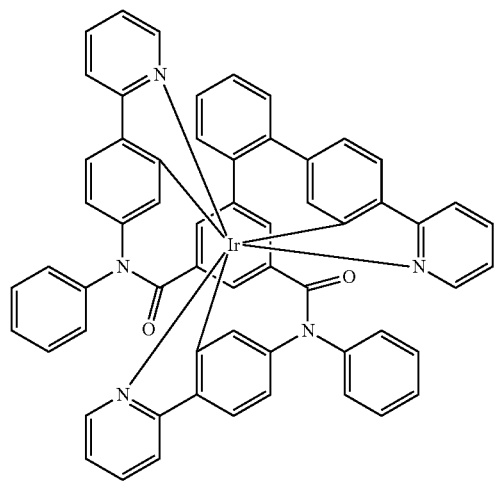
101
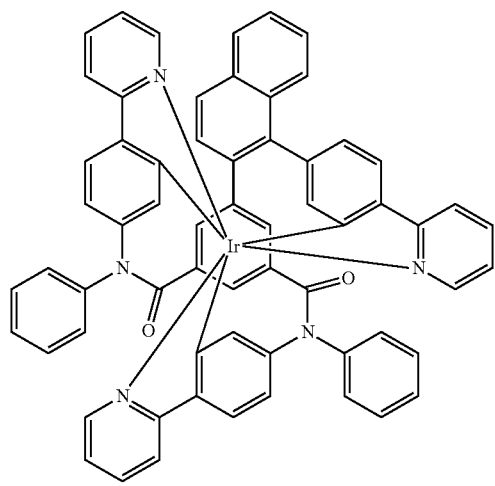
102
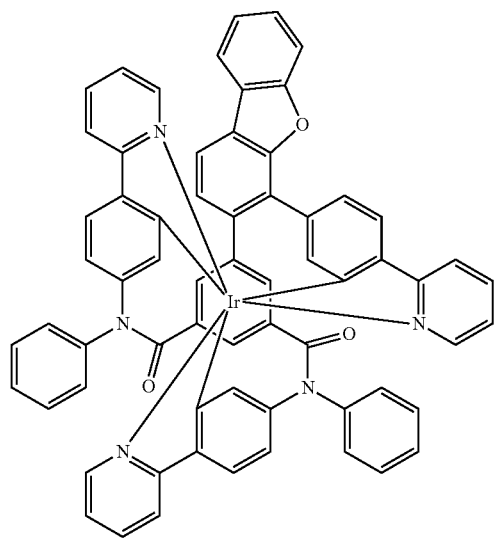
103
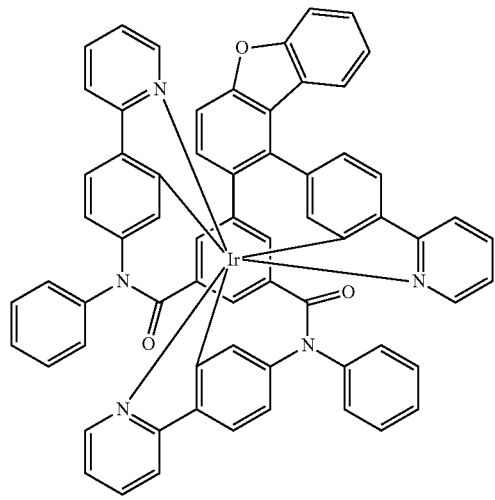
104
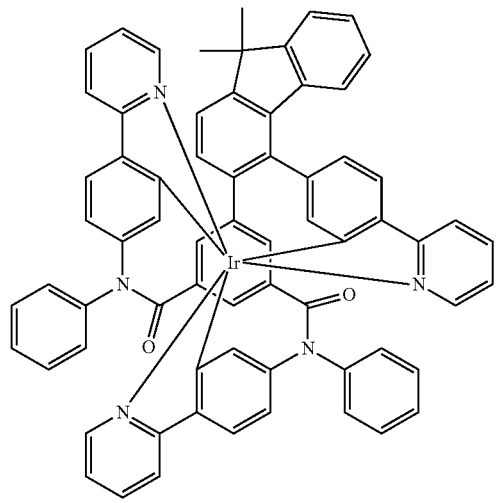

-continued
105
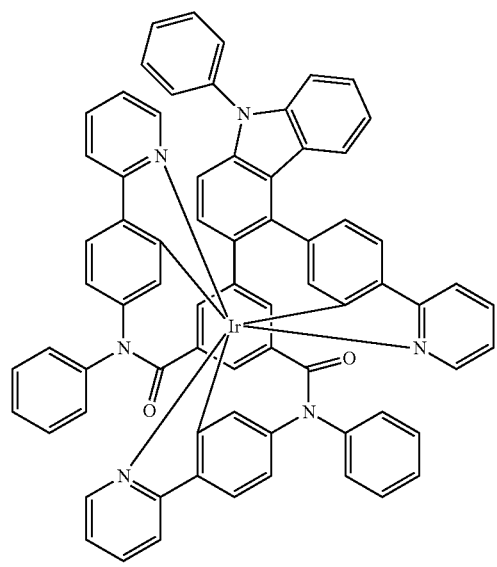
106
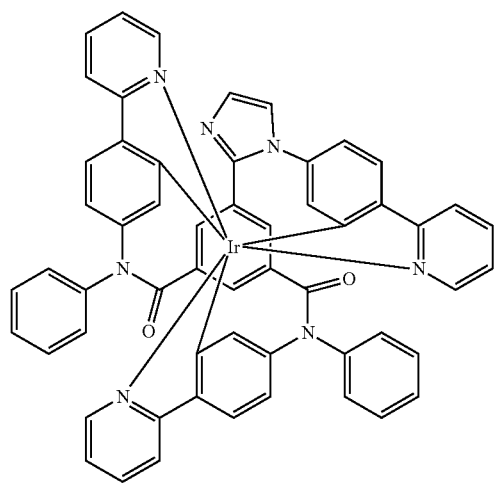
107
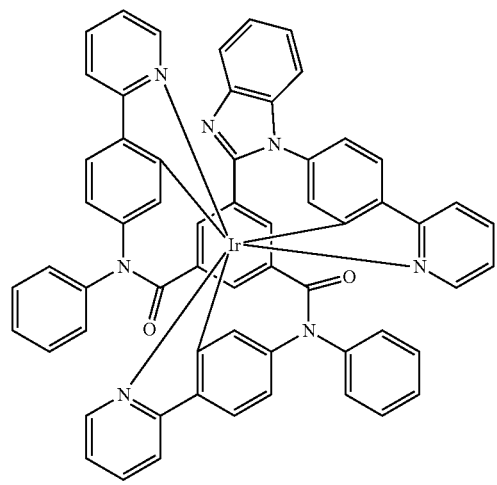
108
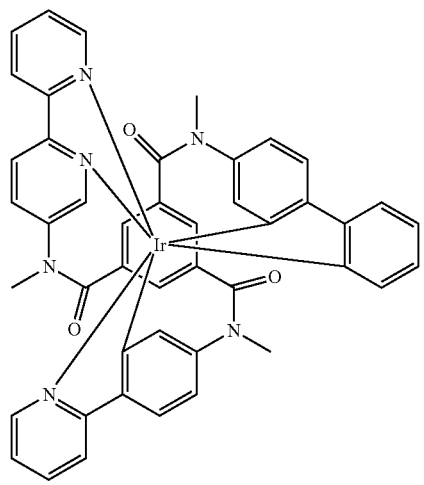
109
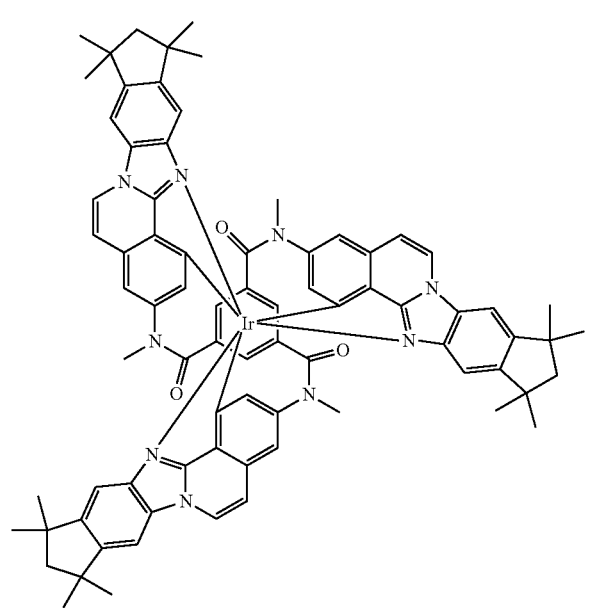
110
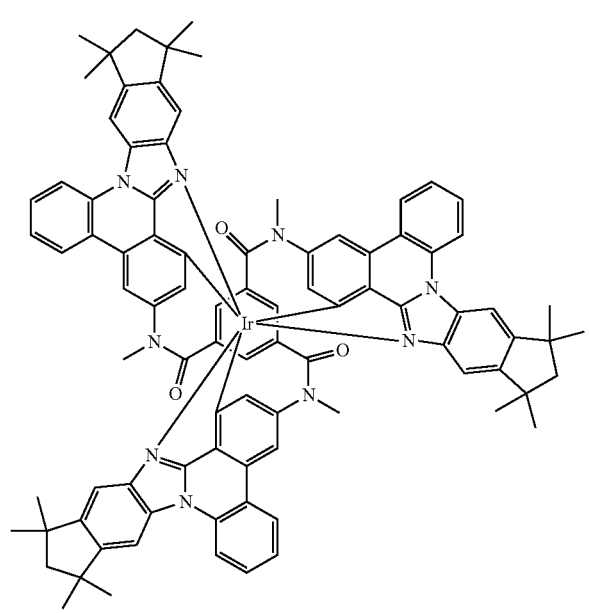

-continued
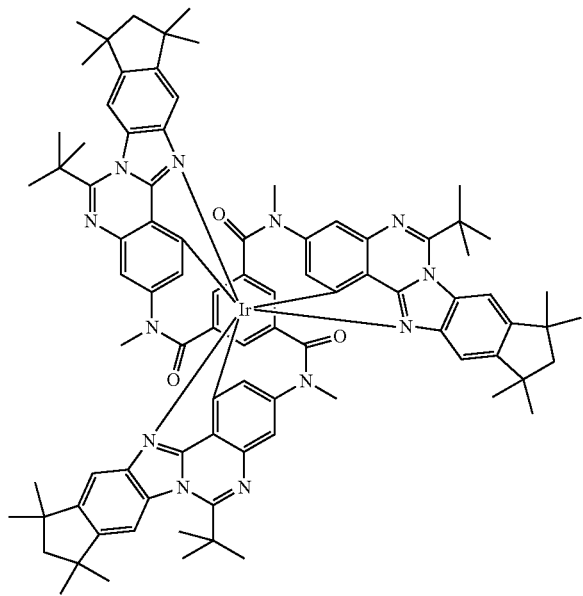
111
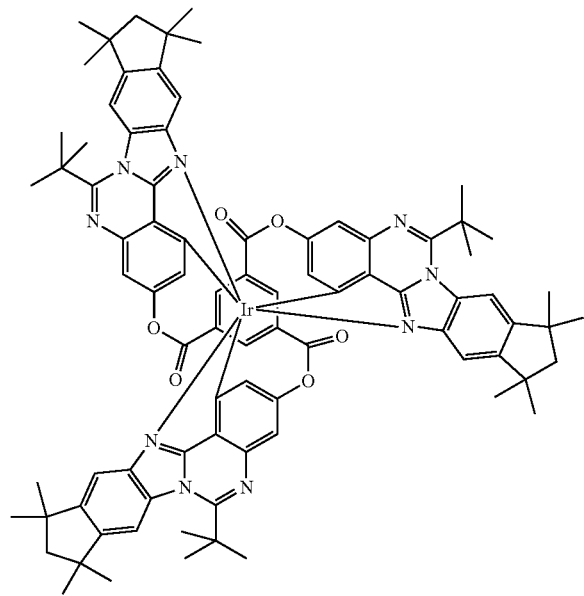
112
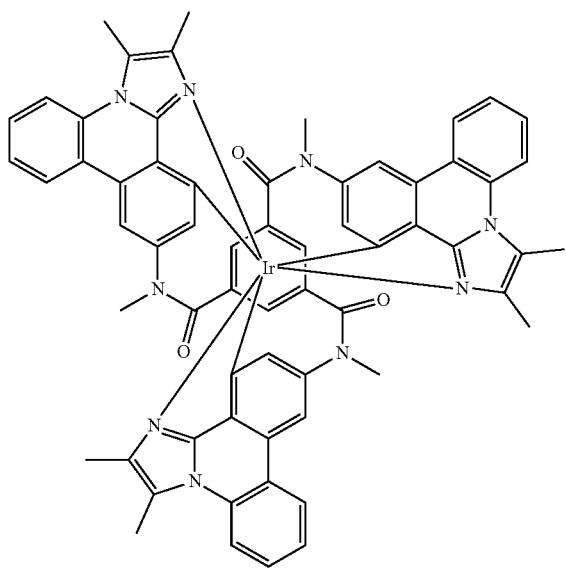
113
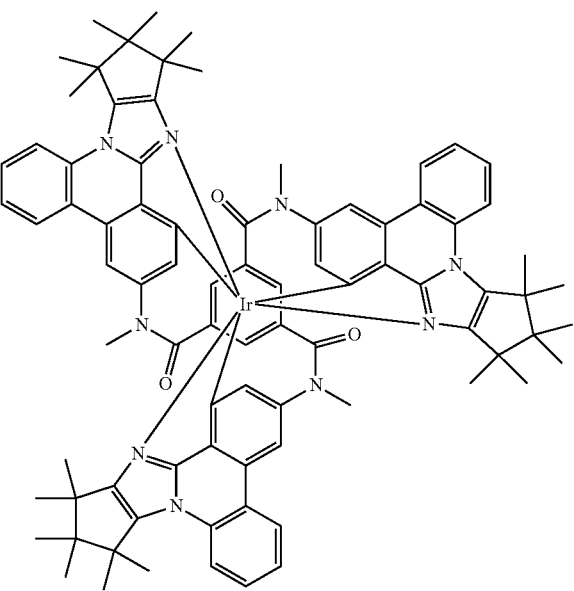
114

115
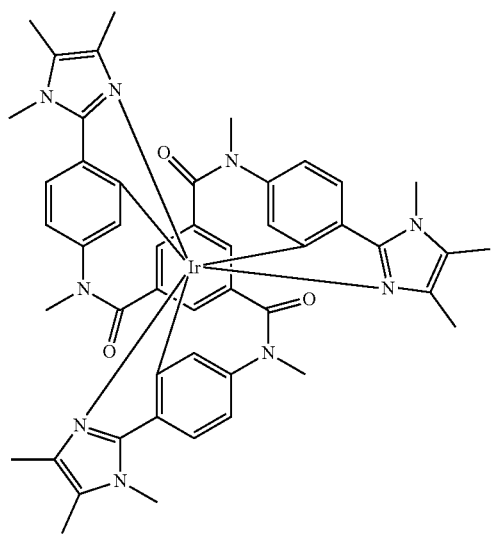
116
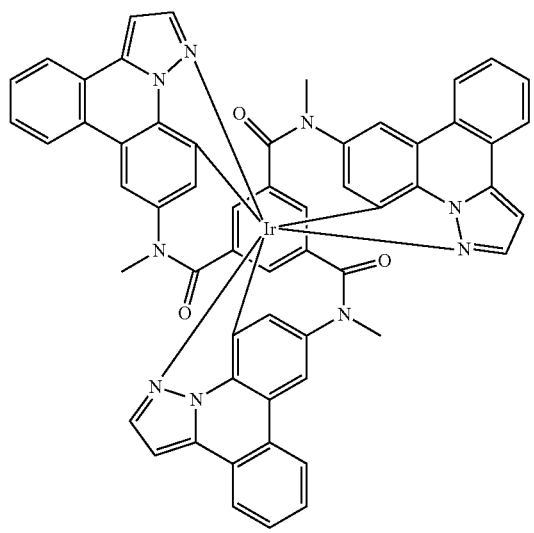
117
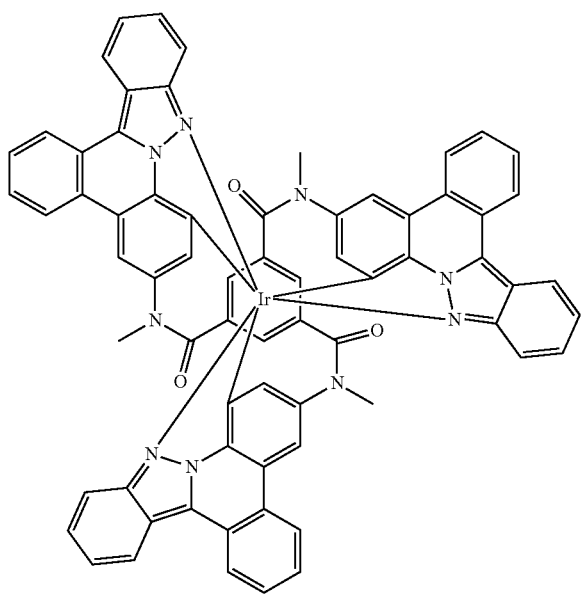
118
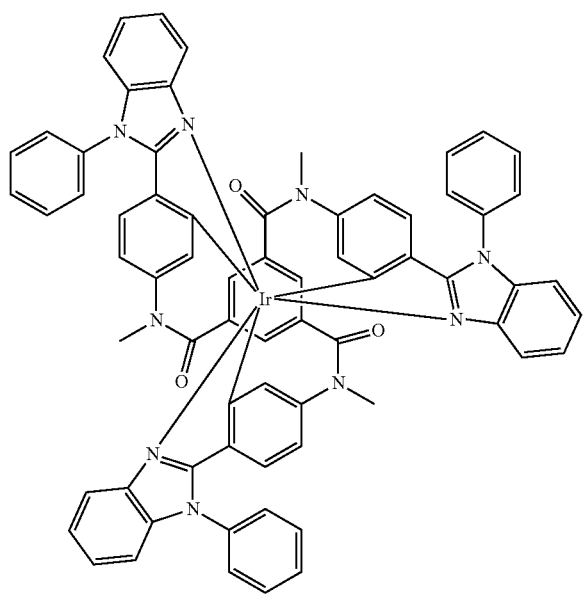

-continued
119
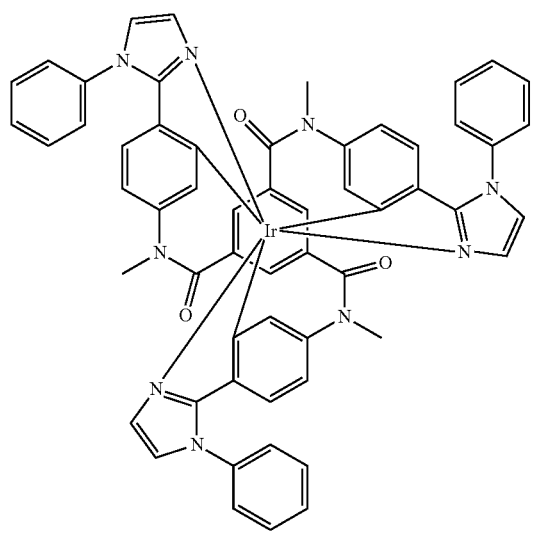
120
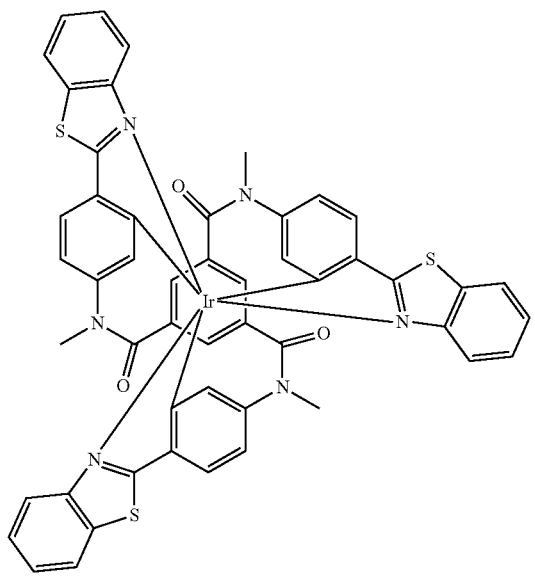
121
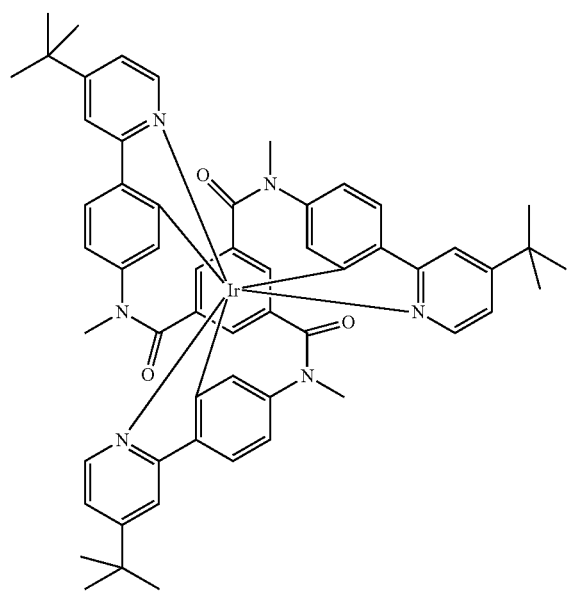
122
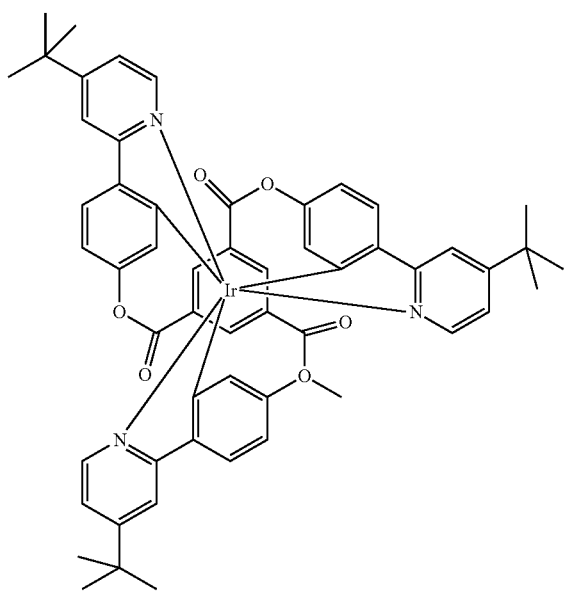

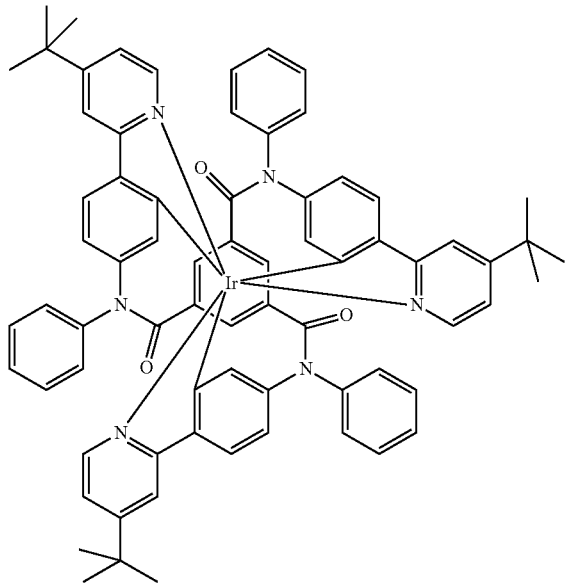

123

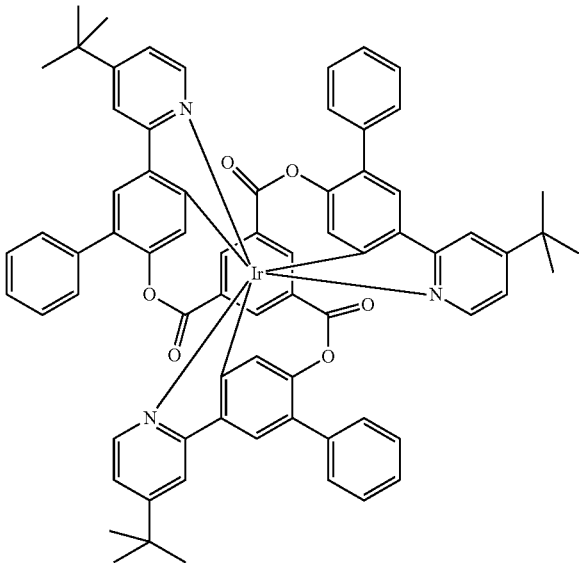

124

The meta l complexes of the invention are preparable in principle by various processes. In general, for this purpose, a metal salt or metal compound is reacted with the corresponding free ligand.

Therefore, the present invention further provides a process for preparing the metal complexes of the invention by reacting the corresponding free ligands with metal alkoxides of the formula (42), with metal ketoketonates of the formula (43), with metal halides of the formula (44) or with metal carboxylates of the formula (45)

M(OR)$_n$  Formula (42)

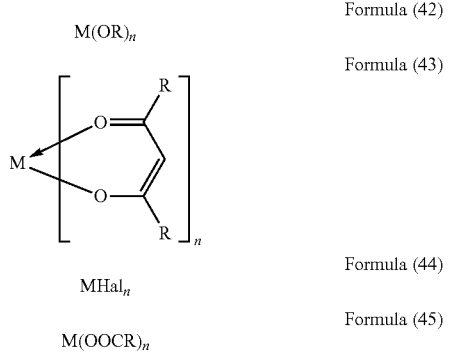

Formula (43)

MHal$_n$  Formula (44)

M(OOCR)$_n$  Formula (45)

where M is the metal in the metal complex of the invention which is synthesized, n is the valency of the metal M, R has the definitions given above, Hal=F, Cl, Br or I and the metal reactants may also be present in the form of the corresponding hydrates. R here is preferably an alkyl group having 1 to 4 carbon atoms.

It is likewise possible to use metal compounds, especially iridium compounds, bearing both alkoxide and/or halide and/or hydroxyl radicals and ketoketonate radicals. These compounds may also be charged. Corresponding iridium compounds of particular suitability as reactants are disclosed in WO 2004/085449. Particularly suitable are [IrCl$_2$(acac)$_2$]-, for example Na[IrCl$_2$(acac)$_2$], metal complexes with acetylacetonate derivatives as ligand, for example Ir(acac)$_3$ or tris(2,2,6,6-tetramethylheptane-3,5-dionato)iridium, and IrCl$_3$.xH$_2$O where x is typically a number from 2 to 4.

The synthesis of the complexes is preferably conducted as described in WO 2002/060910 and in WO 2004/085449. In this case, the synthesis can, for example, also be activated by thermal or photochemical means and/or by microwave radiation. In addition, the synthesis can also be conducted in an autoclave at elevated pressure and/or elevated temperature.

The reactions can be conducted without addition of solvents or melting aids in a melt of the corresponding ligands to be o-metallated. It is optionally possible to add solvents or melting aids. Suitable solvents are protic or aprotic solvents such as aliphatic and/or aromatic alcohols (methanol, ethanol, isopropanol, t-butanol, etc.), oligo- and polyalcohols (ethylene glycol, propane-1,2-diol, glycerol, etc.), alcohol ethers (ethoxyethanol, diethylene glycol, triethylene glycol, polyethylene glycol, etc.), ethers (di- and triethylene glycol dimethyl ether, diphenyl ether, etc.), aromatic, heteroaromatic and/or aliphatic hydrocarbons (toluene, xylene, mesitylene, chlorobenzene, pyridine, lutidine, quinoline, isoquinoline, tridecane, hexadecane, etc.), amides (DMF, DMAC, etc.), lactams (NMP), sulphoxides (DMSO) or sulphones (dimethyl sulphone, sulpholane, etc.). Suitable melting aids are compounds that are in solid form at room temperature but melt when the reaction mixture is heated and dissolve the reactants, so as to form a homogeneous melt. Particularly suitable are biphenyl, m-terphenyl, triphenyls, R- or S-binaphthol or else the corresponding racemate, 1,2-, 1,3- or 1,4-bisphenoxybenzene, triphenylphosphine oxide, 18-crown-6, phenol, 1-naphthol, hydroquinone, etc. Particular preference is given here to the use of hydroquinone.

It is possible by these processes, if necessary followed by purification, for example recrystallization or sublimation, to obtain the inventive compounds of formula (1) in high purity, preferably more than 99% (determined by means of $^1$H NMR and/or HPLC).

The metal complexes of the invention may also be rendered soluble by suitable substitution, for example by comparatively long alkyl groups (about 4 to 20 carbon atoms), especially branched alkyl groups, or optionally substituted aryl groups, for example xylyl, mesityl or branched terphenyl or quaterphenyl groups. Another particular method that leads to a distinct improvement in the solubility of the metal complexes is the use of fused-on aliphatic groups, as shown, for example, by the formulae (34) to (40) disclosed above. Such compounds are then soluble in sufficient concentration at room temperature in standard organic solvents, for example toluene or xylene, to be able to process the complexes from solution. These soluble compounds are of particularly good suitability for processing from solution, for example by printing methods.

The metal complexes of the invention may also be mixed with a polymer. It is likewise possible to incorporate these metal complexes covalently into a polymer. This is especially possible with compounds substituted by reactive leaving groups such as bromine, iodine, chlorine, boronic acid or boronic ester, or by reactive polymerizable groups such as olefins or oxetanes. These may find use as monomers for production of corresponding oligomers, dendrimers or polymers. The oligomerization or polymerization is preferably effected via the halogen functionality or the boronic acid functionality or via the polymerizable group. It is additionally possible to crosslink the polymers via groups of this kind. The compounds of the invention and polymers may be used in the form of a crosslinked or uncrosslinked layer.

The invention therefore further provides oligomers, polymers or dendrimers containing one or more of the above-detailed metal complexes of the invention, wherein one or more bonds of the metal complex of the invention to the polymer, oligomer or dendrimer are present rather than one or more hydrogen atoms and/or substituents. According to the linkage of the metal complex of the invention, it therefore forms a side chain of the oligomer or polymer or is incorporated in the main chain. The polymers, oligomers or dendrimers may be conjugated, partly conjugated or non-conjugated. The oligomers or polymers may be linear, branched or dendritic. For the repeat units of the metal complexes of the invention in oligomers, dendrimers and polymers, the same preferences apply as described above.

For preparation of the oligomers or polymers, the monomers of the invention are homopolymerized or copolymerized with further monomers. Preference is given to copolymers wherein the metal complexes of the invention are present to an extent of 0.01 to 99.9 mol %, preferably 5 to 90 mol %, more preferably 5 to 50 mol %. Suitable and preferred comonomers which form the polymer base skeleton are chosen from fluorenes (for example according to EP 842208 or WO 2000/022026), spirobifluorenes (for example according to EP 707020, EP 894107 or WO 2006/061181), paraphenylenes (for example according to WO 92/18552), carbazoles (for example according to WO 2004/070772 or WO 2004/113468), thiophenes (for example according to EP 1028136), dihydrophenanthrenes (for example according to WO 2005/014689), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers may contain still further units, for example hole transport units, especially those based on triarylamines, and/or electron transport units.

For the processing of the metal complexes of the invention from the liquid phase, for example by spin-coating or by printing methods, formulations of the metal complexes of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, hexamethylindane or mixtures of these solvents.

The present invention therefore further provides a formulation comprising at least one metal complex of the invention or at least one oligomer, polymer or dendrimer of the invention and at least one further compound. The further compound may, for example, be a solvent, especially one of the abovementioned solvents or a mixture of these solvents. The further compound may alternatively be a further organic or inorganic compound which is likewise used in the electronic device, for example a matrix material. This further compound may also be polymeric.

The above-described metal complex of the invention or the preferred embodiments detailed above can be used as active component in an electronic device, or can be used as photocatalysts or as oxygen sensitizers. The present invention thus further provides for the use of a compound of the invention in an electronic device or as photocatalyst or as oxygen sensitizer. The present invention still further provides an electronic device comprising at least one compound of the invention.

An electronic device is understood to mean any device comprising anode, cathode and at least one layer, said layer comprising at least one organic or organometallic compound. The electronic device of the invention thus comprises anode, cathode and at least one layer containing at least one metal complex of the invention. Preferred electronic devices are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), the latter being understood to mean both purely organic solar cells and dye-sensitized solar cells, organic optical detectors, organic photoreceptors, organic field-quench devices (O-FQDs), light-emitting electrochemical cells (LECs), oxygen sensors and organic laser diodes (O-lasers), comprising at least one metal complex of the invention in at least one layer. Particular preference is given to organic electroluminescent devices. This is especially true when the metal is iridium or aluminium. Active components are generally the organic or inorganic materials introduced between the anode and cathode, for example charge injection, charge transport or charge blocker materials, but especially emission materials and matrix materials. The compounds of the invention exhibit particularly good properties as emission material in organic electroluminescent devices. A preferred embodiment of the invention is therefore organic electroluminescent devices. In addition, the compounds of the invention can be used for production of singlet oxygen or in photocatalysis. Especially when the metal is ruthenium, preference is given to use as a photosensitizer in a dye-sensitized solar cell ("Gratzel cell").

The organic electroluminescent device comprises cathode, anode and at least one emitting layer. Apart from these layers, it may comprise still further layers, for example in each case one or more hole injection layers, hole transport layers, hole blocker layers, electron transport layers, electron injection layers, exciton blocker layers, electron blocker layers, charge generation layers and/or organic or inorganic p/n junctions. At the same time, it is possible that one or more hole transport layers are p-doped, for example with metal oxides such as $MoO_3$ or $WO_3$ or with (per)fluorinated electron-deficient aromatic systems, and/or that one or more electron transport layers are n-doped. It is likewise possible for interlayers to be introduced between two emitting layers, these having, for example, an exciton-blocking function and/or controlling the charge balance in the electroluminescent device. However, it should be pointed out that not necessarily every one of these layers need be present.

In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are three-layer systems where the three layers exhibit blue, green and orange or red emission (for the basic construction see, for example, WO 2005/011013), or systems having more than three emitting layers. The system may also be a hybrid system wherein one or more layers fluoresce and one or more other layers phosphoresce. White-emitting organic electroluminescent devices may be used for lighting applications or else with colour filters for full-colour displays.

In a preferred embodiment of the invention, the organic electroluminescent device comprises the metal complex of the invention as emitting compound in one or more emitting layers.

When the metal complex of the invention is used as emitting compound in an emitting layer, it is preferably used in combination with one or more matrix materials. The mixture of the metal complex of the invention and the matrix material contains between 0.1% and 99% by volume, preferably between 1% and 90% by volume, more preferably between 3% and 40% by volume and especially between 5% and 15% by volume of the metal complex of the invention, based on the overall mixture of emitter and matrix material. Correspondingly, the mixture contains between 99.9% and 1% by volume, preferably between 99% and 10% by volume, more preferably between 97% and 60% by volume and especially between 95% and 85% by volume of the matrix material, based on the overall mixture of emitter and matrix material.

The matrix material used may generally be any materials which are known for the purpose according to the prior art. The triplet level of the matrix material is preferably higher than the triplet level of the emitter.

Suitable matrix materials for the compounds of the invention are ketones, phosphine oxides, sulphoxides and sulphones, for example according to WO 2004/013080, WO 2004/093207, WO 2006/005627 or WO 2010/006680, triarylamines, carbazole derivatives, e.g. CBP (N,N-biscarbazolylbiphenyl), m-CBP or the carbazole derivatives disclosed in WO 2005/039246, US 2005/0069729, JP 2004/288381, EP 1205527, WO 2008/086851 or US 2009/0134784, indolocarbazole derivatives, for example according to WO 2007/063754 or WO 2008/056746, indenocarbazole derivatives, for example according to WO 2010/136109 or WO 2011/000455, azacarbazoles, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, diazasilole derivatives, for example according to WO 2010/054729, diazaphosphole derivatives, for example according to WO 2010/054730, triazine derivatives, for example according to WO 2010/015306, WO 2007/063754 or WO 2008/056746, zinc complexes, for example according to EP 652273 or WO 2009/062578, dibenzofuran derivatives, for example according to WO 2009/148015 or WO 2015/169412, or bridged carbazole derivatives, for example according to US 2009/0136779, WO 2010/050778, WO 2011/042107 or WO 2011/088877.

It may also be preferable to use a plurality of different matrix materials as a mixture, especially at least one electron-conducting matrix material and at least one hole-conducting matrix material. A preferred combination is, for example, the use of an aromatic ketone, a triazine derivative or a phosphine oxide derivative with a triarylamine derivative or a carbazole derivative as mixed matrix for the metal complex of the invention. Preference is likewise given to the use of a mixture of a charge-transporting matrix material and an electrically inert matrix material having no significant involvement, if any, in the charge transport, as described, for example, in WO 2010/108579. Preference is likewise given to the use of two electron-transporting matrix materials, for example triazine derivatives and lactam derivatives, as described, for example, in WO 2014/094964.

It is further preferable to use a mixture of two or more triplet emitters together with a matrix. In this case, the triplet emitter having the shorter-wave emission spectrum serves as co-matrix for the triplet emitter having the longer-wave emission spectrum. For example, it is possible to use the metal complexes of the invention as co-matrix for longer-wave-emitting triplet emitters, for example for green- or red-emitting triplet emitters. In this case, it may also be preferable when both the shorter-wave- and the longer-wave-emitting metal complexes are a compound of the invention.

The metal complexes of the invention can also be used in other functions in the electronic device, for example as hole transport material in a hole injection or transport layer, as charge generation material, as electron blocker material, as hole blocker material or as electron transport material, for example in an electron transport layer, according to the choice of metal and the exact structure of the ligand. When the metal complex of the invention is an aluminium complex, it is preferably used in an electron transport layer. It is likewise possible to use the metal complexes of the invention as matrix material for other phosphorescent metal complexes in an emitting layer.

Preferred cathodes are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag, in which case combinations of the metals such as Mg/Ag, Ca/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). Likewise useful for this purpose are organic alkali metal complexes, e.g. Liq (lithium quinolinate). The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/$NiO_x$, Al/$PtO_x$) may also be preferred. For some applications, at least one of the electrodes has to be transparent or partly transparent in order to enable either the irradiation of the organic material (O-SC) or the emission of light (OLED/PLED, O-laser). Preferred anode materials here are conductive mixed metal oxides. Particular preference is given to indium tin oxide (ITO) or indium zinc oxide (IZO). Preference is further given to conductive doped organic materials, especially conductive doped polymers, for example PEDOT, PANI or derivatives of these polymers. It is further preferable when a p-doped hole transport material is applied to the anode as hole injection layer, in which case suitable p-dopants are metal oxides, for example $MoO_3$ or $WO_3$, or (per)fluorinated electron-deficient aromatic systems. Further suitable p-dopants are HAT-CN (hexacyanohexaazatriphenylene) or the compound NPD9 from Novaled. Such a layer simplifies hole injection into materials having a low HOMO, i.e. a large HOMO in terms of magnitude.

In the further layers, it is generally possible to use any materials as used according to the prior art for the layers, and the person skilled in the art is able, without exercising inventive skill, to combine any of these materials with the materials of the invention in an electronic device.

The device is correspondingly (according to the application) structured, contact-connected and finally hermetically sealed, since the lifetime of such devices is severely shortened in the presence of water and/or air.

Additionally preferred is an organic electroluminescent device, characterized in that one or more layers are coated by a sublimation process. In this case, the materials are applied by vapour deposition in vacuum sublimation systems at an initial pressure of typically less than $10^{-5}$ mbar, preferably less than $10^{-6}$ mbar. It is also possible that the initial pressure is even lower or even higher, for example less than $10^{-7}$ mbar.

Preference is likewise given to an organic electroluminescent device, characterized in that one or more layers are coated by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured (for example, M. S. Arnold et al., *Appl. Phys. Lett.* 2008, 92, 053301).

Preference is additionally given to an organic electroluminescent device, characterized in that one or more layers are produced from solution, for example by spin-coating, or by any printing method, for example screen printing, flexographic printing, offset printing or nozzle printing, but more preferably LITI (light-induced thermal imaging, thermal transfer printing) or inkjet printing. For this purpose, soluble compounds are needed, which are obtained, for example, through suitable substitution.

The organic electroluminescent device can also be produced as a hybrid system by applying one or more layers from solution and applying one or more other layers by vapour deposition. For example, it is possible to apply an emitting layer comprising a metal complex of the invention and a matrix material from solution, and to apply a hole blocker layer and/or an electron transport layer thereto by vapour deposition under reduced pressure.

These methods are known in general terms to those skilled in the art and can be applied by those skilled in the art without difficulty to organic electroluminescent devices comprising compounds of formula (1) or the above-detailed preferred embodiments.

The electronic devices of the invention, especially organic electroluminescent devices, are notable for one or more of the following surprising advantages over the prior art:

1. The metal complexes of the invention can be synthesized in very high yield and very high purity with exceptionally short reaction times and at comparatively low reaction temperatures.
2. The metal complexes of the invention, especially those in which $X^2$ is an amide group or an ester group, have very good solubility in polar solvents, such as esters, e.g. ethyl acetate, butyl acetate or hexyl acetate or benzoic esters, amides, e.g. DMF or DMAC, lactones or lactams, e.g. NMP.
3. The metal complexes of the invention have excellent thermal stability, which is also manifested in the sublimation of the complexes.
4. The metal complexes of the invention exhibit neither thermal nor photochemical fac/mer or mer/fac isomerization, which leads to advantages in the use of these complexes.
5. Some of the metal complexes of the invention have a very narrow emission spectrum, which leads to a high colour purity in the emission, as is desirable particularly for display applications.
6. Organic electroluminescent devices comprising the metal complexes of the invention as emitting materials have a very good lifetime.
7. Organic electroluminescent devices comprising the metal complexes of the invention as emitting materials have excellent efficiency.

These abovementioned advantages are not accompanied by a deterioration in the further electronic properties.

The invention is illustrated in detail by the examples which follow, without any intention of restricting it thereby. The person skilled in the art will be able to use the details given, without exercising inventive skill, to produce further electronic devices of the invention and hence to execute the invention over the entire scope claimed.

EXAMPLES

The syntheses which follow, unless stated otherwise, are conducted under a protective gas atmosphere in dried solvents. The metal complexes are additionally handled with exclusion of light or under yellow light. The solvents and reagents can be purchased, for example, from Sigma-ALDRICH or ABCR. The respective figures in square brackets or the numbers quoted for individual compounds relate to the CAS numbers of the compounds known from the literature. With regard to their conformation in the olefin or imine bond, ligands are shown in pictorial form hereinafter as they occur in the metal complex, irrespective of whether they are obtained from the synthesis as the E form, Z form or as a mixture.

Synthesis of the Synthons S:

Example S1

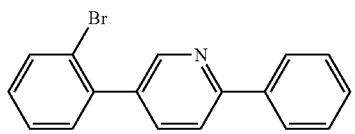 [SMILES: Brc1ccccc1-c1ccc(-c2ccccc2)nc1]

A mixture of 28.1 g (100 mmol) of 2-phenyl-5-[4,4,5,5-tetramethyl-1,3,2-dioxaborolan-2-yl)pyridine [879291-27-7], 28.2 g (100 mmol) of 1-bromo-2-iodobenzene [583-55-1], 31.8 g (300 mmol) of sodium carbonate, 787 mg (3 mmol) of triphenylphosphine, 225 mg (1 mmol) of palladium(II) acetate, 300 ml of toluene, 150 ml of ethanol and 300 ml of water is heated under reflux for 24 h. After cooling, the mixture is extended with 500 ml of toluene, and the organic phase is removed, washed once with 500 ml of water and once with saturated sodium chloride solution and dried over magnesium sulphate. After the solvent has been removed, the residue is recrystallized from ethyl acetate/n-heptane or chromatographed on silica gel (toluene/ethyl acetate, 9:1 v/v). Yield: 22.7 g (73 mmol), 73%. Purity: about 97% by $^1$H NMR.

In an analogous manner, it is possible to synthesize the following compounds:

| Ex. | Boronic ester | Product | Yield |
|---|---|---|---|
| S2 | 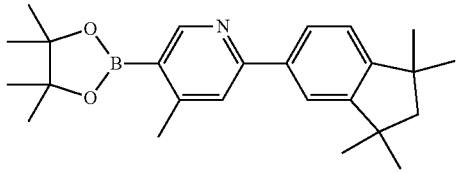 1870010-74-4 | 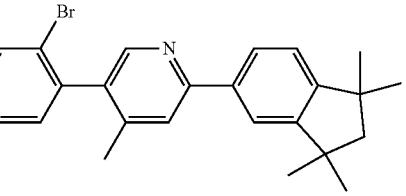 | 51% |
| S3 | 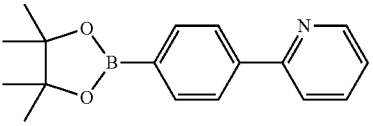 908350-80-1 | 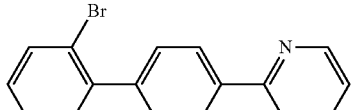 | 72% |
| S4 | 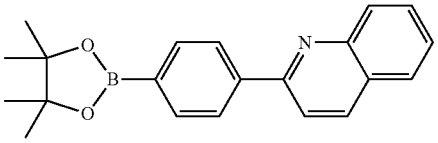 1383803-71-1 | 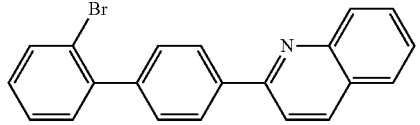 | 68% |

Example S5

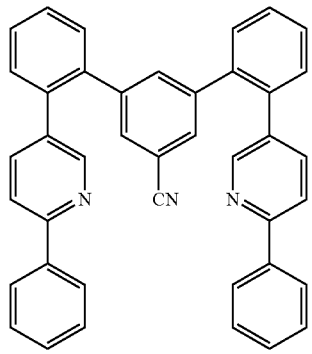

A mixture of 36.4 g (100 mmol) of 2,2'-(5-chloro-1,3-phenylene)bis[4,4,5,5-tetramethyl-1,3,2-dioxaborolane [1417036-49-7], 65.2 g (210 mmol) of S1, 42.4 g (400 mmol) of sodium carbonate, 1.57 g (6 mmol) of triphenylphosphine, 500 mg (2 mmol) of palladium(II) acetate, 500 ml of toluene, 200 ml of ethanol and 500 ml of water is heated under reflux for 48 h. After cooling, the mixture is extended with 500 ml of toluene, and the organic phase is removed, washed once with 500 ml of water and once with 500 ml of saturated sodium chloride solution and dried over magnesium sulphate. After the solvent has been removed, the residue is chromatographed on silica gel (n-heptane/ethyl acetate, 2:1 v/v). Yield: 41.4 g (68 mmol), 68%. Purity: about 95% by $^1$H NMR.

In an analogous manner, it is possible to synthesize the following compounds:

| Ex. | Bromide | Product | Yield |
|---|---|---|---|
| S6 | S2 | | 70% |
| S7 | S3 | | 67% |
| S8 | S4 | | 74% |

145

Example S20

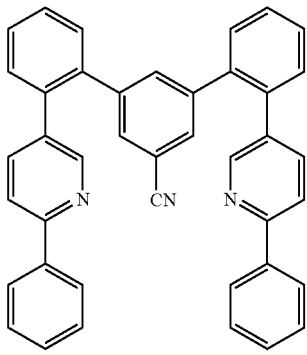

146

A mixture of 28.6 g (50 mmol) of S5, 7.2 g (80 mmol) of copper(I) cyanide [544-92-3], 30 g of glass beads (diameter 3 mm) and 150 ml of NMP is heated to 190° C. with good stirring for 24 h. After cooling, 300 ml of dichloromethane are added, and salts are filtered off with suction through a Celite bed in the form of a dichloromethane slurry. The filtrate is washed five times with 200 ml each time of 5% ammonium solution and once with 200 ml of saturated sodium chloride solution, the dichloromethane is removed under reduced pressure and the residue is extracted by stirring with a hot mixture of 50 ml of ethyl acetate and 100 ml of methanol. Yield: 19.9 g (36 mmol), 71%. Purity: about 95% by $^1$H NMR.

In an analogous manner, it is possible to synthesize the following compounds:

| Ex. | Reactant | Product | Yield |
|---|---|---|---|
| S21 | S6 | | 73% |
| S22 | S7 | | 69% |

| Ex. | Reactant | Product | Yield |
|---|---|---|---|
| S23 | 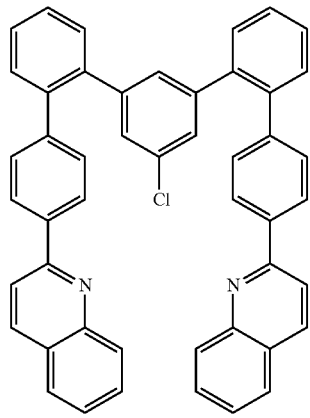 [SMILES: Clc1cc(-c2ccccc2-c2ccc(-c3ccc4ccccc4n3)cc2)cc(-c2ccccc2-c2ccc(-c3ccc4ccccc4n3)cc2)c1] | 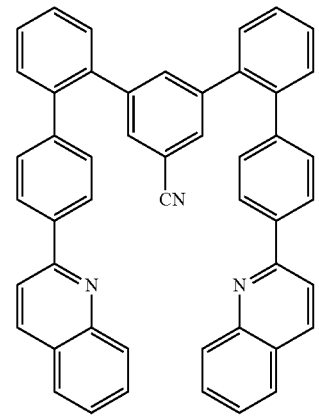 [SMILES: N#Cc1cc(-c2ccccc2-c2ccc(-c3ccc4ccccc4n3)cc2)cc(-c2ccccc2-c2ccc(-c3ccc4ccccc4n3)cc2)c1] | 64% |

Example S40

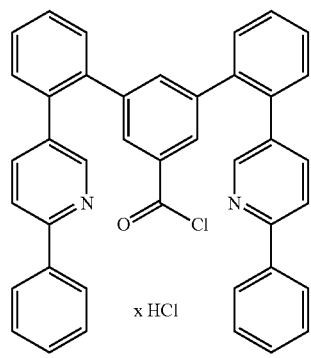 [SMILES: O=C(Cl)c1cc(-c2ccccc2-c2ccc(-c3ccccc3)nc2)cc(-c2ccccc2-c2ccc(-c3ccccc3)nc2)c1]

A mixture of 28.1 g (50 mmol) of S20, 8.0 g (200 mmol) of NaOH, 20 ml of water and 100 ml of ethanol is heated under reflux for 16 h. After cooling, the mixture is adjusted to pH 7 by adding 10% hydrochloric acid, the ethanol is removed under reduced pressure, and the precipitated carboxylic acid is filtered off with suction and washed once with a little cold water. After drying by suction, the carboxylic acid is suspended in 300 ml of toluene, and the toluene is drawn off under reduced pressure. This azeotropic drying operation is repeated twice more. The dried carboxylic acid is suspended in 300 ml of dichloromethane, and then 5.2 ml (60 mmol) of oxalyl chloride are added dropwise. After evolution of gas has ended, the mixture is heated under reflux for another 30 min. The residue obtained after removal of the dichloromethane is converted without further purification. Yield: 20.7 g (33 mmol), 65%. Purity: about 95% by $^1$H NMR.

In an analogous manner, it is possible to synthesize the following compounds:

| Ex. | Reactant | Product | Yield |
|---|---|---|---|
| S41 | 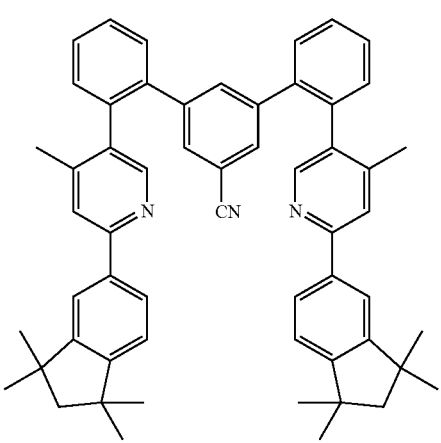 | 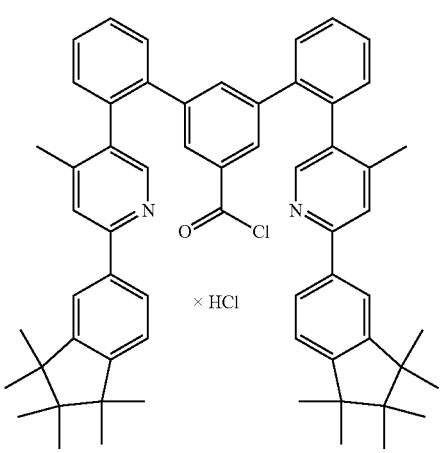 | 68% |

| Ex. | Reactant | Product | Yield |
|---|---|---|---|
| S42 | S22 | ×HCl | 59% |
| S43 | S23 | ×HCl | 61% |

Example S60

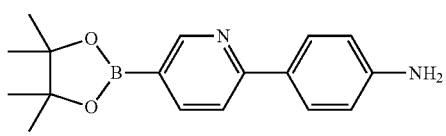 [SMILES: CC1(C)OB(c2ccc(-c3ccc(N)cc3)nc2)OC1(C)C]

A mixture of 24.9 g (100 mmol) of 2-(4-aminophenyl)-5-bromopyridine [1264652-77-8], 26.7 g (105 mmol) of bis(pinacolato)diborane [73183-34-3], 29.5 g (300 mmol) of potassium acetate, anhydrous, 561 mg (2 mmol) of tricyclohexylphosphine, 224 mg (1 mmol) of palladium(II) acetate and 500 ml of dioxane is heated at 90° C. for 16 h. After the solvent has been removed under reduced pressure, the residue is taken up in 500 ml of ethyl acetate and filtered through a Celite bed, the filtrate is concentrated under reduced pressure until commencement of crystallization and about 100 ml of methanol are finally added dropwise in order to complete the crystallization. Yield: 20.1 g (68 mmol), 68%; purity: about 95% by $^1$H NMR.

In an analogous manner, it is possible to synthesize the following compounds:

| Ex. | Reactant | Product | Yield |
|---|---|---|---|
| S61 | 150595-78-1 | | 63% |

| Ex. | Reactant | Product | Yield |
|---|---|---|---|
| S62 | 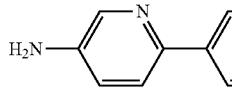 1367930-24-2 | 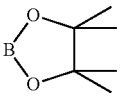 | 58% |

A: Synthesis of the Ligands L:

Example L1

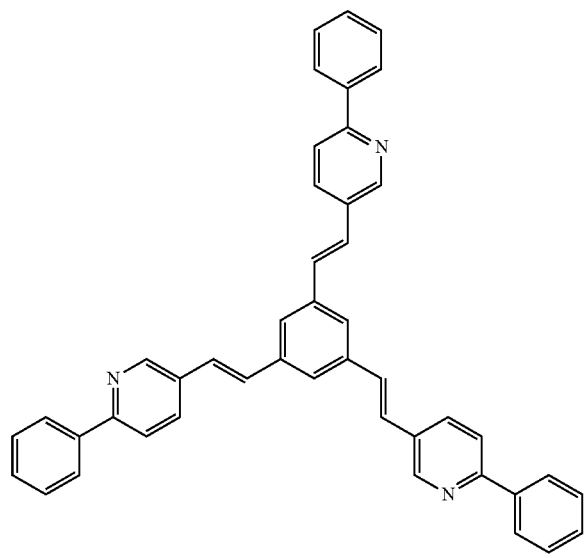 [SMILES: C(=C\c1cc(/C=C/c2ccc(-c3ccccc3)nc2)cc(/C=C/c2ccc(-c3ccccc3)nc2)c1)/c1ccc(-c2ccccc2)nc1]

To a solution of 4.7 g (30 mmol) of 1,3,5-trivinylbenzene [3048-52-0] and 23.4 g (100 mmol) of 5-bromo-2-phenylpyridine [27012-25-5] in 300 ml of THF are successively added 3.1 g (3 mmol) of $Pd_2(dba)_3$*$CHCl_3$ [52552-40-4], 2.6 g (9 mmol) of [(t-Bu)$_3$PH]BF$_4$ [131274-22-1] and 78.1 g (400 mmol) of dicyclohexylmethylamine [7560-83-0], and then the mixture is heated under reflux for 24 h. After cooling, all volatile constituents are removed under reduced pressure, the residue is taken up in 500 ml of dichloromethane and washed three times with 300 ml each time of water and once with 300 ml of sodium chloride solution, the organic phase is dried over magnesium sulphate and filtered through a silica gel bed, and the product is eluted with dichloromethane and then concentrated to dryness under reduced pressure. The crude product thus obtained is recrystallized twice from dichloromethane/methanol. Yield: 11.3 g (6.1 mmol), 61%; purity: about 98% by $^1$H NMR.

The following compounds can be prepared in an analogous manner, it being possible to purify the crude products by Kugelrohr distillation, recrystallization or chromatography. If a mixture of bromides is used, as well as the symmetric ligands, it is also possible by chromatographic separation (CombiFlash Torrent, from Axel Semrau GmbH&Co KG) to obtain ligands having different bidentate sub-ligands (see examples L18 to L27 and L28).

| Ex. | Bromide reactant(s) Olefin* | Product | Yield |
|---|---|---|---|
| L2 | 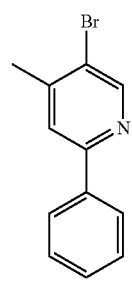 31686-64-3 | 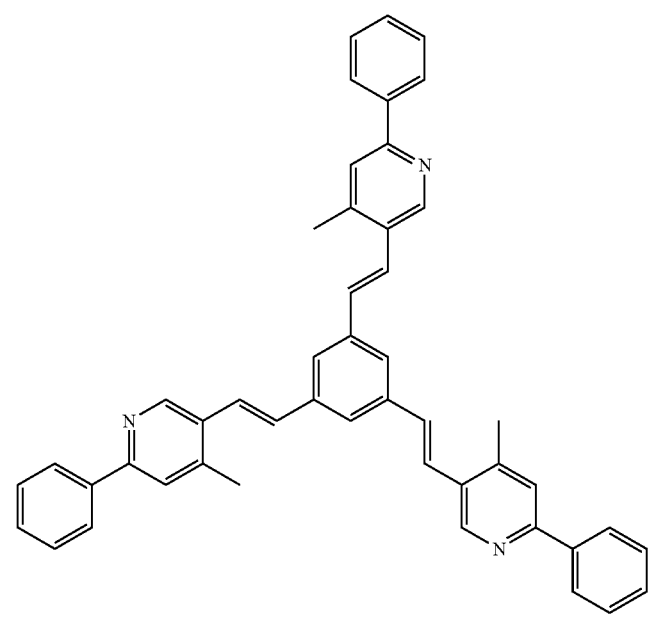 [SMILES: Cc1cc(-c2ccccc2)ncc1/C=C/c1cc(/C=C/c2cnc(-c3ccccc3)cc2C)cc(/C=C/c2cnc(-c3ccccc3)cc2C)c1] | 64% |

-continued

| Ex. | Bromide reactant(s) Olefin* | Product | Yield |
|---|---|---|---|
| L3 | 5-bromo-2-(o-tolyl)pyridine  88345-94-2 | tris-styryl product with 2-(o-tolyl)pyridin-5-yl groups | 56% |
| L4 | 5-bromo-2-(4-tert-butylphenyl)pyridine  1215073-34-9 | tris-styryl product with 2-(4-tert-butylphenyl)pyridin-5-yl groups | 71% |

-continued
| Ex. | Bromide reactant(s) Olefin* | Product | Yield |
|---|---|---|---|
| L5 | 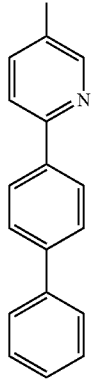 1035556-84-3 | 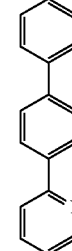 | 74% |
| L6 | 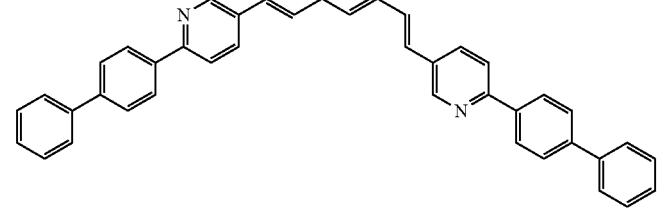 1486482-87-4 | 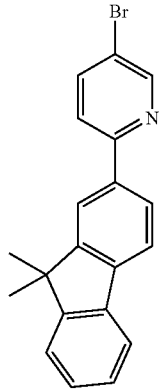 | 68% |

-continued
| Ex. | Bromide reactant(s) Olefin* | Product | Yield |
|---|---|---|---|
| L7 | 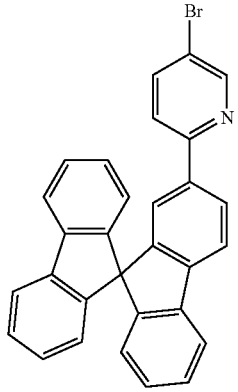 148682-88-5 | 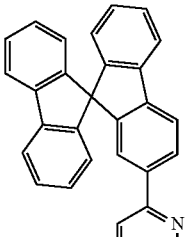 | 70% |
| L8 | 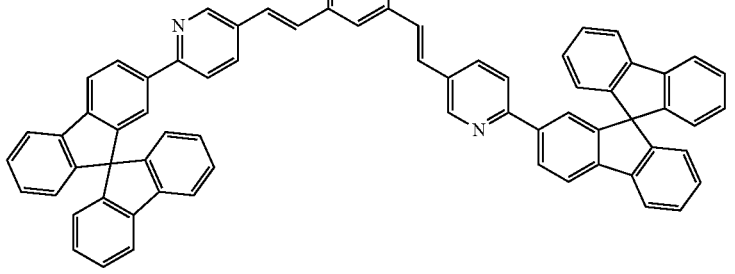 1414352-87-6 | 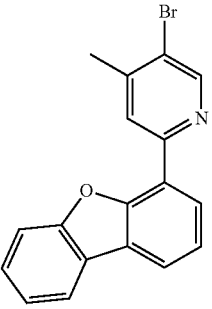 | 59% |

-continued
| Ex. | Bromide reactant(s) Olefin* | Product | Yield |
|---|---|---|---|
| L9 | 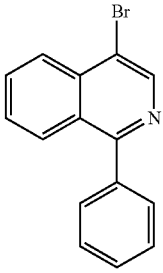<br>22960-25-4 | 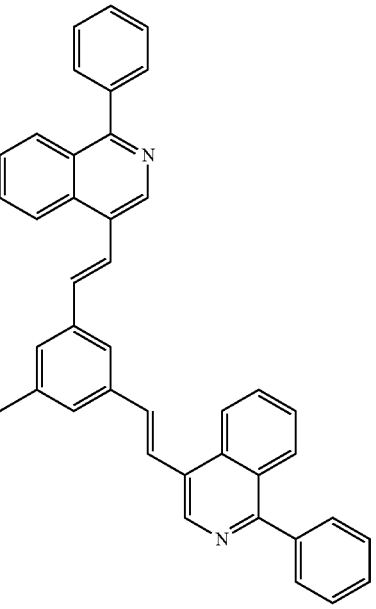 | 65% |
| L10 | 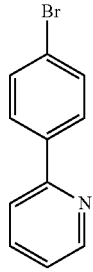<br>63996-36-1 | 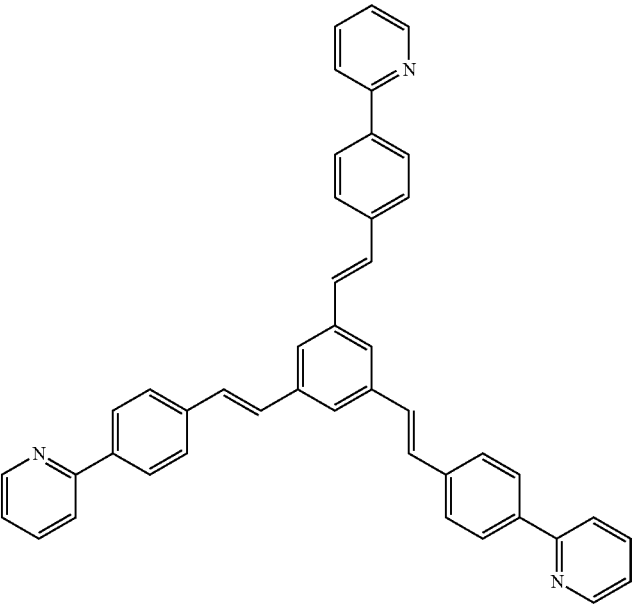 [SMILES: C(=C\c1cc(/C=C/c2ccc(-c3ccccn3)cc2)cc(/C=C/c2ccc(-c3ccccn3)cc2)c1)/c1ccc(-c2ccccn2)cc1] | 71% |

-continued

| Ex. | Bromide reactant(s) Olefin* | Product | Yield |
|---|---|---|---|
| L11 | 1246851-70-6 | | 64% |
| L12 | 504413-43-8 | | 57% |

-continued
| Ex. | Bromide reactant(s) Olefin* | Product | Yield |
|---|---|---|---|
| L13 | 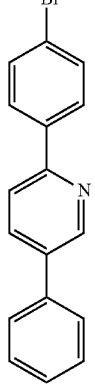 927898-46-2 | 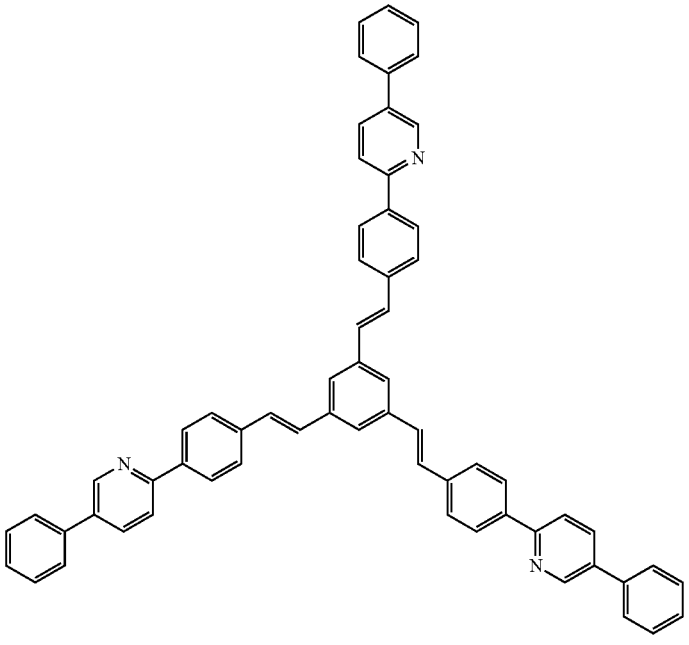 [SMILES: C(=C\c1cc(/C=C/c2ccc(-c3ccc(-c4ccccc4)cn3)cc2)cc(/C=C/c2ccc(-c3ccc(-c4ccccc4)cn3)cc2)c1)/c1ccc(-c2ccc(-c3ccccc3)cn2)cc1] | 69% |
| L14 | 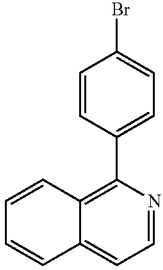 936498-10-1 | 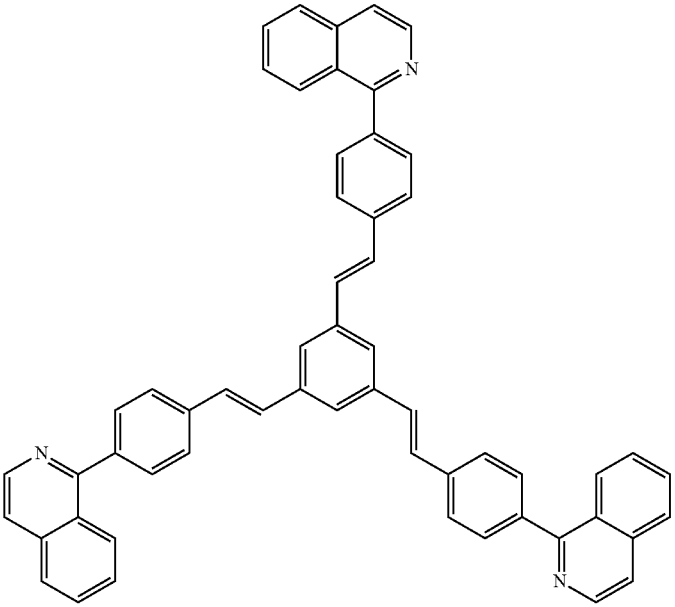 [SMILES: C(=C\c1cc(/C=C/c2ccc(-c3nccc4ccccc34)cc2)cc(/C=C/c2ccc(-c3nccc4ccccc34)cc2)c1)/c1ccc(-c2nccc3ccccc23)cc1] | 64% |

-continued
| Ex. | Bromide reactant(s) Olefin* | Product | Yield |
|---|---|---|---|
| L15 | 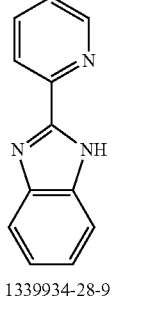<br>1339934-28-9 | 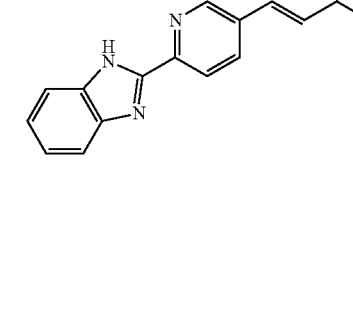 | 71% |
| L16 | 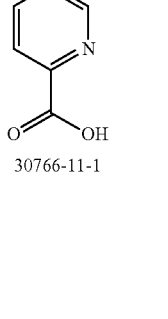<br>30766-11-1 |  | 38% |
| L17 | 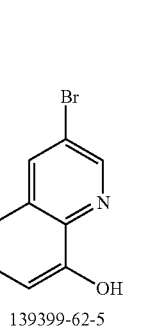<br>139399-62-5 | 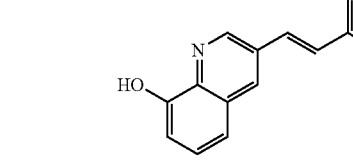 | 44% |

-continued
| Ex. | Bromide reactant(s) Olefin* | Product | Yield |
|---|---|---|---|
| L18 and L19 | 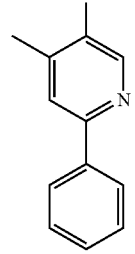 31686-64-3 |  L18 | 14% |
| | 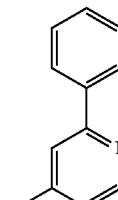 1414352-87-6 | 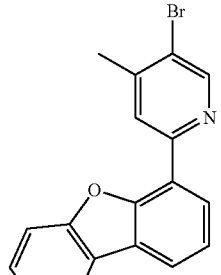 L19 | 16% |

-continued
| Ex. | Bromide reactant(s) Olefin* | Product | Yield |
|---|---|---|---|
| L20 and L21 | 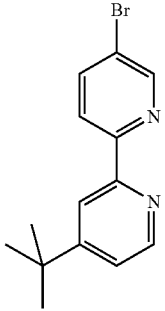<br>1246851-70-6 | 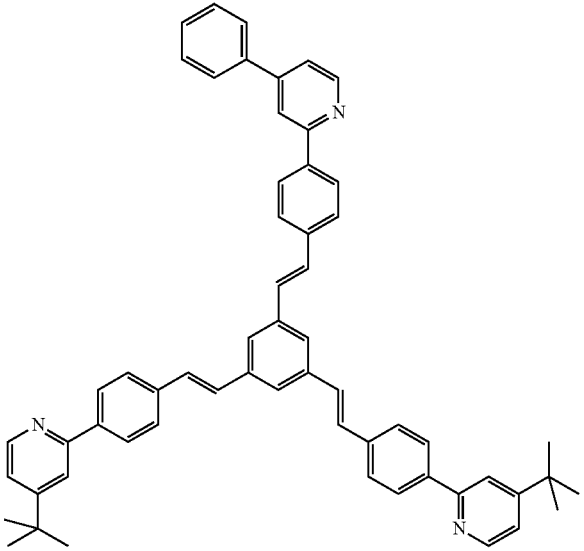<br>L20 | 14% |
| | 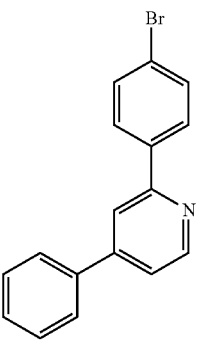<br>504413-43-8 | 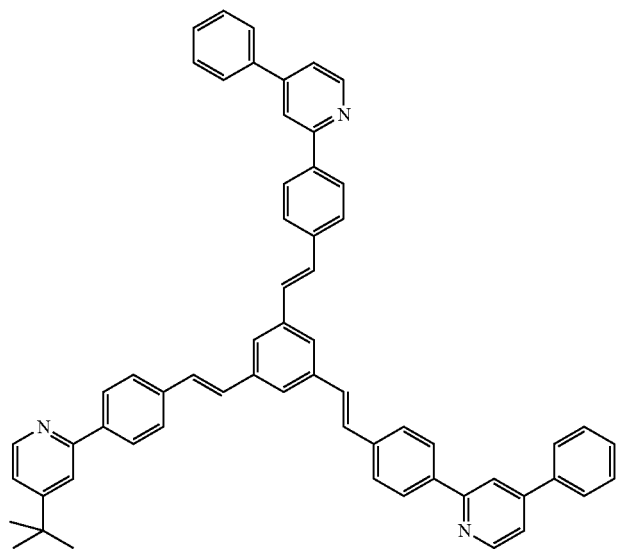<br>L21 | 12% |

-continued
| Ex. | Bromide reactant(s) Olefin* | Product | Yield |
|---|---|---|---|
| L22 and L23 | 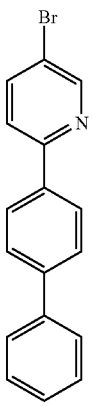<br>1035556-84-3 | 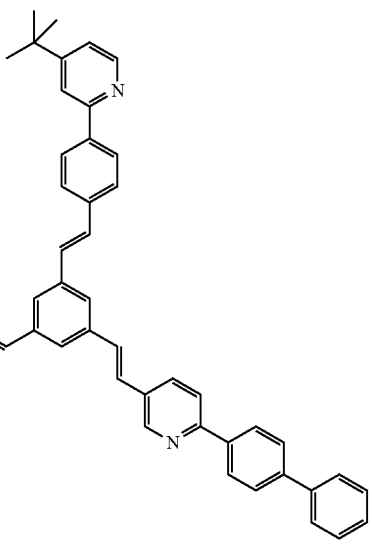<br>L22 | 11% |
| | 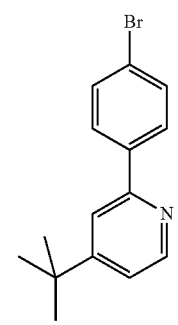<br>1246851-70-6 | 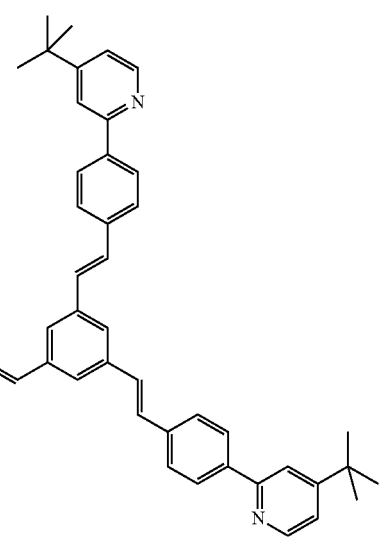<br>L23 | 12% |

-continued

| Ex. | Bromide reactant(s) Olefin* | Product | Yield |
|---|---|---|---|
| L24 and L25 | 1035556-84.3 | L24 | 10% |
|  | 30766-11-1 | L25 | 12% |

-continued
| Ex. | Bromide reactant(s) Olefin* | Product | Yield |
|---|---|---|---|
| L26 and L27 | 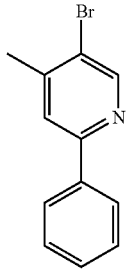<br>31686-64-3 | 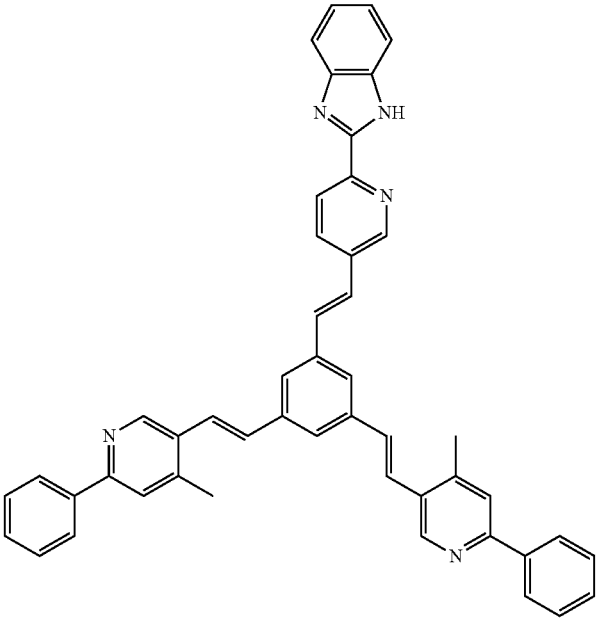<br>L26 | 16% |
| | 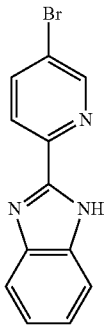<br>1339934-28-9 | 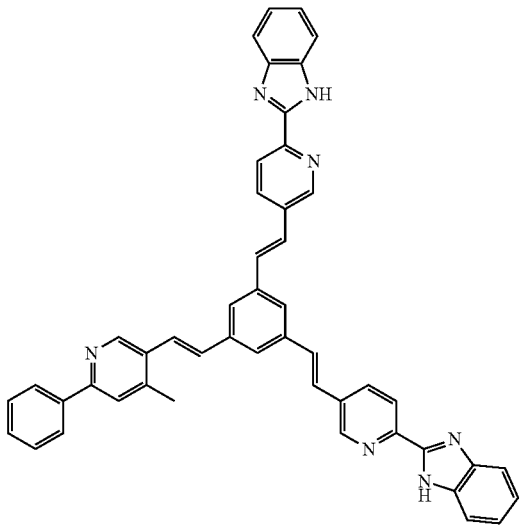<br>L27 | 15% |

-continued
| Ex. | Bromide reactant(s) Olefin* | Product | Yield |
|---|---|---|---|
| L28 | 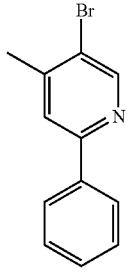 31686-64-3<br><br>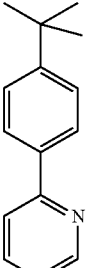 1414352-87-6<br><br>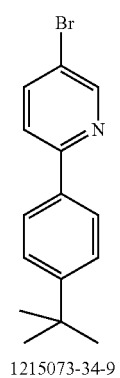 1215073-34-9 | 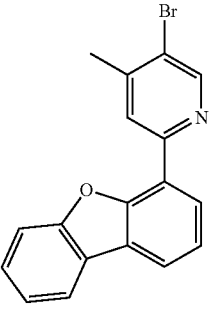 L28 | 16% |

| Ex. | Bromide reactant(s) Olefin* | Product | Yield |
|---|---|---|---|
| L29 | 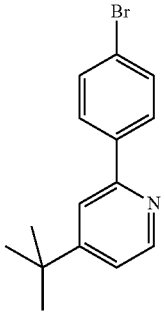 1246851-70-6 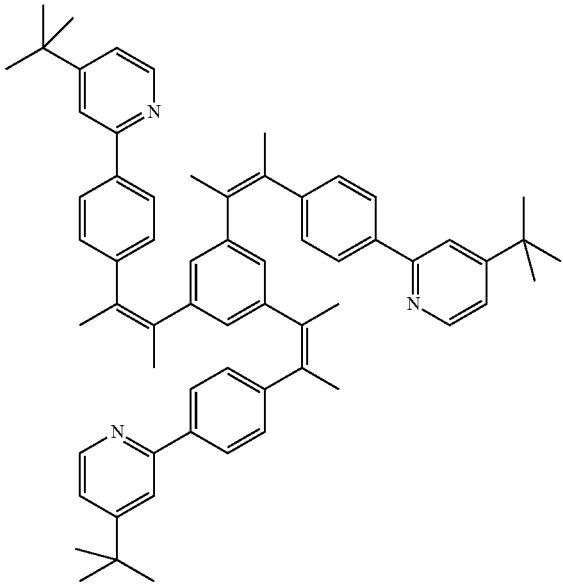 [SMILES: C/C(=C(\C)c1cc(/C(C)=C(/C)c2ccc(-c3cc(C(C)(C)C)ccn3)cc2)cc(/C(C)=C(/C)c2ccc(-c3cc(C(C)(C)C)ccn3)cc2)c1)c1ccc(-c2cc(C(C)(C)C)ccn2)cc1] 52385-35-0 | 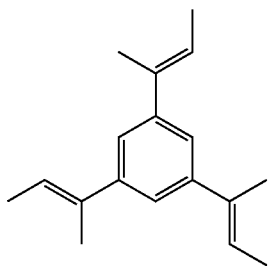 | 19% |
| L30 | 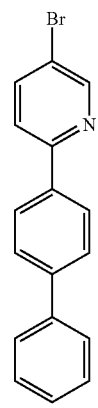 135556-84.3 | 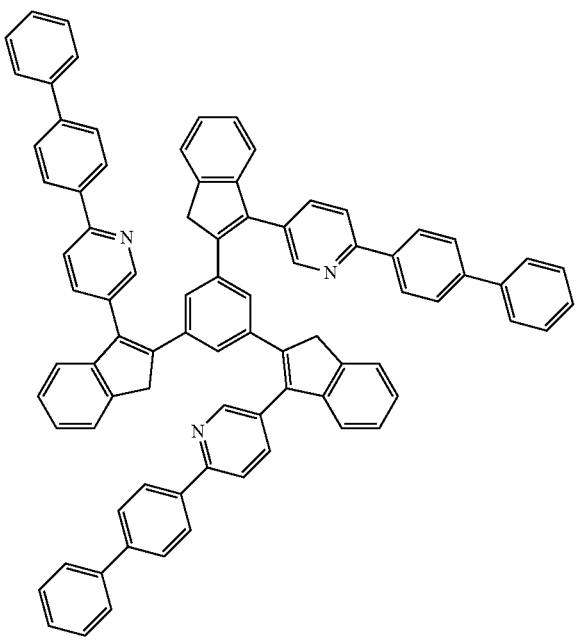 [SMILES: c1ccc(-c2ccc(-c3ccc(C4=C(c5cc(C6=C(c7ccc(-c8ccc(-c9ccccc9)cc8)nc7)c7ccccc7C6)cc(C6=C(c7ccc(-c8ccc(-c9ccccc9)cc8)nc7)c7ccccc7C6)c5)Cc5ccccc54)cn3)cc2)cc1] | 21% |

-continued
| Ex. | Bromide reactant(s) Olefin* | Product | Yield |
|---|---|---|---|
| | 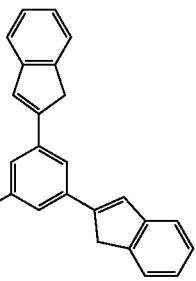 1421374-63-1 | | |
| L31 | 504413-43-8 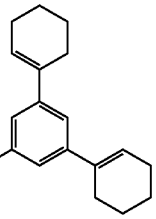 52467-23-9 | 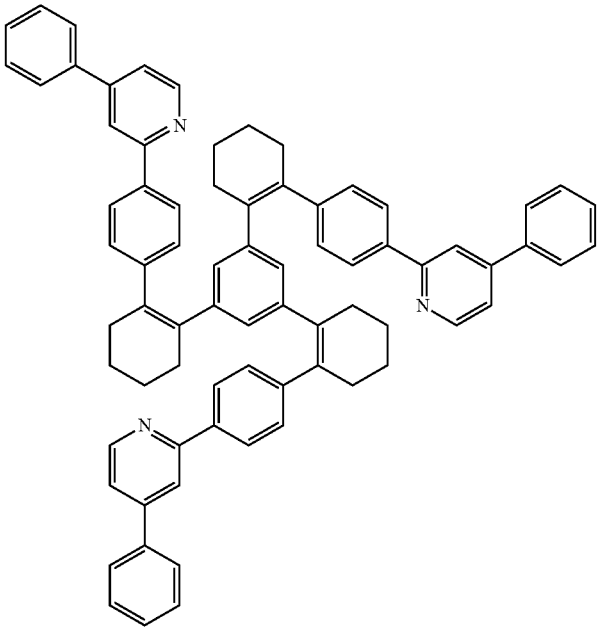 [SMILES: c1ccc(-c2ccnc(-c3ccc(C4=C(c5cc(C6=C(c7ccc(-c8cc(-c9ccccc9)ccn8)cc7)CCCC6)cc(C6=C(c7ccc(-c8cc(-c9ccccc9)ccn8)cc7)CCCC6)c5)CCCC4)cc3)c2)cc1] | 24% |
| L50 | S5 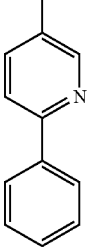 1132943-42-0 | 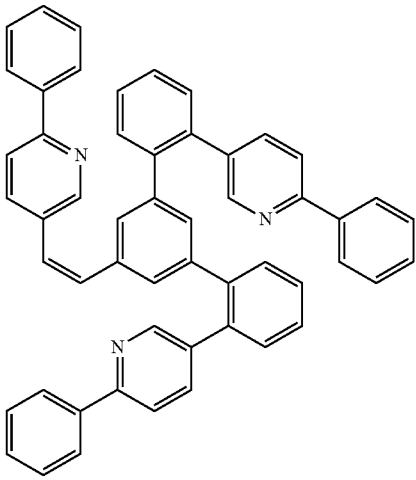 [SMILES: C(=C/c1cc(-c2ccccc2-c2ccc(-c3ccccc3)nc2)cc(-c2ccccc2-c2ccc(-c3ccccc3)nc2)c1)/c1ccc(-c2ccccc2)nc1] | 44% |

-continued
| Ex. | Bromide reactant(s) Olefin* | Product | Yield |
|---|---|---|---|
| L51 | S6 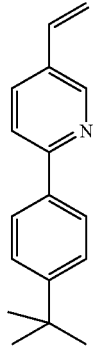 1094356-87-2 | 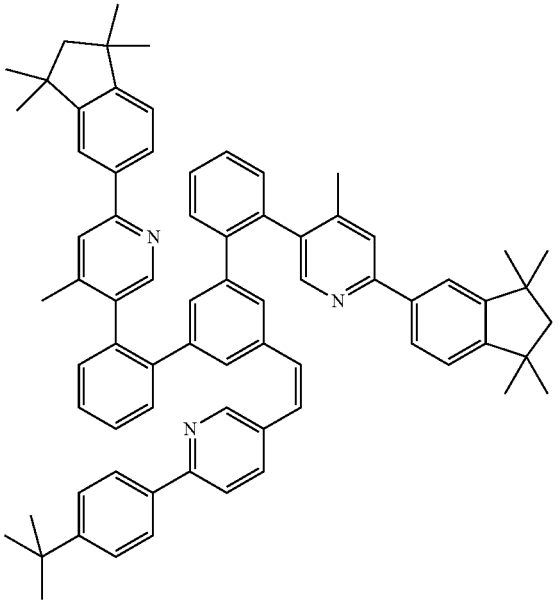 [SMILES: Cc1cc(-c2ccc3c(c2)C(C)(C)CC3(C)C)ncc1-c1ccccc1-c1cc(/C=C\c2ccc(-c3ccc(C(C)(C)C)cc3)nc2)cc(-c2ccccc2-c2cnc(-c3ccc4c(c3)C(C)(C)CC4(C)C)cc2C)c1] | 46% |
| L52 | S7 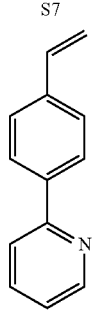 69135-05-3 | 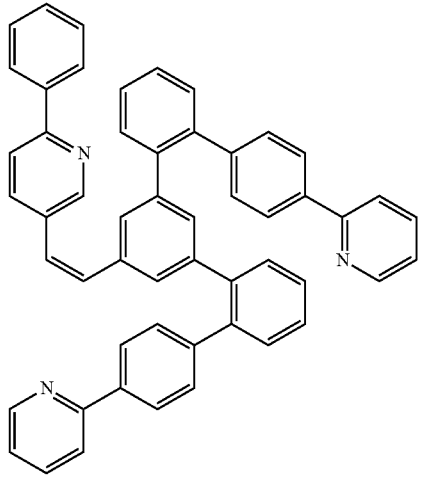 [SMILES: C(=C/c1cc(-c2ccccc2-c2ccc(-c3ccccn3)cc2)cc(-c2ccccc2-c2ccc(-c3ccccn3)cc2)c1)/c1ccc(-c2ccccc2)nc1] | 39% |

| Ex. | Bromide reactant(s) Olefin* | Product | Yield |
|---|---|---|---|
| L53 | S8<br>1011301-24-8 | 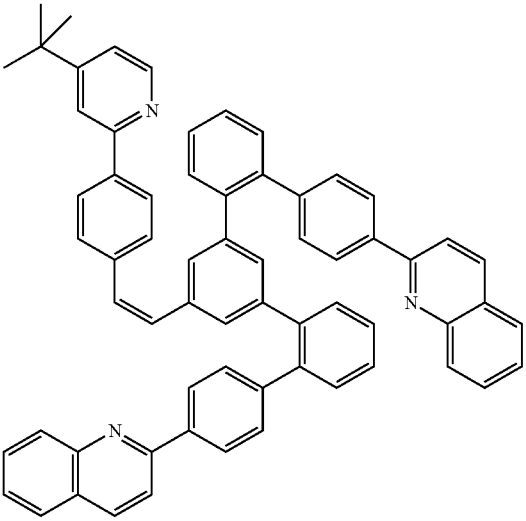 [SMILES: CC(C)(C)c1ccnc(-c2ccc(/C=C\c3cc(-c4ccccc4-c4ccc(-c5ccc6ccccc6n5)cc4)cc(-c4ccccc4-c4ccc(-c5ccc6ccccc6n5)cc4)c3)cc2)c1] | 37 |

*if different from 1,3,5-trivinylbenzene

Example L100

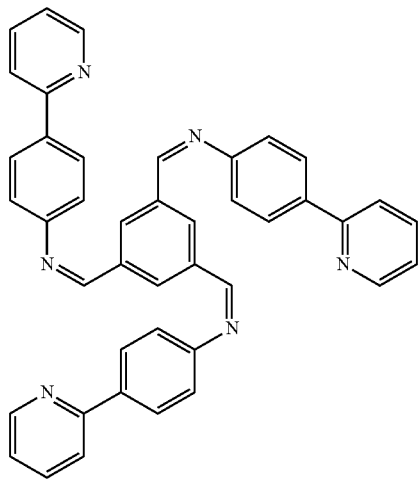 [SMILES: C(=N/c1ccc(-c2ccccn2)cc1)/c1cc(/C=N\c2ccc(-c3ccccn3)cc2)cc(/C=N\c2ccc(-c3ccccn3)cc2)c1]

Example L101

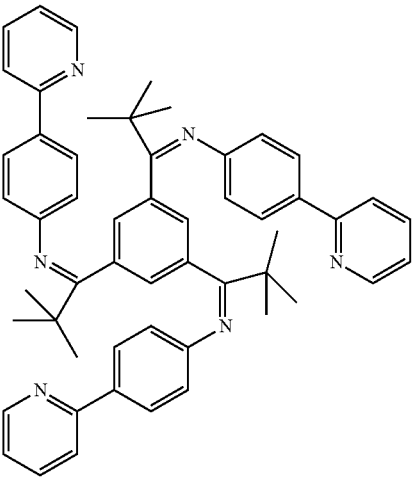 [SMILES: CC(C)(C)/C(=N/c1ccc(-c2ccccn2)cc1)c1cc(/C(=N\c2ccc(-c3ccccn3)cc2)C(C)(C)C)cc(/C(=N\c2ccc(-c3ccccn3)cc2)C(C)(C)C)c1]

Variant A, for Aldehydes:

Procedure analogous to J. G. Muntaner et al., Org. & Biomol. Chem., 2014, 12, 286. To a solution of 24.3 g (100 mmol) of 4-(2-pyridyl)anilinium dihydrochloride [856849-12-2] in 200 ml of ethanol are added 97 ml of a 2 N sodium ethoxide solution in ethanol. Then 4.9 g (30 mmol) of 1,3,5-benzenetricarboxaldehyde [3163-76-6] are added and the mixture is heated under reflux for 6 h. Subsequently, the ethanol is distilled off almost to dryness, the oily residue is taken up in 300 ml of DCM, insoluble fractions are filtered off using a Celite bed in the form of a DCM slurry, the DCM is removed under reduced pressure and the crude product is recrystallized from acetonitrile/cyclohexane. Yield: 15.5 g (25 mmol), 83%. Purity: about 97% by $^1$H NMR.

Variant B, for Ketones:

Procedure analogous to P. Sulmon et al., Synthesis 1985, 192.

To a suspension of 24.3 g (100 mmol) of 4-(2-pyridyl)anilinium dihydrochloride in 200 ml of diethyl ether are added three drops of methanol and then, in portions, 8.0 g (200 mmol) of sodium hydride, 60% by weight dispersion in mineral oil (caution: evolution of hydrogen!). After 3 h at room temperature, the evolution of hydrogen has ended. 10.1 g (30 mmol) of 1,3,5-tripivaloylbenzene [23471-32-1] are added and the reaction mixture is cooled down to 0° C. in an ice/salt bath. Then 95 ml of 1 N titanium tetrachloride solution in DCM are added dropwise, and the mixture is stirred for a further 2 h, allowed to warm up to room temperature and then heated under reflux for 18 h. After cooling, the precipitated solid is filtered off with suction and washed three times with 100 ml of DCM, the filtrate is concentrated to dryness, and the oily residue is taken up in 300 ml of DCM, washed three times with 100 ml each time of 2 N aqueous KOH solution and then dried over magnesium sulphate. The DCM is removed under reduced pressure and the residue is chromatographed with cyclohexane:ethyl acetate:triethylamine (90:9:1, v/v) on silica gel (deactivated with triethylamine). Yield: 4.9 g (6 mmol), 21%. Purity: about 97% by $^1$H NMR.

Example L102

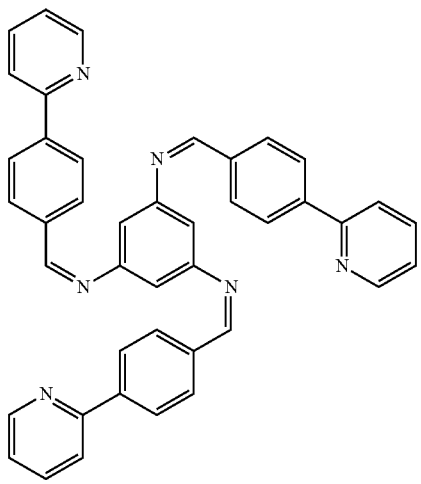 [SMILES: C(=N/c1cc(/N=C\c2ccc(-c3ccccn3)cc2)cc(/N=C\c2ccc(-c3ccccn3)cc2)c1)/c1ccc(-c2ccccn2)cc1]

A mixture of 3.7 g (30 mmol) of 1,3,5-triaminobenzene [108-72-5], 18.3 g (100 mmol) of 4-(2-pyridinyl)benzaldehyde [127406-56-8], 951 mg (5 mmol) of 4-toluenesulphonic acid monohydrate [6192-52-5] and 300 ml of mesitylene is heated under reflux until the separation of water has ended. After cooling, the mesitylene is removed under reduced pressure and the residue is chromatographed with cyclohexane:ethyl acetate:triethylamine (90:9:1, v/v) on silica gel (deactivated with triethylamine). Yield: 14.3 g (23 mmol), 77%. Purity: about 97% by $^1$H NMR.

Example L200

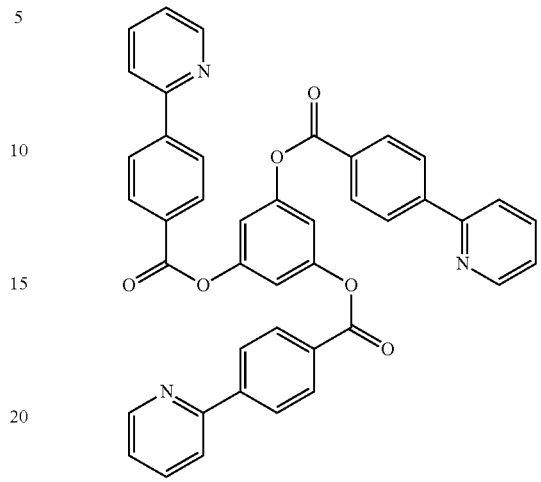

To a well-stirred solution of 3.8 g (30 mmol) of benzene-1,3,5-triol [108-73-6] in 100 ml of dichloromethane are added 28 ml of triethylamine and then, in a dropwise manner a solution of 21.8 g (100 mmol) of 4-(2-pyridinyl)benzoyl chloride [190850-37-4] in 100 ml of dichloromethane, and then the mixture is stirred under reflux for 12 h. After cooling, the volatile constituents are removed under reduced pressure and the residue is extracted by stirring with 300 ml of hot methanol, and the product is filtered off with suction, washed three times with 50 ml each time of methanol and finally recrystallized from ethyl acetate/methanol. Yield: 14.7 g (22 mmol), 73%. Purity: about 97% by $^1$H NMR.

The following compounds can be prepared in an analogous manner, it being possible to purify the crude products by Kugelrohr distillation, recrystallization or chromatography. If a mixture of alcohols, amines or acid chlorides is used, as well as the symmetric ligands, it is also possible by chromatographic separation (CombiFlash Torrent, from Axel Semrau GmbH&Co KG) to obtain ligands having different bidentate sub-ligands.

| Ex. | Reactant | Product | Yield |
|---|---|---|---|
| L201 | 108-73-6<br>257876-10-3 | | 68% |

-continued

| Ex. | Reactant | Product | Yield |
|---|---|---|---|
| L202 | 1,3,5-triaminobenzene (108-72-5); 4-(pyridin-2-yl)benzoyl chloride (190850-37-4) | N,N',N''-(benzene-1,3,5-triyl)tris(4-(pyridin-2-yl)benzamide) | 75% |
| L203 | 108-72-5; 6-phenylnicotinoyl chloride (257876-10-3) | N,N',N''-(benzene-1,3,5-triyl)tris(6-phenylnicotinamide) | 71% |
| L204 | benzene-1,3,5-tricarbonyl trichloride (442-95-1); 4-(pyridin-2-yl)phenol (51035-40-6) | tris(4-(pyridin-2-yl)phenyl) benzene-1,3,5-tricarboxylate | 64% |

| Ex. | Reactant | Product | Yield |
|---|---|---|---|
| L205 | 442-95-1<br>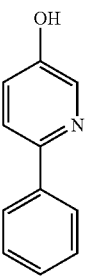<br>66131-77-9 | 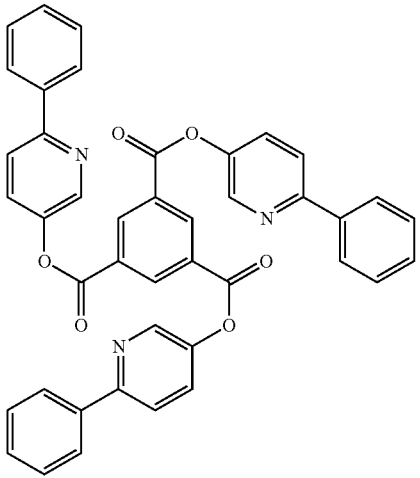 [SMILES: O=C(Oc1ccc(-c2ccccc2)nc1)c1cc(C(=O)Oc2ccc(-c3ccccc3)nc2)cc(C(=O)Oc2ccc(-c3ccccc3)nc2)c1] | 68% |
| L206 | 442-95-1<br>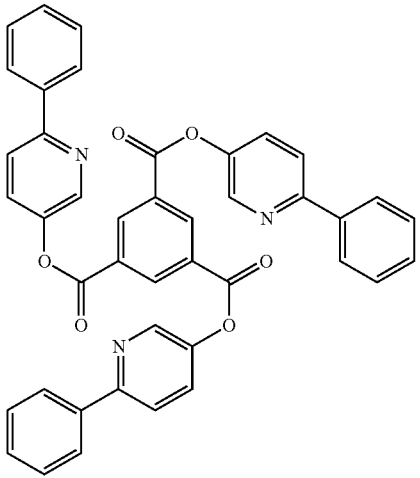 [SMILES: O=C(Oc1ccc(-c2ccccc2)nc1)c1cc(C(=O)Oc2ccc(-c3ccccc3)nc2)cc(C(=O)Oc2ccc(-c3ccccc3)nc2)c1]<br>18471-73-3 | 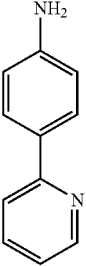 | 71% |
| L207 | 442-95-1<br>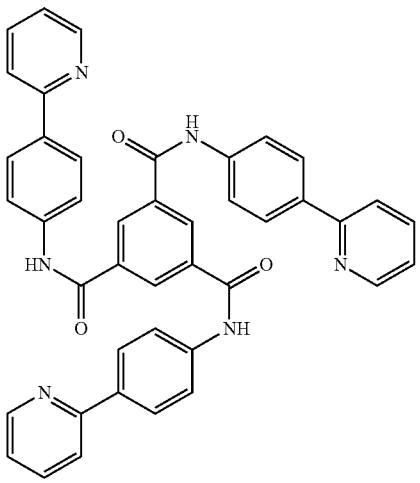 [SMILES: O=C(Nc1ccc(-c2ccccn2)cc1)c1cc(C(=O)Nc2ccc(-c3ccccn3)cc2)cc(C(=O)Nc2ccc(-c3ccccn3)cc2)c1]<br>126370-67-0 | 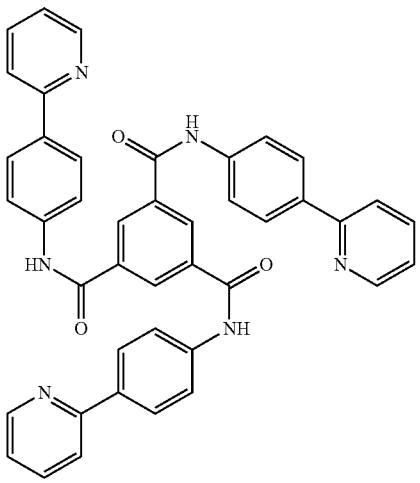 [SMILES: O=C(Nc1ccc(-c2ccccn2)cc1)c1cc(C(=O)Nc2ccc(-c3ccccn3)cc2)cc(C(=O)Nc2ccc(-c3ccccn3)cc2)c1] | 75% |

| Ex. | Reactant | Product | Yield |
|---|---|---|---|
| L208 | 108-73-6<br>90828-20-2 | | 66% |
| L209 | 108-72-5<br>37041-29-5 | | 69% |
| L210 | 108-73-6<br>854167-98-9 | | 71% |

| Ex. | Reactant | Product | Yield |
|---|---|---|---|
| L211 | 108-72-5<br>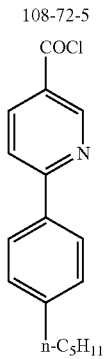<br>111647-50-8 | 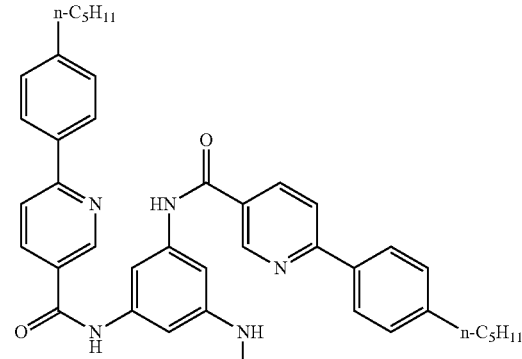 | 58% |
| L212 | 442-95-1<br>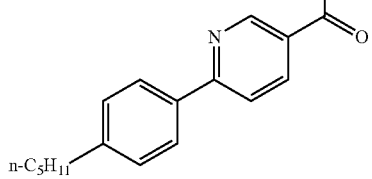<br>53164-95-7 |  | 61% |
| L213 | 442-95-1<br>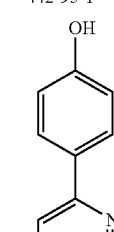<br>371201-06-8 | 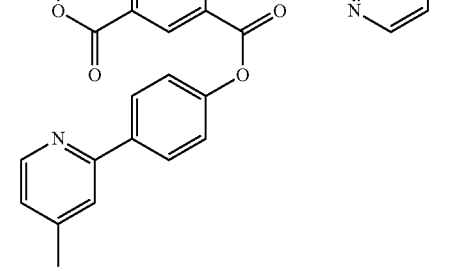 | 60% |

-continued

| Ex. | Reactant | Product | Yield |
|---|---|---|---|
| L214 | 442-95-1<br>149353-76-4 | | 66% |
| L215 | 442-95-1<br>1032825-10-7 | | 68% |
| L216 | 442-95-1<br>30696-03-8 | | 67% |

| Ex. | Reactant | Product | Yield |
|---|---|---|---|
| L217 | 442-95-1<br>884500-88-3 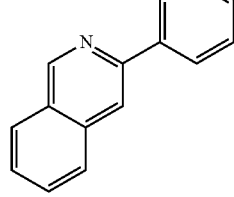 | 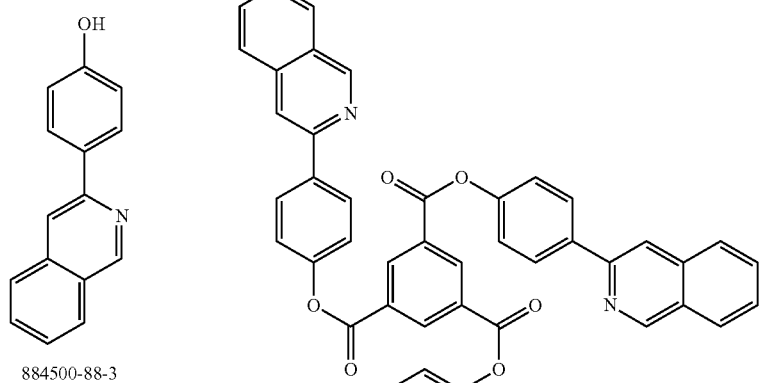 | 73% |
| L218 | 442-95-1<br>855839-55-3 | 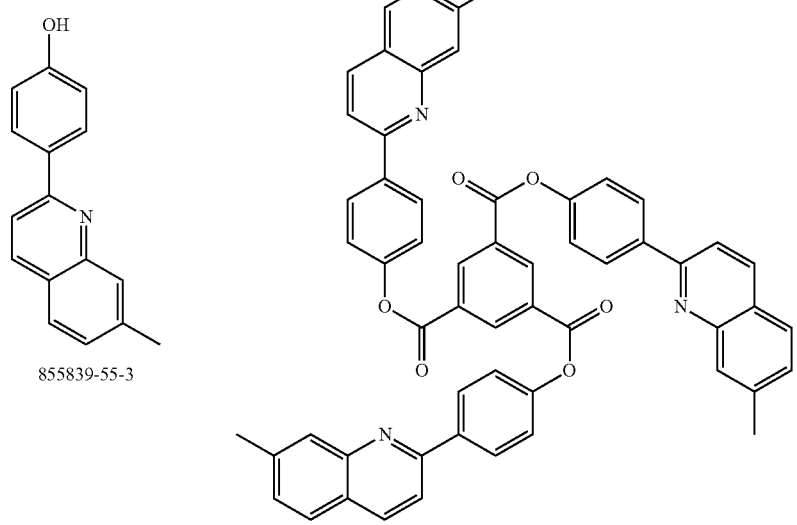 | 69% |

| Ex. | Reactant | Product | Yield |
|---|---|---|---|
| L219 | 442-95-1<br><br>775344-00-8 | | 70% |
| L220 | 442-95-1<br><br>54231-47-9 | | 67% |
| L221 | 442-95-1<br><br>139218-75-0 | | 55% |

| Ex. | Reactant | Product | Yield |
|---|---|---|---|
| L222 | 442-95-1<br>1087269-19-9 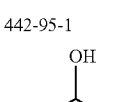 | 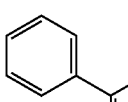 | 58% |
| L223 | 442-95-1<br>57442-05-4 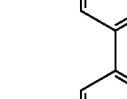 | | 72% |

| Ex. | Reactant | Product | Yield |
|---|---|---|---|
| L224 | 442-95-1<br>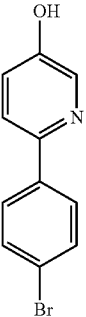<br>150595-78-1 | 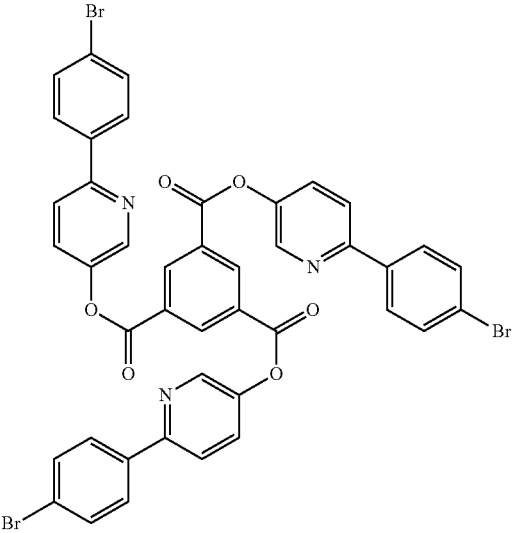 [SMILES: O=C(Oc1ccc(-c2ccc(Br)cc2)nc1)c1cc(C(=O)Oc2ccc(-c3ccc(Br)cc3)nc2)cc(C(=O)Oc2ccc(-c3ccc(Br)cc3)nc2)c1] | 69% |
| L225 | 442-95-1<br>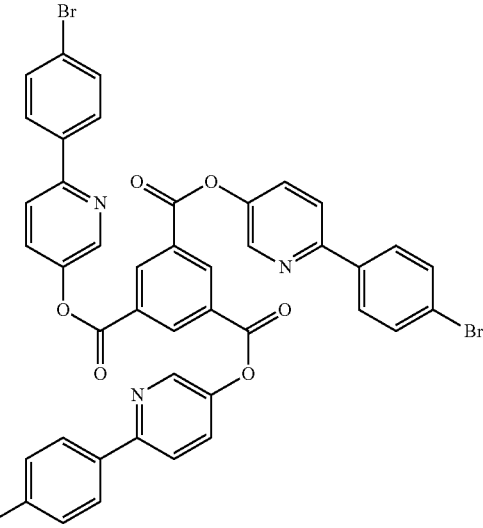<br>1261970-83-5 | 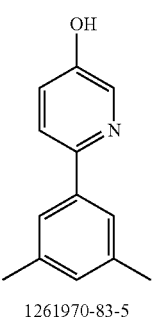 | 64% |
| L226 | 442-95-1<br>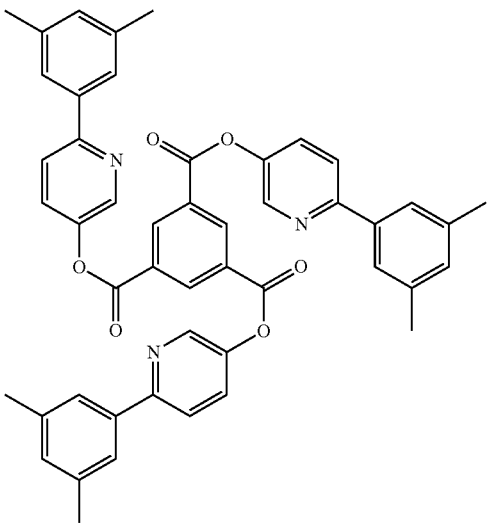<br>942134-44-3 | 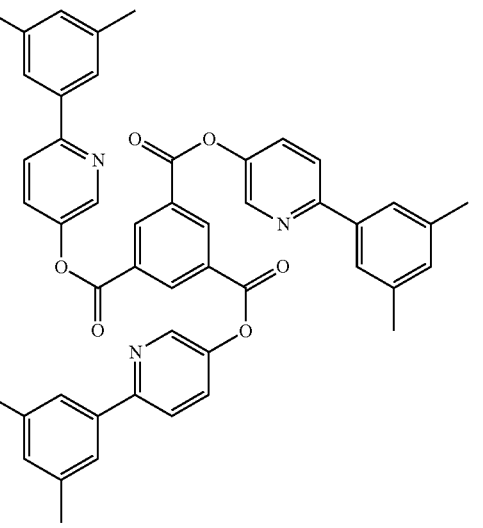 | 61% |

| Ex. | Reactant | Product | Yield |
|---|---|---|---|
| L227 | 442-95-1<br><br>906101-30-2 | 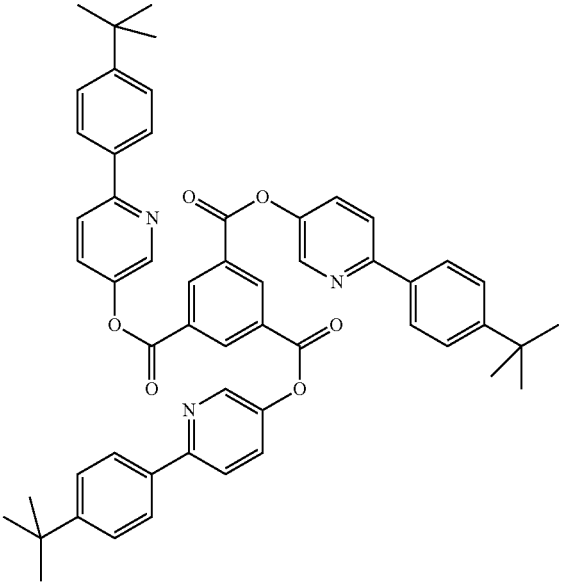 [SMILES: CC(C)(C)c1ccc(-c2ccc(OC(=O)c3cc(C(=O)Oc4ccc(-c5ccc(C(C)(C)C)cc5)nc4)cc(C(=O)Oc4ccc(-c5ccc(C(C)(C)C)cc5)nc4)c3)cn2)cc1] | 70% |
| L228 | 442-95-1<br><br>1551357-67-5 | 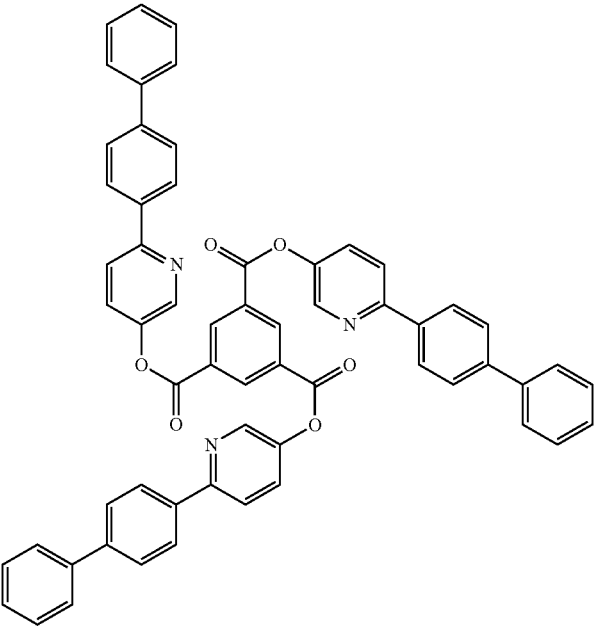 [SMILES: O=C(Oc1ccc(-c2ccc(-c3ccccc3)cc2)nc1)c1cc(C(=O)Oc2ccc(-c3ccc(-c4ccccc4)cc3)nc2)cc(C(=O)Oc2ccc(-c3ccc(-c4ccccc4)cc3)nc2)c1] | 75% |

| Ex. | Reactant | Product | Yield |
|---|---|---|---|
| L229 | 442-95-1<br>1876770-00-1 | | 57% |
| L230 | 442-95-1<br>1903525-21-2 | | 70% |
| L231 | 442-95-1<br>1698352-04-3 | | 66% |

-continued
| Ex. | Reactant | Product | Yield |
|---|---|---|---|
| L232 | 442-95-1 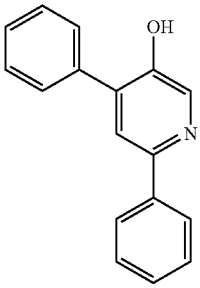 76570-31-5 | 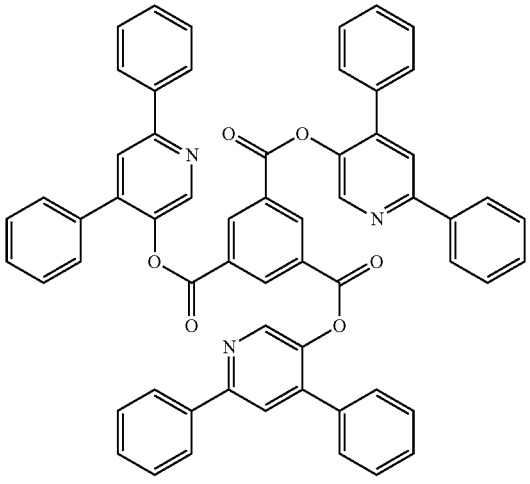 [SMILES: O=C(Oc1cnc(-c2ccccc2)cc1-c1ccccc1)c1cc(C(=O)Oc2cnc(-c3ccccc3)cc2-c2ccccc2)cc(C(=O)Oc2cnc(-c3ccccc3)cc2-c2ccccc2)c1] | 71% |
| L233 | 442-95-1 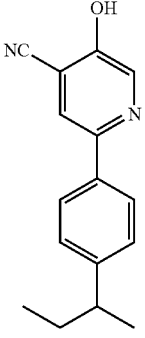 1894503-17-3 | 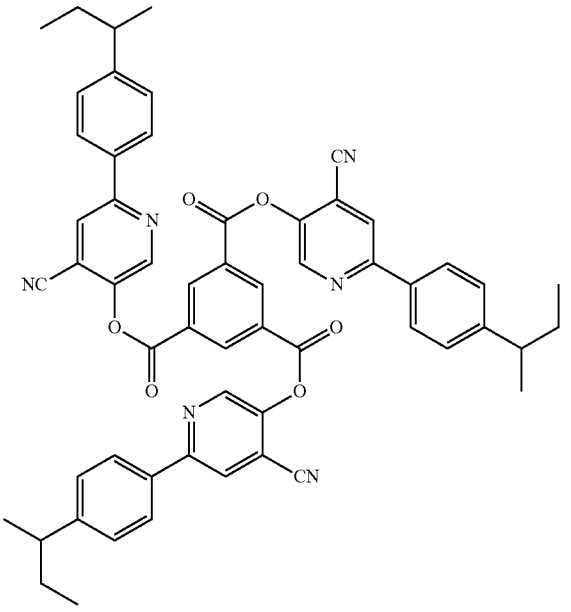 [SMILES: CCC(C)c1ccc(-c2cc(C#N)c(OC(=O)c3cc(C(=O)Oc4cnc(-c5ccc(C(C)CC)cc5)cc4C#N)cc(C(=O)Oc4cnc(-c5ccc(C(C)CC)cc5)cc4C#N)c3)cn2)cc1] | 64% |
| L234 | 442-95-1 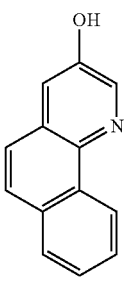 91804-13-6 | 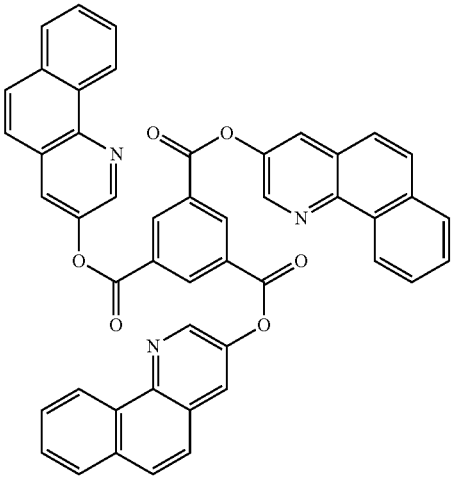 [SMILES: O=C(Oc1cnc2c(ccc3ccccc32)c1)c1cc(C(=O)Oc2cnc3c(ccc4ccccc43)c2)cc(C(=O)Oc2cnc3c(ccc4ccccc43)c2)c1] | 68% |

| Ex. | Reactant | Product | Yield |
|---|---|---|---|
| L235 | 442-95-1<br>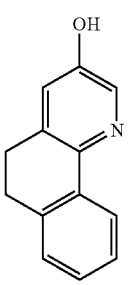<br>84731-41-9 | 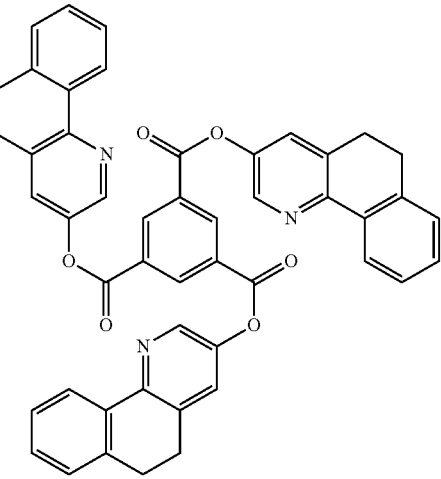 | 63% |
| L236 | 442-95-1<br>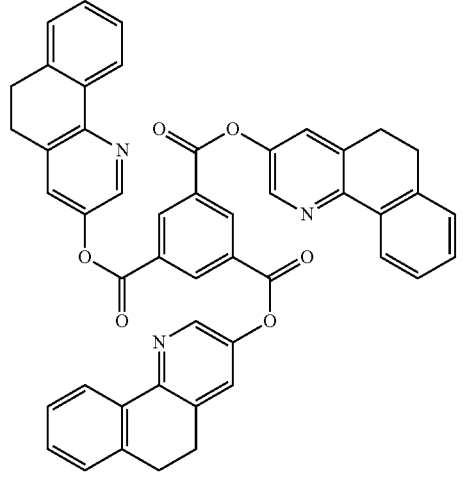 [SMILES: O=C(Oc1cnc2c(c1)CCc1ccccc1-2)c1cc(C(=O)Oc2cnc3c(c2)CCc2ccccc2-3)cc(C(=O)Oc2cnc3c(c2)CCc2ccccc2-3)c1]<br>1702400-65-4 | 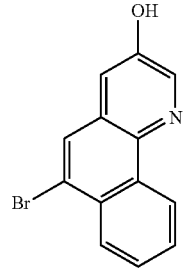 | 72% |
| L237 | 442-95-1<br>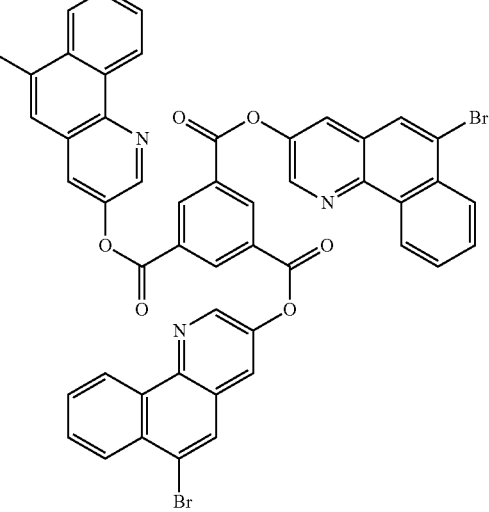<br>66404-96-4 | 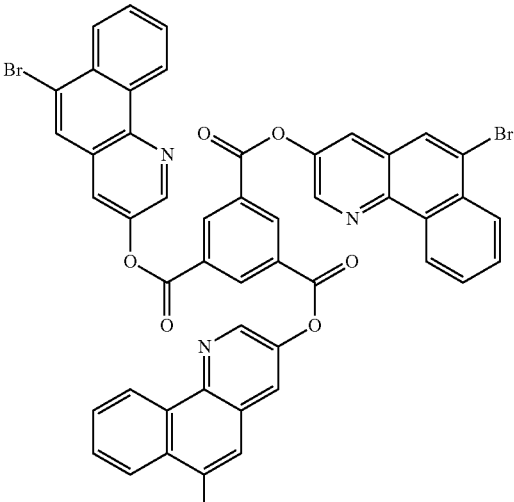 | 69% |

| Ex. | Reactant | Product | Yield |
|---|---|---|---|
| L238 | 442-95-1 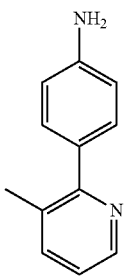 885955-74-8 | 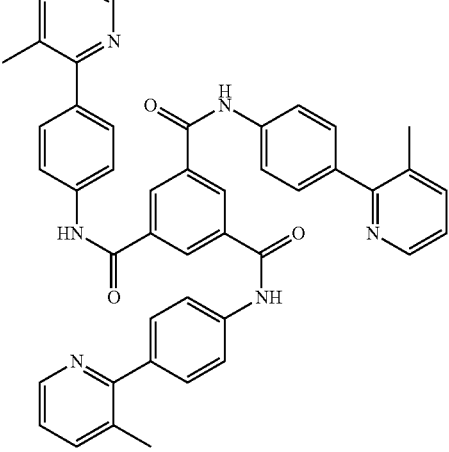 | 70% |
| L239 | 442-95-1 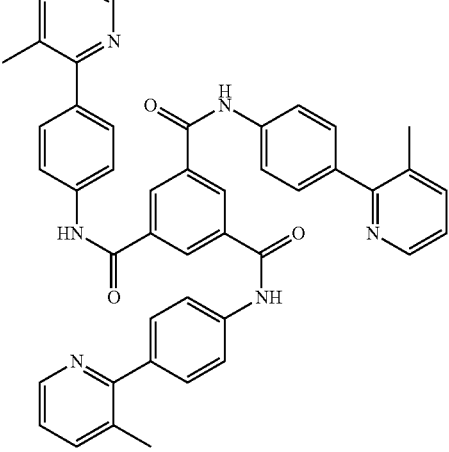 58992-84-0 | 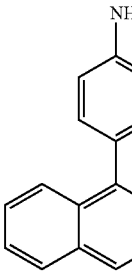 | 76% |
| L240 | 442-95-1 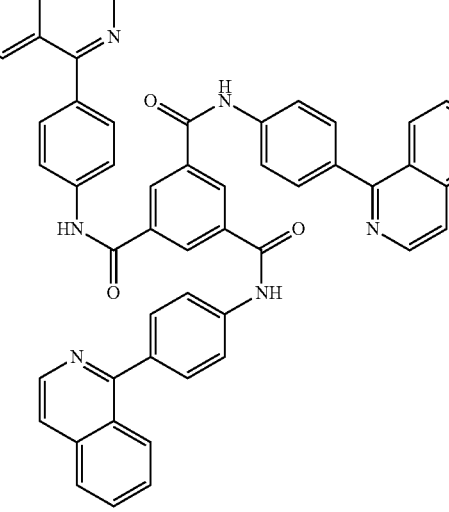 1224953-47-2 | 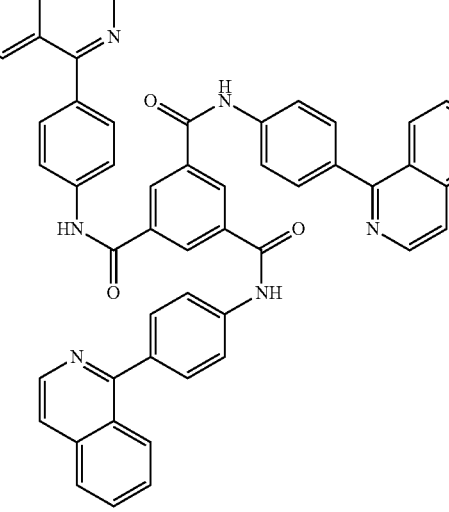 | 75% |

| Ex. | Reactant | Product | Yield |
|---|---|---|---|
| L241 | 442-95-1<br>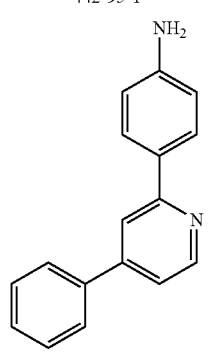<br>1351665-31-0 | 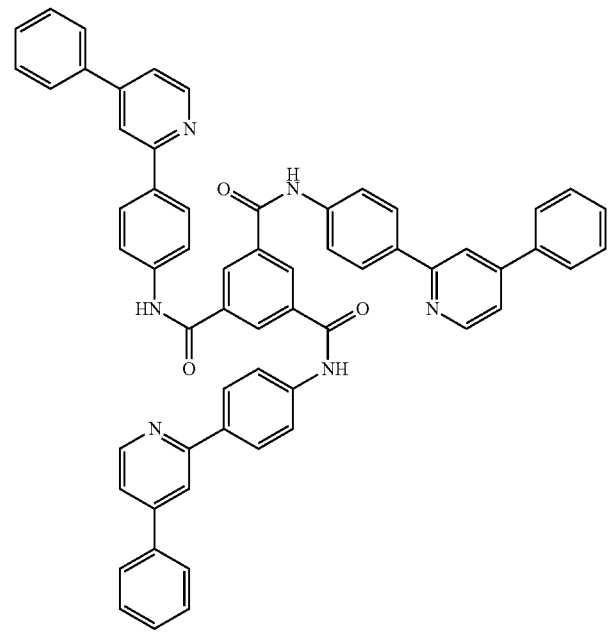 [SMILES: O=C(Nc1ccc(-c2cc(-c3ccccc3)ccn2)cc1)c1cc(C(=O)Nc2ccc(-c3cc(-c4ccccc4)ccn3)cc2)cc(C(=O)Nc2ccc(-c3cc(-c4ccccc4)ccn3)cc2)c1] | 69% |
| L242 | 442-95-1<br>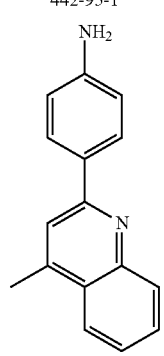<br>580-38-1 | 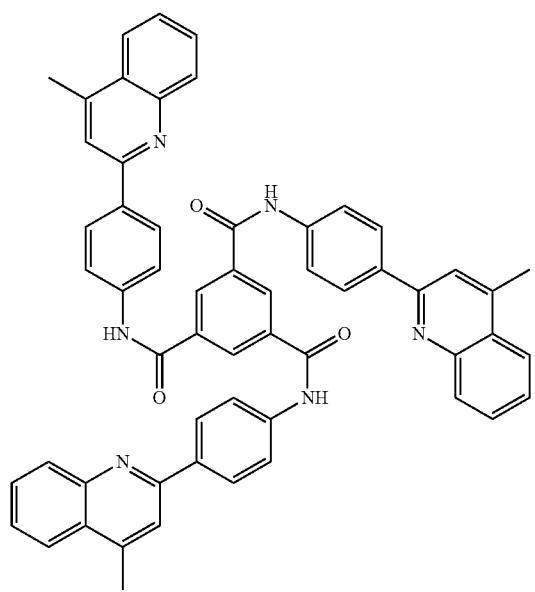 [SMILES: Cc1cc(-c2ccc(NC(=O)c3cc(C(=O)Nc4ccc(-c5cc(C)c6ccccc6n5)cc4)cc(C(=O)Nc4ccc(-c5cc(C)c6ccccc6n5)cc4)c3)cc2)nc2ccccc12] | 71% |

| Ex. | Reactant | Product | Yield |
|---|---|---|---|
| L243 | 442-95-1<br>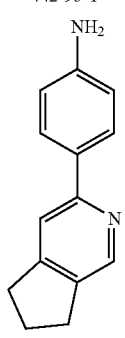<br>1798331-49-3 | 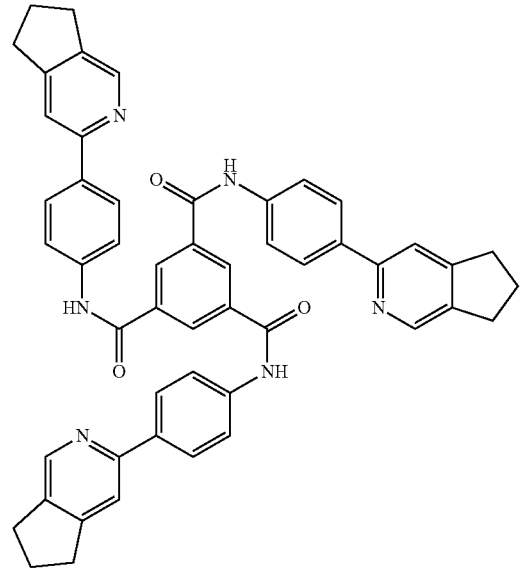 [SMILES: O=C(Nc1ccc(-c2cc3c(cn2)CCC3)cc1)c1cc(C(=O)Nc2ccc(-c3cc4c(cn3)CCC4)cc2)cc(C(=O)Nc2ccc(-c3cc4c(cn3)CCC4)cc2)c1] | 64% |
| L244 | 442-95-1<br>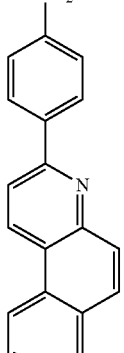<br>94211-88-8 | 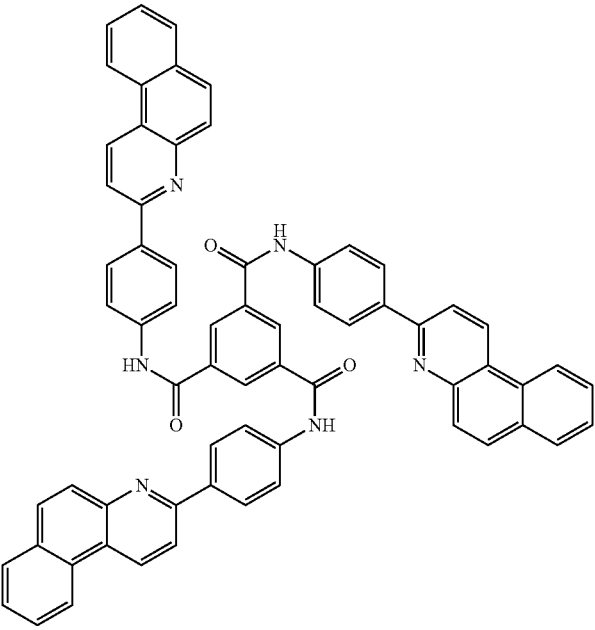 [SMILES: O=C(Nc1ccc(-c2ccc3c(ccc4ccccc43)n2)cc1)c1cc(C(=O)Nc2ccc(-c3ccc4c(ccc5ccccc54)n3)cc2)cc(C(=O)Nc2ccc(-c3ccc4c(ccc5ccccc54)n3)cc2)c1] | 76% |

| Ex. | Reactant | Product | Yield |
|---|---|---|---|
| L245 | 442-95-1 <br> 530086-92-1 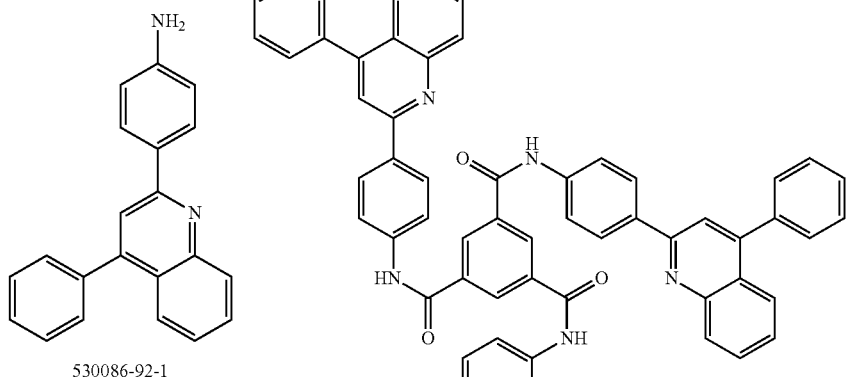 | 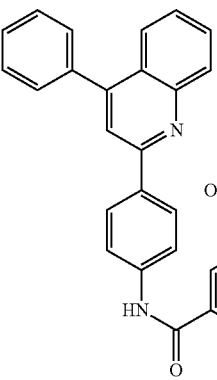 | 72% |
| L246 | 442-95-1 <br> 344285-96-7 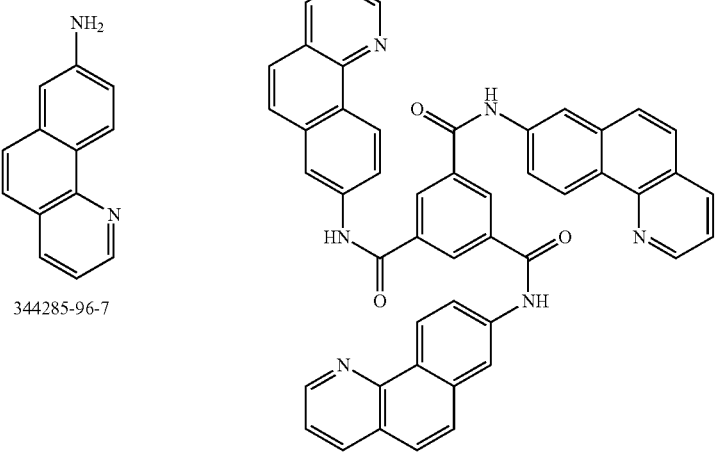 | 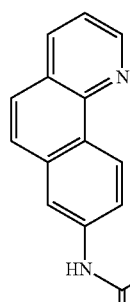 | 75% |

| Ex. | Reactant | Product | Yield |
|---|---|---|---|
| L247 | 442-95-1<br><br>13102354-6 | | 67% |
| L248 | 442-95-1<br><br>1159407-94-9 | | 69% |
| L249 | 442-95-1<br><br>126370-67-0 | | 67% |

| Ex. | Reactant | Product | Yield |
|---|---|---|---|
| L250 | 442-95-1 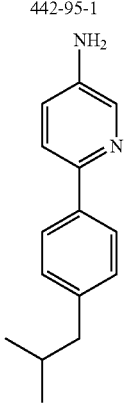 1554504-03-8 | 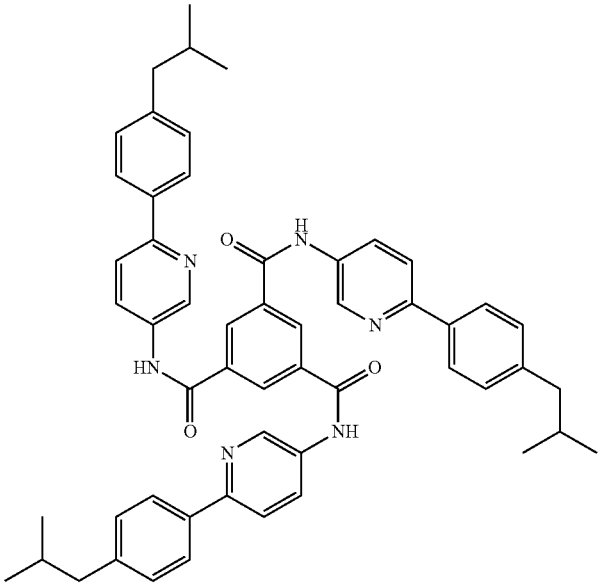 [SMILES: CC(C)Cc1ccc(-c2ccc(NC(=O)c3cc(C(=O)Nc4ccc(-c5ccc(CC(C)C)cc5)nc4)cc(C(=O)Nc4ccc(-c5ccc(CC(C)C)cc5)nc4)c3)cn2)cc1] | 63% |
| L251 | 442-95-1 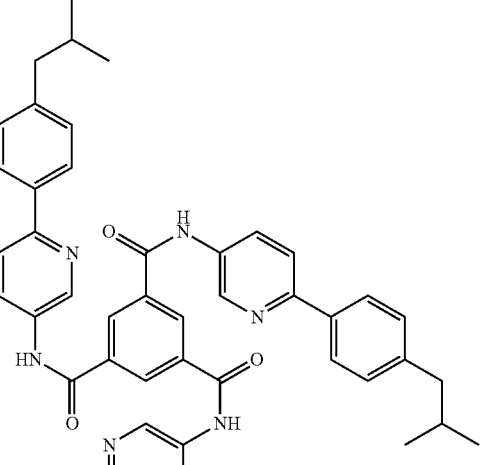 1551869-82-9 | 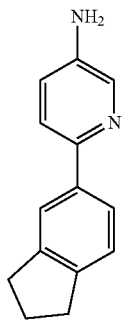 | 68% |

| Ex. | Reactant | Product | Yield |
|---|---|---|---|
| L252 | 442-95-1<br>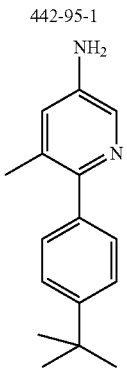<br>1192165-48-2 | 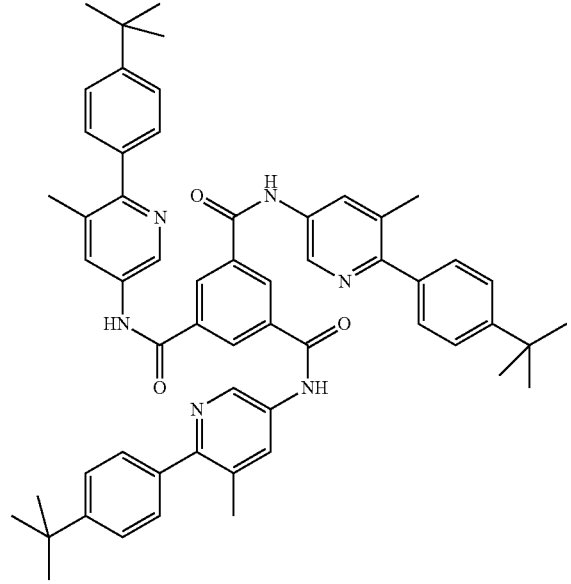 [SMILES: Cc1cc(NC(=O)c2cc(C(=O)Nc3cnc(-c4ccc(C(C)(C)C)cc4)c(C)c3)cc(C(=O)Nc3cnc(-c4ccc(C(C)(C)C)cc4)c(C)c3)c2)cnc1-c1ccc(C(C)(C)C)cc1] | 69% |
| L253 | 442-95-1<br>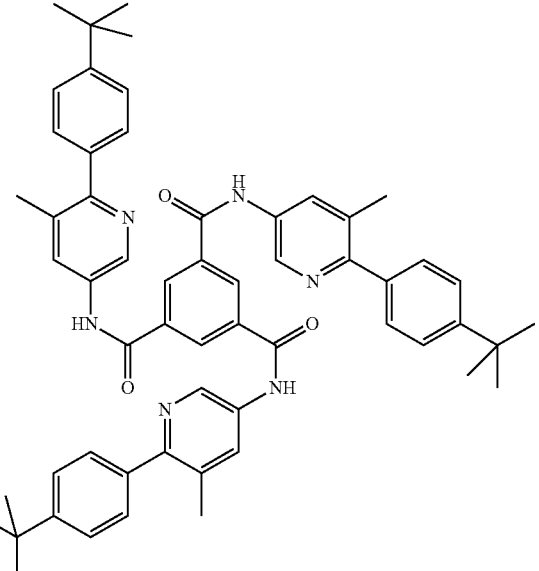<br>151585-47-6 | 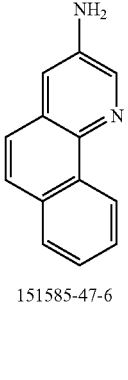 | 74% |
| L254 | 442-95-1<br>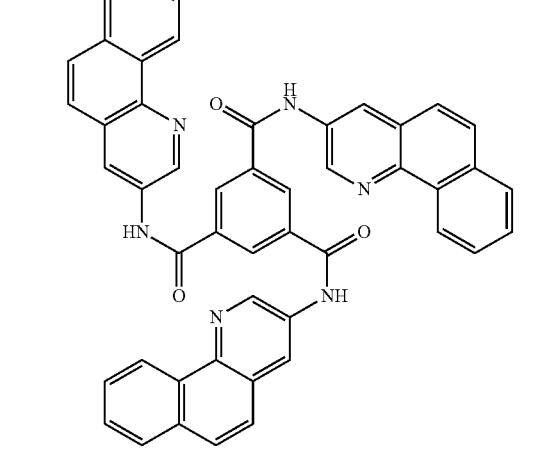<br>66728-99-2 | 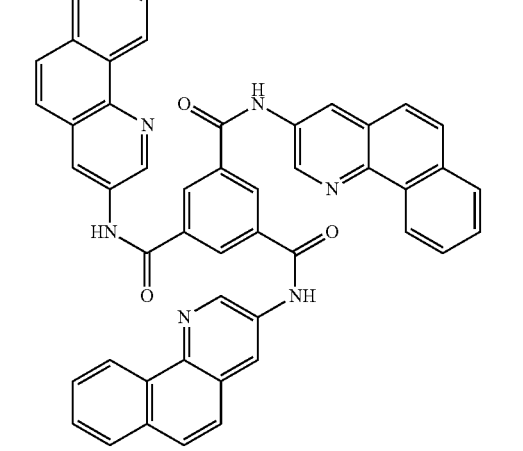 | 77% |

| Ex. | Reactant | Product | Yield |
|---|---|---|---|
| L255 | 442-95-1<br />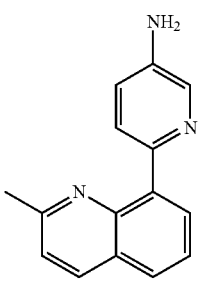<br />1357166-67-6 | 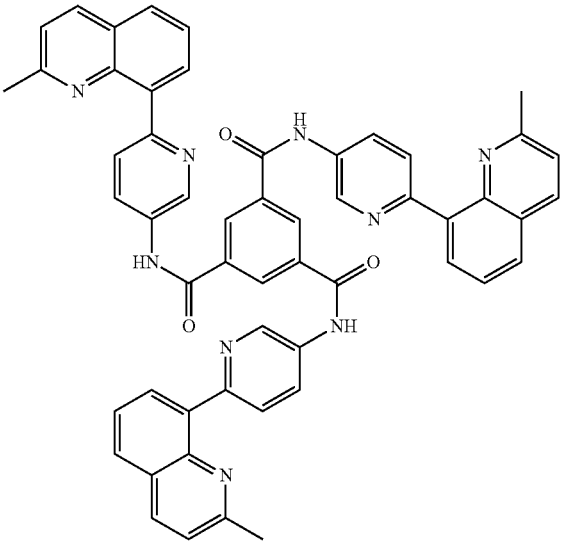 [SMILES: Cc1ccc2cccc(-c3ccc(NC(=O)c4cc(C(=O)Nc5ccc(-c6cccc7ccc(C)nc67)nc5)cc(C(=O)Nc5ccc(-c6cccc7ccc(C)nc67)nc5)c4)cn3)c2n1] | 73% |
| L256 | 442-95-1<br />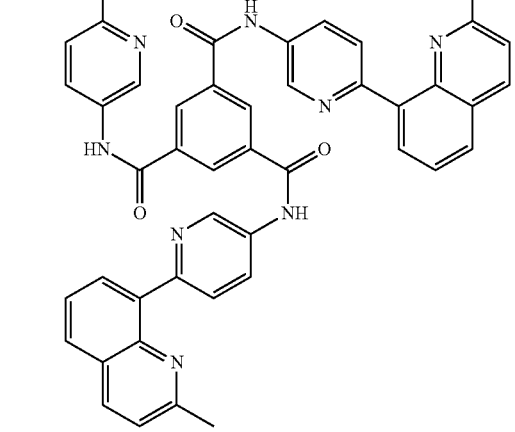<br />151585-47-6 | 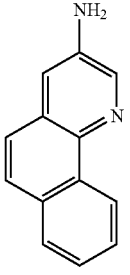 | 17% |
| L257 | 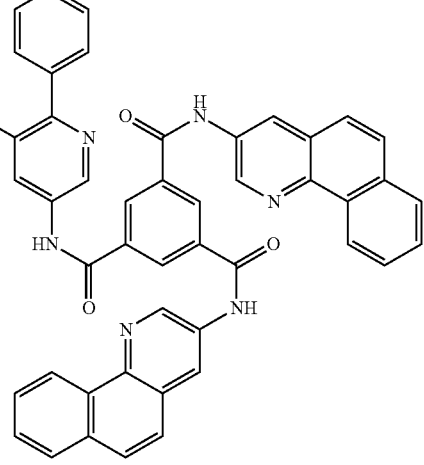<br />126370-67-0 | 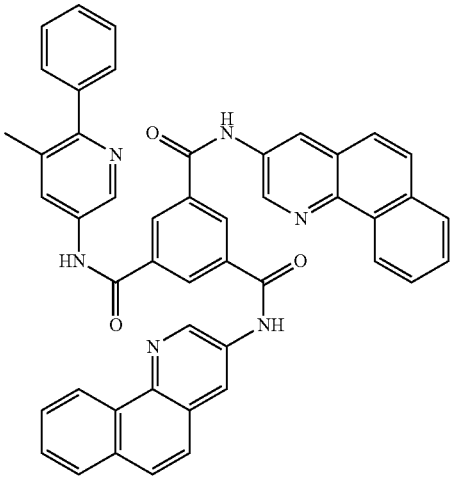 | 15% |

-continued
| Ex. | Reactant | Product | Yield |
|---|---|---|---|
| L258 | 442-95-1<br><br>1870003-70-5<br>addition as DMF solution | | 30% |
| L259 | 442-95-1<br><br>1870003-72-7<br>addition as DMF solution | | 38% |
| L260 | S40<br>126370-67-0 | | 70% |
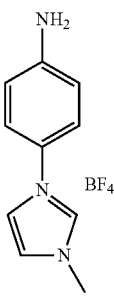

-continued

| Ex. | Reactant | Product | Yield |
|---|---|---|---|
| L261 | S41 942134-44-3 | | 67% |
| L262 | S42 371201-06-8 | | 72% |

-continued
| Ex. | Reactant | Product | Yield |
|---|---|---|---|
| L263 | S43<br>57442-05-4 | 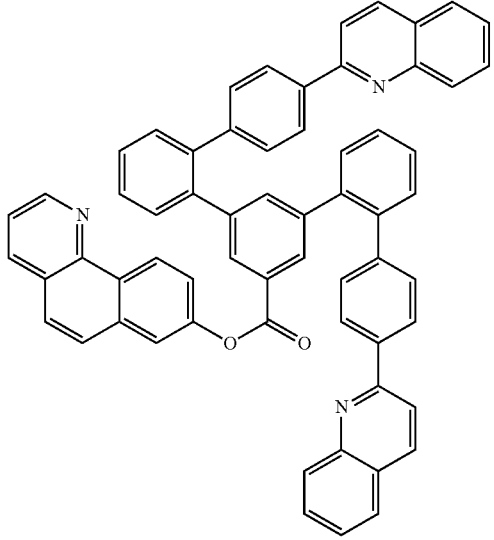 [SMILES: O=C(Oc1ccc2c(ccc3cccnc32)c1)c1cc(-c2ccccc2-c2ccc(-c3ccc4ccccc4n3)cc2)cc(-c2ccccc2-c2ccc(-c3ccc4ccccc4n3)cc2)c1] | 76% |
| L264 | S40<br>1551869-82-9 | 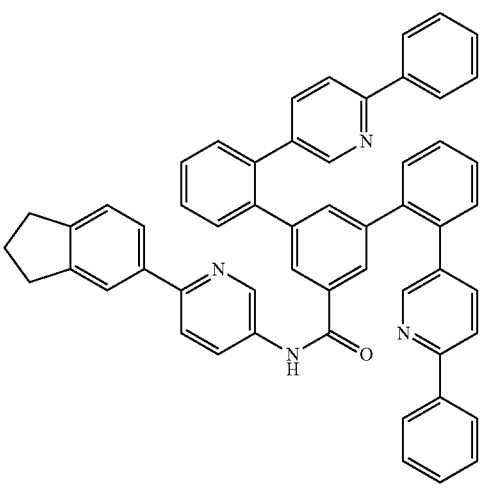 [SMILES: O=C(Nc1ccc(-c2ccc3c(c2)CCC3)nc1)c1cc(-c2ccccc2-c2ccc(-c3ccccc3)nc2)cc(-c2ccccc2-c2ccc(-c3ccccc3)nc2)c1] | 75% |

| Ex. | Reactant | Product | Yield |
|---|---|---|---|
| L265 | S41<br>1554504-03-8 | 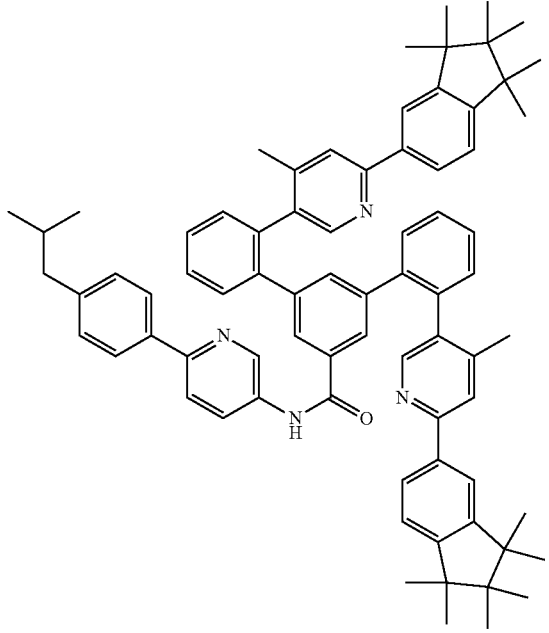 [SMILES: Cc1cc(-c2ccc3c(c2)C(C)(C)C(C)(C)C3(C)C)ncc1-c1ccccc1-c1cc(C(=O)Nc2ccc(-c3ccc(CC(C)C)cc3)nc2)cc(-c2ccccc2-c2cnc(-c3ccc4c(c3)C(C)(C)C(C)(C)C4(C)C)cc2C)c1] | 68% |
| L266 | S42<br>1351665-31-0 | 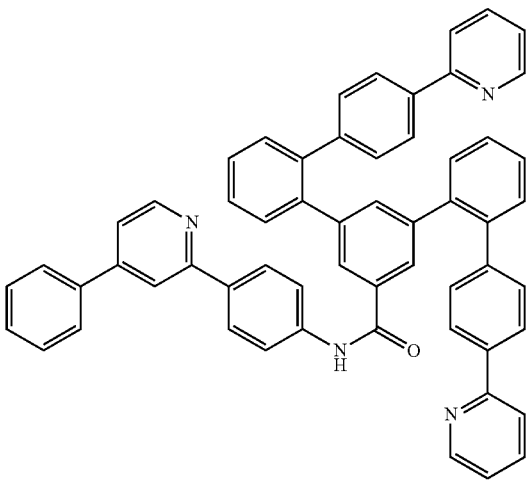 [SMILES: O=C(Nc1ccc(-c2cc(-c3ccccc3)ccn2)cc1)c1cc(-c2ccccc2-c2ccc(-c3ccccn3)cc2)cc(-c2ccccc2-c2ccc(-c3ccccn3)cc2)c1] | 73% |

| Ex. | Reactant | Product | Yield |
|---|---|---|---|
| L267 | S43<br>885955-74-8 | 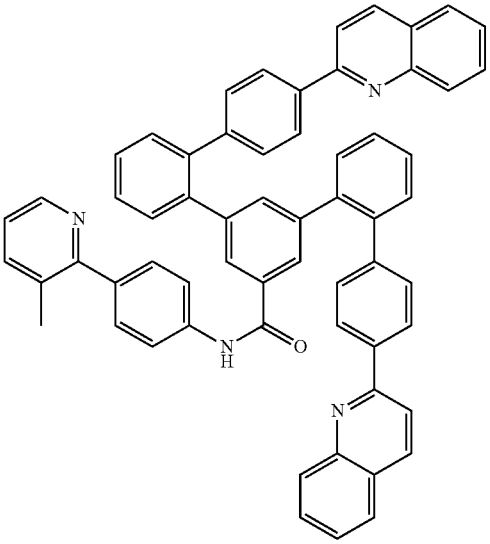 | 76% |
| L268 | 442-95-1<br>1255636-82-8 | 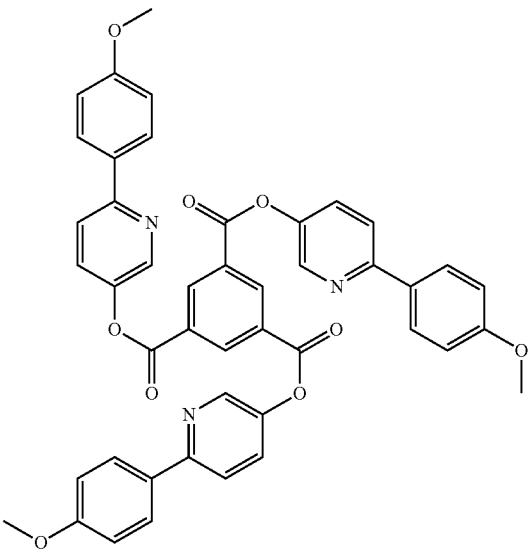 | 68% |

Example L300

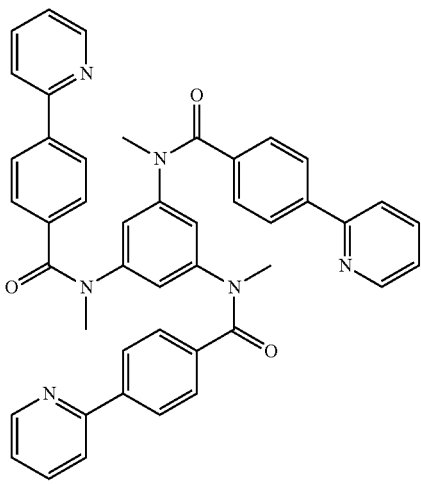 [SMILES: CN(C(=O)c1ccc(-c2ccccn2)cc1)c1cc(N(C)C(=O)c2ccc(-c3ccccn3)cc2)cc(N(C)C(=O)c2ccc(-c3ccccn3)cc2)c1]

To a suspension of 6.7 g (10 mmol) of L202 in 150 ml of dimethylacetamide are added 1.2 g (50 mmol) of sodium hydride in portions, and the mixture is stirred at room temperature for 30 min. Then 2.1 ml (33 mmol) of methyl iodide [74-88-4] are added and the mixture is heated to 60° C. for 16 h. 20 ml of conc. ammonia solution are added dropwise, the mixture is stirred for another 30 min, the solvent is substantially removed under reduced pressure, and the residue is taken up in 300 ml of dichloromethane, washed once with 200 ml of 5% by weight aqueous ammonia, twice with 100 ml each time of water and once with 100 ml of saturated sodium chloride solution, and then dried over magnesium sulphate. The dichloromethane is removed under reduced pressure and the crude product is recrystallized from ethyl acetate/methanol. Yield: 4.2 g (7.3 mmol), 73%. Purity: about 97% by $^1$H NMR.

The compounds which follow can be prepared in an analogous manner, using the electrophiles specified in place of methyl iodide. In the case of use of secondary alkyl halides, 60 mmol of NaH and 60 mmol of the secondary alkylating agent are used. The crude products can be purified by Kugelrohr distillation, recrystallization or chromatography.

| Ex. | Reactants | Product | Yield |
|---|---|---|---|
| L301 | L203<br>74-88-4 | | 78% |
| L302 | L206<br>74-88-4 | | 70% |

-continued

| Ex. | Reactants | Product | Yield |
|---|---|---|---|
| L303 | L207<br>74-88-4 | | 68% |
| L304 | L209<br>74-88-4 | | 70% |
| L305 | L211<br>74-88-4 | | 68% |

| Ex. | Reactants | Product | Yield |
|---|---|---|---|
| L306 | L238<br>73084-03-4 | 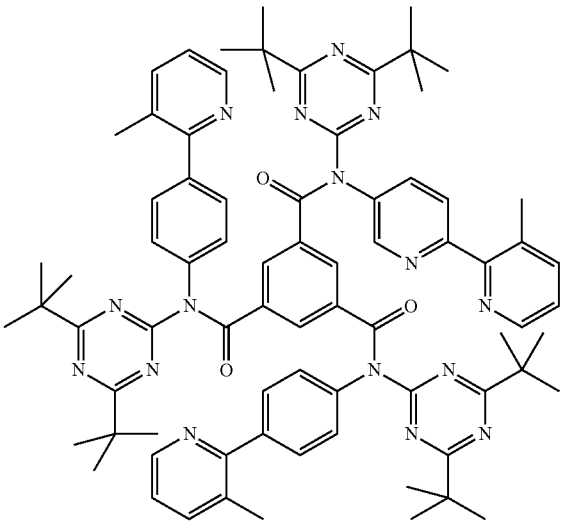 [SMILES: Cc1cccnc1-c1ccc(N(C(=O)c2cc(C(=O)N(c3ccc(-c4ncccc4C)cc3)c3nc(C(C)(C)C)nc(C(C)(C)C)n3)cc(C(=O)N(c3ccc(-c4ncccc4C)nc3)c3nc(C(C)(C)C)nc(C(C)(C)C)n3)c2)c2nc(C(C)(C)C)nc(C(C)(C)C)n2)cc1] | 46% |
| L307 | L239<br>29394-58-9 | 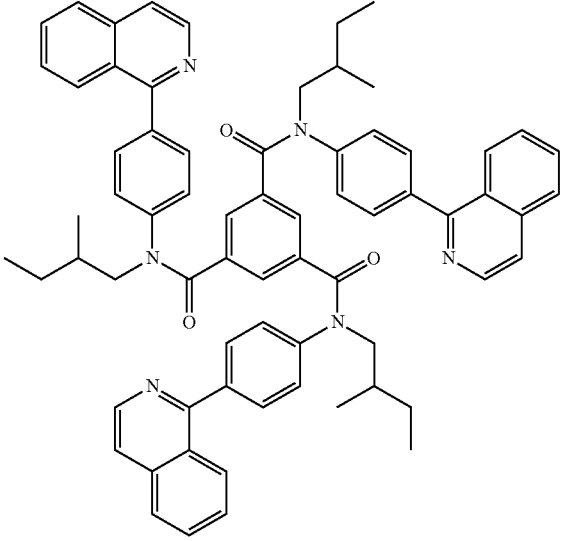 [SMILES: CCC(C)CN(C(=O)c1cc(C(=O)N(CC(C)CC)c2ccc(-c3nccc4ccccc34)cc2)cc(C(=O)N(CC(C)CC)c2ccc(-c3nccc4ccccc34)cc2)c1)c1ccc(-c2nccc3ccccc23)cc1] | 64% |
| L308 | L240<br>74-88-4 | 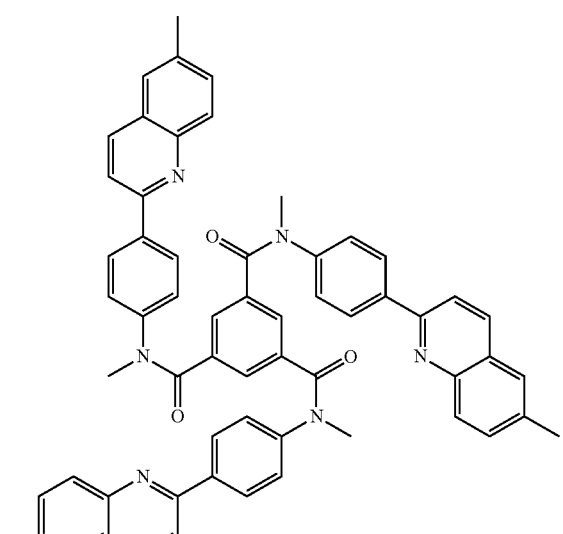 | 73% |

-continued
| Ex. | Reactants | Product | Yield |
|---|---|---|---|
| L309 | L241<br>75-03-6 | 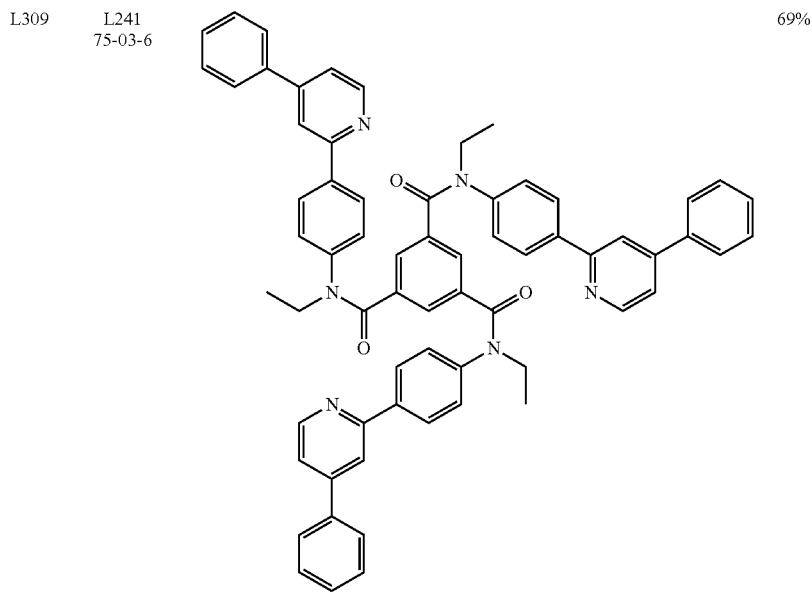 | 69% |
| L310 | L242<br>24424-99-5 | 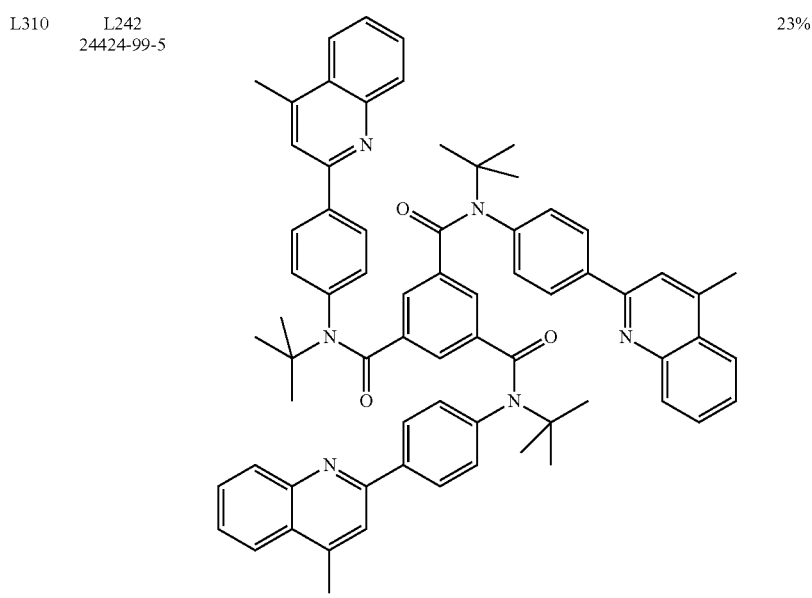 | 23% |

-continued
| Ex. | Reactants | Product | Yield |
|---|---|---|---|
| L311 | L243<br>74-88-4 | 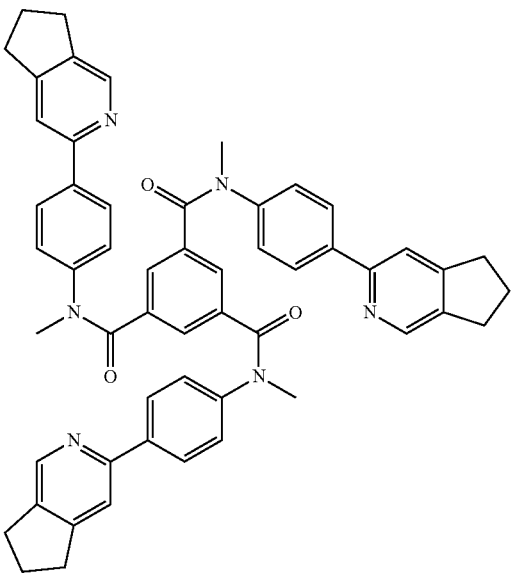 [SMILES: CN(C(=O)c1cc(C(=O)N(C)c2ccc(-c3cc4c(cn3)CCC4)cc2)cc(C(=O)N(C)c2ccc(-c3cc4c(cn3)CCC4)cc2)c1)c1ccc(-c2cc3c(cn2)CCC3)cc1] | 76% |
| L312 | L244<br>865-50-9 | 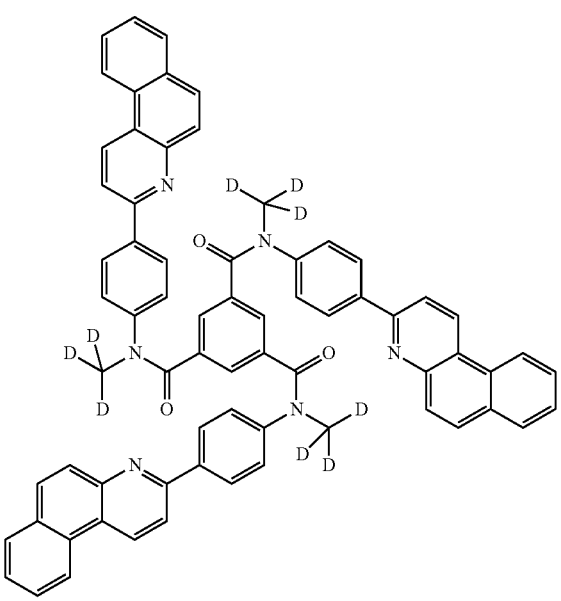 [SMILES: [2H]C([2H])([2H])N(C(=O)c1cc(C(=O)N(c2ccc(-c3ccc4c(ccc5ccccc54)n3)cc2)C([2H])([2H])[2H])cc(C(=O)N(c2ccc(-c3ccc4c(ccc5ccccc54)n3)cc2)C([2H])([2H])[2H])c1)c1ccc(-c2ccc3c(ccc4ccccc43)n2)cc1] | 74% |

| Ex. | Reactants | Product | Yield |
|---|---|---|---|
| L313 | L245<br>75-26-3 | 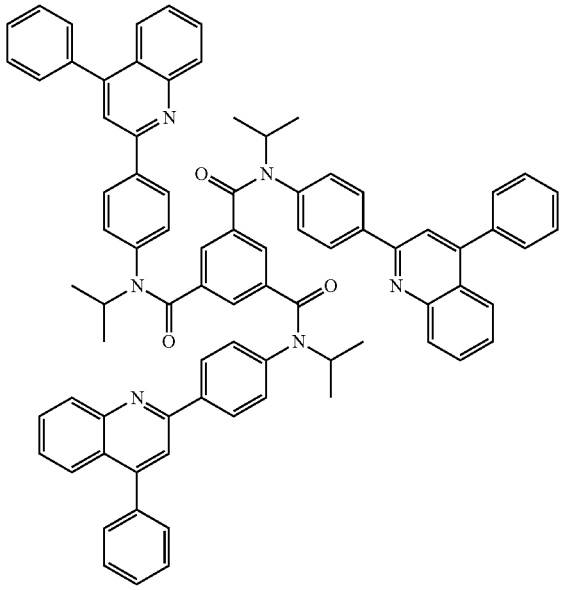 [SMILES: CC(C)N(C(=O)c1cc(C(=O)N(c2ccc(-c3cc(-c4ccccc4)c4ccccc4n3)cc2)C(C)C)cc(C(=O)N(c2ccc(-c3cc(-c4ccccc4)c4ccccc4n3)cc2)C(C)C)c1)c1ccc(-c2cc(-c3ccccc3)c3ccccc3n2)cc1] | 38% |
| L314 | L247<br>513-38-2 | 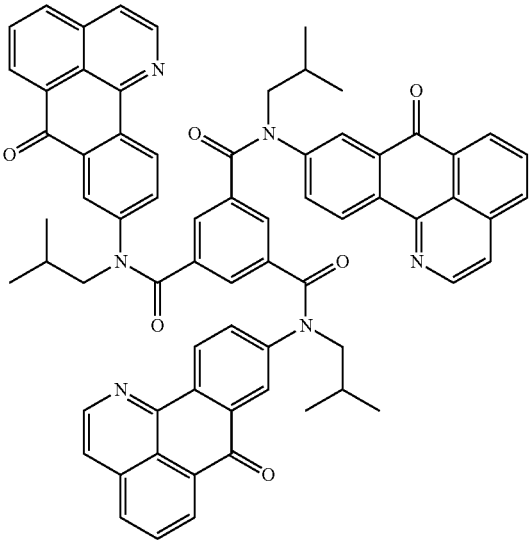 [SMILES: CC(C)CN(C(=O)c1cc(C(=O)N(CC(C)C)c2ccc3c(c2)C(=O)c2cccc4ccnc-3c24)cc(C(=O)N(CC(C)C)c2ccc3c(c2)C(=O)c2cccc4ccnc-3c24)c1)c1ccc2c(c1)C(=O)c1cccc3ccnc-2c13] | 63% |

-continued

| Ex. | Reactants | Product | Yield |
|---|---|---|---|
| L315 | L250<br>15501-33-4 | | 66% |
| L316 | L251<br>620-05-3 | | 72% |
| L317 | L253<br>15501-33-4 | | 64% |

| Ex. | Reactants | Product | Yield |
|---|---|---|---|
| L318 | L254<br>74-88-4 | 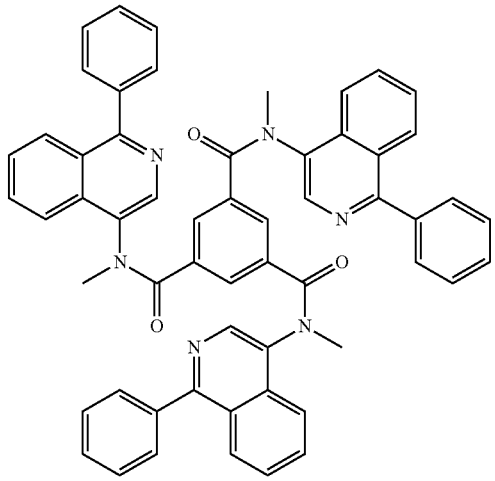 [SMILES: CN(C(=O)c1cc(C(=O)N(C)c2cnc(-c3ccccc3)c3ccccc23)cc(C(=O)N(C)c2cnc(-c3ccccc3)c3ccccc23)c1)c1cnc(-c2ccccc2)c2ccccc12] | 70% |
| L319 | L255<br>75-77-4 | 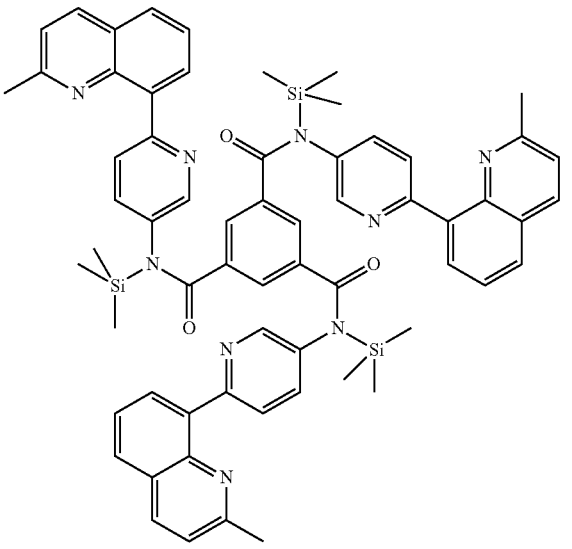 [SMILES: Cc1ccc2cccc(-c3ccc(N(C(=O)c4cc(C(=O)N(c5ccc(-c6cccc7ccc(C)nc67)nc5)[Si](C)(C)C)cc(C(=O)N(c5ccc(-c6cccc7ccc(C)nc67)nc5)[Si](C)(C)C)c4)[Si](C)(C)C)cn3)c2n1] | 58% |
| L320 | L256<br>74-88-4 | 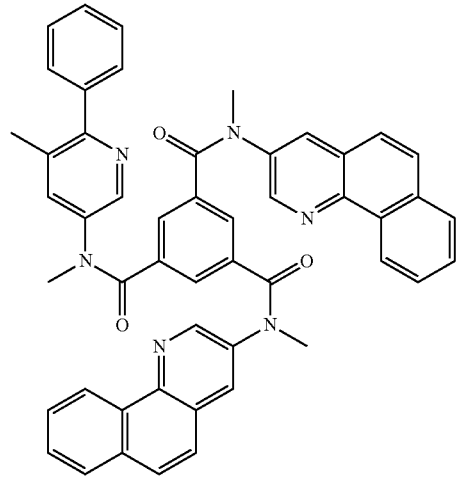 [SMILES: Cc1cc(N(C)C(=O)c2cc(C(=O)N(C)c3cnc4c(ccc5ccccc54)c3)cc(C(=O)N(C)c3cnc4c(ccc5ccccc54)c3)c2)cnc1-c1ccccc1] | 73% |

-continued
| Ex. | Reactants | Product | Yield |
|---|---|---|---|
| L321 | L257<br>15501-33-4 | 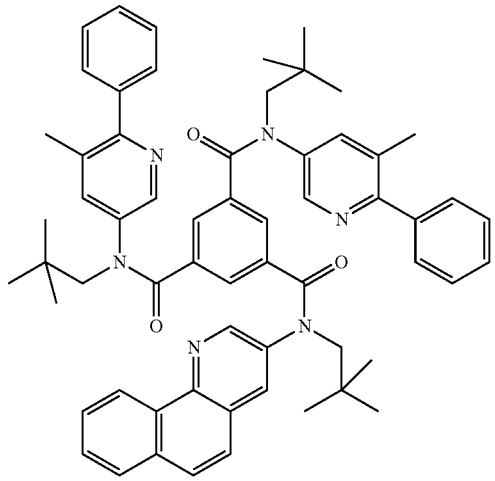 [SMILES: Cc1cc(N(CC(C)(C)C)C(=O)c2cc(C(=O)N(CC(C)(C)C)c3cnc(-c4ccccc4)c(C)c3)cc(C(=O)N(CC(C)(C)C)c3cnc4c(ccc5ccccc54)c3)c2)cnc1-c1ccccc1] | 65% |
| L322 | L258<br>74-88-4<br>Cs₂CO₃ base<br>acetone solvent | 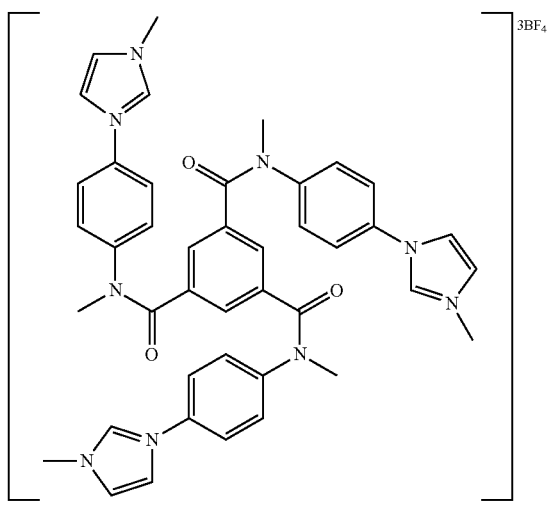 3BF₄ | 43% |
| L323 | L264<br>12 mmol<br>74-88-4<br>15 mmol<br>NaH | 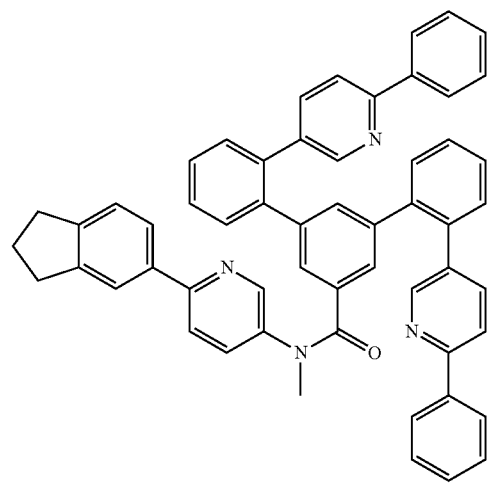 [SMILES: CN(C(=O)c1cc(-c2ccccc2-c2ccc(-c3ccccc3)nc2)cc(-c2ccccc2-c2ccc(-c3ccccc3)nc2)c1)c1ccc(-c2ccc3c(c2)CCC3)nc1] | 71% |

-continued
| Ex. | Reactants | Product | Yield |
|---|---|---|---|
| L324 | L265<br>10 mmol<br>15501-33-4<br>15 mmol NaH | 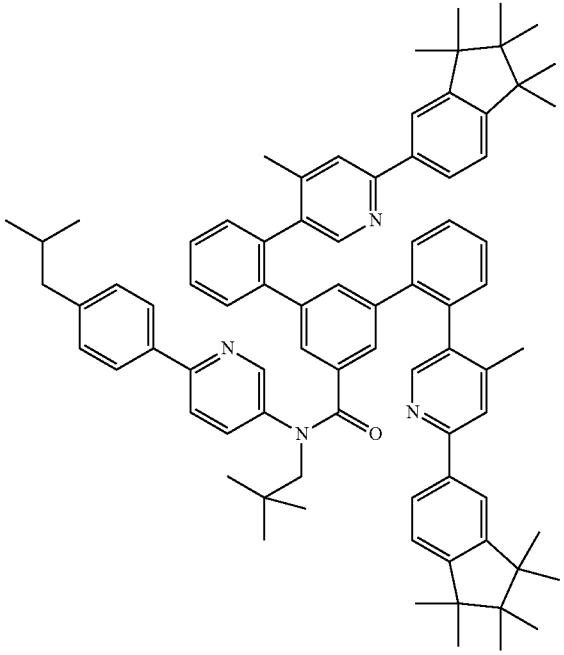 [SMILES: Cc1cc(-c2ccc3c(c2)C(C)(C)C(C)(C)C3(C)C)ncc1-c1ccccc1-c1cc(C(=O)N(CC(C)(C)C)c2ccc(-c3ccc(CC(C)C)cc3)nc2)cc(-c2ccccc2-c2cnc(-c3ccc4c(c3)C(C)(C)C(C)(C)C4(C)C)cc2C)c1] | 68% |
| L325 | L266<br>12 mmol<br>15501-33-4<br>15 mmol NaH | 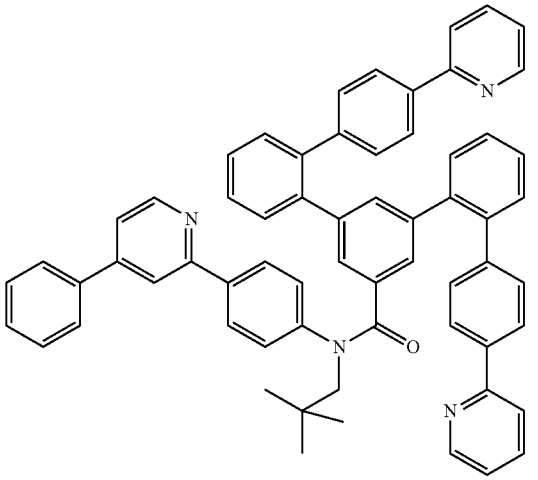 [SMILES: CC(C)(C)CN(C(=O)c1cc(-c2ccccc2-c2ccc(-c3ccccn3)cc2)cc(-c2ccccc2-c2ccc(-c3ccccn3)cc2)c1)c1ccc(-c2cc(-c3ccccc3)ccn2)cc1] | 66% |

-continued
| Ex. | Reactants | Product | Yield |
|---|---|---|---|
| L326 | L267<br>12 mmol<br>74-88-4<br>15 mmol<br>NaH | 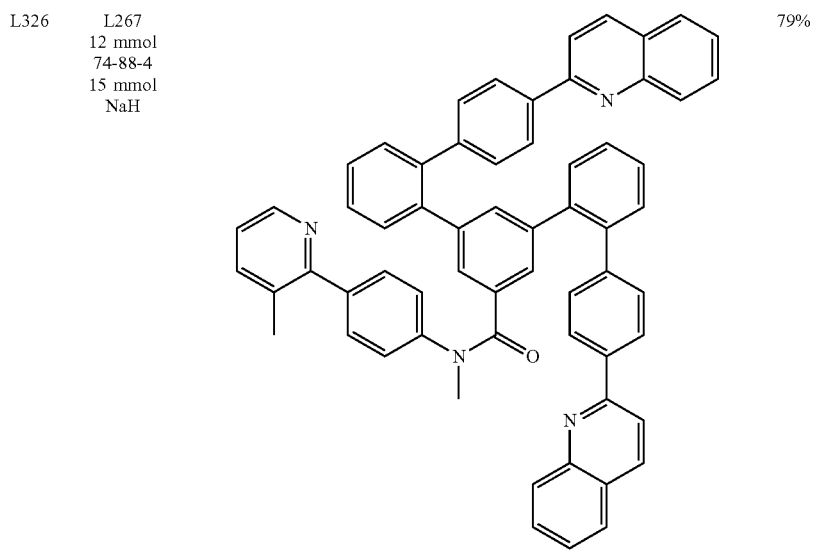 | 79% |
| L327 | L206<br>534-00-9 | 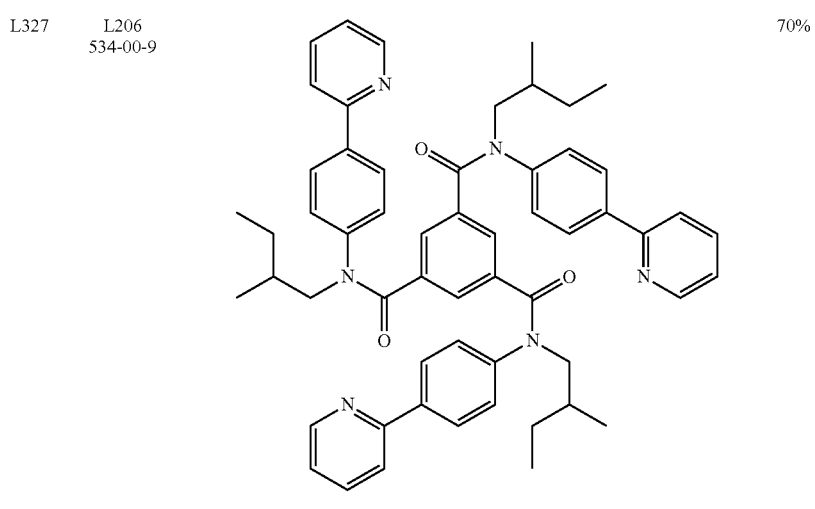 | 70% |

Example L400

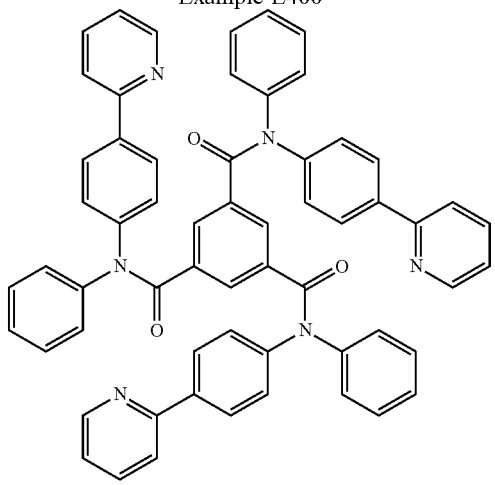

A mixture of 6.7 g (10 mmol) of L206, 4.5 ml (40 mmol) of iodobenzene [591-50-4], 12.7 g (60 mmol) of tripotassium phosphate, 292 mg (1.5 mmol) of copper(I) iodide, 553 mg (3 mmol) of 2,2,6,6-tetramethyl-3,5-heptanedione [1118-71-4], 50 g of glass beads (diameter 3 mm) and 150 ml of o-xylene is heated to 130° C. for 24 h. After cooling, the solvent is removed under reduced pressure, the residue is taken up in 500 ml of dichloromethane, the salts are filtered off using a Celite bed in the form of a slurry, and the filtrate is washed three times with 100 ml of 5% by weight ammonia solution and once with 100 ml of water, and then dried over magnesium sulphate. The crude product obtained after the solvent has been removed is recrystallized from ethyl acetate/methanol. Yield: 6.1 g (6.8 mmol), 68%. Purity: about 97% by $^1$H NMR.

The compounds which follow can be prepared in an analogous manner, with adjustment of the stoichiometry of the reactants to the number of NH functions. The crude products can be purified by Kugelrohr distillation, Ex. Reactants Product Yield

| Ex. | Reactants | Product | Yield |
|---|---|---|---|
| L401 | L246<br>37055-53-1 | | 55% |
| L402 | L248<br>20442-79-9 | | 58% |

| Ex. | Reactants | Product | Yield |
|---|---|---|---|
| L403 | L249 857784-97-5 | 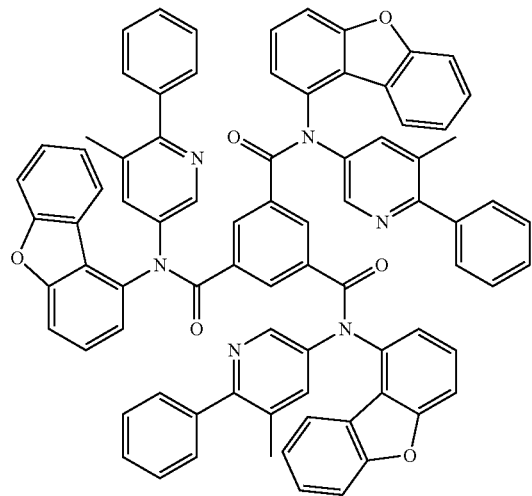 [SMILES: Cc1cc(N(C(=O)c2cc(C(=O)N(c3cnc(-c4ccccc4)c(C)c3)c3cccc4oc5ccccc5c34)cc(C(=O)N(c3cnc(-c4ccccc4)c(C)c3)c3cccc4oc5ccccc5c34)c2)c2cccc3oc4ccccc4c23)cnc1-c1ccccc1] | 31% |
| L404 | L252 1643766-87-3 | 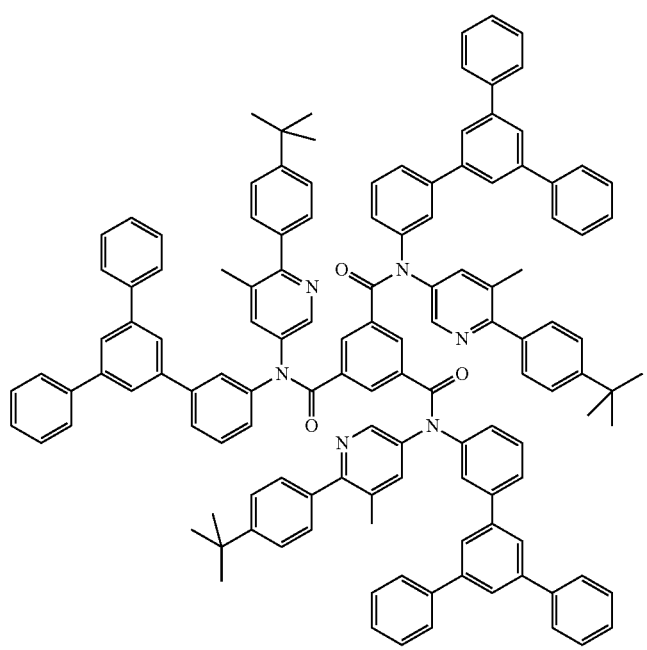 [SMILES: Cc1cc(N(C(=O)c2cc(C(=O)N(c3cccc(-c4cc(-c5ccccc5)cc(-c5ccccc5)c4)c3)c3cnc(-c4ccc(C(C)(C)C)cc4)c(C)c3)cc(C(=O)N(c3cccc(-c4cc(-c5ccccc5)cc(-c5ccccc5)c4)c3)c3cnc(-c4ccc(C(C)(C)C)cc4)c(C)c3)c2)c2cccc(-c3cc(-c4ccccc4)cc(-c4ccccc4)c3)c2)cnc1-c1ccc(C(C)(C)C)cc1] | 60% |

-continued

| Ex. | Reactants | Product | Yield |
|---|---|---|---|
| L405 | L264<br>591-50-4 | | 73% |
| L406 | L265<br>5896-29-7 | | 64% |

-continued
| Ex. | Reactants | Product | Yield |
|---|---|---|---|
| L407 | L266<br>1778649-24-3 | 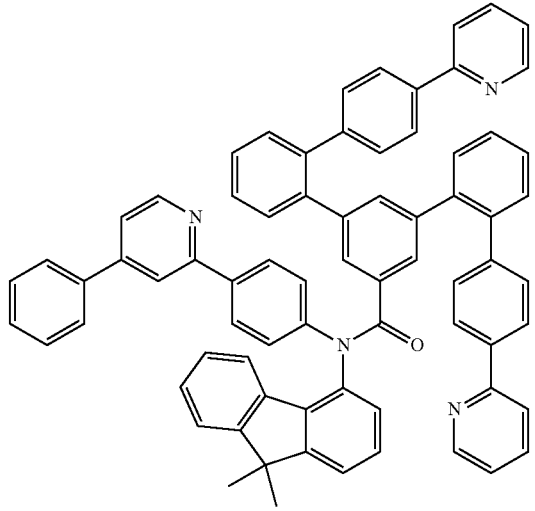 [SMILES: CC1(C)c2ccccc2-c2c(N(C(=O)c3cc(-c4ccccc4-c4ccc(-c5ccccn5)cc4)cc(-c4ccccc4-c4ccc(-c5ccccn5)cc4)c3)c3ccc(-c4cc(-c5ccccc5)ccn4)cc3)cccc21] | 37% |
| L408 | L267<br>374077-23-3 | 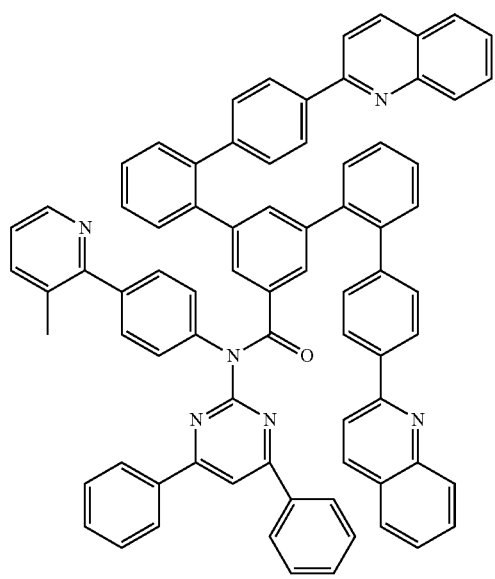 [SMILES: Cc1cccnc1-c1ccc(N(C(=O)c2cc(-c3ccccc3-c3ccc(-c4ccc5ccccc5n4)cc3)cc(-c3ccccc3-c3ccc(-c4ccc5ccccc5n4)cc3)c2)c2nc(-c3ccccc3)cc(-c3ccccc3)n2)cc1] | 56% |

Example L500

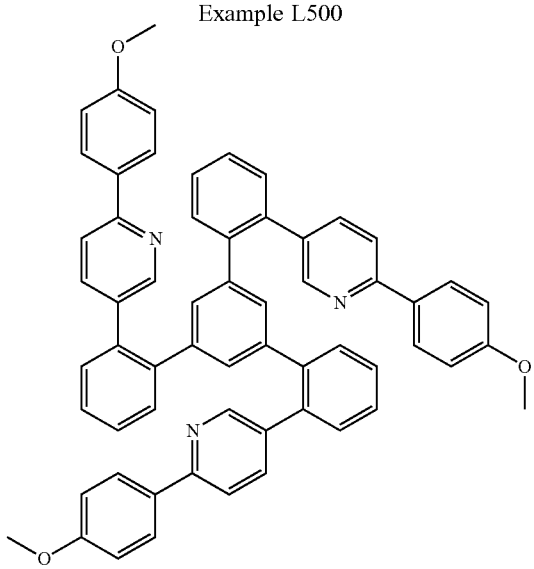

A well-stirred mixture of 16.3 g (30 mmol) of 1,3,5-tris (2-bromophenyl)benzene [380626-56-2], 31.1 g (100 mmol) of 2-(4-methoxyphenyl)-5-(4,4,5,5-tetramethyl-[1,3,2]dioxaborolan-2-yl)pyridine [1374263-53-2], 42.5 g (200 mmol) of tripotassium phosphate, 534 mg (1.3 mmol) of S-Phos [657408-07-6], 224 mg (1.0 mmol) of palladium(II) acetate, 300 ml of toluene, 100 ml of dioxane and 300 ml of water is heated under reflux for 16 h. After cooling, the aqueous phase is removed and the organic phase is concentrated to dryness. The brown foam is taken up in 300 ml of ethyl acetate and filtered through a silica gel bed in the form of an ethyl acetate slurry (diameter 15 cm, length 20 cm) in order to remove brown components. After concentrating to 100 ml, 300 ml of methanol are added dropwise to the warm solution with very good stirring, in the course of which a beige solid crystallizes out. The solid is filtered off with suction, washed twice with 100 ml each time of methanol and dried under reduced pressure. Yield: 20.5 g (24 mmol), 80%. Purity: about 95% by $^1$H NMR.

In an analogous manner, it is possible to prepare the following compounds

| Ex. | Reactants | Product | Yield |
|---|---|---|---|
| L501 | L60 | (structure with NH$_2$ groups) | 54% |
| L502 | L61 | (structure with OH groups) | 57% |

-continued

| Ex. | Reactants | Product | Yield |
|---|---|---|---|
| L503 | L62 | 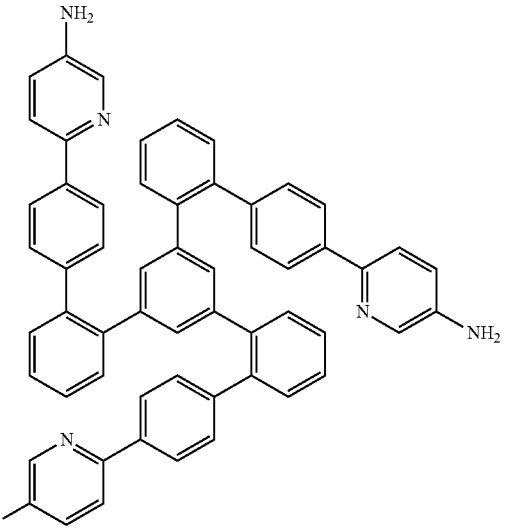 | 49% |

B: Synthesis of the Metal Complexes:

Example Ir(L1)

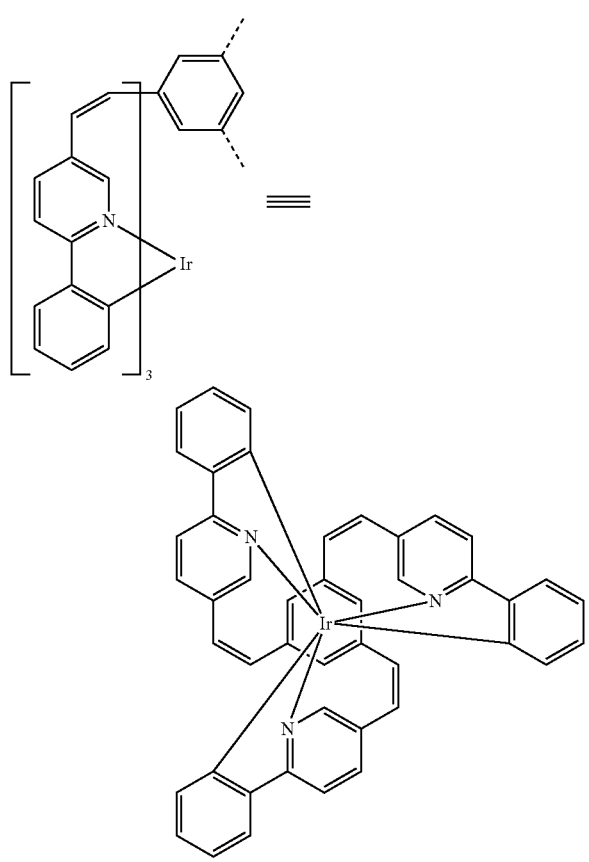

Variant A:

A mixture of 6.16 g (10 mmol) of ligand L1, 4.90 g (10 mmol) of trisacetylacetonatoiridium(III) [15635-87-7] and 150 g of hydroquinone [123-31-9] is initially charged in a 500 ml two-neck round-bottomed flask with a glass-sheathed magnetic core. The flask is provided with a water separator (for media of lower density than water) and an air condenser with argon blanketing and placed into a metal heating bath. The apparatus is purged with argon from the top via the argon blanketing system for 15 min, allowing the argon to flow out of the side neck of the two-neck flask. Through the side neck of the two-neck flask, a glass-sheathed Pt-100 thermocouple is introduced into the flask and the end is positioned just above the magnetic stirrer core. Then the apparatus is thermally insulated with several loose windings of domestic aluminium foil, the insulation being run up to the middle of the riser tube of the water separator. Then the apparatus is heated rapidly with a heated laboratory stirrer system to 250° C., measured with the Pt-100 thermal sensor which dips into the molten stirred reaction mixture. Over the next 1.5 h, the reaction mixture is kept at 250° C., in the course of which a small amount of condensate is distilled off and collects in the water separator. After cooling, the melt cake is mechanically comminuted and extracted by boiling with 500 ml of methanol. The beige suspension thus obtained is filtered through a double-ended frit, and the beige solid is washed once with 50 ml of methanol and then dried under reduced pressure. The beige solid thus obtained is dissolved in 200 ml of dichloromethane and filtered through about 1 kg of silica gel in the form of a dichloromethane slurry (column diameter about 18 cm) with exclusion of air in the dark, leaving dark-coloured components at the start. The core fraction is cut out and concentrated on a rotary evaporator, with simultaneous continuous dropwise addition of MeOH until crystallization. After removal with suction, washing with a little MeOH and drying under reduced pressure, the orange product is purified further by continuous hot extraction five times with toluene/acetonitrile 3:1 (v/v) and hot extraction twice with ethyl acetate (amount initially charged in each case about 150 ml, extraction thimble: standard Soxhlet thimbles made from cellulose from Whatman) with careful exclusion of air and light. Finally, the product is subjected to heat treatment under high vacuum at 280° C. or alternatively fractional sublimation at about 340° C. Yield: 2.66 g (3.3 mmol), 33%. Purity: >99.9% by HPLC.

The metal complexes shown below can in principle be purified by chromatography, recrystallization, hot extraction. The removal of residual solvents and further purification can be effected by treatment under reduced pressure/high vacuum at typically 250-330° C., or by sublimation/fractional sublimation.

The metal complexes are typically obtained as a 1:1 mixture of the Λ and Δ isomers/enantiomers. Images of complexes adduced hereinafter typically show only one isomer. If ligands having three different sub-ligands are used, or chiral ligands are used as a racemate, the metal complexes derived are obtained as a diastereomer mixture. These can be separated by fractional crystallization or by chromatographic means. If chiral ligands are used in enantiomerically pure form, the metal complexes derived are obtained as a diastereomer mixture, the separation of which by fractional crystallization or chromatography leads to pure enantiomers.

In an analogous manner, it is possible to prepare the following compounds:

| Ex. | Ligand | Product Variant Reaction time* Reaction temperature* Extractant* | Yield |
|---|---|---|---|
| Ir(L2) | L2 | Ir(L2) as A | 35% |
| Ir(L3) | L3 | Ir(L3) as A | 27% |
| Ir(L4) | L4 | Ir(L4) 250° C. 2 h butyl acetate | 39% |
| Ir(L5) | L5 | Ir(L5) as A | 33% |
| Ir(L6) | L6 | Ir(L6) as A | 29% |
| Ir(L7) | L7 | Ir(L7) 260° C. 2 h toluene | 31% |
| Ir(L8) | L8 | Ir(L8) 250° C. 2 h o-xylene | 25% |
| Ir(L9) | L9 | Ir(L9) 240° C. 2 h DCM | 37% |
| Ir(L10) | L10 | 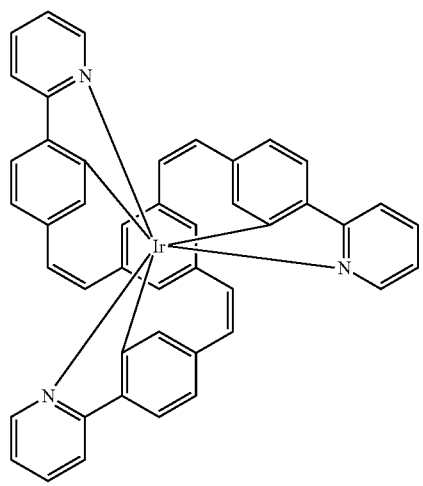 Ir(L10) as A | 35% |
| Ir(L11) | L11 | Ir(L11) as A | 35% |
| Ir(L12) | L12 | Ir(L12) as A | 38% |
| Ir(L13) | L13 | Ir(L13) as A | 31% |

-continued
| Ex. | Ligand | Product<br>Variant<br>Reaction time*<br>Reaction temperature*<br>Extractant* | Yield |
|---|---|---|---|
| Ir(L14) | L14 | Ir(L14)<br>250° C.<br>1.5 h<br>DCM | 28% |
| Ir(L15) | L15 | 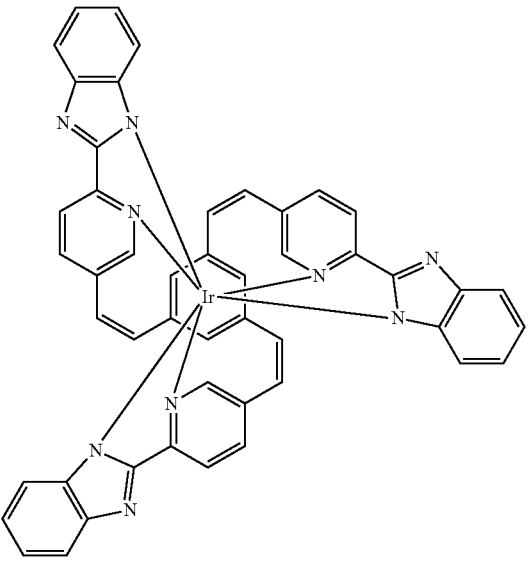<br>Ir(L15)<br>240° C.<br>2 h<br>o-xylene | 21% |
| Ir(L16) | L16 | 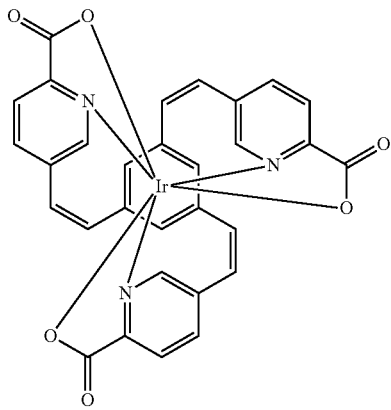<br>Ir(L16)<br>240° C.<br>2 h<br>butyl acetate | 41% |
| Ir(L17) | L17 | Ir(L17)<br>240° C.<br>2 h<br>DCM | 43% |

-continued
| Ex. | Ligand | Product<br>Variant<br>Reaction time*<br>Reaction temperature*<br>Extractant* | Yield |
|---|---|---|---|
| Ir(L18) | L18 | 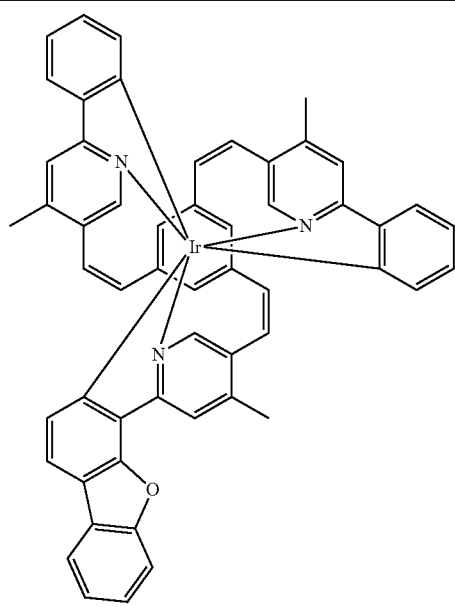<br>Ir(L18)<br>250° C.<br>1.5 h<br>ethyl acetate | 36% |
| Ir(L19) | L19 | Ir(L19)<br>as Ir(L18) | 39% |
| Ir(L20) | L20 | Ir(L20)<br>as Ir(L18) | 36% |
| Ir(L21) | L21 | Ir(L21)<br>as Ir(L18) | 35% |
| Ir(L22) | L22 | 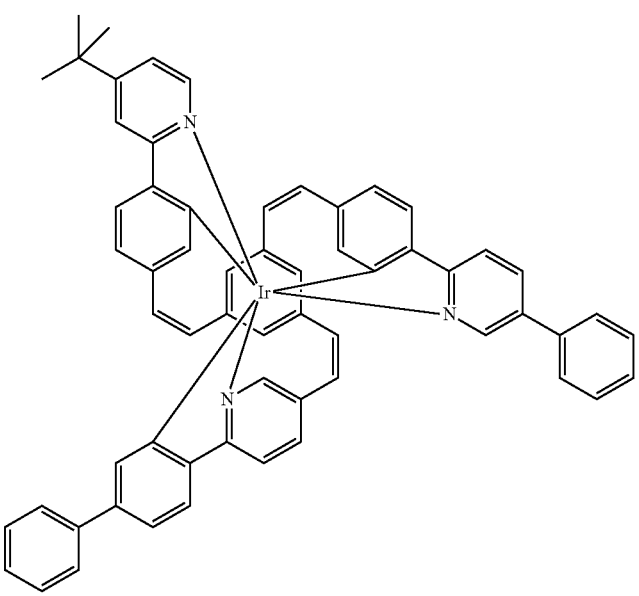<br>Ir(L22)<br>as Ir(L18) | 30% |
| Ir(L23) | L23 | Ir(L23)<br>as Ir(L18) | 33% |

-continued

| Ex. | Ligand | Product<br>Variant<br>Reaction time*<br>Reaction temperature*<br>Extractant* | Yield |
|---|---|---|---|
| Ir(L24) | L24 | Ir(L24)<br>250° C.<br>1.5 h<br>DCM | 27% |
| Ir(L25) | L25 | Ir(L25)<br>250° C.<br>1.5 h<br>anisole | 29% |
| Ir(L26) | L26 | Ir(L26)<br>250° C.<br>1.5 h<br>DCM | 30% |
| Ir(L27) | L27 | Ir(L27)<br>as Ir(L26) | 28% |
| Ir(L28) | L28 | 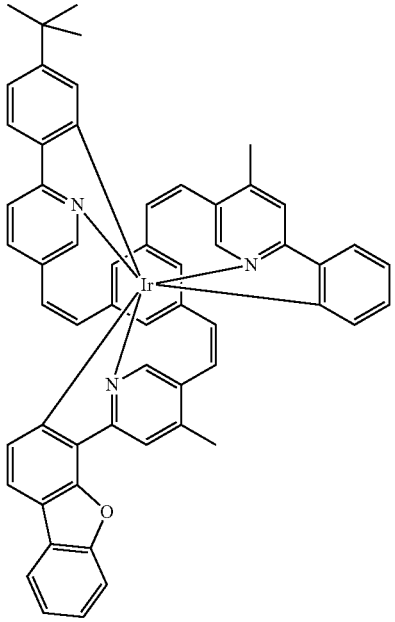<br>Ir(L28)<br>250° C.<br>1.5 h<br>chromatographic separation of<br>the diastereomers<br>toluene:DCM 90:10<br>silica gel | 22%<br>17% |
| Ir(L29) | L29 | Ir(L29)<br>as Ir(L18) | 12% |
| Ir(L30) | L30 | Ir(L30)<br>as Ir(L18) | 46% |
| Ir(L31) | L31 | Ir(L31)<br>as Ir(L18) | 31% |

-continued
| Ex. | Ligand | Product<br>Variant<br>Reaction time*<br>Reaction temperature*<br>Extractant* | Yield |
|---|---|---|---|
| Ir(L50) | L50 | 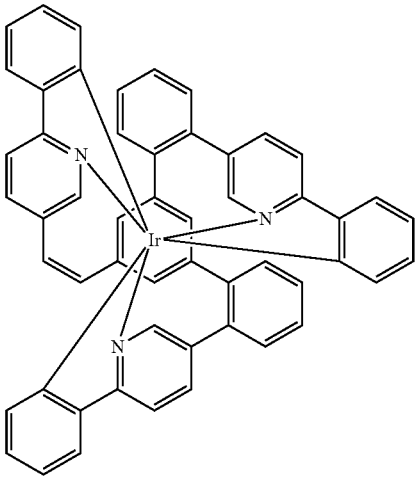<br>Ir(L50)<br>250° C.<br>1.5 h<br>DCM | 45% |
| Ir(L51) | L51 | Ir(L51)<br>as Ir(L50) | 40% |
| Ir(L52) | L52 | Ir(L52)<br>as Ir(L50) | 43% |
| Ir(L53) | L53 | Ir(L53)<br>as Ir(L50) | 36% |
| Ir(L100) | L100 | 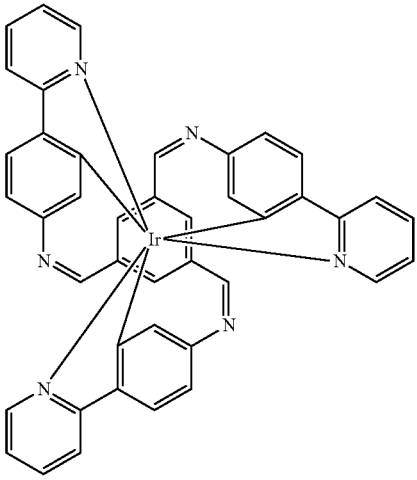<br>Ir(L100)<br>270° C.<br>3 h<br>DCM | 18% |
| Ir(L101) | L101 | Ir(L101)<br>as Ir(L100) | 23% |
| Ir(L102) | L102 | Ir(L102)<br>as Ir(L100) | 15% |

-continued

| Ex. | Ligand | Product<br>Variant<br>Reaction time*<br>Reaction temperature*<br>Extractant* | Yield |
|---|---|---|---|
| Ir(L200) | L200 | Ir(L200)<br>250° C.<br>2 h<br>DCM | 32% |
| Ir(L201) | L201 | Ir(L201)<br>as Ir(L200) | 38% |
| Ir(L204) | L204 | Ir(L204)<br>as Ir(L200) | 43% |
| Ir(L205) | L205 | Ir(L205)<br>as Ir(L200) | 35% |
| Ir(L208) | L208 | Ir(L208)<br>as Ir(L200) | 43% |
| Ir(L209) | L209 | Ir(L209)<br>260° C.<br>2 h<br>o-xylene | 23% |
| Ir(L210) | L210 | Ir(L210)<br>260° C.<br>2 h<br>toluene | 27% |
| Ir(L211) | L211 | Ir(L211)<br>as Ir(L200) | 46% |
| Ir(L212) | L212 | Ir(L212)<br>as Ir(L200) | 38% |
| Ir(L213) | L213 | Ir(L213)<br>as Ir(L200) | 35% |
| Ir(L214) | L214 | Ir(L214)<br>as Ir(L200) | 24% |
| Ir(L215) | L215 | Ir(L215)<br>as Ir(L200) | 41% |
| Ir(L216) | L216 | Ir(L216)<br>as Ir(L210) | 27% |
| Ir(L217) | L217 | Ir(L217)<br>as Ir(L200) | 39% |
| Ir(L218) | L218 | Ir(L218)<br>as Ir(L210) | 28% |
| Ir(L219) | L219 | Ir(L219)<br>as Ir(L200) | 39% |
| Ir(L220) | L220 | Ir(L220)<br>as Ir(L210) | 28% |
| Ir(L221) | L221 | Ir(L221)<br>as Ir(L200) | 41% |
| Ir(L222) | L222 | Ir(L222)<br>as Ir(L210) | 27% |
| Ir(L223) | L223 | Ir(L223)<br>as Ir(L209) | 27% |
| Ir(L224) | L224 | Ir(L224)<br>as Ir(L200) | 44% |
| Ir(L225) | L225 | Ir(L225)<br>as Ir(L210) | 28% |

-continued
| Ex. | Ligand | Product Variant Reaction time* Reaction temperature* Extractant* | Yield |
|---|---|---|---|
| Ir(L226) | L226 | Ir(L226) as Ir(L200) | 36% |
| Ir(L227) | L227 | Ir(L227) as Ir(L200) | 36% |
| Ir(L228) | L228 | Ir(L228) as Ir(L200) | 43% |
| Ir(L229) | L229 | Ir(L229) as Ir(L210) | 25% |
| Ir(L230) | L230 | Ir(L230) as Ir(L210) | 27% |
| Ir(L231) | L231 | Ir(L231) as Ir(L200) | 39% |
| Ir(L332) | L232 | Ir(L332) as Ir(L200) | 40% |
| Ir(L233) | L233 | Ir(L233) as Ir(L210) ethyl acetate | 26% |
| Ir(L234) | L234 | Ir(L234) as Ir(L209) | 26% |
| Ir(L235) | L235 | Ir(L235) as Ir(L209) | 23% |
| Ir(L236) | L236 | Ir(L236) as Ir(L209) | 25% |
| Ir(L237) | L237 | Ir(L237) as Ir(L209) | 25% |
| Ir(L259) | L259 | | 16% |
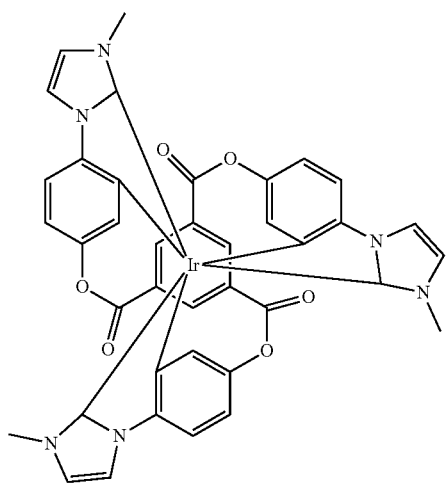
Ir(L259)
addition of 33 mmol of NaO-t-Bu
250° C.
2 h
toluene -continued
| Ex. | Ligand | Product<br>Variant<br>Reaction time*<br>Reaction temperature*<br>Extractant* | Yield |
|---|---|---|---|
| Ir(L260) | L260 | 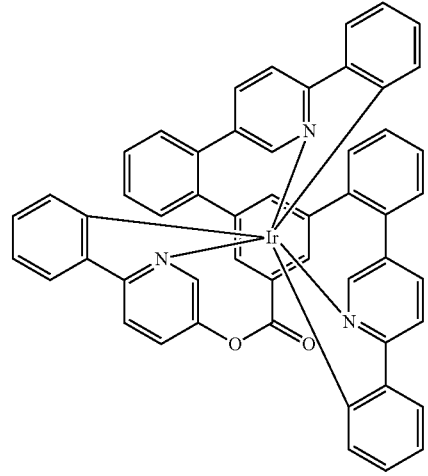<br>Ir(L260)<br>as Ir(L200) | 64% |
| Ir(L268) | L268 | 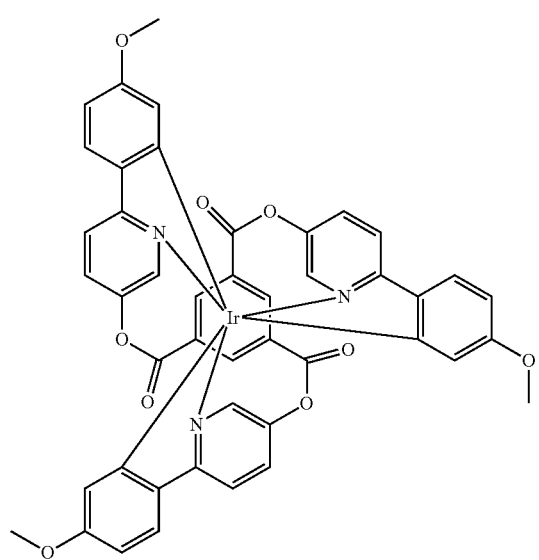<br>Ir(L268)<br>as Ir(L200) | 48% |

-continued

| Ex. | Ligand | Product Variant Reaction time* Reaction temperature* Extractant* | Yield |
|---|---|---|---|
| Ir(L300) | L300 | Ir(L300) 250° C. 2 h DCM | 49% |
| Ir(L301) | L301 | Ir(L301) as Ir(L300) | 57% |
| Ir(L302) | L302 | Ir(L302) as Ir(L300) | 38% |
| Ir(L303) | L303 | Ir(L303) as Ir(L300) | 52% |
| Ir(L304) | L304 | Ir(L304) 260° C. 2 h o-xylene | 34% |
| Ir(L305) | L305 | Ir(L305) as Ir(L300) | 46% |
| Ir(L306) | L306 | Ir(L306) as Ir(L300) | 47% |
| Ir(L307) | L307 | Ir(L307) as Ir(L300) | 44% |
| Ir(L308) | L308 | Ir(L308) 260° C. 2 h toluene | 32% |
| Ir(L309) | L309 | Ir(L309) as Ir(L300) | 40% |
| Ir(L310) | L310 | Ir(L310) as Ir(L308) | 33% |
| Ir(L311) | L311 | Ir(L311) as Ir(L300) | 43% |
| Ir(L312) | L312 | Ir(L312) as Ir(L308) | 30% |
| Ir(L313) | L313 | Ir(L313) as Ir(L308) | 35% |
| Ir(L314) | L314 | Ir(L314) as Ir(L308) | 36% |
| Ir(L315) | L315 | Ir(L315) as Ir(L300) | 45% |
| Ir(L316) | L316 | Ir(L316) as Ir(L300) | 47% |
| Ir(L317) | L317 | Ir(L317) as Ir(L304) | 31% |
| Ir(L318) | L318 | Ir(L318) as Ir(L300) | 41% |
| Ir(L319) | L319 | Ir(L319) as Ir(L300) | 43% |
| Ir(L320) | L320 | Ir(L320) as Ir(L304) | 30% |
| Ir(L321) | L321 | Ir(L321) as Ir(L304) | 33% |

| Ex. | Ligand | Product<br>Variant<br>Reaction time*<br>Reaction temperature*<br>Extractant* | Yield |
|---|---|---|---|
| Ir(L322) | L322 | 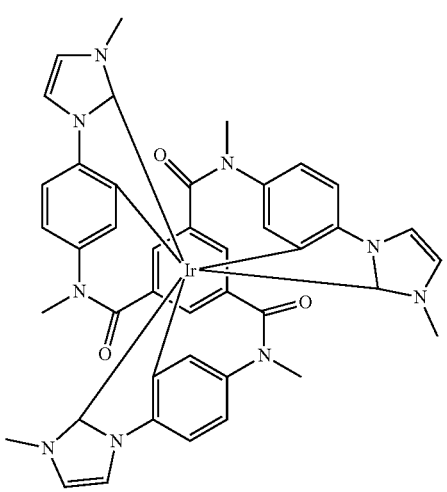<br>Ir(L322)<br>addition of 33 mmol of NaO-t-Bu<br>250° C.<br>2 h<br>toluene | 21% |
| Ir(L323) | L323 | 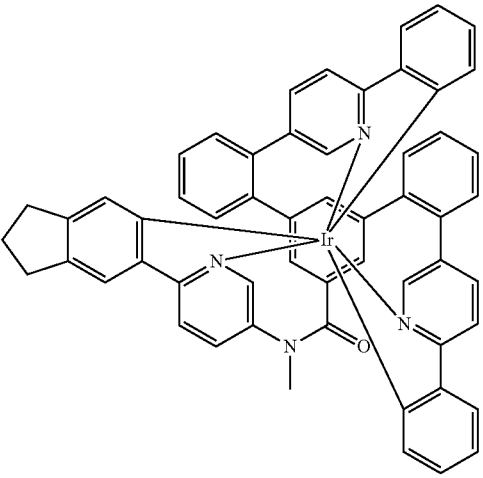<br>Ir(L322)<br>as Ir(L300) | 56% |
| Ir(L324) | L324 | Ir(L324)<br>as Ir(L300) | 60% |
| Ir(L325) | L325 | Ir(L325)<br>as Ir(L300) | 55% |
| Ir(L326) | L326 | Ir(L326)<br>as Ir(L300) | 57% |
| Ir(L327) | L327 | Ir(L327)<br>as Ir(L300)<br>Diastereomer mixture | 55% |
| Ir(L400) | L400 | Ir(L400)<br>as Ir(L300) | 56% |
| Ir(L401) | L401 | Ir(L401)<br>as Ir(L300) | 55% |
| Ir(L402) | L402 | Ir(L402)<br>as Ir(L300) | 50% |
| Ir(L403) | L403 | Ir(L403)<br>as Ir(L300) | 37% |

-continued
| Ex. | Ligand | Product<br>Variant<br>Reaction time*<br>Reaction temperature*<br>Extractant* | Yield |
|---|---|---|---|
| Ir(L404) | L404 | Ir(L404)<br>as Ir(L300) | 52% |
| Ir(L405) | L405 | Ir(L405)<br>as Ir(L300) | 49% |
| Ir(L406) | L406 | Ir(L406)<br>as Ir(L300) | 51% |
| Ir(L407) | L407 | Ir(L407)<br>as Ir(L300) | 47% |
| Ir(L408) | L408 | Ir(L408)<br>as Ir(L300) | 34% |
| Ir(L500) | L(500) | 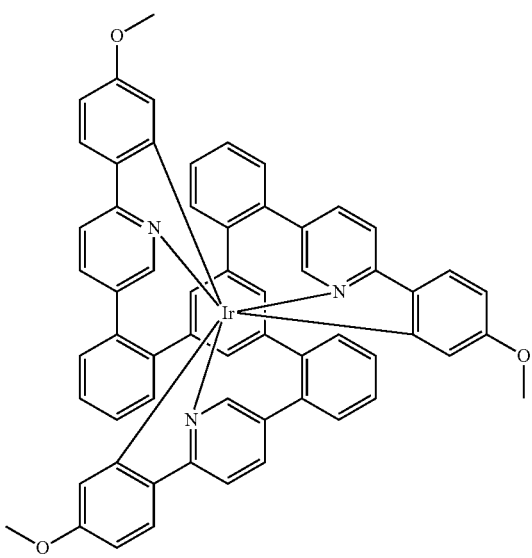<br>Ir(L500)<br>250° C.<br>1.5 h<br>1 x hot extraction of the crude product with<br>DCM | 85% |
| Ir(L501) | L(501) | Ir(L501)<br>as Ir(L500) | 56% |
| Ir(L502) | L(502) | Ir(L502)<br>as Ir(L500) | 49% |
| Ir(L503) | L(503) | Ir(L503)<br>as Ir(L500) | 46% |
*: if different Metal Complexes of Ligands L15, L16, L17:

Procedure analogous to example Ir(L1) using the metal compounds specified in the table. Hot extraction with ethyl acetate or dichloromethane.

| Ex. | Ligand Metal salt | Product | Yield |
|---|---|---|---|
| Al(L15) | L15 Al(O-$^i$C$_3$H$_7$)$_3$ [555-31-7] | Al(L15) | 23% |
| Al(L16) | L16 Al(O-$^i$C$_3$H$_7$)$_3$ | Al(L16) | 27% |
| Al(L17) | L17 Al(O-$^i$C$_3$H$_7$)$_3$ | Al(L17) | 22% |

-continued

| Ex. | Ligand Metal salt | Product | Yield |
|---|---|---|---|
| Ga(L17) | L17<br>Ga(O-$^i$C$_3$H$_7$)$_3$<br>[4452-61-3] | Ga(L17) | 37% |
| La(L16) | L16<br>LaCl$_3$ | La(L16) | 41% |
| Fe(L15) | L15<br>FeCl$_3$ | Fe(L15) | 46% |
| Fe(L16) | L16<br>FeCl$_3$ | Fe(L16) | 44% |
| Ru(L15) | L15<br>RuCl$_3$ | Ru(L15) | 38% |

D: Functionalization of the Metal Complexes:

1) Halogenation of the Iridium Complexes:

To a solution or suspension of 10 mmol of a complex bearing A×C—H groups (with A=1, 2, 3) in the para position to the iridium in 500 ml to 2000 ml of dichloromethane according to the solubility of the metal complexes is added, in the dark and with exclusion of air, at −30 to +30° C., A x 10.5 mmol of N-halosuccinimide (halogen: Cl, Br, I), and the mixture is stirred for 20 h. Complexes of sparing solubility in DCM may also be converted in other solvents (TCE, THF, DMF, chlorobenzene, etc.) and at elevated temperature. Subsequently, the solvent is substantially removed under reduced pressure. The residue is extracted by boiling with 100 ml of methanol, and the solids are filtered off with suction, washed three times with 30 ml of methanol and then dried under reduced pressure. This gives the iridium complexes brominated in the para position to the iridium. Complexes having a HOMO (CV) of about −5.1 to −5.0 eV and of smaller magnitude have a tendency to oxidation (Ir(III)>Ir(IV)), the oxidizing agent being bromine released from NBS. This oxidation reaction is apparent by a distinct green hue in the otherwise yellow to red solutions/suspensions of the emitters. In such cases, a further equivalent of NBS is added. For workup, 300-500 ml of methanol and 2 ml of hydrazine hydrate as reducing agent are added, which causes the green solutions/suspensions to turn yellow (reduction of Ir(IV)>Ir(III)). Then the solvent is substantially drawn off under reduced pressure, 300 ml of methanol are added, and the solids are filtered off with suction, washed three times with 100 ml each time of methanol and dried under reduced pressure.

Substoichiometric brominations, for example mono- and dibrominations of complexes having 3 C—H groups in the para position to iridium, usually proceed less selectively than the stoichiometric brominations. The crude products of these brominations can be separated by chromatography (CombiFlash Torrent from A. Semrau).

Synthesis of Ir(L200-3Br):

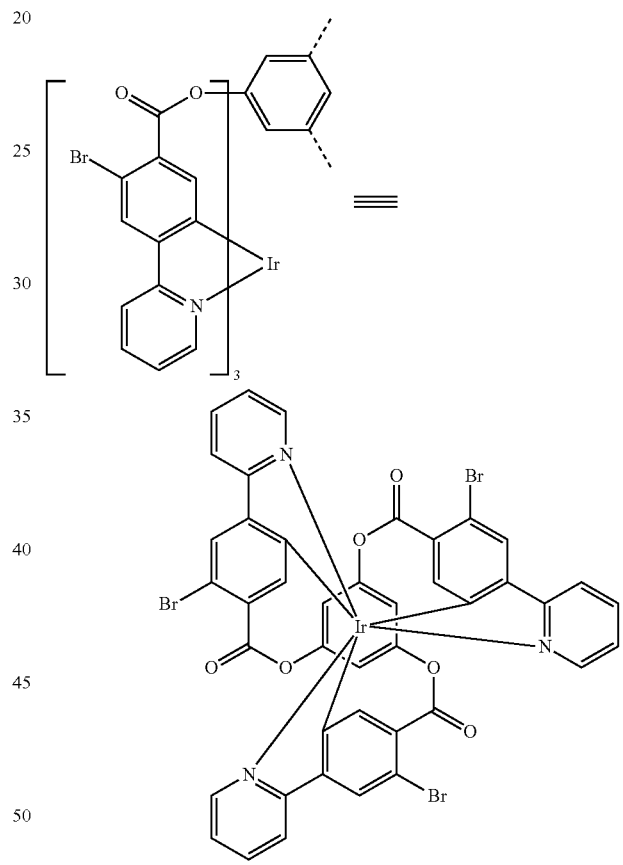

To a suspension, stirred at room temperature, of 8.6 g (10 mmol) of Ir(L200) in 500 ml of DCM are added 5.6 g (31.5 mmol) of N-bromosuccinimide all at once and then the mixture is stirred for a further 20 h. After removing about 400 ml of the DCM under reduced pressure, 200 ml of methanol are added to the yellow suspension, and the solids are filtered off with suction, washed three times with about 50 ml of methanol each time and then dried under reduced pressure. Yield: 10.6 g (9.3 mmol), 93%; purity: >99.0% by NMR.

In an analogous manner, it is possible to prepare the following compounds:

| Ex. | Reactant > brominated complex | Yield |
|---|---|---|
| | Tribromination | |
| Ir(L201-3Br) | 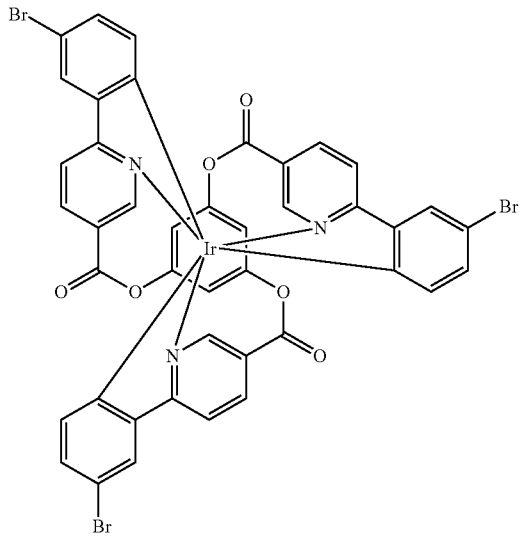
Ir(L201) > Ir(L201-3Br) | 94% |
| Ir(L204-3Br) | 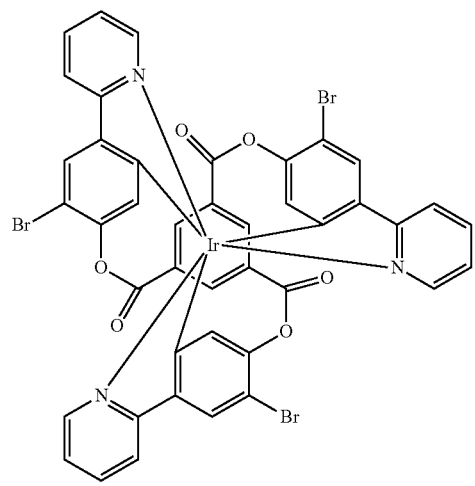
Ir(L204) > Ir(L204-3Br) | 90% |

-continued

| Ex. | Reactant > brominated complex | Yield |
|---|---|---|
| Ir(L205-3Br) | Ir(L205) > Ir(L205-3Br) | 95% |
| Ir(L223-3Br) | Ir(L223) > Ir(L223-3Br) | 92% |

-continued

| Ex. | Reactant > brominated complex | Yield |
|---|---|---|
| Ir(L232-3Br) | Ir(L232) > Ir(L232-3Br) | 91% |
| Ir(L235-3Br) | Ir(L235) > Ir(L235-3Br) | 88% |

-continued

| Ex. | Reactant > brominated complex | Yield |
|---|---|---|
| Ir(L262-3Br) | Ir(L262) > Ir(L262-3Br) | 91% |
| Ir(L300-3Br) | Ir(L300) > Ir(L300-3Br) | 90% |
| Ir(L301-3Br) | Ir(L301) > Ir(L301-3Br) | 93% |

-continued
| Ex. | Reactant > brominated complex | Yield |
|---|---|---|
| Ir(L302-3Br) | 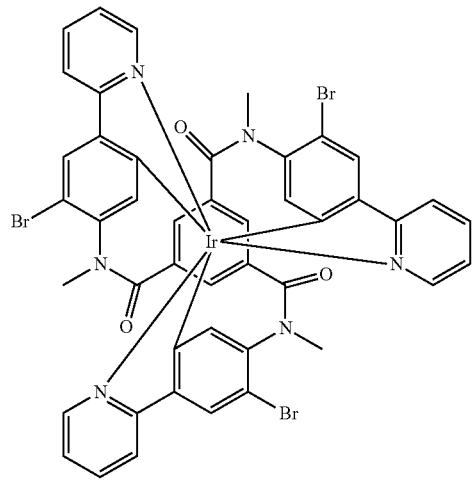<br>Ir(L302) > Ir(L302-3Br) | 87% |
| Ir(L303-3Br) | 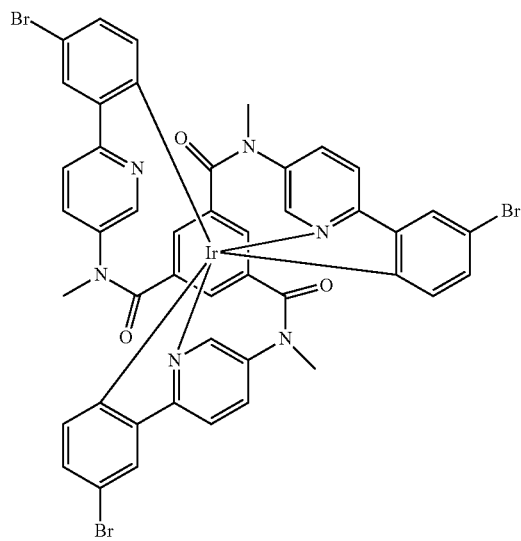<br>Ir(L303) > Ir(L303-3Br) | 92% |

-continued

| Ex. | Reactant > brominated complex | Yield |
|---|---|---|
| Ir(L317-3Br) | Ir(L317) > Ir(L317-3Br) | 93% |
| Ir(L320-3Br) | Ir(L320) > Ir(L320-3Br) | 87% |

US 11,031,562 B2
313                                                                                                                   314
-continued

| Ex. | Reactant > brominated complex | Yield |
|---|---|---|
| Ir(L326-3Br) | Ir(L326) > Ir(L326-3Br) | 88% |
| Ir(L400-3Br) | Ir(L400) > Ir(L400-3Br) | 76% |

-continued
| Ex. | Reactant > brominated complex | Yield |
|---|---|---|
| Ir(L403-3Br) | 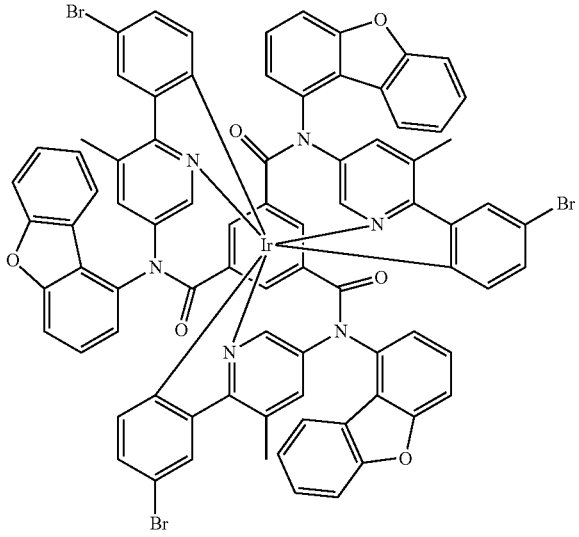 Ir(L403) > Ir(L403-3Br) | 86% |
| IrK1-3Br | 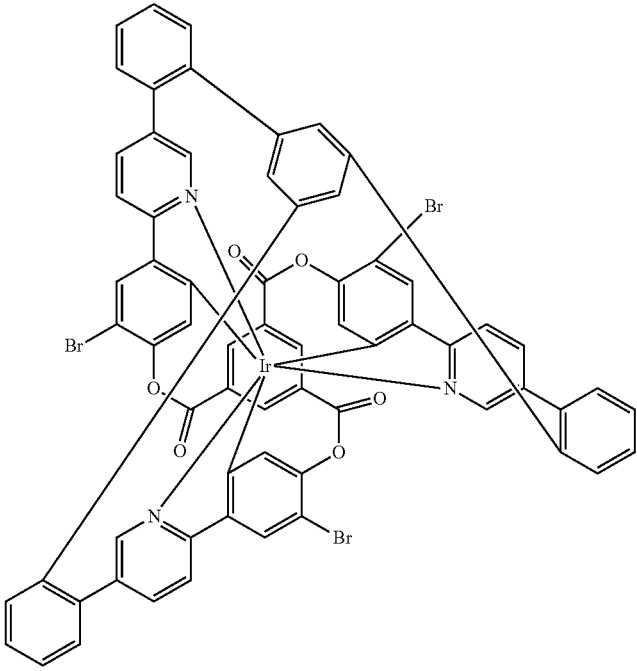 IrK1 > IrK1-3Br | 79% |

-continued
| Ex. | Reactant > brominated complex | Yield |
|---|---|---|
| IrK4-3Br | 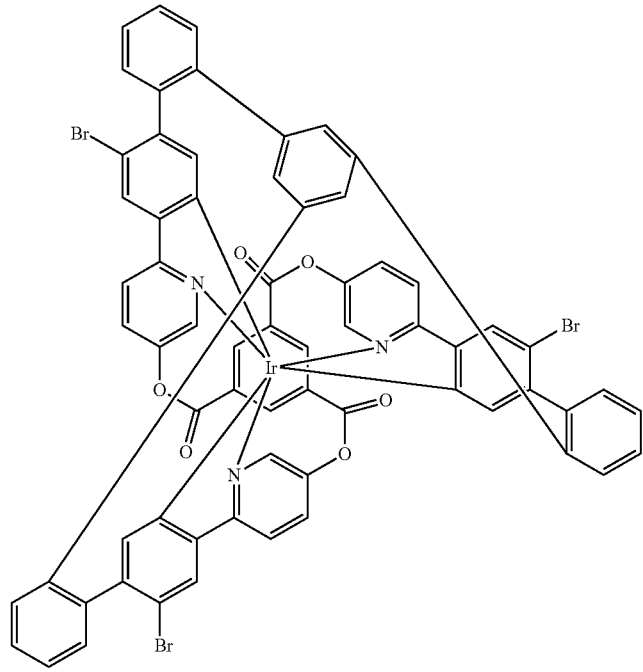<br>IrK4 > IrK4-3Br | 90% |
| IrK12-3Br | 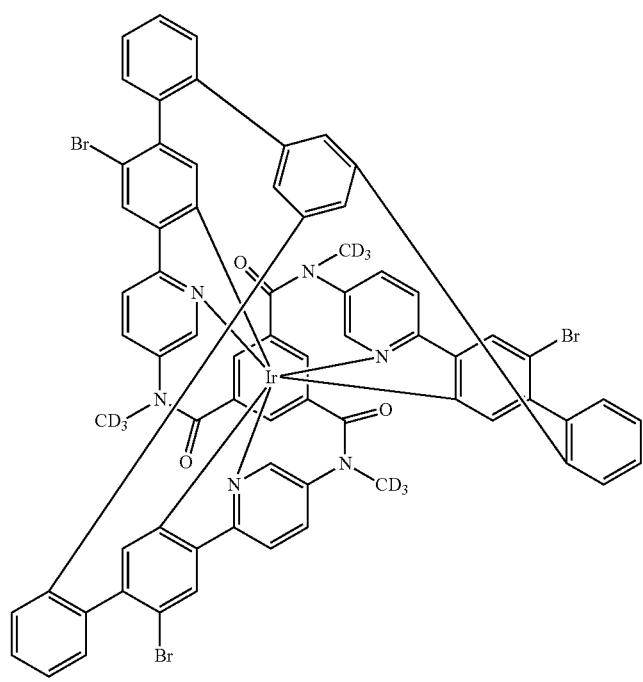<br>IrK12 > IrK12-3Br | 92% |

-continued
| Ex. | Reactant > brominated complex | Yield |
|---|---|---|
| IrK21-3Br | 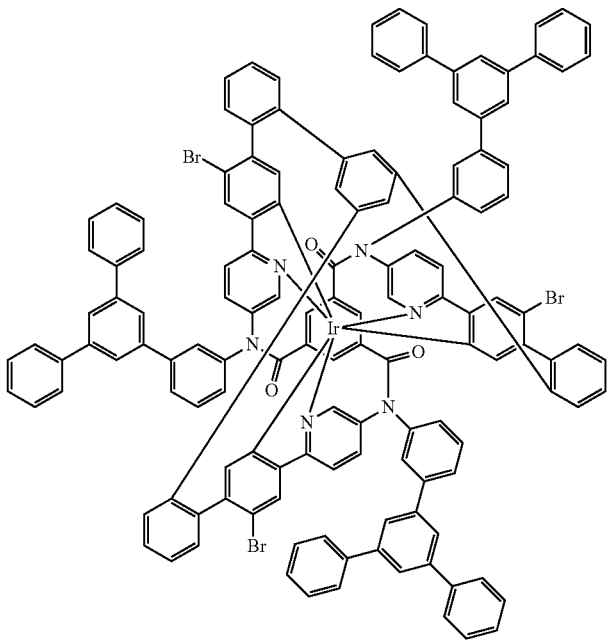 IrK21 > IrK21-3Br | 88% |
| Dibromides | | |
|---|---|---|
| Ir(L301-2Br) | 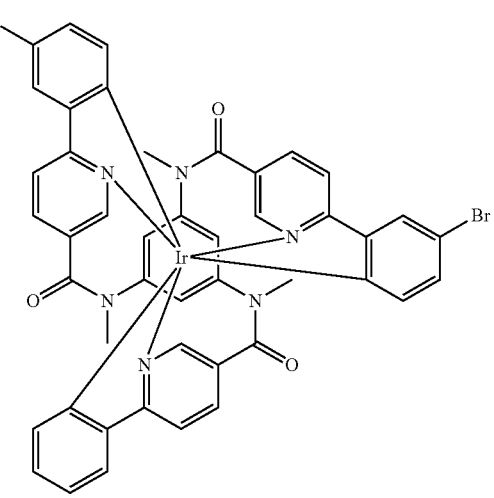 Ir(L301) > Ir(L301-2Br) 2 eq NBS, DCM, 0° C. chromatography with DCM on silica gel | 26% |

-continued
| Ex. | Reactant > brominated complex | Yield |
|---|---|---|
| Ir(L323-2Br) | 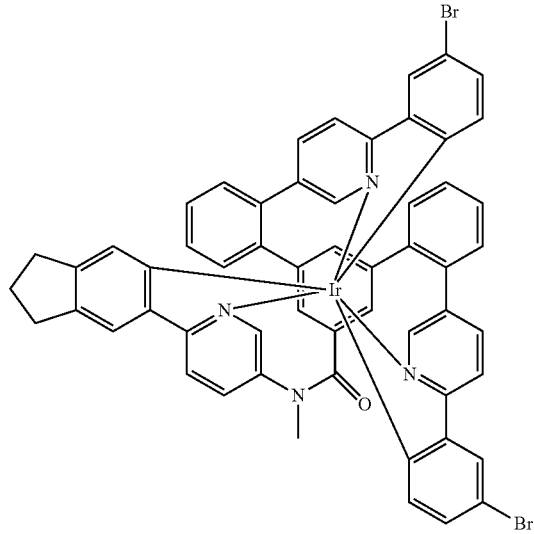
Ir(L323) > Ir(L323-2Br) | 90% |
| Ir(L405-2Br) | 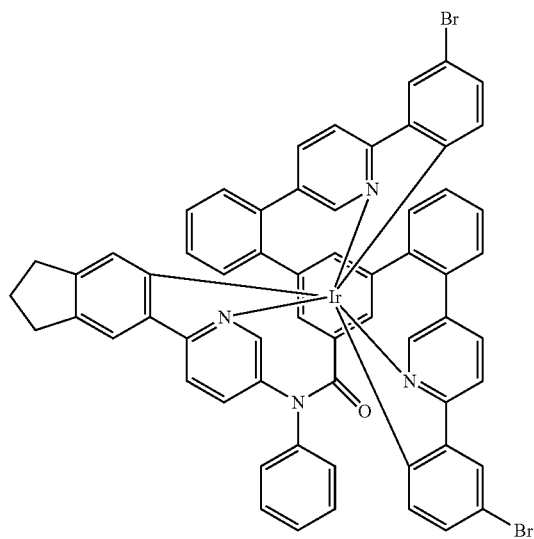
Ir(L405) > Ir(L405-2Br) | 92% |

-continued

| Ex. | Reactant > brominated complex | Yield |
|---|---|---|
| | Monobromides | |
| Ir(L301-2Br) | Ir(L301) > Ir(L301-1Br)<br>1 eq NBS, DCM, 0° C.<br>chromatography with DCM on silica gel | 22% |

2) Suzuki Coupling with the Brominated Iridium Complexes:

Variant A, Biphasic Reaction Mixture:

To a suspension of 10 mmol of a brominated complex, 12-20 mmol of boronic acid or boronic ester per Br function and 40-80 mmol of tripotassium phosphate in a mixture of 300 ml of toluene, 100 ml of dioxane and 300 ml of water are added 0.6 mmol of tri-o-tolylphosphine and then 0.1 mmol of palladium(II) acetate, and the mixture is heated under reflux for 16 h. After cooling, 500 ml of water and 200 ml of toluene are added, the aqueous phase is removed, and the organic phase is washed three times with 200 ml of water and once with 200 ml of saturated sodium chloride solution and dried over magnesium sulphate. The mixture is filtered through a Celite bed and washed through with toluene, the toluene is removed almost completely under reduced pressure, 300 ml of methanol are added, and the precipitated crude product is filtered off with suction, washed three times with 50 ml each time of methanol and dried under reduced pressure. The crude product is columned on silica gel. The metal complex is finally heat-treated or sublimed. The heat treatment is effected under high vacuum (p about $10^{-6}$ mbar) within the temperature range of about 200-300° C. The sublimation is effected under high vacuum (p about $10^{-6}$ mbar) within the temperature range of about 300-400° C., the sublimation preferably being conducted in the form of a fractional sublimation.

Variant B, Monophasic Reaction Mixture:

To a suspension of 10 mmol of a brominated complex, 12-20 mmol of boronic acid or boronic ester per Br function and 60-100 mmol of the base (potassium fluoride, tripotassium phosphate (anhydrous or monohydrate or trihydrate), potassium carbonate, caesium carbonate etc.) and 100 g of glass beads (diameter 3 mm) in 100 ml-500 ml of an aprotic solvent (THF, dioxane, xylene, mesitylene, dimethylacetamide, NMP, DMSO, etc.) are added 0.6 mmol of tri-o-tolylphosphine and then 0.1 mmol of palladium(II) acetate, and the mixture is heated at elevated temperature (90-130° C.) or under reflux for 1-24 h. Alternatively, it is possible to use other phosphines such as triphenylphosphine, tri-tert-butylphosphine, Sphos, Xphos, RuPhos, XanthPhos, etc., the preferred phosphine:palladium ratio in the case of these phosphines being 3:1 to 1.2:1. The solvent is removed under reduced pressure, the product is taken up in a suitable solvent (toluene, dichloromethane, ethyl acetate, etc.) and purification is effected as described in Variant A.

Synthesis of Ir100:

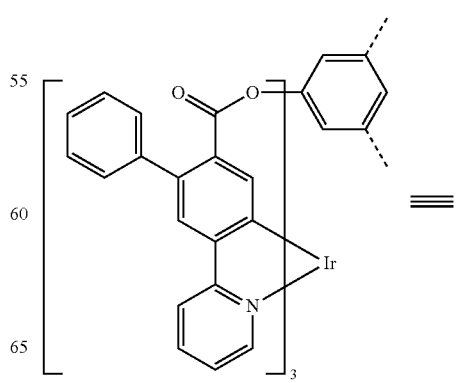

-continued

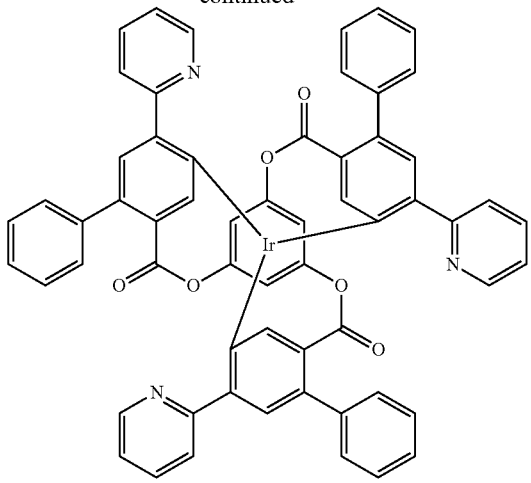

Variant A:

Use of 11.0 g (10.0 mmol) of Ir(L200-3Br) and 7.3 g (60.0 mmol) of phenylboronic acid [98-80-6], 12.7 g (60 mmol) of tripotassium phosphate (anhydrous), 183 mg (0.6 mmol) of tri-o-tolylphosphine [6163-58-2], 23 mg (0.1 mmol) of palladium(II) acetate, 300 ml of toluene, 100 ml of dioxane and 300 ml of water, reflux, 16 h. Chromatographic separation on silica gel with toluene/ethyl acetate (7:3, v/v), followed by hot extraction five times with ethyl acetate. Yield: 5.7 g (5.2 mmol), 52%; purity: about 99.9% by HPLC.

Variant B:

As A, except using 13.8 g (60 mmol) of tripotassium phosphate monohydrate, 693 g (0.6 mmol) of tetrakis(triphenylphosphine)palladium(0), 150 ml of DMSO, 90° C., 24 h. After cooling, pour into 500 ml of methanol, filter off solids with suction, wash three times with 50 ml each time of methanol and dry the solid under reduced pressure. Further purification is effected by chromatography and via hot extraction as described above. Yield: 6.2 g (5.7 mmol), 62%; purity: about 99.9% by HPLC.

In an analogous manner, it is possible to prepare the following compounds:

| Ex. | Bromide/boronic acid/variant Product | Yield |
|---|---|---|
| Ir101 | Ir(201-3Br)/5122-95-2/A 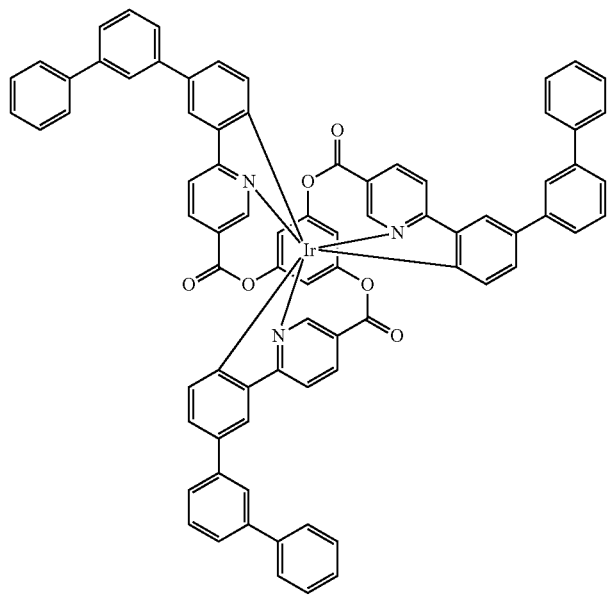 | 60% |

-continued
| Ex. | Bromide/boronic acid/variant Product | Yield |
|---|---|---|
| Ir102 | Ir(L204-3Br)/1233200-59-3/A | 62% |
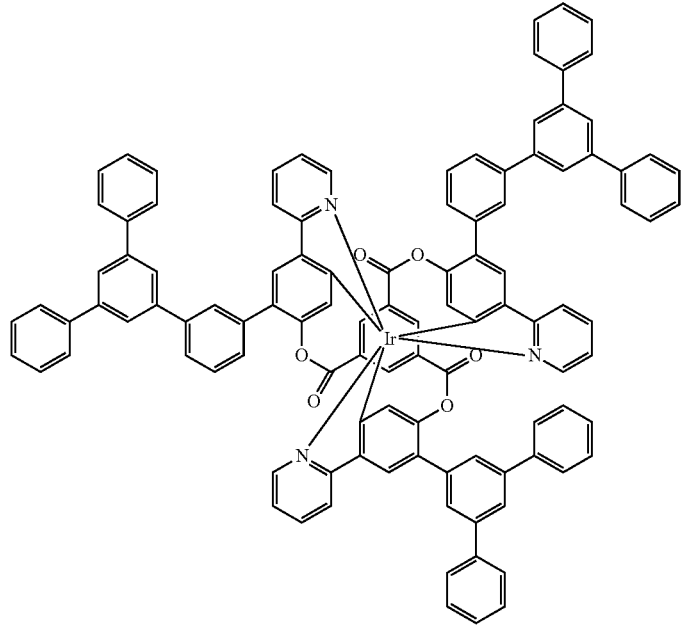
| Ir103 | Ir(L205-3Br)/100124-06-9/A | 58% |
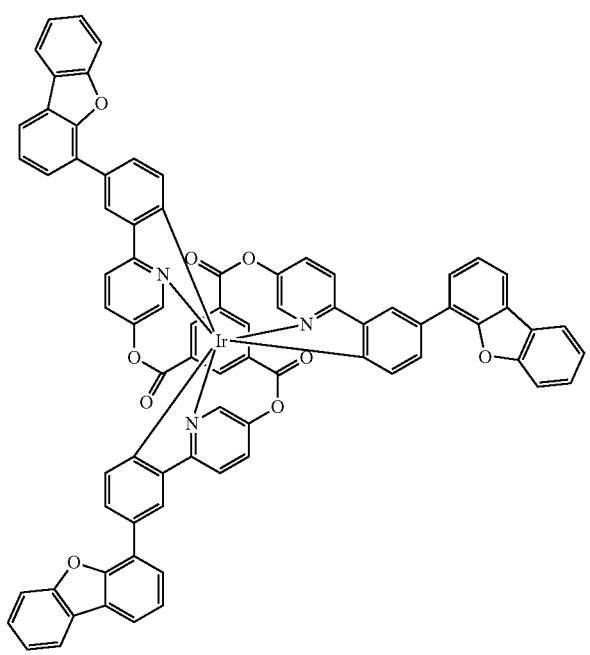

-continued
| | Bromide/boronic acid/variant | |
| Ex. | Product | Yield |
| Ir104 | Ir(L223-3Br)/84110-40-7/B<br>SPhos: Pd(ac)$_2$/2:1/K$_3$PO$_4$*3H$_2$O<br>Toluene/chromatographic separation with toluene | 46% |
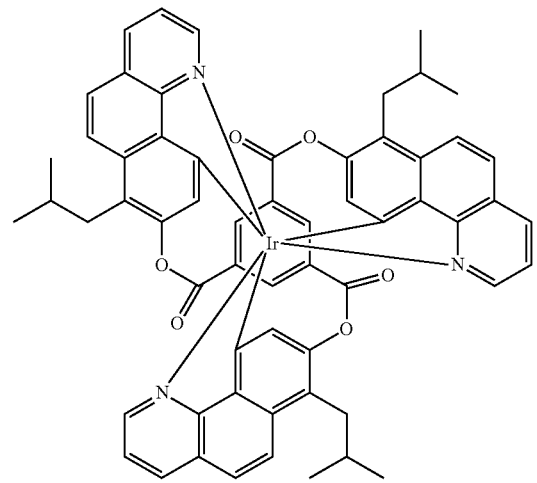
| Ir105 | Ir(L232-3Br)/162607-19-4/A | 68% |
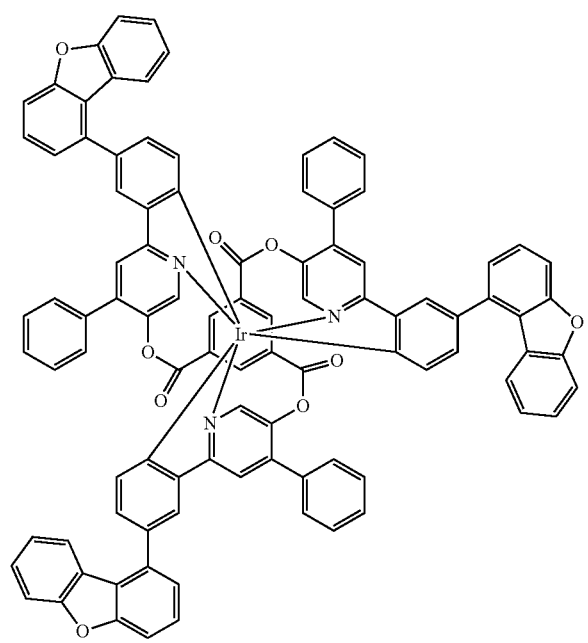

| Ex. | Bromide/boronic acid/variant Product | Yield |
|---|---|---|
| Ir106 | Ir(L235-3Br)/98-80-6/A | 55% |
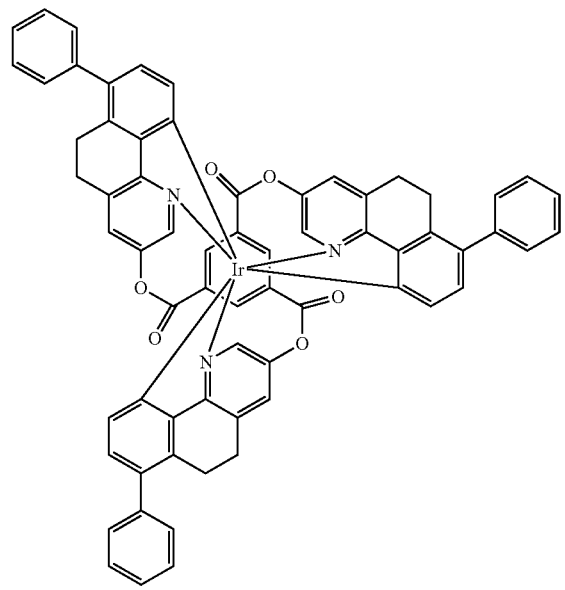
| Ir107 | Ir(L262-3Br)/854952-58-2/A | 57% |
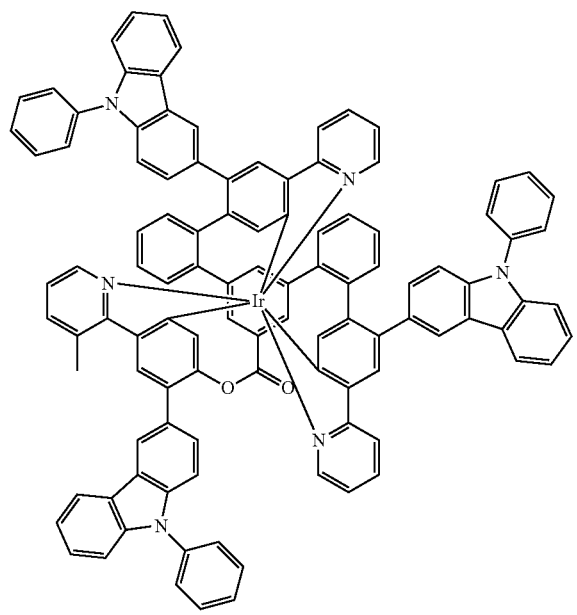

-continued
| Ex. | Bromide/boronic acid/variant<br>Product | Yield |
|---|---|---|
| Ir108 | Ir(L300-3Br)/5122-95-2/B<br>9 mol % Pd(PPh₃)₄/K₃PO₄ × 1 H₂O/DMSO/80° C./60 h<br>Chromatographic purification with DCM<br>and 5 × hot extraction with ethyl acetate | 47% |
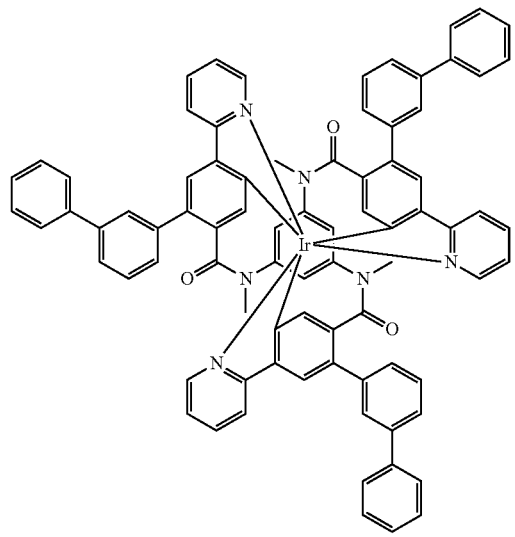
| | | |
|---|---|---|
| Ir109 | Ir(L301-3Br)/1421789-05-0/conditions as Ir108 | 66% |
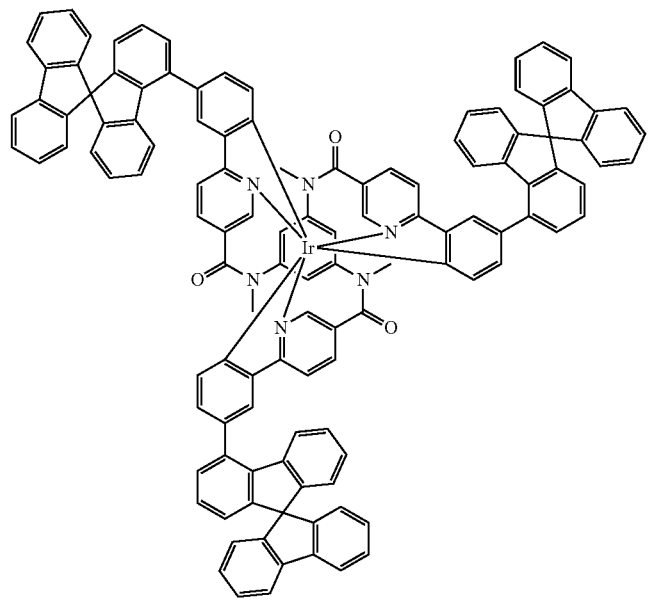

-continued
| Ex. | Bromide/boronic acid/variant Product | Yield |
|---|---|---|
| Ir110 | Ir(L302-3Br)/1703019-86-6/conditions as Ir110 Hot extraction with toluene | 45% |
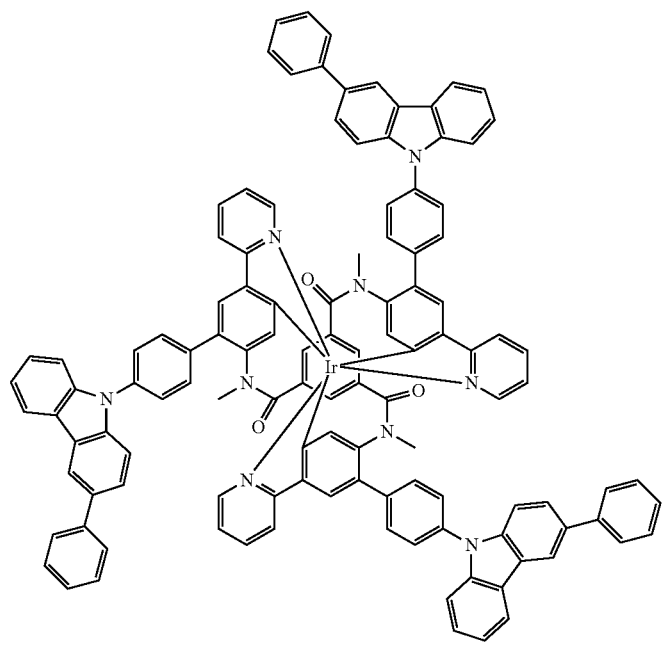
| Ir111 | Ir(L303-3Br)/1313018-07-3/A | 69% |
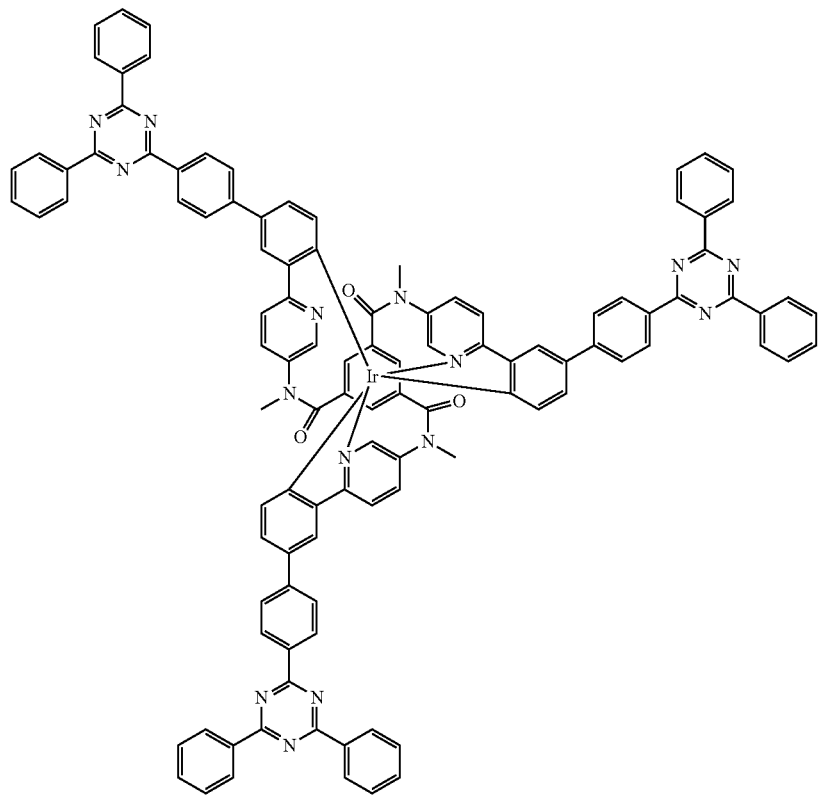

-continued
| Ex. | Bromide/boronic acid/variant Product | Yield |
|---|---|---|
| Ir112 | Ir(L317-3Br)/1680179-22-9/conditions as Ir108 | 65% |
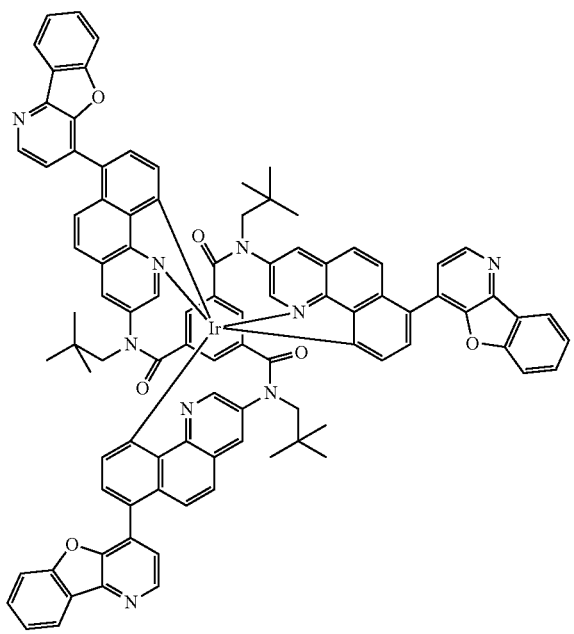
| Ir113 | Ir(L320-3Br)/333432-28-3/conditions as Ir108 | 68% |
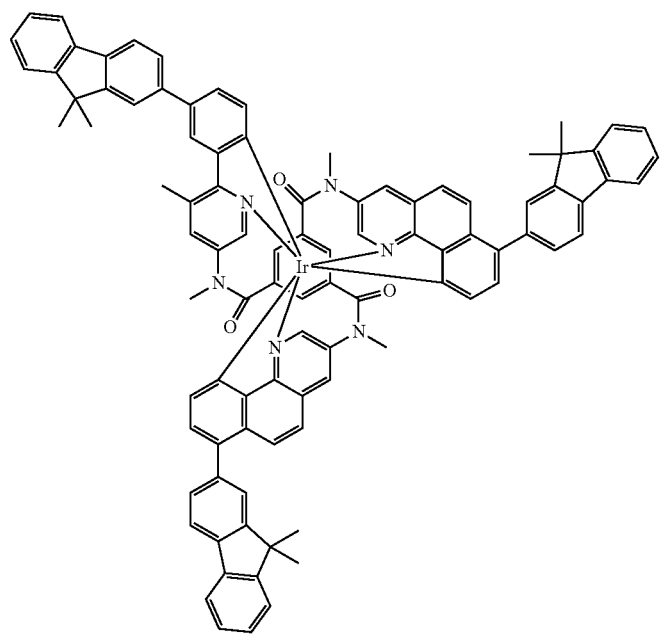

-continued
| Ex. | Bromide/boronic acid/variant Product | Yield |
|---|---|---|
| Ir114 | Ir(L326)-3Br/153624-42-1/conditions as Ir108 | 47% |
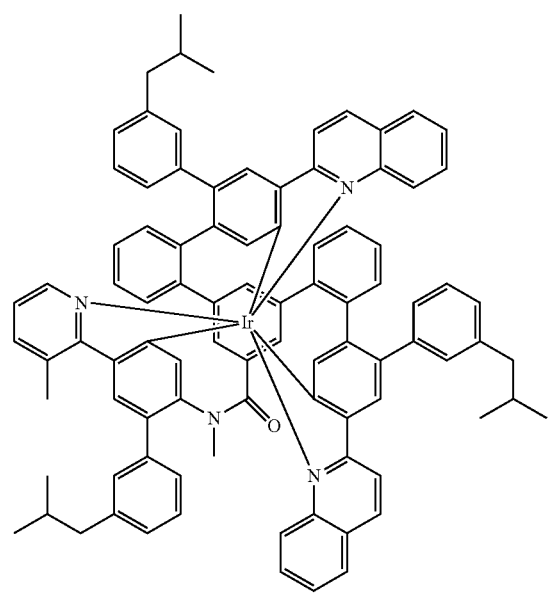
| Ir115 | Ir(L400-3Br)/98-80-6/A | 38% |
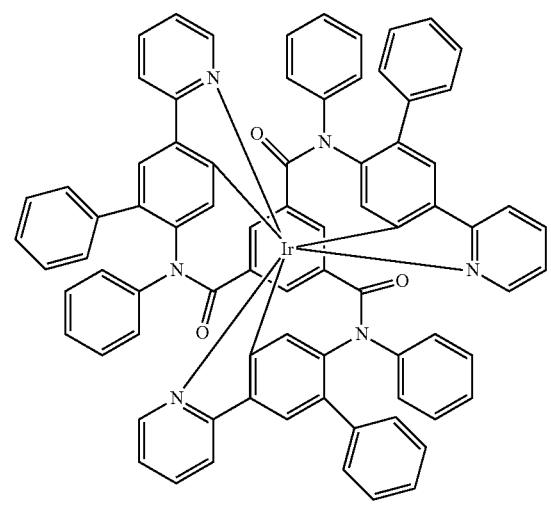

-continued
| Ex. | Bromide/boronic acid/variant Product | Yield |
|---|---|---|
| Ir116 | Ir(L403-3Br)/1357066-50-2/ | 59% |
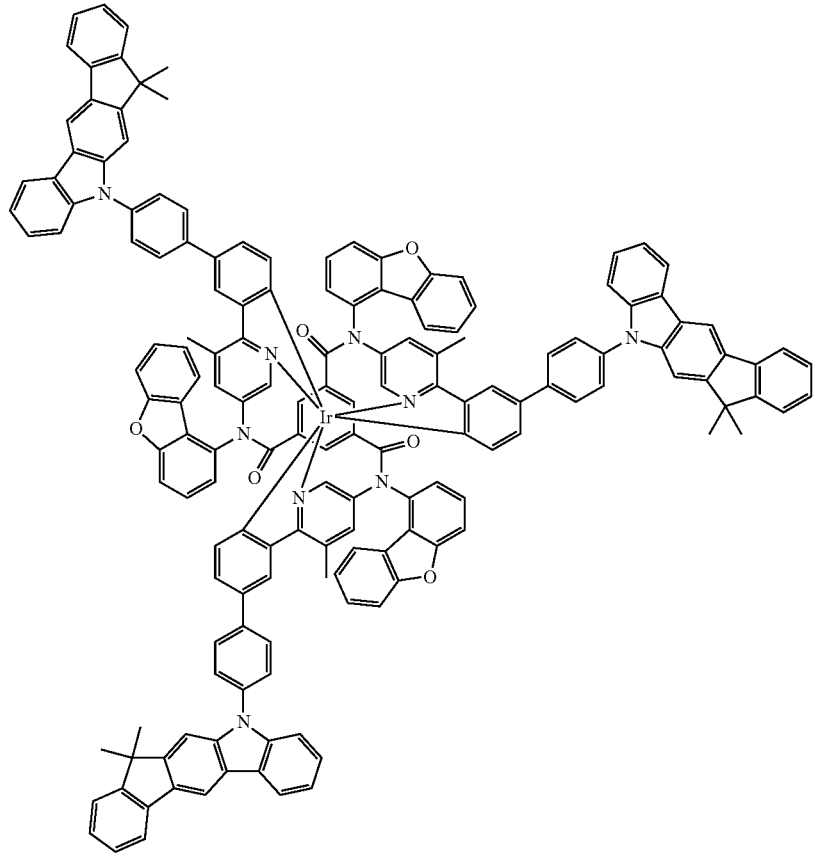
| Ir117 | Ir(L301-2Br)/854952-58-2/conditions as Ir108 | 62% |
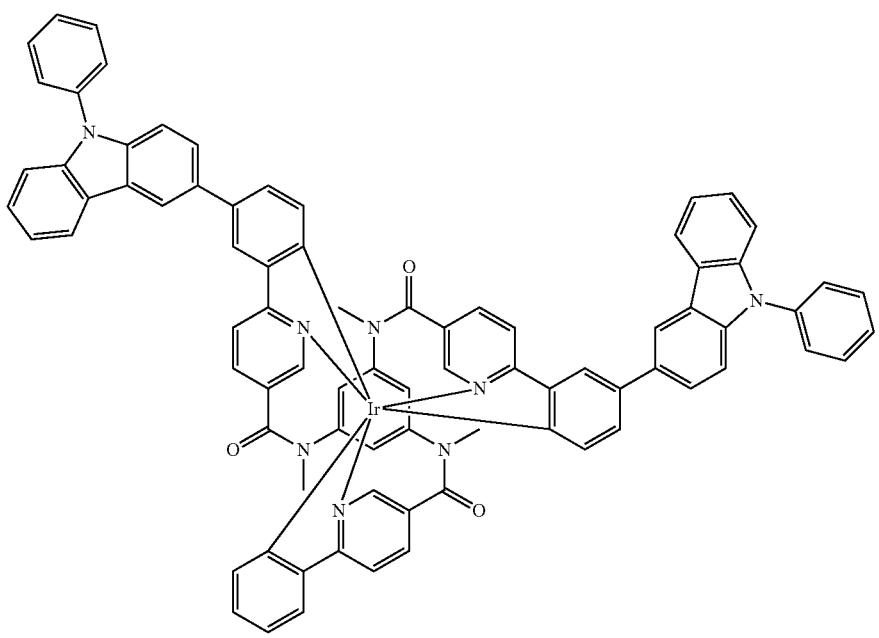

-continued
| Ex. | Bromide/boronic acid/variant Product | Yield |
|---|---|---|
| Ir118 | Ir(L323-3Br)/796071-96-0/conditions as Ir108 | 63% |
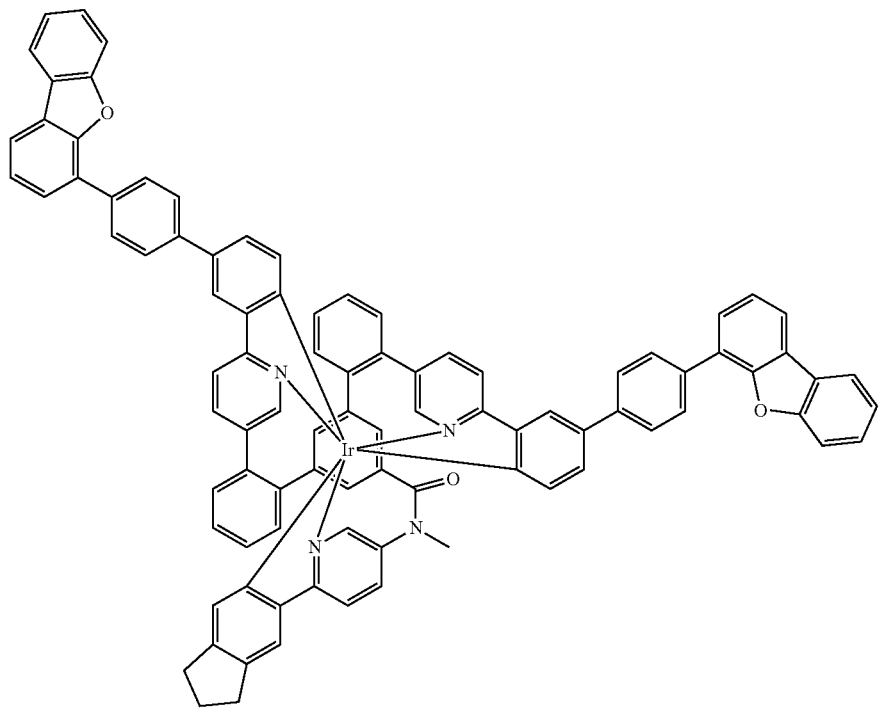
| Ir119 | Ir(L405-3Br)/197223-39-5/conditions as Ir108 | 57% |
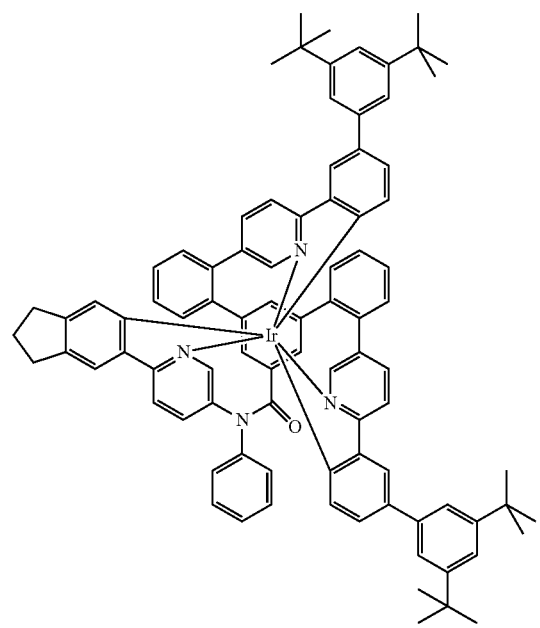

-continued
| Ex. | Bromide/boronic acid/variant<br>Product | Yield |
|---|---|---|
| Ir120 | Ir(L301)/796071-96-0/conditions as Ir108 | 49% |
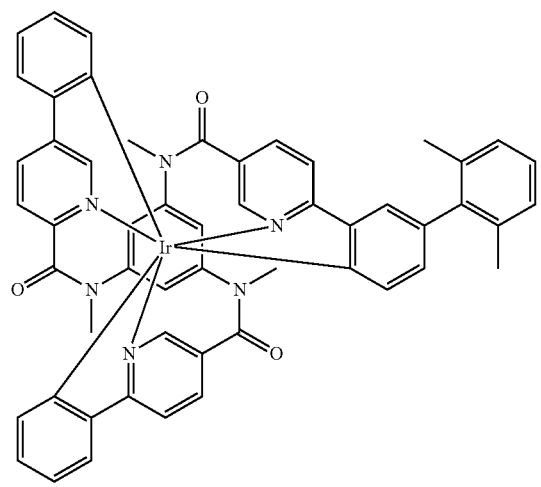
| Ir121 | Ir(L215-3B)/3842-55-5/conditions as Ir108 | 59% |
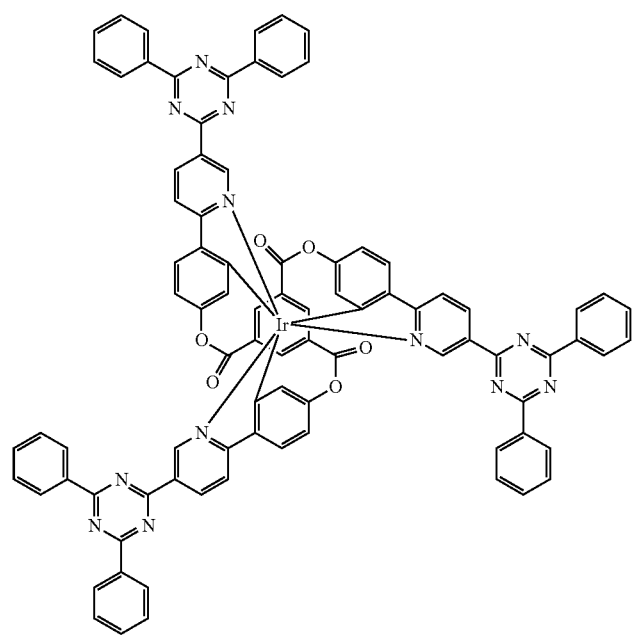

-continued

| Ex. | Bromide/boronic acid/variant Product | Yield |
|---|---|---|
| Ir122 | Ir(L215-3B)/253158-13-3/conditions as Ir108 | 63% |
| Ir123 | Ir(L215-3B)/1689576-03-1/conditions as Ir108 | 60% |

-continued
| Ex. | Bromide/boronic acid/variant<br>Product | Yield |
|---|---|---|
| Ir124 | Ir(L215-3B)/73-84-03-4/conditions as Ir108 | 65% |
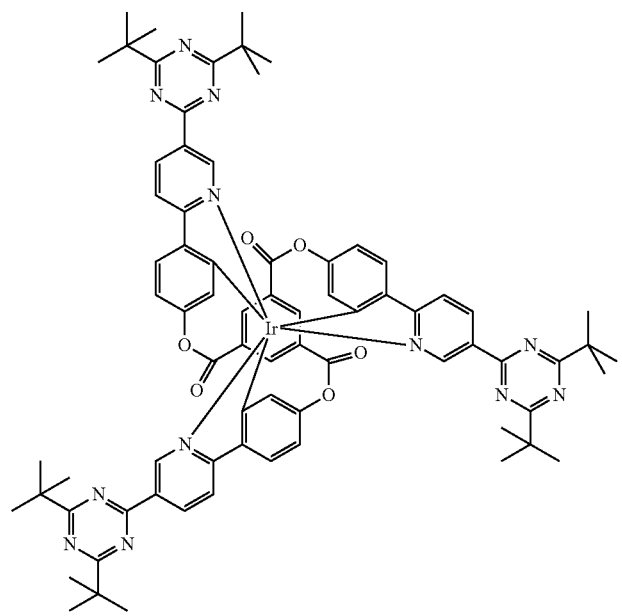
| Ir125 | Ir(L303-3B)/89827-45-2/conditions as Ir108 | 67% |
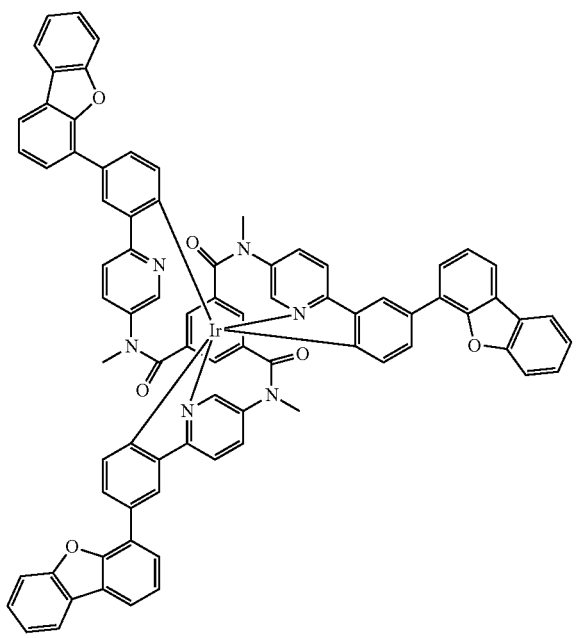

-continued
| Ex. | Bromide/boronic acid/variant Product | Yield |
|---|---|---|
| Ir126 | Ir(L405-2B)/1802584-76-4/conditions as Ir108 | 47% |
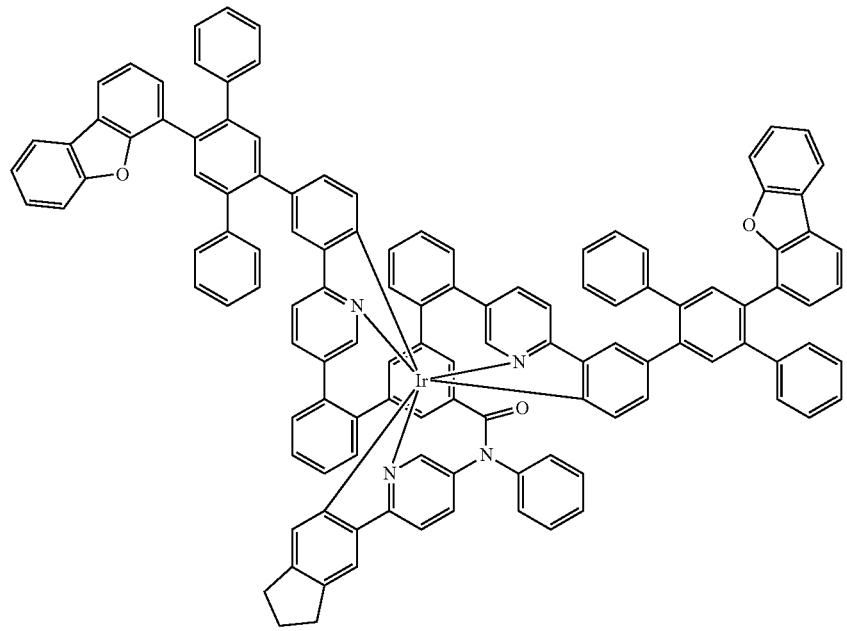
| Ir127 | Ir(K1-3Br)//98-80-6/conditions as Ir108 | 39% |
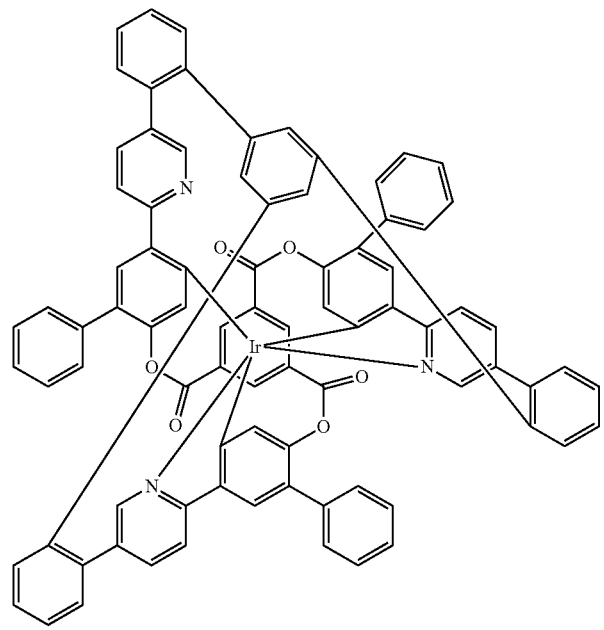

-continued
| Ex. | Bromide/boronic acid/variant Product | Yield |
|---|---|---|
| Ir128 | Ir(K4-3Br)//1233200-59-3/conditions as Ir108 | 45% |
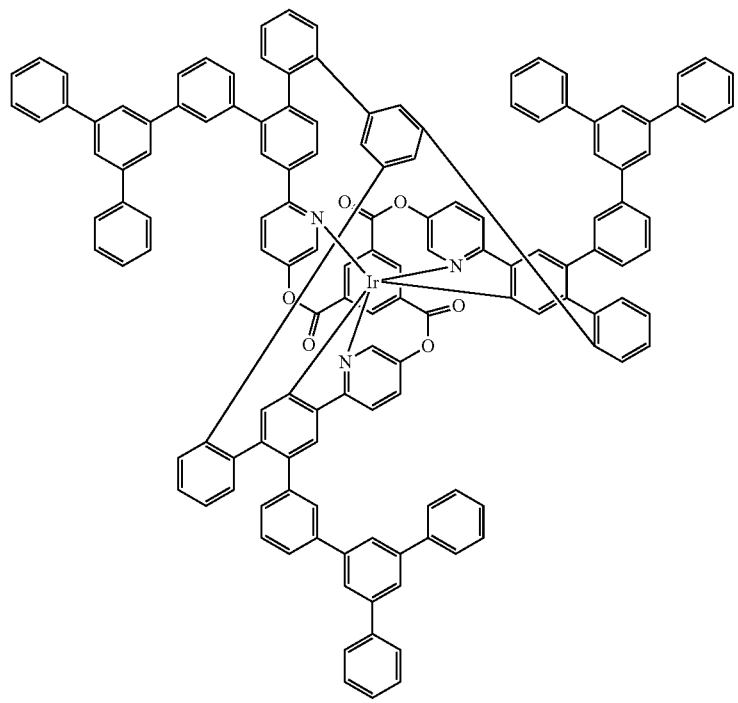
| Ir129 | Ir(K12-3Br)/796071-96-0/conditions as Ir108 | 43% |
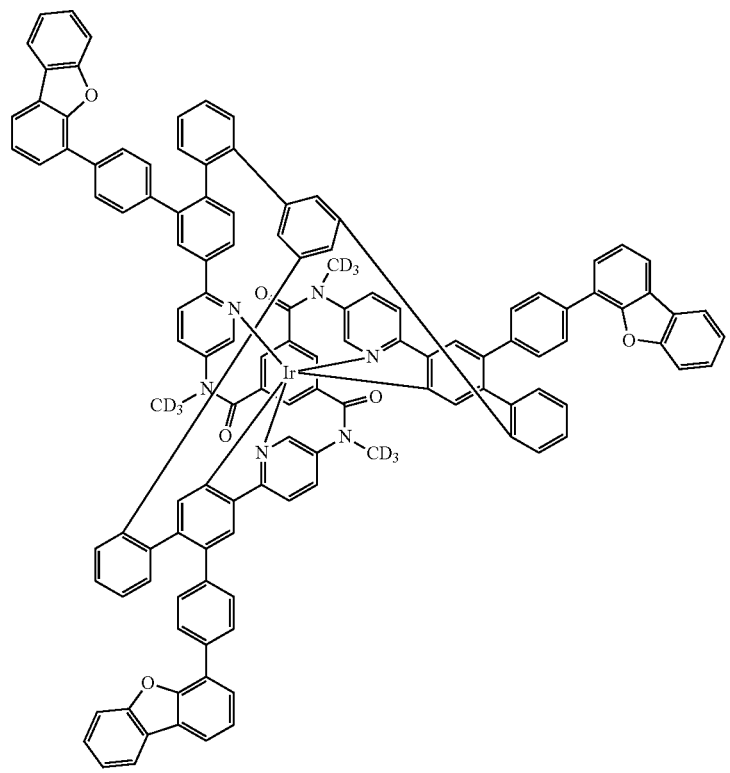

| Ex. | Bromide/boronic acid/variant Product | Yield |
|---|---|---|
| Ir130 | Ir(K21-3Br)/1233200-59-3/conditions as Ir108 | 37% |

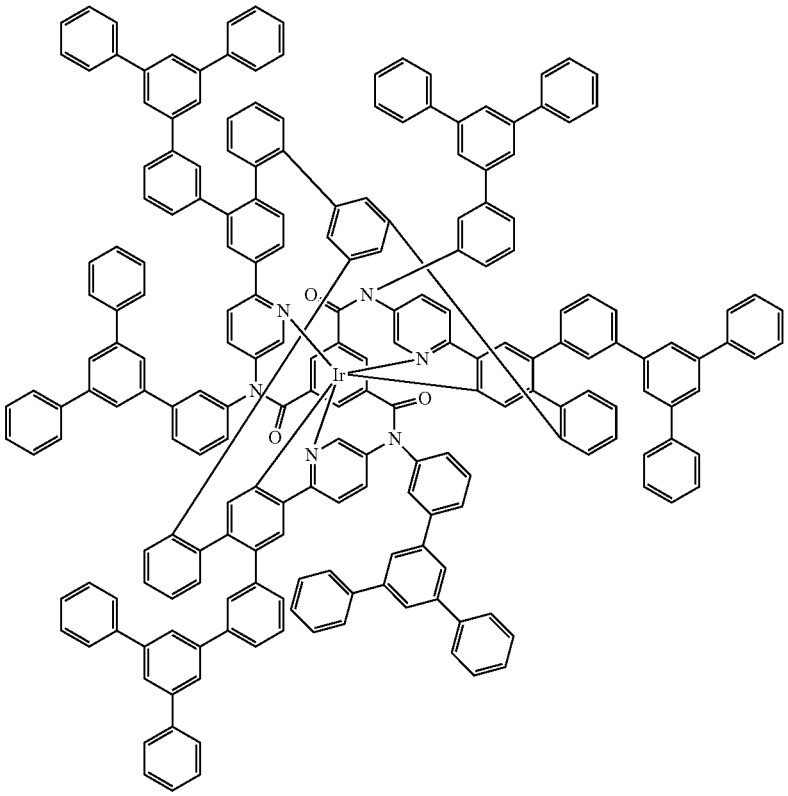

3) Borylation of the Iridium Complexes:

A mixture of 10 mmol of the brominated complex, 12 mmol of bis(pinacolato)diborane [73183-34-3] per bromine function, 30 mmol of anhydrous potassium acetate per bromine function, 0.2 mmol of tricyclohexylphosphine, 0.1 mmol of palladium(II) acetate and 300 ml of solvent (dioxane, DMSO, NMP, toluene, etc.) is stirred at 80-160° C. for 4-16 h. After the solvent has been removed under reduced pressure, the residue is taken up in 300 ml of dichloromethane, THF or ethyl acetate and filtered through a Celite bed, the filtrate is concentrated under reduced pressure until commencement of crystallization and about 100 ml of methanol are finally added dropwise in order to complete the crystallization. The compounds can be recrystallized from dichloromethane, ethyl acetate or THF with addition of methanol.

Synthesis of Ir(L215-3B):

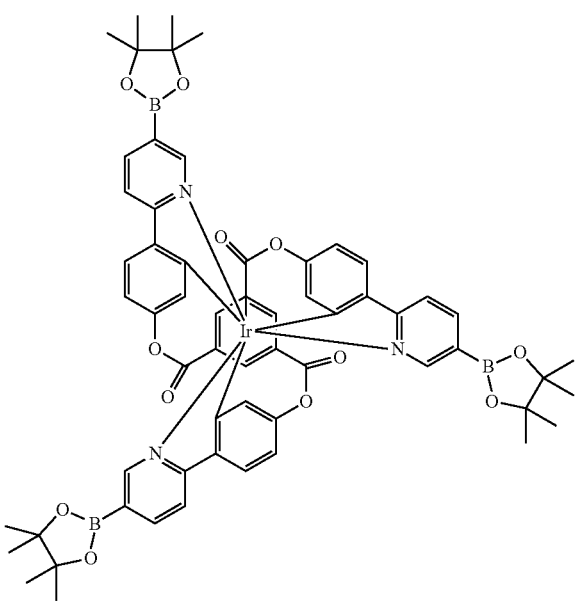

Use of 11.0 g (10 mmol) of Ir(L215) and 9.1 g (36 mmol) of bis(pinacolato)diborane [73183-34-3], dioxane/toluene 1:1 v/v, 120° C., 16 h, taking up and Celite filtration in THF, recrystallization from ethyl acetate:methanol. Yield: 7.3 g (6.0 mmol), 60%; purity: about 99.8% by HPLC.

In an analogous manner, it is possible to prepare the following compounds:

| Ex. | Product Reactant | Yield |
|---|---|---|
| Ir(L303-3B) | Ir(L303-3Br) | 49% |
| Ir(L405-2B) | Ir(L405-2Br) | 57% |

4) Synthesis of Cryptates:
IrK1

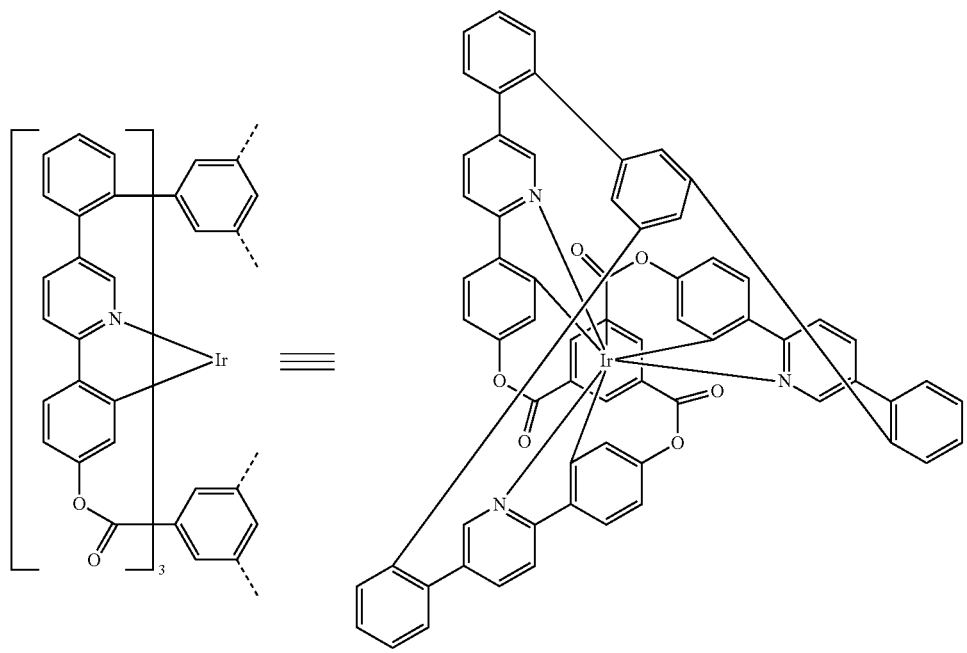

Step A:

A mixture of 5.2 g (5 mmol) of Ir(L500) and 100 g of pyridinium hydrochloride is heated to 190° C. with good stirring for 5 h. After cooling to 80° C., a mixture of 300 ml of water and 20 ml of acetic acid is added dropwise, the mixture is left to cool while stirring, and the precipitated solids are filtered off with suction, washed three times with water and dried under reduced pressure. For azeotropic drying, the solid is suspended in 200 ml of ethanol, and the ethanol is drawn off on a rotary evaporator. The azeotropic drying is repeated twice more with 200 ml each time of toluene, then the solid is subjected to extractive stirring with 300 ml of hot n-heptane, filtered off with suction, washed with a little n-heptane and then dried under reduced pressure at 150° C.

Step B:

The triphenol thus obtained (4.7 g, 4.7 mmol, 93%) is dissolved in a mixture of 300 ml of THF and 10 ml of pyridine and cooled down to 0° C., and then a solution of 1.3 g (4.8 mmol) of benzene-1,3,5-tricarbonyl trichloride [4422-95-1] in 100 ml of THF is added dropwise. The mixture is allowed to warm up to room temperature, stirred for a further 2 h, then heated to 40° C. and stirred for a further 16 h. Then the solvent is removed under reduced pressure, the residue is extracted by stirring with 200 ml of methanol, and the solids are filtered off with suction, washed three times with 50 ml each time of methanol and dried under reduced pressure. The product is purified further by continuous hot extraction five times with ethyl acetate (amount initially charged in each case about 150 ml, extraction thimble: standard Soxhlet thimbles made from cellulose from Whatman) with careful exclusion of air and light. Finally, the product is fractionally sublimed at about 360° C. Yield: 2.8 g (2.4 mmol), 48%. Purity: >99.9% by HPLC.

In an analogous manner, it is possible to prepare the following compounds:

| Ex. | Product Reactant | Yield |
|---|---|---|
| IrK2 | 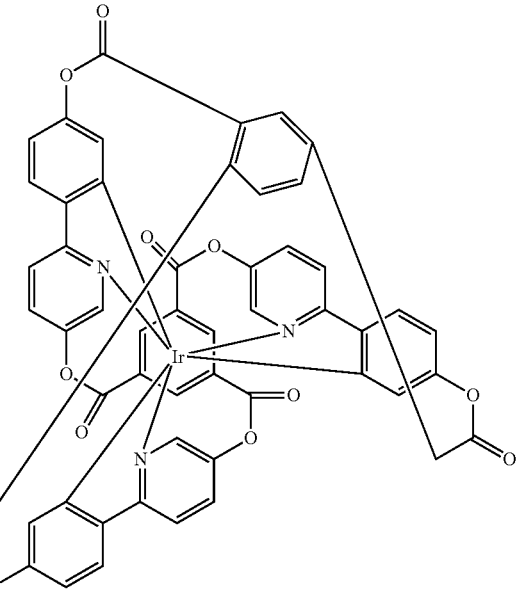<br>Ir(L268) | 36% |
| IrK3 | 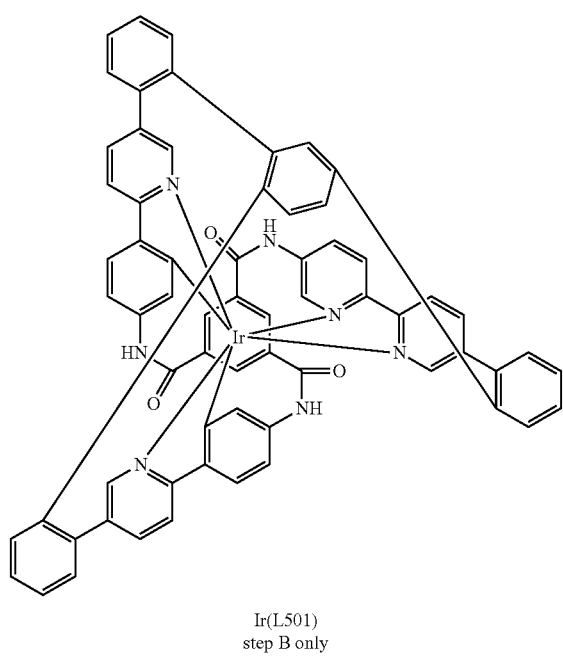<br>Ir(L501)<br>step B only | |

-continued
| Ex. | Product Reactant | Yield |
|---|---|---|
| IrK4 | 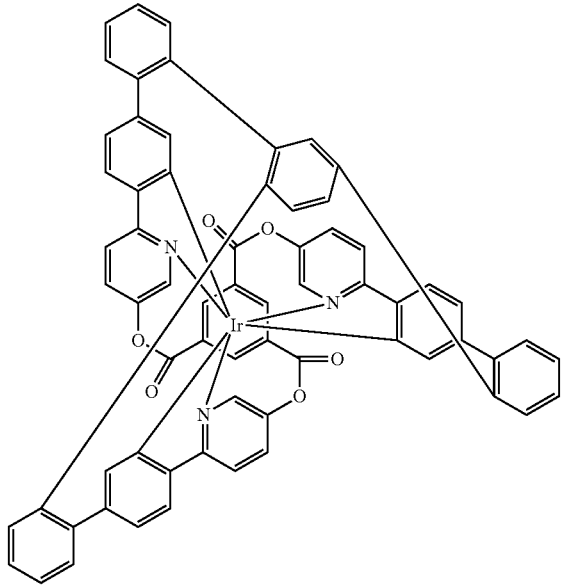<br>Ir(L502)<br>step B only | |
| IrK5 | 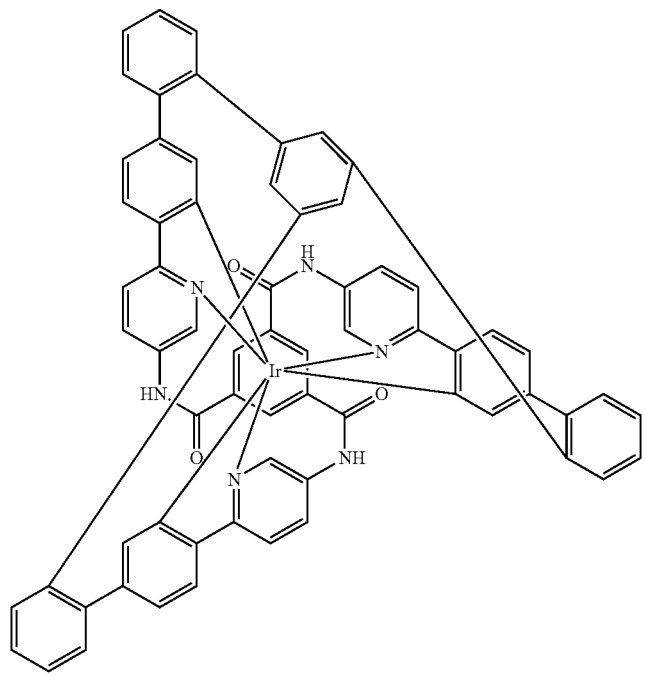<br>Ir(L503)<br>step B only | |

IrK10: Alkylation of IrK3
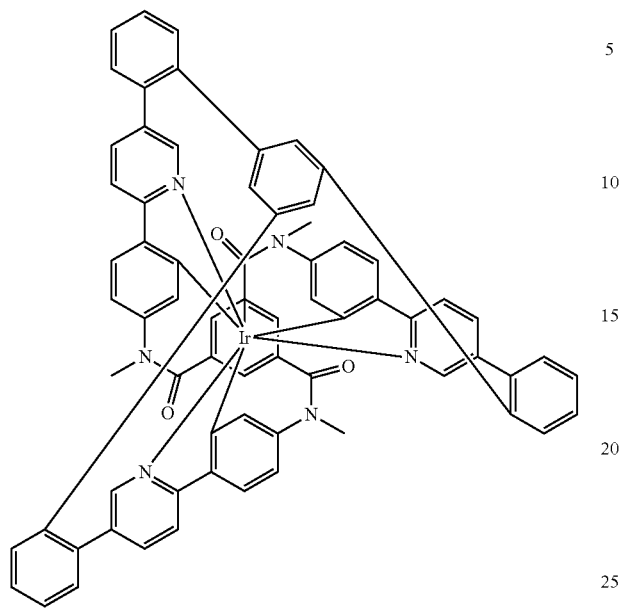
The alkylation is effected analogously to the synthesis of L300. Yield 71%.
In an analogous manner, it is possible to prepare the following compounds:
| Ex. | Product Reactant | Yield |
|---|---|---|
| IrK11 | IrK3 15501-33-4 | 62% |

| Ex. | Product Reactant | Yield |
|---|---|---|
| IrK12 | 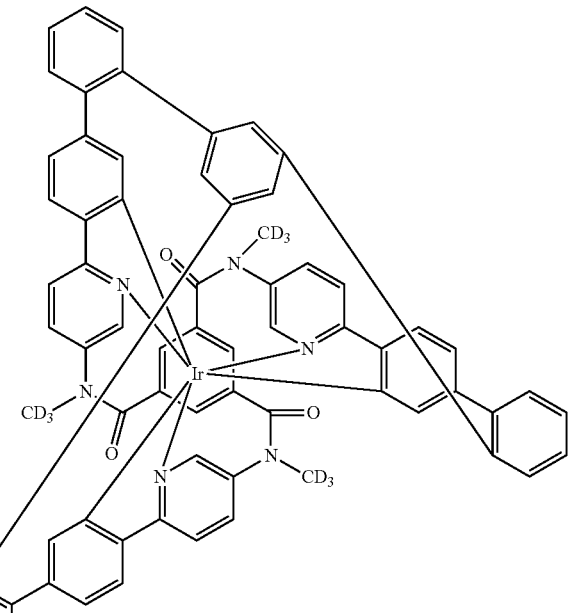<br>IrK5<br>865-50-9 | 69% |
IrK20: Arylation of IrK3
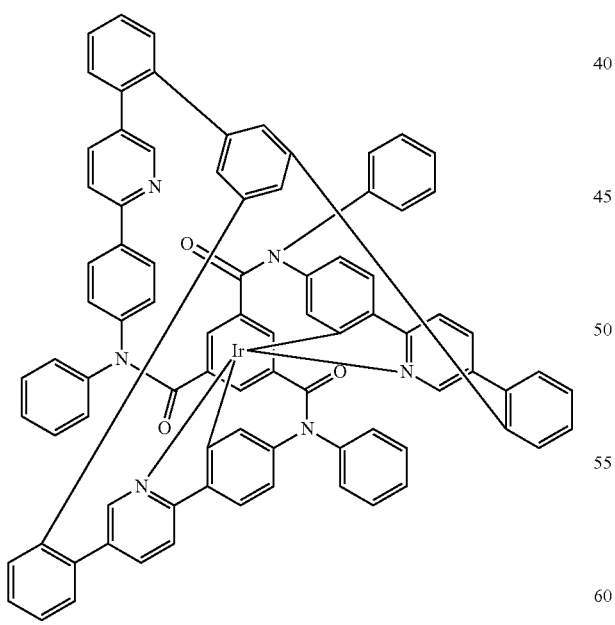
The arylation is effected analogously to the synthesis of L300. Yield 51%.
In an analogous manner, it is possible to prepare the following compounds:

| Ex. | Product Reactant | Yield |
|---|---|---|
| IrK21 | 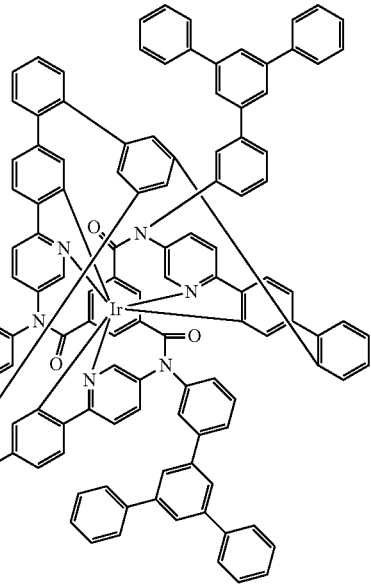<br>IrK5<br>1643766-87-3 | 55% |

5) Separation of the Diastereomers of Ir(L327):

5.0 g of the diastereomer mixture of Ir(L327) is separated with toluene:ethyl acetate (9:1) on silica gel (about 600 g, column geometry about 8×70 cm) into the two enantiomerically pure diastereomers A-Ir(L327) (2.2 g) and A-Ir(L327) (2.3 g).

Example: Thermal and Photophysical Properties and Oxidation and Reduction Potentials Table 1 collates the thermal and photochemical properties and oxidation and reduction potentials (CV, Ox. in DCM, Red. in THF) of the comparative materials IrPPy, Ir1 to 5 (for structures see Table 2) and the selected materials of the invention.

The compounds of the invention have improved thermal stability and photostability compared to the materials according to the prior art. While materials according to the prior art exhibit brown discolouration and ashing after thermal storage at 360° C. for 7 days and secondary components in the region of >1 mol % can be detected in the $^1$H NMR, the complexes of the invention are substantially inert under these conditions. This thermal robustness is crucial especially for the processing of the materials under high vacuum (vapour small-molecule devices). In addition, the compounds of the invention have very good photostability in anhydrous $C_6D_6$ solution under irradiation with light of wavelength about 455 nm. More particularly, in contrast to prior art complexes containing bidentate ligands, no facial-meridional isomerization is detectable in the $^1$H NMR. As can be inferred from Table 1, the compounds of the invention in solution (room temperature, degassed solutions) show universally very high PL quantum efficiencies.

TABLE 1

| Complex | Therm. stab. Photo. stab. | PL-max. | PLQE Lömi | HOMO LUMO |
|---|---|---|---|---|
| Comparative examples, for structures see Table 13 | | | | |
| IrPPy | decomposition | 509 | 0.97 | — |
|  | decomposition |  | toluene | — |
| Ir1 | — | 513 | 0.97 | −5.09 |
|  | — |  | toluene | −1.99 |
| Ir2 | decomposition | 516 | 0.97 | −5.05 |
|  | decomposition |  | toluene | −1.71 |
| Ir3* | decomposition | 510 | 0.76 | — |
|  | decomposition |  | BuCN | — |
| Ir4** | decomposition | 580 | 0.54 | — |
|  | decomposition |  | DMF | — |
| Ir5** | decomposition | 532 | 0.81 | — |
|  | decomposition |  | DMF | — |
| Inventive examples | | | | |
| Ir(L204) | no decomp. | 495 | 0.94 | −5.54 |
|  | no decomp. |  | toluene | −2.40 |
| Ir(L302) | no decomp. | 513 | 0.96 | −5.26 |
|  | no decomp. |  | toluene | −2.10 |
| Ir(L200) | no decomp. | 552 | 0.94 | −5.66 |
|  | no decomp. |  | toluene | −2.64 |
| Ir(L300) | no decomp. | 539 | 0.95 | −5.34 |
|  | no decomp. |  | toluene | −2.29 |
| Ir(L205) | no decomp. | 577 | 0.93 | −5.43 |
|  | no decomp. |  | toluene | −2.55 |
| Ir(L303) | no decomp. | 535 | 0.97 | −5.27 |
|  | no decomp. |  | toluene | −2.43 |
| Ir(L201) | no decomp. | 583 | 0.89 | −5.61 |
|  | no decomp. |  | toluene | −2.42 |
| Ir(L301) | no decomp. | 557 | 0.91 | −5.32 |
|  | no decomp. |  | toluene | −2.53 |

*G. St-Pierre et al., Dalton Trans, 2011, 40, 11726.
**A. Ruggi et al., Eur. J. Inorg. Chem 2012, 1025.

TABLE 2

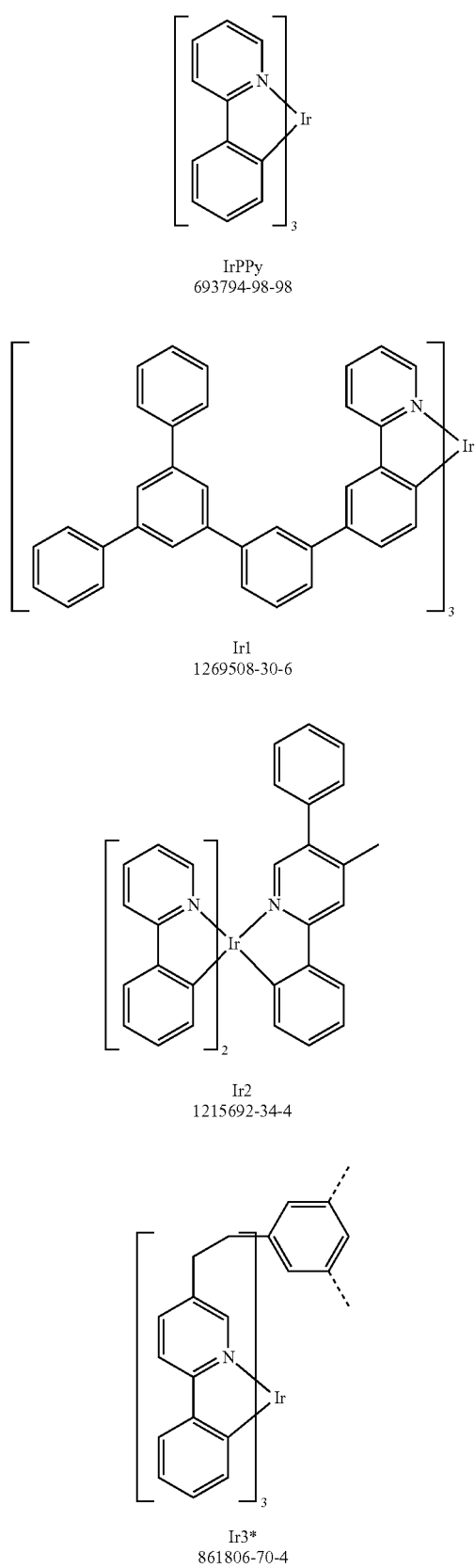

IrPPy
693794-98-98

Ir1
1269508-30-6

Ir2
1215692-34-4

Ir3*
861806-70-4

TABLE 2-continued

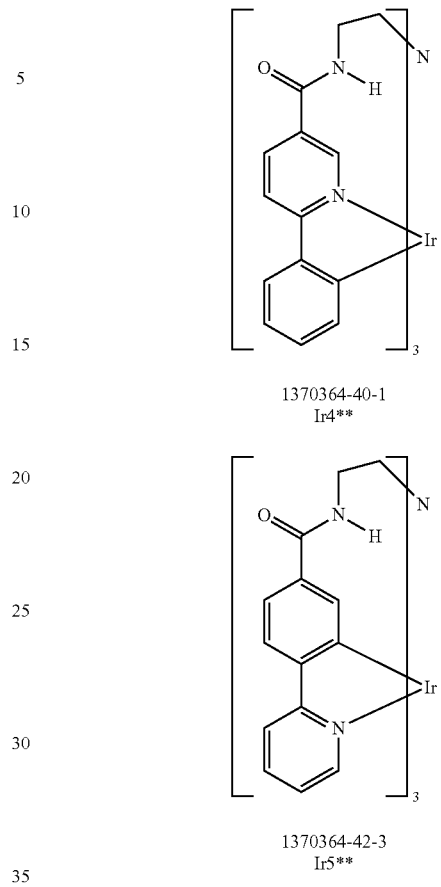

1370364-40-1
Ir4**

1370364-42-3
Ir5**

Production of the OLEDs

1) Vacuum-Processed Devices:

OLEDs of the invention and OLEDs according to the prior art are produced by a general method according to WO 2004/058911, which is adapted to the circumstances described here (variation in layer thickness, materials used).

In the examples which follow, the results for various OLEDs are presented. Glass plaques with structured ITO (50 nm, indium tin oxide) form the substrates to which the OLEDs are applied. The OLEDs basically have the following layer structure: substrate/hole transport layer 1 (HTL1) consisting of HTM doped with 5% NDP-9 (commercially available from Novaled), 20 nm/hole transport layer 2 (HTL2)/optional electron blocker layer (EBL)/emission layer (EML)/optional hole blocker layer (HBL)/electron transport layer (ETL)/optional electron injection layer (EIL) and finally a cathode. The cathode is formed by an aluminium layer of thickness 100 nm.

First of all, vacuum-processed OLEDs are described. For this purpose, all the materials are applied by thermal vapour deposition in a vacuum chamber. In this case, the emission layer always consists of at least one matrix material (host material) and an emitting dopant (emitter) which is added to the matrix material(s) in a particular proportion by volume by co-evaporation. Details given in such a form as M3:M2: Ir(L1) (55%:35%:10%) mean here that the material M3 is present in the layer in a proportion by volume of 55%, M2 in a proportion of 35% and Ir(L1) in a proportion of 10%. Analogously, the electron transport layer may also consist of a mixture of two materials. The exact structure of the OLEDs can be found in Table 1. The materials used for production of the OLEDs are shown in Table 6.

The OLEDs are characterized in a standard manner. For this purpose, the electroluminescence spectra, the power efficiency (measured in cd/A) and the voltage (measured at 1000 cd/m² in V) are determined from current-voltage-brightness characteristics (IUL characteristics). For selected experiments, the lifetime is determined. The lifetime is defined as the time after which the luminance has fallen from a particular starting luminance to a certain proportion. The figure LD50 means that the lifetime specified is the time at which the luminance has dropped to 50% of the starting luminance, i.e. from, for example, 1000 cd/m² to 500 cd/m². According to the emission colour, different starting brightnesses were selected. The values for the lifetime can be converted to a figure for other starting luminances with the aid of conversion formulae known to those skilled in the art. In this context, the lifetime for a starting luminance of 1000 cd/m² is a standard figure.

Use of Compounds of the Invention as Emitter Materials in Phosphorescent OLEDs

One use of the compounds of the invention is as phosphorescent emitter materials in the emission layer in OLEDs. The iridium compounds according to Table 4 are used as a comparison according to the prior art. The results for the OLEDs are collated in Table 2.

TABLE 1

Structure of the OLEDs

| Ex. | HTL2 thickness | EBL thickness | EML thickness | HBL thickness | ETL thickness |
|---|---|---|---|---|---|
| Ref.-D1 | HTM 40 nm | — | M1:IrPPy (90%:10%) 35 nm | — | ETM1:ETM2 (50%:50%) 30 nm |
| Ref.-D2 | HTM 40 nm | — | M1:Ir2 (90%:10%) 35 nm | — | ETM1:ETM2 (50%:50%) 30 nm |
| Ref.-D3 | HTM 40 nm | — | M1:Ir3 (90%:10%) 35 nm | — | ETM1:ETM2 (50%:50%) 30 nm |
| D1 | HTM 40 nm | — | M1:Ir(L1) (90%:10%) 35 nm | — | ETM1:ETM2 (50%:50%) 30 nm |
| D2 | HTM 40 nm | — | M1:Ir(L4) (90%:10%) 35 nm | HBM1 10 nm | ETM1:ETM2 (50%:50%) 30 nm |
| D3 | HTM 40 nm | — | M1:Ir(L10) (90%:10%) 35 nm | HBM1 10 nm | ETM1:ETM2 (50%:50%) 30 nm |
| D4 | HTM 60 nm | — | M2:Ir(L14) (85%:15%) 40 nm | — | ETM1:ETM2 (50%:50%) 30 nm |
| D5 | HTM 40 nm | — | M2:M3:Ir(L1) (60%:30%:10%) 35 nm | — | ETM1:ETM2 (50%:50%) 30 nm |
| D6 | HTM 30 nm | — | M1:M3:Ir(L204) (30%:60%:10%) 30 nm | — | ETM1:ETM2 (50%:50%) 30 nm |
| D7 | HTM 40 nm | — | M1:M3:Ir(L302) (30%:60%:10%) 35 nm | — | ETM1:ETM2 (50%:50%) 30 nm |
| D8 | HTM 40 nm | — | M1:M3:Ir(L200) (30%:60%:10%) 35 nm | — | ETM1:ETM2 (50%:50%) 30 nm |
| D9 | HTM 40 nm | — | M1:M3:Ir(L300) (25%:60%:15%) 35 nm | — | ETM1:ETM2 (50%:50%) 30 nm |
| D10 | HTM 40 nm | — | M1:M3:Ir(L205) (30%:60%:10%) 40 nm | — | ETM1:ETM2 (50%:50%) 30 nm |

TABLE 1-continued

Structure of the OLEDs

| Ex. | HTL2 thickness | EBL thickness | EML thickness | HBL thickness | ETL thickness |
|---|---|---|---|---|---|
| D11 | HTM 40 nm | — | M1:M3:Ir(L303) (30%:60%:10%) 40 nm | — | ETM1:ETM2 (50%:50%) 30 nm |
| D12 | HTM 45 nm | — | M1:M3:Ir(L201) (30%:60%:10%) 40 nm | — | ETM1:ETM2 (50%:50%) 30 nm |
| D13 | HTM 40 nm | — | M1:M3:Ir(L301) (25%:60%:15%) 40 nm | — | ETM1:ETM2 (50%:50%) 30 nm |
| D14 | HTM 45 nm | — | M6:M3:Ir(L208) (35%:60%:5%) 40 nm | — | ETM1:ETM2 (50%:50%) 30 nm |
| D15 | HTM 45 nm | — | M6:M3:Ir(L210) (40%:55%:5%) 40 nm | — | ETM1:ETM2 (50%:50%) 30 nm |
| D16 | HTM 30 nm | — | M1:M3:Ir(L212) (30%:60%:10%) 30 nm | — | ETM1:ETM2 (50%:50%) 30 nm |
| D17 | HTM 30 nm | — | M1:M3:Ir(L213) (30%:60%:10%) 30 nm | — | ETM1:ETM2 (50%:50%) 30 nm |
| D18 | HTM 45 nm | — | M6:Ir(L216) (95%:5%) 35 nm | — | ETM1:ETM2 (50%:50%) 30 nm |
| D19 | HTM 45 nm | — | M6:Ir(L218) (95%:5%) 35 nm | — | ETM1:ETM2 (50%:50%) 30 nm |
| D20 | HTM 45 nm | — | M6:Ir(L220) (95%:5%) 35 nm | — | ETM1:ETM2 (50%:50%) 30 nm |
| D21 | HTM 40 nm | — | M1:M3:Ir(L223) (25%:60%:15%) 30 nm | — | ETM1:ETM2 (50%:50%) 30 nm |
| D22 | HTM 40 nm | — | M1:M3:Ir(L225) (25%:60%:15%) 30 nm | — | ETM1:ETM2 (50%:50%) 30 nm |
| D23 | HTM 40 nm | — | M1:M3:Ir(L235) (25%:60%:15%) 30 nm | — | ETM1:ETM2 (50%:50%) 30 nm |
| D24 | HTM 40 nm | M7 5 nm | M7:Ir(L259) (85%:15%) 30 nm | HBM1 10 nm | ETM1:ETM2 (50%:50%) 30 nm |
| D25 | HTM 40 nm | — | M1:M3:Ir(L260) (25%:60%:15%) 30 nm | — | ETM1:ETM2 (50%:50%) 30 nm |
| D26 | HTM 45 nm | — | M6:Ir(L308) (95%:5%) 35 nm | — | ETM1:ETM2 (50%:50%) 30 nm |
| D27 | HTM 45 nm | — | M6:Ir(L310) (95%:5%) 35 nm | — | ETM1:ETM2 (50%:50%) 30 nm |
| D28 | HTM 45 nm | — | M6:Ir(L260) (95%:5%) 35 nm | — | ETM1:ETM2 (50%:50%) 30 nm |
| D29 | HTM 45 nm | — | M6:IrK4 (93%:7%) 30 nm | — | ETM1:ETM2 (50%:50%) 30 nm |
| D30 | HTM 45 nm | — | M1:M3:IrK11 (30%:60%:10%) 30 nm | — | ETM1:ETM2 (50%:50%) 30 nm |
| D31 | HTM 45 nm | — | M1:M3:IrK20 (30%:60%:10%) 30 nm | — | ETM1:ETM2 (50%:50%) 30 nm |

TABLE 2

Results for the vacuum-processed OLEDs

| Ex. | EQE (%) 1000 cd/m² | Voltage (V) 1000 cd/m² | CIE x/y 1000 cd/m² | LD50 (h) 1000 cd/m² |
|---|---|---|---|---|
| Ref.-D1 | 16.0 | 2.7 | 0.33/062 | 60000 |
| Ref.-D2 | 17.5 | 2.6 | 0.35/0.61 | 170000 |
| Ref.-D3 | 17.9 | 3.0 | 0.34/0.62 | 190000 |
| D1 | 18.1 | 2.7 | 0.60/0.38 | 240000 |
| D2 | 18.9 | 2.9 | 0.59/0.40 | 280000 |
| D3 | 19.2 | 2.9 | 0.57/0.41 | 270000 |
| D4 | 17.4 | 2.9 | 0.67/0.33 | 330000 |
| D5 | 18.6 | 2.8 | 0.61/0.38 | 290000 |
| D6 | 18.9 | 3.4 | 0.18/0.44 | 60000 |
| D7 | 19.5 | 3.3 | 0.30/0.62 | 330000 |
| D8 | 19.7 | 3.1 | 0.37/0.57 | 370000 |
| D9 | 20.1 | 3.0 | 0.35/0.60 | 350000 |
| D10 | 19.2 | 3.1 | 0.55/0.44 | 330000 |
| D11 | 19.5 | 3.1 | 0.39/0.58 | 350000 |
| D12 | 19.9 | 3.0 | 0.60/0.40 | 380000 |
| D13 | 20.2 | 3.1 | 0.48/0.52 | 290000 |
| D14 | 18.7 | 3.0 | 0.70/0.30 | 430000 |
| D15 | 20.1 | 2.9 | 0.69/0.31 | 480000 |
| D16 | 19.0 | 3.4 | 0.19/0.45 | 70000 |
| D17 | 19.4 | 3.5 | 0.18/0.43 | 80000 |
| D18 | 21.4 | 2.9 | 0.63/0.36 | 450000 |
| D19 | 21.5 | 2.9 | 0.64/0.36 | 430000 |
| D20 | 21.4 | 3.1 | 0.64/0.36 | — |
| D21 | 18.8 | 3.0 | 0.45/0.54 | 390000 |
| D22 | 19.5 | 3.0 | 0.54/0.45 | 300000 |
| D23 | 20.0 | 3.1 | 0.56/0.44 | 410000 |
| D24 | 13.7 | 5.1 | 0.16/0.21 | — |
| D25 | 21.3 | 3.1 | 0.33/0.62 | 380000 |
| D26 | 21.0 | 3.1 | 0.65/0.35 | 390000 |
| D27 | 21.2 | 3.2 | 0.66/0.34 | 420000 |
| D28 | 19.5 | 3.1 | 0.64/0.36 | 380000 |
| D29 | 20.6 | 3.2 | 0.66/0.34 | 480000 |
| D30 | 21.0 | 3.1 | 0.35/061 | 430000 |
| D31 | 21.4 | 3.2 | 0.35/061 | 460000 |

Solution-Processed Devices:

A: From Soluble Functional Materials

The iridium complexes of the invention may also be processed from solution and lead therein to OLEDs which are much simpler in terms of process technology compared to the vacuum-processed OLEDs, but nevertheless have good properties. The production of such components is based on the production of polymeric light-emitting diodes (PLEDs), which has already been described many times in the literature (for example in WO 2004/037887). The structure is composed of substrate/ITO/hole injection layer (60 nm)/interlayer (20 nm)/emission layer (60 nm)/hole blocker layer (10 nm)/electron transport layer (40 nm)/cathode. For this purpose, substrates from Technoprint (soda-lime glass) are used, to which the ITO structure (indium tin oxide, a transparent conductive anode) is applied. The substrates are cleaned in a cleanroom with DI water and a detergent (Deconex 15 PF) and then activated by a UV/ozone plasma treatment. Thereafter, likewise in a cleanroom, a 60 nm hole injection layer is applied by spin-coating. The required spin rate depends on the degree of dilution and the specific spin-coater geometry. In order to remove residual water from the layer, the substrates are baked on a hotplate at 200° C. for 30 minutes. The interlayer used serves for hole transport; in this case, HL-X092 from Merck is used. The interlayer may alternatively also be replaced by one or more layers which merely have to fulfil the condition of not being leached off again by the subsequent processing step of EML deposition from solution. For production of the emission layer, the triplet emitters of the invention are dissolved together with the matrix materials in toluene or chlorobenzene. The typical solids content of such solutions is between 16 and 25 g/l when, as here, the layer thickness of 60 nm which is typical of a device is to be achieved by means of spin-coating. The solution-processed devices of type 1 contain an emission layer composed of M4:M5:IrL (30%:55%:15%), and those of type 2 contain an emission layer composed of M4:M5:IrLa:IrLb (30%:34%:30%:6%); in other words, they contain two different Ir complexes. The emission layer is spun on in an inert gas atmosphere, argon in the present case, and baked at 160° C. for 10 min. Vapour-deposited above the latter are the hole blocker layer (10 nm ETM1) and the electron transport layer (40 nm ETM1 (50%)/ETM2 (50%)) (vapour deposition systems from Lesker or the like, typical vapour deposition pressure $5 \times 10^{-6}$ mbar). Finally, a cathode of aluminium (100 nm) (high-purity metal from Aldrich) is applied by vapour deposition. In order to protect the device from air and air humidity, the device is finally encapsulated and then characterized. The OLED examples cited are yet to be optimized; Table 3 summarizes the data obtained.

TABLE 3

Results with materials processed from solution

| Ex. | Emitter Device | EQE (%) 1000 cd/m² | Voltage (V) 1000 cd/m² | CIE x/y | LD50 (h) 1000 cd/m² |
|---|---|---|---|---|---|
| Orange and red OLEDs | | | | | |
| Sol-D1 | Ir(L9) type 1 | 15.5 | 6.3 | 0.67/0.33 | 50000 |
| Sol-D2 | Ir1 Ir(L9) type 2 | 15.9 | 6.1 | 0.67/0.33 | 160000 |
| Sol-D3 | Ir1 Ir(L215) type 2 | 14.9 | 5.8 | 0.70/0.30 | — |
| Sol-D4 | Ir1 Ir(L217) type 2 | 16.9 | 5.9 | 0.61/0.38 | 180000 |
| Sol-D5 | Ir1 Ir(L220) type 2 | 18.9 | 5.6 | 0.67/0.33 | 200000 |
| Sol-D6 | Ir1 Ir(L232) type 2 | 19.8 | 5.7 | 0.65/0.35 | 190000 |
| Sol-D7 | Ir1 Ir(L233) type 2 | 18.4 | 5.5 | 0.70/0.30 | 140000 |
| Sol-D8 | Ir1 Ir(L267) type 2 | 19.0 | 5.7 | 0.64/0.35 | 170000 |
| Sol-D9 | Ir1 Ir(L307) type 2 | 18.5 | 5.9 | 0.67/0.32 | 150000 |
| Sol-D10 | Ir1 Ir(L313) type 2 | 19.4 | 5.6 | 0.66/0.34 | 190000 |
| Sol-D11 | Ir1 Ir(L320) type 2 | 19.0 | 5.7 | 0.65/0.35 | 180000 |
| Sol-D12 | Ir1 Ir(L401) type 2 | 19.0 | 5.7 | 0.48/0.50 | 210000 |
| Sol-D13 | Ir1 Ir(L408) type 2 | 19.4 | 5.5 | 0.63/0.36 | 190000 |
| Sol-D14 | Ir1 Ir(L227) type 2 | 19.9 | 5.6 | 0.57/0.43 | 180000 |
| Sol-D15 | Ir1 Ir(L228) type 2 | 19.9 | 5.6 | 0.59/0.40 | 200000 |
| Sol-D16 | Ir1 Ir(L229) type 2 | 20.7 | 5.7 | 0.58/0.42 | 170000 |

TABLE 3-continued

Results with materials processed from solution

| Ex. | Emitter Device | EQE (%) 1000 cd/m² | Voltage (V) 1000 cd/m² | CIE x/y | LD50 (h) 1000 cd/m² |
|---|---|---|---|---|---|
| Sol-D17 | Ir1 Ir(L231) type 2 | 20.6 | 5.7 | 0.61/0.38 | — |
| Sol-D18 | Ir1 Ir(L261) type 2 | 19.5 | 5.5 | 0.57/0.43 | 190000 |
| Sol-D19 | Ir1 Ir103 type 2 | 19.6 | 5.6 | 0.58/0.41 | 220000 |
| Sol-D20 | Ir1 Ir104 type 2 | 19.1 | 5.6 | 0.45/0.53 | 220000 |
| Sol-D21 | Ir1 Ir106 type 2 | 20.7 | 5.8 | 0.60/0.39 | 260000 |
| Sol-D22 | Ir(L315) Ir112 type 2 | 20.0 | 5.3 | 0.57/0.41 | 330000 |
| Sol-D23 | Ir110 Ir114 type 2 | 19.6 | 5.3 | 0.63/0.37 | 330000 |
| Sol-D24 | Ir110 Ir121 type 2 | 18.4 | 5.3 | 0.65/0.35 | 320000 |
| Sol-D25 | Ir110 Ir122 type 2 | 18.2 | 5.4 | 0.64/0.36 | 310000 |
| Sol-D26 | Ir110 Ir123 type 2 | 18.4 | 5.3 | 0.65/0.35 | 300000 |
| Sol-D27 | Ir110 Ir124 type 2 | 18.5 | 5.3 | 0.62/0.37 | 310000 |
| Sol-D28 | Ir111 Ir128 type 2 | 18.5 | 5.3 | 0.55/0.44 | 300000 |
| Green and yellow OLEDs | | | | | |
| Sol-Ref.-D1 | Ir1 type 1 | 19.4 | 5.2 | 0.37/0.61 | 190000 |
| Sol-Ref.-D2 | Ir4 type 1 | 5.6 | 6.8 | 0.43/0.55 | <1000 |
| Sol-Ref.-D3 | Ir5 type 1 | 7.2 | 6.6 | 0.40/0.58 | <1000 |
| Sol-D100 | Ir(L4) type 1 | 19.7 | 5.1 | 0.39/0.60 | 240000 |
| Sol-D101 | Ir(L18) type 1 | 20.7 | 5.3 | 0.43/0.56 | 270000 |
| Sol-D102 | Ir(L102) type 1 | 19.6 | 5.1 | 0.34/0.62 | 200000 |
| Sol-D103 | Ir(L227) type 1 | 19.5 | 5.1 | 0.36/0.60 | 220000 |
| Sol-D104 | Ir(L211) type 1 | 19.8 | 5.1 | 0.40/0.59 | 260000 |
| Sol-D105 | Ir(L311) type 1 | 19.8 | 5.3 | 0.36/0.62 | 270000 |
| Sol-D106 | Ir(L315) type 1 | 20.3 | 5.4 | 0.35/0.63 | 310000 |
| Sol-D107 | Ir(L323) type 1 | 20.0 | 5.3 | 0.38/0.60 | 280000 |
| Sol-D108 | Ir(L324) type 1 | 20.5 | 5.3 | 0.40/0.59 | 260000 |
| Sol-D109 | Ir(L325) type 1 | 20.0 | 5.2 | 0.46/0.53 | 290000 |
| Sol-D110 | Ir(L402) type 1 | 20.8 | 5.1 | 0.36/0.62 | 240000 |
| Sol-D111 | Ir(L403) type 1 | 20.2 | 5.4 | 0.37/0.61 | 220000 |
| Sol-D112 | Ir(L406) type 1 | 21.3 | 5.2 | 0.39/0.69 | 300000 |
| Sol-D113 | Ir(L407) type 1 | 21.1 | 5.1 | 0.45/0.55 | 310000 |
| Sol-D114 | Ir100 type 1 | 21.1 | 5.1 | 0.44/0.55 | 300000 |
| Sol-D115 | Ir103 type 1 | 21.1 | 5.1 | 0.35/0.62 | 340000 |
| Sol-D116 | Ir108 type 1 | 20.9 | 5.3 | 0.41/0.58 | 290000 |
| Sol-D117 | Ir110 type 1 | 21.5 | 5.1 | 0.34/0.61 | 320000 |
| Sol-D118 | Ir111 type 1 | 19.5 | 5.0 | 0.33/0.61 | 270000 |
| Sol-D119 | Ir118 type 1 | 21.5 | 5.2 | 0.42/0.57 | 290000 |
| Sol-D118 | Ir127 type 1 | 20.5 | 5.4 | 0.32/0.62 | 380000 |
| Sol-D119 | Ir130 type 1 | 20.0 | 5.3 | 0.39/0.60 | 350000 |

TABLE 4

Structural formulae of the materials used

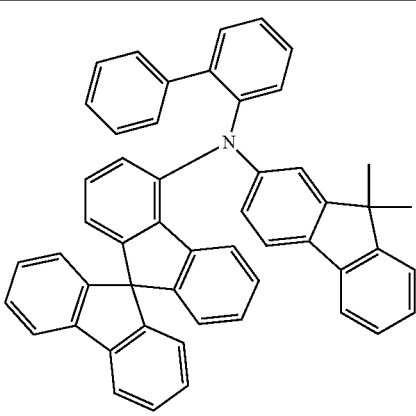

HTM 1450933-44-4

TABLE 4-continued
Structural formulae of the materials used
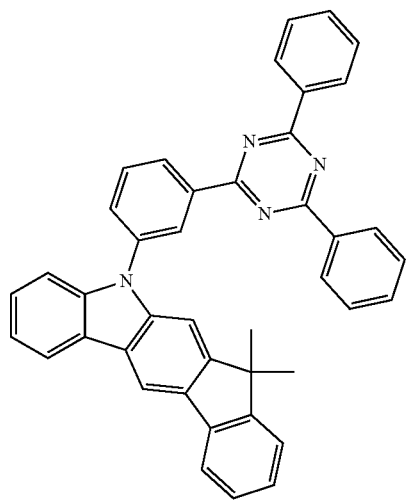
M1
1257248-13-7
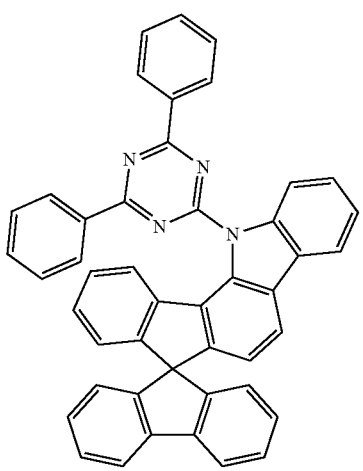
M2
1615703-29-1
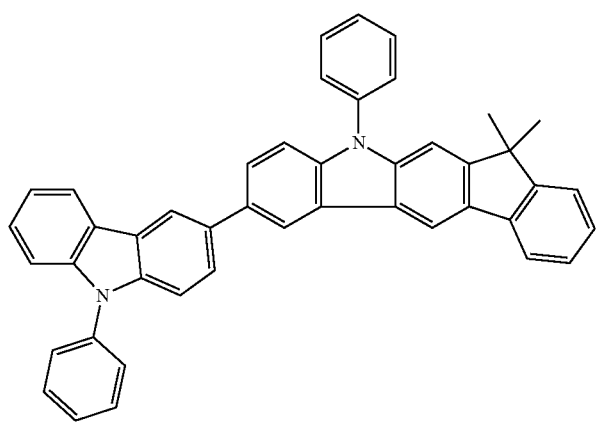
M3
1357150-54-9

TABLE 4-continued
Structural formulae of the materials used
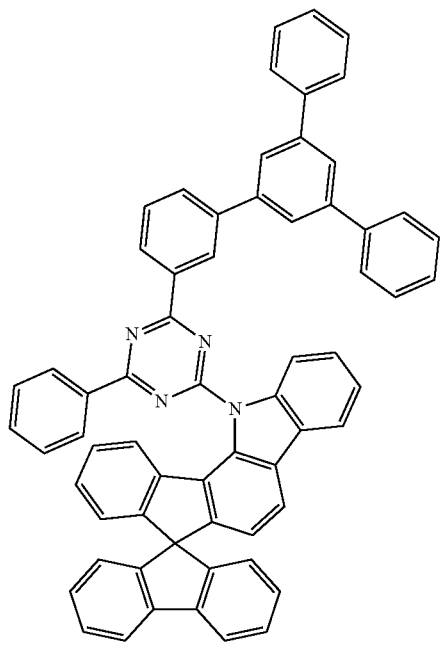
M4
1616231-60-7
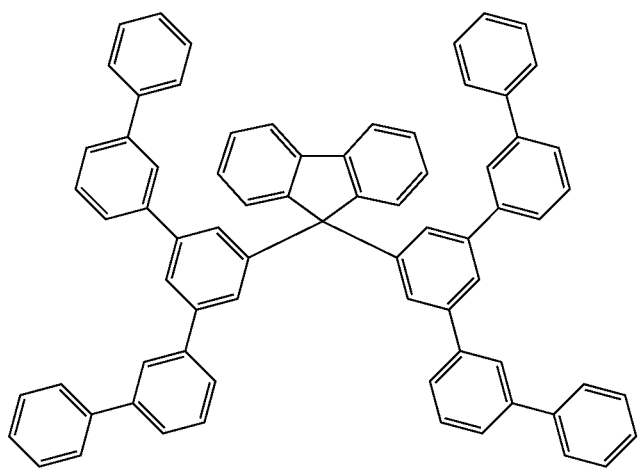
M5
1246496-85-4
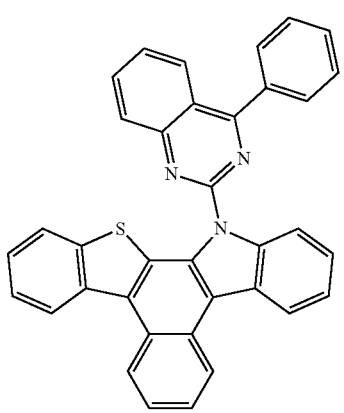 [SMILES: c1ccc(-c2nc(-n3c4ccccc4c4c5ccccc5c5c6ccccc6sc5c43)nc3ccccc23)cc1]
M6

TABLE 4-continued
Structural formulae of the materials used
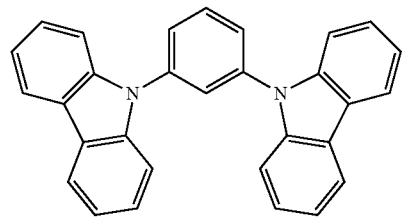 [SMILES: c1cc(-n2c3ccccc3c3ccccc32)cc(-n2c3ccccc3c3ccccc32)c1]
M7
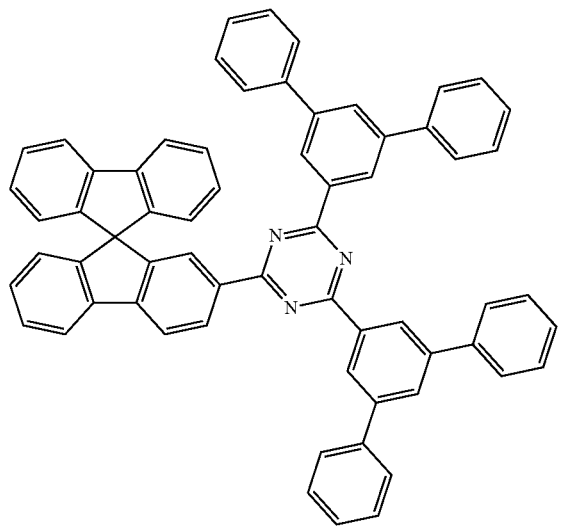
1233200-52-6
ETM1 = HBM1
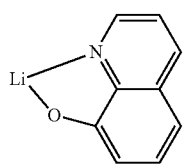
25387-93-3
ETM2
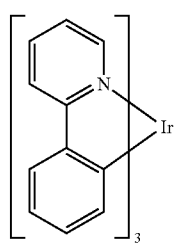
693794-98-8
IrPPy TABLE 4-continued
Structural formulae of the materials used
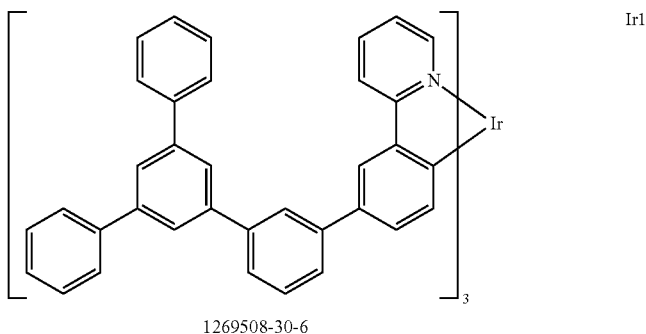
Ir1
1269508-30-6
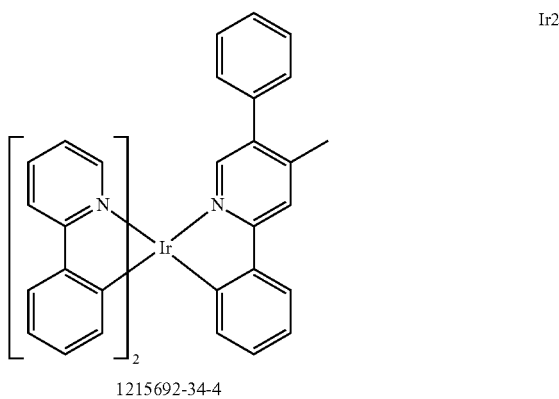
Ir2
1215692-34-4
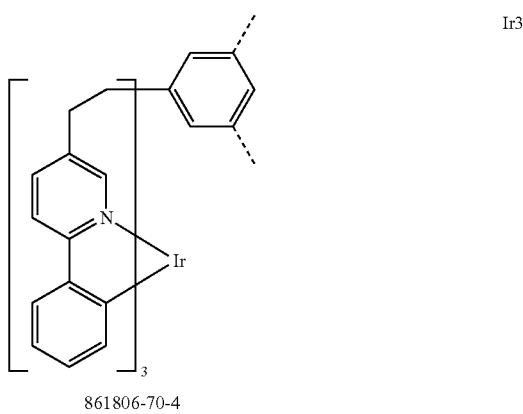
Ir3
861806-70-4
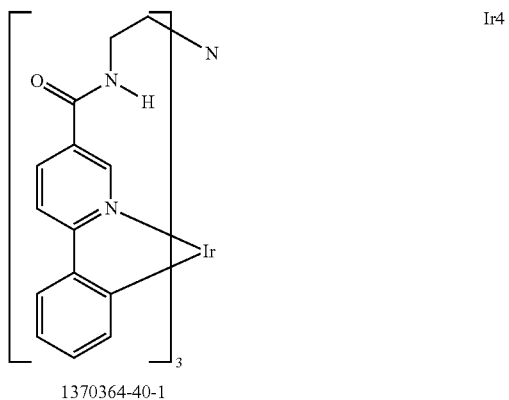
Ir4
1370364-40-1

TABLE 4-continued

Structural formulae of the materials used

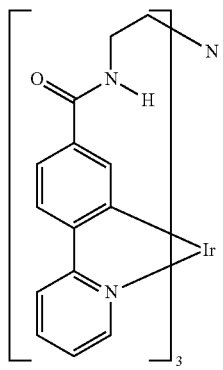

Ir5

1370364-42-3

The invention claimed is:

1. A monometallic compound comprising a hexadentate tripodal ligand wherein three bidentate sub-ligands which are optionally the same or different coordinate to a metal and the three bidentate sub-ligands are joined to one another via a bridge of formula (1):

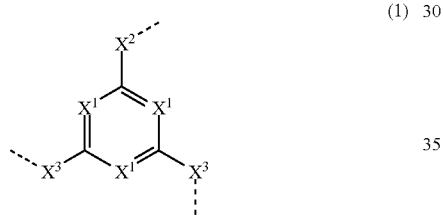

(1)

wherein the dotted bonds denote the bonds of the bridge of formula (1) to the three bidentate sub-ligands;

$X^1$ is, identically or differently in each instance, CR or N;

$X^2$ is, identically or differently in each instance, —CR'=CR'—, —CR'=N—, —C(=O)—O—, —C(=O)—NR''—, —C(=O)—S—, —C(=S)—O—, —C(=S)—NR''— or —C(=S)—S—;

$X^3$ is, identically or differently in each instance, $X^2$ or a —CR=CR— group;

R and R'
is, identically or differently in each instance, H, D, F, Cl, Br, I, N(R$^1$)$_2$, CN, NO$_2$, OR$^1$, SR$^1$, COOH, C(=O)N(R$^1$)$_2$, Si(R$^1$)$_3$, B(OR$^1$)$_2$, C(=O)R$^1$, P(=O)(R$^1$)$_2$, S(=O)R$^1$, S(=O)$_2$R$^1$, OSO$_2$R$^1$, a straight-chain alkyl group having 1 to 20 carbon atoms or an alkenyl or alkynyl group having 2 to 20 carbon atoms or a branched or cyclic alkyl group having 3 to 20 carbon atoms, wherein the alkyl, alkenyl, and alkynyl groups in each instance are optionally substituted by one or more radicals R$^1$, and wherein one or more nonadjacent CH$_2$ groups are optionally replaced by R$^1$C=CR1, C≡C, Si(R$^1$)$_2$, C=O, NR$^1$, O, S, or CONR$^1$, an aromatic or heteroaromatic ring system having 5 to 40 aromatic ring atoms and in each instance is optionally substituted by one or more radicals R$^1$;

and wherein, when $X^2$ is —CR'=CR'—, two radicals R' together optionally define an aliphatic or heteroaliphatic ring system; and wherein, $X^3$ is —CR=CR—, two radicals R together optionally define an aliphatic, heteroaliphatic, aromatic, or heteroaromatic ring system;

R'' is, identically or differently in each instance, H, D, a straight-chain alkyl group having 1 to 20 carbon atoms or a branched or cyclic alkyl group having 3 to 20 carbon atoms, wherein the alkyl group in each instance is optionally substituted by one or more radicals R$^1$ and wherein one or more nonadjacent CH$_2$ groups are optionally replaced by Si(R$^1$)$_2$, or an aromatic or heteroaromatic ring system having 5 to 40 aromatic ring atoms and in each instance is optionally substituted by one or more radicals R$^1$;

R$^1$ is, identically or differently in each instance, H, D, F, Cl, Br, I, N(R$^2$)$_2$, CN, NO$_2$, OR$^2$, SR$^2$, Si(R$^2$)$_3$, B(OR$^2$)$_2$, C(=O)R$^2$, P(=O)(R$^2$)$_2$, S(=O)R$^2$, S(=O)$_2$R$^2$, OSO$_2$R$^2$, a straight-chain alkyl group having 1 to 20 carbon atoms or an alkenyl or alkynyl group having 2 to 20 carbon atoms or a branched or cyclic alkyl group having 3 to 20 carbon atoms, wherein the alkyl, alkenyl, and alkynyl groups in each instance are optionally substituted by one or more radicals R$^2$, wherein one or more nonadjacent CH$_2$ groups are optionally replaced by R$^2$C=CR$^2$, C≡C, Si(R$^2$)$_2$, C=O, NR$^2$, O, S, or CONR$^2$, an aromatic or heteroaromatic ring system having 5 to 40 aromatic ring atoms and in each instance is optionally substituted by one or more radicals R$^2$; and wherein two or more radicals R$^1$ together optionally define an aliphatic, heteroaliphatic, aromatic or heteroaromatic ring system;

R$^2$ is, identically or differently in each instance, H, D, F, or an aliphatic, aromatic, and/or heteroaromatic organic radical having 1 to 20 carbon atoms, wherein one or more hydrogen atoms are optionally replaced by F; and wherein the three bidentate ligands, in addition to the bridge of formula (1), are also optionally ring-closed by a further bridge so as to form a cryptate, wherein the metal is Ir(III) and two of the bidentate sub-ligands each coordinate to the iridium via one carbon atom and one nitrogen atom or via two carbon atoms and the third bidentate sub-ligand coordinates to the iridium via one carbon atom and one nitrogen atom or via two carbon atoms or via two nitrogen atoms or via one nitrogen atom and one oxygen atom or via two oxygen atoms.

2. The compound of claim 1, wherein the bridge of formula (1) is selected from the group consisting of bridges of formula (2'):

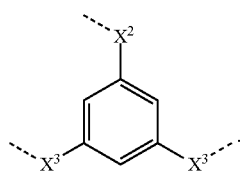

(2')

3. The compound of claim 1, wherein the bridge of formula (1) is selected from the group consisting of bridges of Formulae (2a) through (5e):

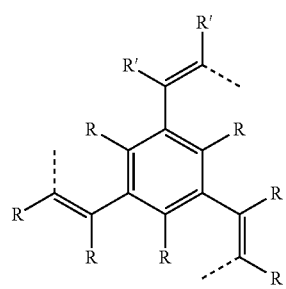

Formula (2a)

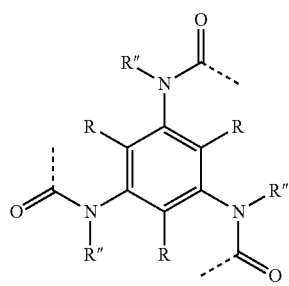

Formula (2b)

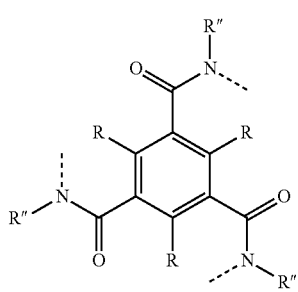

Formula (2c)

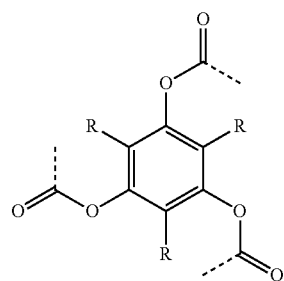

Formula (2d)

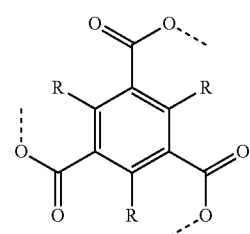

Formula (2e)

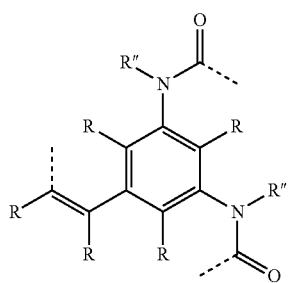

Formula (2f)

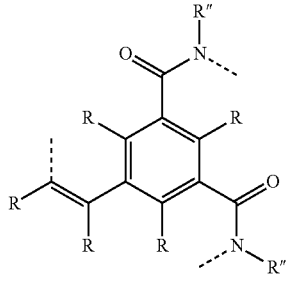

Formula (2g)

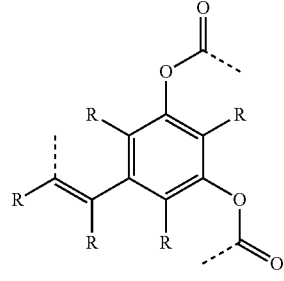

Formula (2h)

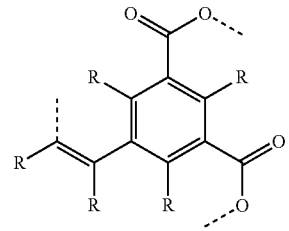

Formula (2i)

391
-continued
Formula (2j)
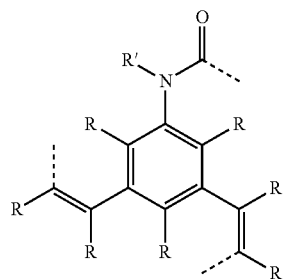
Formula (2k)
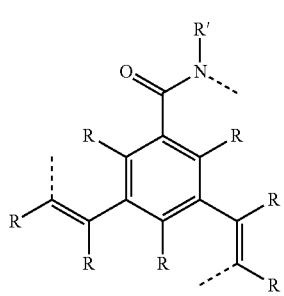
Formula (2l)
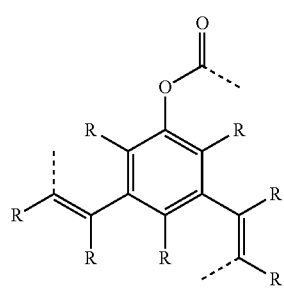
Formula (2m)
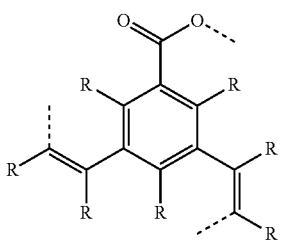
Formula (3a)
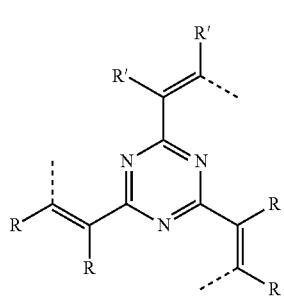
392
-continued
Formula (3b)
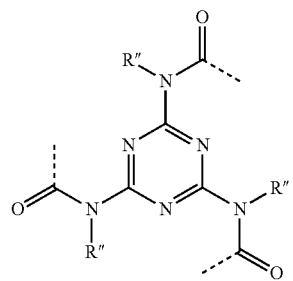
Formula (3c)
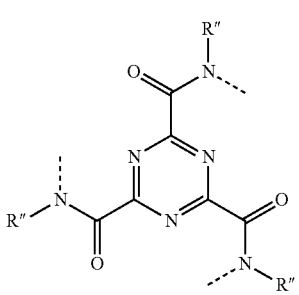
Formula (3d)
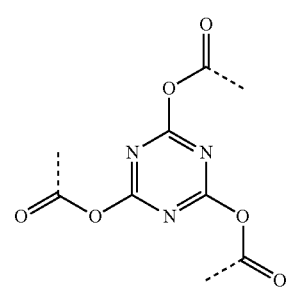
Formula (3e)
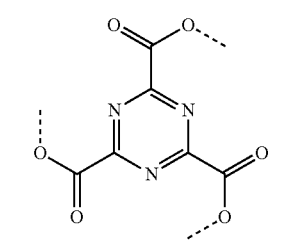
Formula (3f)
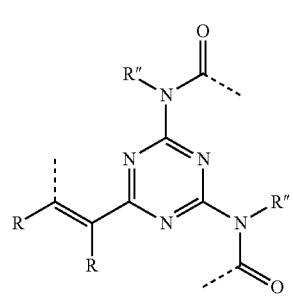

-continued
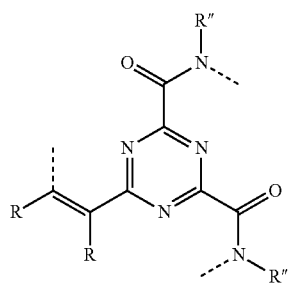
Formula (3g)
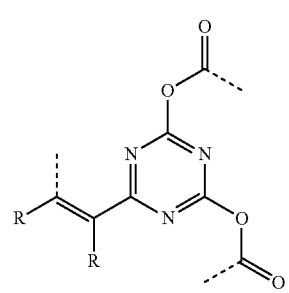
Formula (3h)
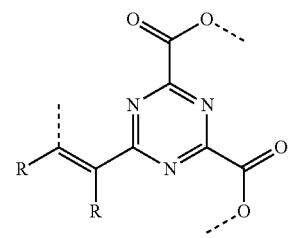
Formula (3i)
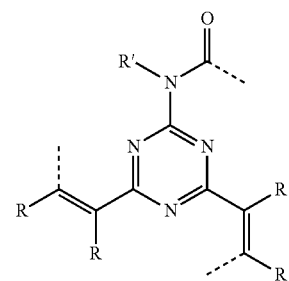
Formula (3j)
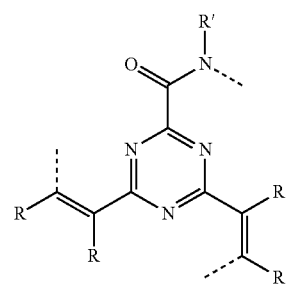
Formula (3k)
-continued
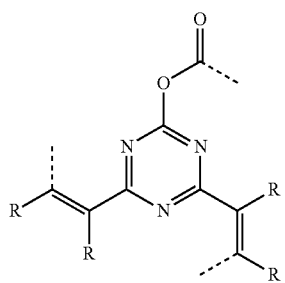
Formula (3l)
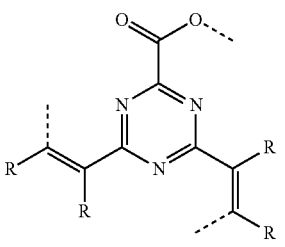
Formula (3m)
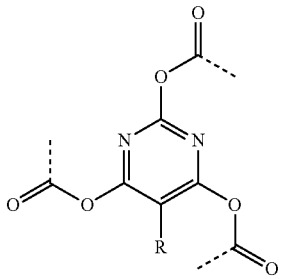
Formula (4d)
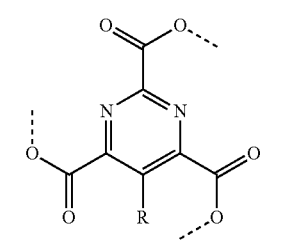
Formula (4e)
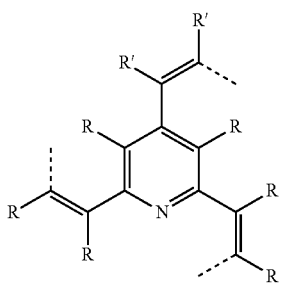
Formula (5a)
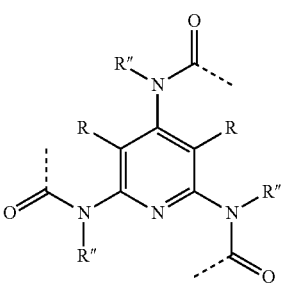
Formula (5b)

-continued

Formula (5c)

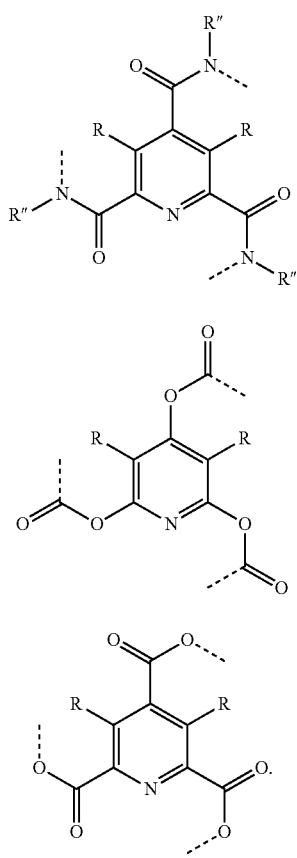

Formula (5d)

Formula (5e)

4. The compound of claim 1, wherein the bidentate sub-ligands are each monoanionic, and wherein either the three bidentate sub-ligands selected are the same or two of the bidentate sub-ligands selected are the same and the third bidentate sub-ligand selected is different from the first two bidentate sub-ligands, and wherein the coordinating atoms in the bidentate sub-ligands are the same or different in each instance and are selected from the group consisting of C, N, and O.

5. The compound of claim 1, wherein the bidentate sub-ligands are the same or different in each instance and are selected from the group consisting of structures of Formulae (L-1), (L-2), (L-3), and (L-4):

Formula (L-1)

CyD
|
CyC

Formula (L-2)

CyC
|
CyD

Formula (L-3)

CyD
|
CyD

-continued

Formula (L-4)

CyC
|
CyC wherein the dotted bond denotes the bond of the sub-ligand to the bridge of formula (1);

CyC is, identically or differently in each instance, an optionally substituted aryl or heteroaryl group having 5 to 14 aromatic ring atoms and coordinates to the metal via a carbon atom and is bonded to CyC or CyD via a covalent bond;

CyD is, identically or differently in each instance, an optionally substituted heteroaryl group having 5 to 14 aromatic ring atoms and coordinates to the metal via a nitrogen atom or via a carbene carbon atom and is bonded to CyC or CyD via a covalent bond;

wherein two or more of optional substituents together optionally define a ring system.

6. The compound of claim 5, wherein CyC is, identically or differently in each instance, selected from the group consisting of structures of formulae (CyC-1) through (CyC-20):

(CyC-1)
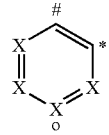

(CyC-2)
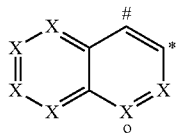

(CyC-3)
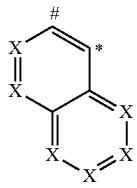

(CyC-4)
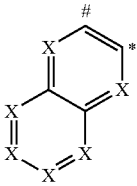

(CyC-5)
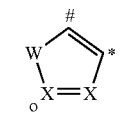

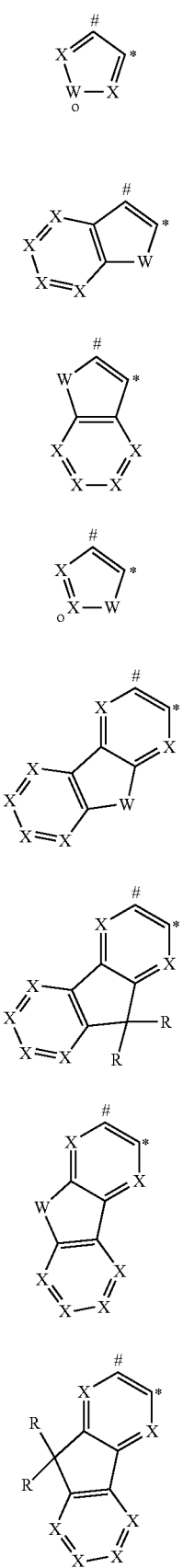
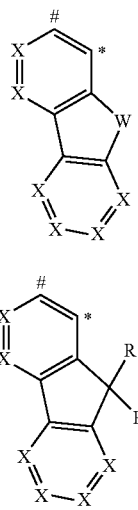
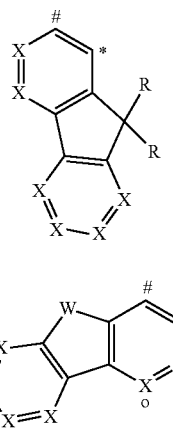
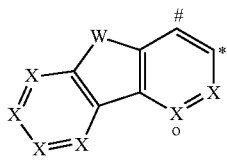
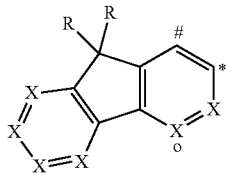
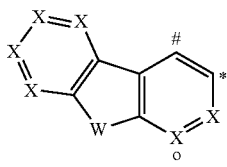
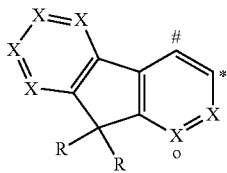
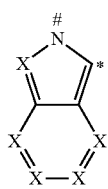
wherein these structures bind in each instance to the position on CyD indicated by # in formula (L-1) or (L-2) or on CyC in formula (L-4), and coordinates to the metal at the position indicated by *; and
wherein CyD is, identically or differently in each instance, selected from the group consisting of structures of formulae (CyD-1) through (CyD-14):

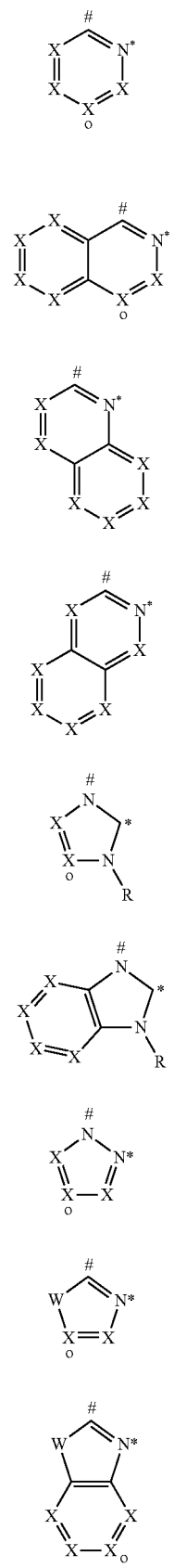

(CyD-1)

(CyD-2)

(CyD-3)

(CyD-4)

(CyD-5)

(CyD-6)

(CyD-7)

(CyD-8)

(CyD-9)

-continued

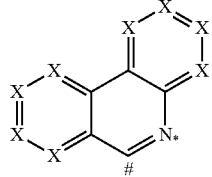 (CyD-10)

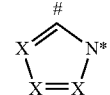 (CyD-11)

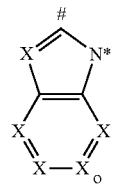 (CyD-12)

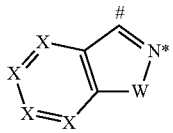 (CyD-13)

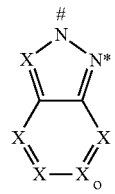 (CyD-14)

wherein these structures bind in each instance to the position on CyC indicated by # in Formula (L-1) or (L-2) or on CyD in Formula (L-3), and coordinates to the metal at the position indicated by *; and wherein X is, identically or differently in each instance, CR or N, with the proviso that not more than two X per cycle are N;

W is, identically or differently in each instance, NR, O, or S; and these structures are bonded to the bridge of formula (1) via the position denoted by "o" in the structures and X is C.

7. The compound of claim 6, wherein the bidentate sub-ligands are, identically or differently in each instance, selected from the group consisting of structures (L-1-1) through (L-44):

(L-1-1)
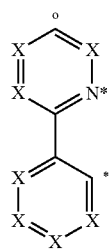
(L-1-2)
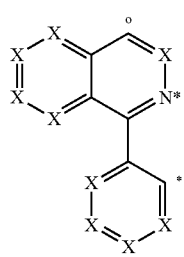
(L-2-1)
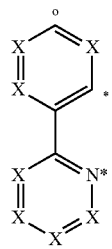
(L-2-2)
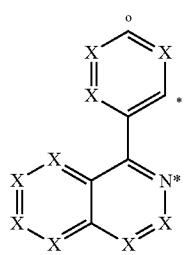
(L-2-3)
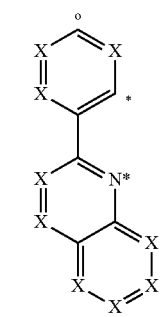
-continued
(L-5)
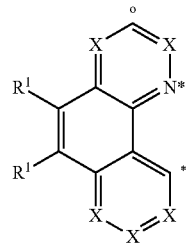
(L-6)
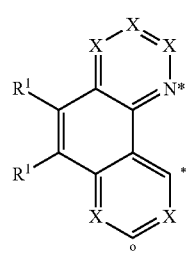
(L-7)
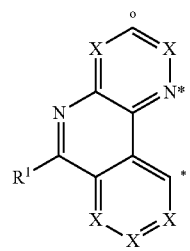
(L-8)
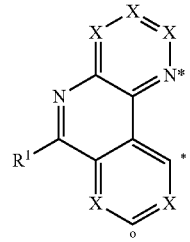
(L-9)
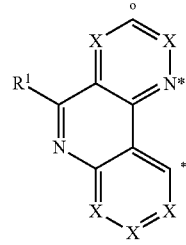
(L-10)
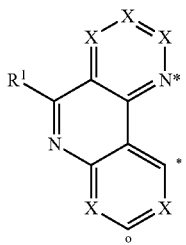

(L-11) 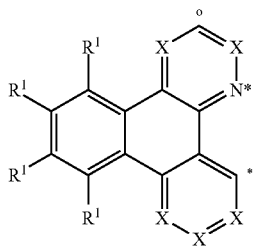
(L-12) 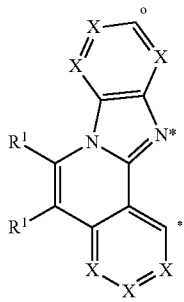
(L-13) 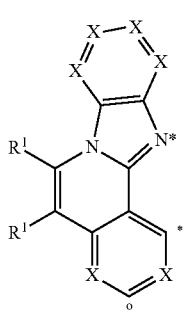
(L-14) 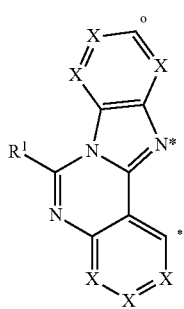
(L-15) 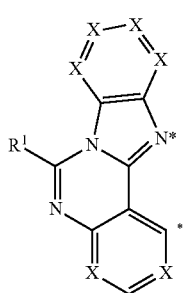
(L-16) 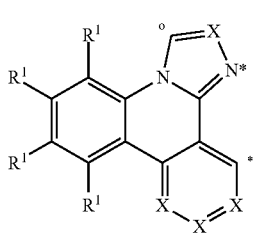
(L-17) 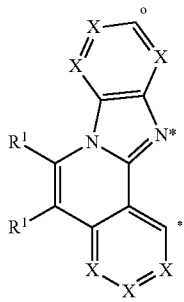
(L-18) 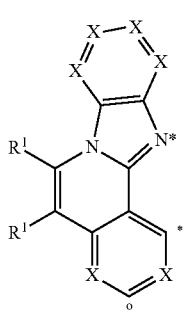
(L-19) 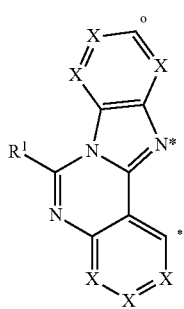
(L-20) 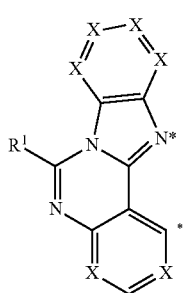
(L-21) 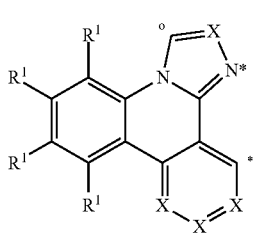

(L-22) 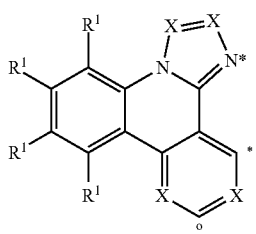
(L-23) 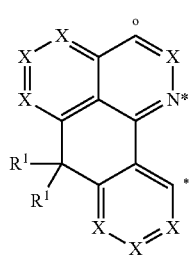
(L-24) 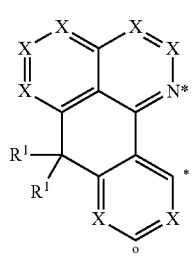
(L25) 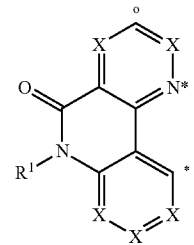
(L-26) 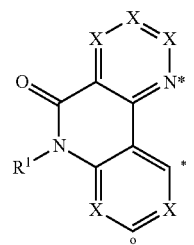
(L-27) 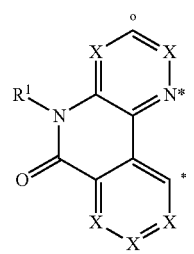
(L-28) 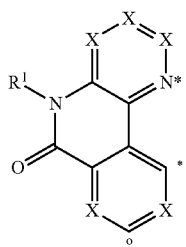
(L-29) 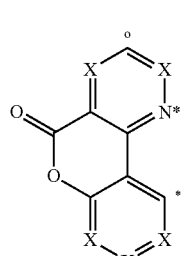
(L30) 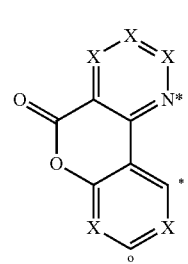
(L-31) 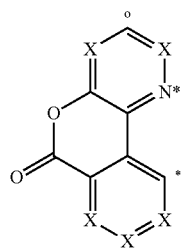
(L-32) 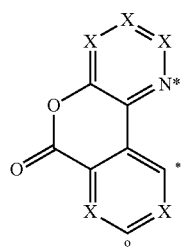
(L-33) 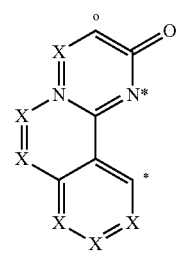

-continued (L-34)
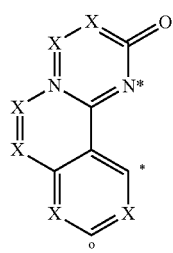

(L-41)
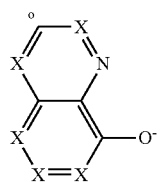

(L-42)
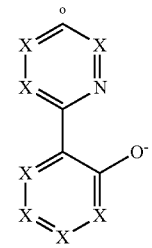

(L-43)
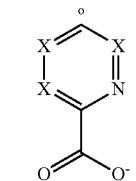

(L-44)
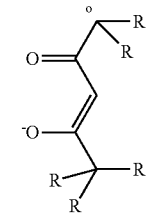

wherein
* indicates the position of the coordination to the metal; and
"o" denotes the position of the bond to the bridge of formula (1).

8. The compound of claim 1, wherein the compound comprises two radicals R or R' which are bonded to adjacent carbon atoms and together define a ring of Formulae (34) through (40):

Formula (34)
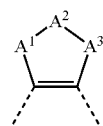

Formula (35)
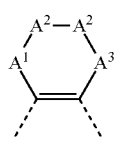

Formula (36)
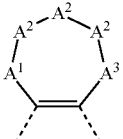

Formula (37)
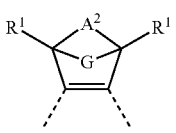

Formula (38)
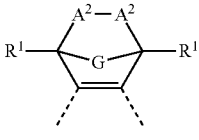

Formula (39)
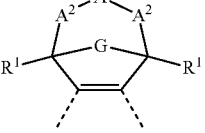

Formula (40)
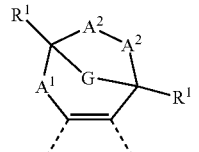

wherein
the dotted bonds denote the linkage of the two carbon atoms in the ligand
$A^1$ and $A^3$
is, identically or differently in each instance, $C(R^3)_2$, O, S, $NR^3$ or $C(=O)$;
$A^2$ is $C(R^1)^2$, O, S, $NR^3$, or $C(=O)$;
G is an alkylene group having 1, 2, or 3 carbon atoms, which is optionally substituted by one or more radicals $R^2$, —CR2=CR2—, or an ortho-bonded arylene or heteroarylene group having 5 to 14 aromatic ring atoms and is optionally substituted by one or more $R^2$ radicals;
$R^3$ is, identically or differently in each instance, H, D, F, a straight-chain alkyl or alkoxy group having 1 to 10 carbon atoms or a branched or cyclic alkyl or alkoxy group having 3 to 10 carbon atoms, wherein the alkyl or alkoxy group in each instance is optionally substituted by one or more radicals $R^2$, and wherein one or more nonadjacent $CH_2$ groups are optionally replaced by $R^2C=CR^2$, $C≡C$, $Si(R^2)^2$, $C=O$, $NR^2$, O, S, or $CONR^2$, an aromatic or heteroaromatic ring system having 5 to 24 aromatic ring atoms and in each instance is optionally substituted by one or more radicals $R^2$, or an aryloxy or heteroaryloxy group having 5 to 24 aromatic ring atoms and is optionally substituted by one or more $R^2$ radicals; and wherein two radicals $R^3$ bonded to the same carbon atom together optionally define an aliphatic or aromatic ring system so as to form a spiro system; and wherein $R^3$ with an adjacent radical R or $R^1$ optionally defines an aliphatic ring system;

with the proviso that no two heteroatoms in these rings are bonded directly to one another and no two C=O groups are bonded directly to one another.

9. A process for preparing the compound of claim 1, comprising reacting a free ligand with a metal alkoxide of Formula (42), a metal ketoketonate of Formula (43), a metal halide of Formula (44), a metal carboxylate of Formula (45), or a metal compound bearing both alkoxide and/or halide and/or hydroxyl radicals and ketoketonate radicals $$M(OR)_n \quad \text{Formula (42)}$$

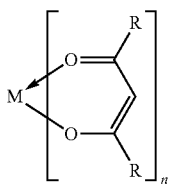

Formula (43)

$$MHal_n \quad \text{Formula (44)}$$

$$M(OOCR)_n \quad \text{Formula (45)}$$

wherein
M is the metal in the metal complex;
n is the valency of M;
Hal is F, Cl, Br, or I; and
wherein metal reactants are optionally present in the form of hydrates.

10. An oligomer, polymer, or dendrimer comprising one or more compounds of claim 1, wherein one or more bonds of the compound to the polymer, oligomer, or dendrimer are present in place of one or more hydrogen atoms and/or substituents.

11. A formulation comprising at least one compound of claim 1 and at least one solvent.

12. A formulation comprising at least one oligomer, polymer, or dendrimer of claim 10 and at least one solvent.

13. An electronic device comprising at least one compound of claim 1.

14. An electronic device comprising at least one oligomer, polymer, or dendrimer of claim 10.

15. The electronic device of claim 13, wherein the electronic device is an organic electroluminescent device and the at least one compound is used as emitting compound in one or more emitting layers or as hole blocker material in a hole blocker layer or as electron transport material in an electron transport layer.

* * * * *